(12) United States Patent
Wada et al.

(10) Patent No.: US 8,404,427 B2
(45) Date of Patent: Mar. 26, 2013

(54) PHOTOSENSITIVE COMPOSITION, AND PATTERN-FORMING METHOD AND RESIST FILM USING THE PHOTOSENSITIVE COMPOSITION

(75) Inventors: Kenji Wada, Shizuoka (JP); Kunihiko Kodama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 102 days.

(21) Appl. No.: 12/786,127

(22) Filed: May 24, 2010

(65) Prior Publication Data

US 2010/0239978 A1   Sep. 23, 2010

Related U.S. Application Data

(63) Continuation-in-part of application No. 11/642,533, filed on Dec. 21, 2006, now Pat. No. 7,749,679.

(30) Foreign Application Priority Data

Dec. 28, 2005  (JP) ................................ 2005-379028

(51) Int. Cl.
  *G03F 7/028* (2006.01)
  *G03F 7/039* (2006.01)
  *G03F 7/26* (2006.01)
(52) U.S. Cl. ...................... 430/270.1; 430/326; 430/921
(58) Field of Classification Search ............... 430/270.1, 430/921, 326
See application file for complete search history.

(56) References Cited

U.S. PATENT DOCUMENTS

| | | | |
|---|---|---|---|
| 5,141,969 A | 8/1992 | Saeva et al. | |
| 5,550,171 A | 8/1996 | Kuczynski | |
| 5,688,628 A | 11/1997 | Oie et al. | |
| 6,093,753 A | 7/2000 | Takahashi | |
| 6,395,446 B1 | 5/2002 | Seki et al. | |
| 6,531,568 B1 | 3/2003 | Shibuya et al. | |
| 6,720,128 B2 * | 4/2004 | Adegawa et al. | 430/270.1 |
| 6,939,664 B2 * | 9/2005 | Huang et al. | 430/270.1 |
| 7,318,991 B2 * | 1/2008 | Ishihara et al. | 430/270.1 |
| 7,749,679 B2 * | 7/2010 | Wada et al. | 430/270.1 |
| 2003/0077543 A1 | 4/2003 | Sato | |
| 2003/0203305 A1 | 10/2003 | Yasunami et al. | |
| 2003/0215742 A1 | 11/2003 | Barclay et al. | |
| 2004/0185378 A1 | 9/2004 | Kodama et al. | |
| 2005/0202351 A1 | 9/2005 | Houlihan et al. | |
| 2006/0008736 A1 * | 1/2006 | Kanda et al. | 430/270.1 |
| 2006/0147836 A1 | 7/2006 | Hatakeyama et al. | |
| 2007/0111140 A1 | 5/2007 | Hatakeyama et al. | |
| 2008/0161520 A1 | 7/2008 | Ishihara et al. | |

FOREIGN PATENT DOCUMENTS

| | | |
|---|---|---|
| JP | 57-153433 A | 9/1982 |
| JP | 60-004165 A | 1/1985 |
| JP | 2-199177 A | 8/1990 |
| JP | 4-502374 A | 4/1992 |
| JP | 7-220990 A | 8/1995 |
| JP | 9-118663 A | 5/1997 |
| JP | 10-048814 A | 2/1998 |
| JP | 11-501909 A | 2/1999 |
| JP | 2000-275845 A | 10/2000 |
| JP | 2002-131897 A | 5/2002 |
| JP | 2002-255930 A | 9/2002 |
| JP | 2002-268223 A | 9/2002 |
| JP | 2002-293816 A | 10/2002 |
| JP | 2003-149812 A | 5/2003 |
| JP | 2003-246786 A | 9/2003 |
| JP | 2004-277303 A | 10/2004 |
| JP | 2005-336452 A | 12/2005 |
| JP | 2006-011005 A | 1/2006 |
| WO | 91/06039 A1 | 5/1991 |
| WO | 03/074509 A1 | 9/2003 |
| WO | 2004-068242 A1 | 8/2004 |
| WO | 2004-077158 A1 | 9/2004 |

OTHER PUBLICATIONS

Japanese Office Action issued on Jan. 4, 2011 in the corresponding Japanese Patent Application No. 2005-379028.

Terada, T. et., al. "Antitumor Agents. I. DNA Topoisomerase II Inhibitory Activity and the Structural Relationship of Podophyllotoxin Derivatives as Antitomor Agents", Chemical and Pharmaceutical Bulletin, vol. 40, No. 10, pp. 2720-2727 (1992).

Ohkawa, K. et., al. "Photoresponsive peptide and polypeptide systems 15: Synthesis of photo-crosslinkable poly (amino acid)s by watery process and its application as a reinforcement for polyion complex fibers", Journal of Materials Science, vol. 38, No. 15, Aug. 1, 2003, pp. 3191-3198.

Japanese Office Action issued on May 24, 2011 in the corresponding Japanese Patent Application No. 2005-379028.

Lin, B. J. "Semiconductor Foundry, Lithography, and Partners", Proceedings of SPIE vol. 4688 (2002), pp. 11-24.

Watanabe Yoshihiko et al., "A New Fragmentation Reaction of Gamma-Oxosulfonium Methylides" Chemistry Letters, 1992, pp. 159-162.

* cited by examiner

*Primary Examiner* — Anca Eoff
(74) *Attorney, Agent, or Firm* — Sughrue Mion, PLLC

(57) ABSTRACT

A photosensitive composition containing a compound having a specific structure, a pattern-forming method using the photosensitive composition, and a compound having a specific structure used in the photosensitive composition.

43 Claims, No Drawings

PHOTOSENSITIVE COMPOSITION, AND PATTERN-FORMING METHOD AND RESIST FILM USING THE PHOTOSENSITIVE COMPOSITION

CROSS-REFERENCE TO RELATED APPLICATION

This is a Continuation-In-Part application of U.S. application Ser. No. 11/642,533 filed in the United States on Dec. 21, 2006; the entire content of which is hereby incorporated by reference.

BACKGROUND OF THE INVENTION

1. Field of the Invention

The present invention relates to a photosensitive composition capable of changing the property by reaction upon irradiation with actinic ray or radiation, and a pattern-forming method and resist film using the photosensitive composition, and the compounds used in the photosensitive composition. More specifically, the invention relates to a photosensitive composition for use in a manufacturing process of semiconductors, e.g., IC, the manufacture of circuit substrates for liquid crystals, thermal heads and the like, and other photo-fabrication processes, lithographic printing plates, and acid-hardening compositions, and also the invention relates to a pattern-forming process and resist film using the photosensitive composition.

2. Description of the Related Art

Chemical amplification resist compositions are pattern-forming materials capable of generating an acid at the area irradiated with actinic ray such as a far ultraviolet ray or radiation, changing the solubility in a developer of the irradiated area with the actinic ray or radiation and the solubility of the non-irradiated area by the reaction with the acid as a catalyst, and forming a pattern on a substrate.

When a KrF excimer laser is used as the exposure light source, resins having poly(hydroxystyrene) that is small in absorption in the region of 248 nm as a fundamental skeleton are mainly used, so that a high sensitivity, high resolution and good pattern is formed as compared with conventionally used naphthoquinonediazide/novolak resins.

On the other hand, when a light source of further shorter wavelength, e.g., an ArF excimer laser (193 nm), is used as the exposure light source, since compounds having an aromatic group substantially show large absorption in the region of 193 nm, resists containing a resin having a highly transparent alicyclic hydrocarbon structure have been developed for an ArF excimer laser.

Various compounds have been found as to acid generators that are main constitutional components of chemical amplification resists, e.g., triaryl sulfonium salts and arylalkyl sulfonium salts are reported (e.g., refer to JP-A-2000-275845 and JP-A-10-48814).

As generating acids, e.g., in JP-A-2002-131897 and JP-A-2003-149812, specific fluorinated organic sulfonic acids are used. In JP-T-11-501909 (The term "JP-T" as used herein refers to a "published Japanese translation of a PCT application".), JP-A-2002-268223 and JP-A-2003-246786, imido anion acid generators capable of generating highly acidic imido upon irradiation with actinic ray or radiation are used.

However, these compounds are still insufficient in various points and the improvement in line edge roughness, pattern profile and the like is required.

In the optical microscope, as a technique of enhancing resolution, a method of filling in between a projection lens and a sample with a liquid having a high refractive index (hereinafter referred to as "immersion liquid"), i.e., an immersion method is conventionally known.

As "the effect of immersion", resolution and the depth of focus can be expressed by the following expressions in the case of immersion, with $\lambda_0$ as the wavelength of the exposure light in the air, n as the refractive index of immersion liquid to the air, and $NA_0=\sin \theta$ with $\theta$ as convergence half angle of the ray of light:

Resolution=$k_1 \cdot (\lambda_0/n)/NA_0$

Depth of focus=$\pm k_2 \cdot (\lambda_0/n)/NA_0^2$

That is, the effect of immersion is equivalent to the case of using exposure wavelength of the wavelength of 1/n. In other words, in the case of the projection optical system of the same NA, the depth of focus can be made n magnifications by immersion. This is effective for every pattern form, and further, it is possible to combine an immersion method with super resolution techniques such as a phase shift method and a transformation lighting method now under discussion.

The example of the apparatus applying this effect to the transfer of a micro-fine image pattern of a semiconductor element are introduced in JP-A-57-153433 (the term "JP-A" as used herein refers to an "unexamined published Japanese patent application") and JP-A-7-220990.

The latest technical advancement of immersion exposure is reported in SPIE Proc., 4688, 11 (2002), J. Vac. Sci. Tecnol. B, 17 (1999), SPIE Proc., 3999, 2 (2000), and WO 2004/077158. When an ArF excimer laser is used as the light source, it is thought that pure water (having a refractive index of 1.44 at 193 nm) is most promising as the immersion liquid in the light of the safety in handling, the transmittance and the refractive index at 193 nm. When an F2 excimer laser is used as the light source, a solution containing fluorine is discussed from the balance of the transmittance and the refractive index at 157 nm, but a sufficiently satisfactory solution from the viewpoint of the environmental safety and at the point of refractive index has not been found yet. From the extent of the effect of immersion and the degree of completion of resist, it is thought that immersion exposure technique will be carried on an ArF exposure apparatus earliest.

It is appointed that when a chemical amplification resist is applied to immersion exposure, the resist layer is brought into contact with the immersion liquid at the time of exposure, so that the resist layer decomposes and ingredients that adversely influence the immersion liquid ooze from the resist layer. WO 2004/068242 discloses that resist performance decomposes by the immersion of a resist for ArF exposure in water before and after exposure and appoints this is a problem in immersion exposure.

SUMMARY OF THE INVENTION

An object of the invention is to provide a photosensitive composition that shows good line edge roughness and pattern profile, and improved in the contrast of sensitivity and dissolution in EUV exposure. Another object is to provide a pattern-forming method and resist film using the photosensitive composition. A further object is to provide compounds for use in the photosensitive composition. Still further objects of the invention are to provide a photosensitive composition suitable for immersion exposure having good performances as described above even in immersion exposure, to provide a pattern-forming method using the photosensitive composition, and to provide compounds for use in the photosensitive composition.

The present invention is as follows.

(1) A photosensitive composition, which comprises (A) a sulfonium salt compound represented by formula (I):

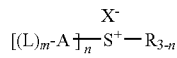
(I)

wherein A represents an (m+1)-valent linking group, when a plurality of A's are present, the plurality of A's may be the same or different, and the plurality of A's may be bonded to each other to form a cyclic structure;

R represents a monovalent organic group, when two R's are present, the two R's may be the same or different, and the two R's may be bonded to each other to form a cyclic structure;

L represents a lactone ring structure, when a plurality of L's are present, the plurality of L's may be the same or different;

$X^-$ represents an anion;

n represents an integer of from 1 to 3; and m represents an integer of 1 or 2.

(2) The photosensitive composition as described in (1) above, wherein the (m+1)-valent linking group represented by A has an aromatic ring.

(3) The photosensitive composition as described in (1) or (2) above, wherein the anion represented by $X^-$ in formula (I) is an organic sulfonate anion ($R^1$—$SO_3^-$), an organic carboxylate anion ($R^1$—$CO_2^-$), an organic imidate anion ($N^-(SO_2—R^1)_2$, $N^-(SO_2—R^1)(CO—R^1)$) or an organic methidate anion ($C^-(SO_2—R^1)_3$), wherein $R^1$ represents a monovalent organic group.

(4) A pattern-forming method, which comprises:

forming a photosensitive film with a photosensitive composition as described in any of (1) to (3) above; and exposing and developing the photosensitive film.

(5) A compound, which is represented by formula (I):

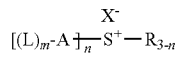
(I)

wherein A represents an (m+1)-valent linking group, when a plurality of A's are present, the plurality of A's may be the same or different, and the plurality of A's may be bonded to each other to form a cyclic structure;

R represents a monovalent organic group, when two R's are present, the two R's may be the same or different, and the two R's may be bonded to each other to form a cyclic structure;

L represents a lactone ring structure, when a plurality of L's are present, the plurality of L's may be the same or different;

$X^-$ represents an anion;

n represents an integer of from 1 to 3; and m represents an integer of 1 or 2.

As preferred embodiments of the invention, the following constitutions are exemplified.

(6) The photosensitive composition as described in any of (1) to (3) above, which further comprises (B) a compound capable of generating an acid upon irradiation with actinic ray or radiation.

(7) The photosensitive composition as described in (6) above, wherein the compound of component (B) is a sulfonium salt of a fluoro-substituted alkanesulfonic acid, a fluorine-substituted benzenesulfonic acid or a fluorine-substituted imidic acid.

(8) The positive photosensitive composition as described in any of (1) to (3), (6) and (7) above, which further comprises (C) a resin capable of decomposing by an action of an acid to increase solubility in an alkali developing solution.

(9) The positive photosensitive composition as described in (8) above, wherein the resin of component (C) has a fluorine atom on a main chain or side chain.

(10) The positive photosensitive composition as described in (8) above, wherein the resin of component (C) has a hexafluoroisopropanol structure.

(11) The positive photosensitive composition as described in (8) above, wherein the resin of component (C) has a hydroxystyrene structural unit.

(12) The positive photosensitive composition as described in (8) above, wherein the resin of component (C) has at least one repeating unit selected from 2-alkyl-2-adamantyl(meth)acrylate and dialkyl(1-adamantyl)methyl(meth)acrylate.

(13) The positive photosensitive composition as described in (8) above, wherein the resin of component (C) has a monocyclic or polycyclic alicyclic hydrocarbon structure.

(14) The positive photosensitive composition as described in (13) above, wherein the resin of component (C) has at least one repeating unit selected from 2-alkyl-2-adamantyl(meth)acrylate and dialkyl(1-adamantyl)methyl(meth)acrylate, at least one repeating unit having a lactone structure and at least one repeating unit having a hydroxyl group.

(15) The positive photosensitive composition as described in (14) above, wherein the resin of component (C) further has a repeating unit having a carboxyl group.

(16) The positive photosensitive composition as described in (8) above, wherein the resin of component (C) has a silicon atom on a main chain or side chain.

(17) The positive photosensitive composition as described in (8) above, wherein the resin of component (C) has a repeating unit having a lactone structure.

(18) The positive photosensitive composition as described in any of (8) to (17) above, which further comprises (D) a dissolution inhibiting compound capable of decomposing by an action of an acid to increase solubility in an alkali developing solution and having a molecular weight of 3,000 or less.

(19) The positive photosensitive composition as described in any (1) to (3), (6) and (7) above, which further comprises (E) a resin soluble in an alkali developing solution and (D) a dissolution inhibiting compound capable of decomposing by an action of an acid to increase solubility in an alkali developing solution and having a molecular weight of 3,000 or less.

(20) The negative photosensitive composition as described in any of (1) to (3), (6) and (7) above, which further comprises (E) a resin soluble in an alkali developing solution and (F) an acid crosslinking agent capable of crosslinking with the resin soluble in an alkali developing solution by an action of an acid.

(21) The photosensitive composition as described in any of (1) to (3) and (6) to (20) above, which further comprises at least one of (G) a basic compound and (H) a fluorine and/or silicon surfactant.

(22) The photosensitive composition as described in (21) above, wherein the basic compound (G) is a compound having a structure selected from an imidazole structure, a diazabicyclo structure, an onium hydroxide structure, an onium carboxylate structure, a trialkylamine structure, an aniline structure and a pyridine structure, an alkylamine derivative having at least one of a hydroxyl group and an ether bond or an aniline derivative having at least one of a hydroxyl group and an ether bond.

DETAILED DESCRIPTION OF THE INVENTION

The invention will be described in detail below.

In the description of a group (an atomic group) in the specification of the invention, the description not referring to substitution or unsubstitution includes both a group not having a substituent and a group having a substituent. For example, "an alkyl group" includes not only an alkyl group having no substituent (an unsubstituted alkyl group) but also an alkyl group having a substituent (a substituted alkyl group).

A positive photosensitive composition in the invention, preferably a positive resist composition, contains (A) a sulfonium salt compound represented by formula (I), and (C) a resin capable of decomposing by the action of an acid to increase solubility in an alkali developing solution, and if necessary, further contains (B) a compound capable of generating an acid upon irradiation with actinic ray or radiation, and (D) a dissolution inhibiting compound capable of decomposing by the action of an acid to increase solubility in an alkali developing solution having a molecular weight of 3,000 or less, alternatively, contains (A) a sulfonium salt compound represented by formula (I), (E) a resin soluble in an alkali developing solution, and (D) a dissolution inhibiting compound capable of decomposing by the action of an acid to increase solubility in an alkali developing solution having a molecular weight of 3,000 or less, and if necessary, further contains (B) a compound capable of generating an acid upon irradiation with actinic ray or radiation.

A negative photosensitive composition in the invention, preferably a negative resist composition, contains (A) a sulfonium salt compound represented by formula (I), (E) a resin soluble in an alkali developing solution, and (F) an acid crosslinking agent capable of crosslinking with the resin soluble in an alkali developing solution by the action of an acid, and if necessary, further contains (B) a compound capable of generating an acid upon irradiation with actinic ray or radiation.

[1] (A) A sulfonium salt compound represented by formula (I):

A photosensitive composition in the invention contains a sulfonium salt compound represented by the following formula (I) (also referred to as "compound (A)"). The sulfonium salt compound represented by formula (I) is not a polymer.

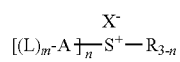

(I)

In formula (I), A represents an (m+1)-valent linking group, when a plurality of A's are present, the plurality of A's may be the same or different, and they may be bonded to each other to form a cyclic structure; R represents a monovalent organic group, when two R's are present, the two R's may be the same or different, and they may be bonded to each other to form a cyclic structure; L represents a lactone ring structure, when a plurality of L's are present, the plurality of L's may be the same or different; $X^-$ represents an anion; n represents an integer of from 1 to 3; and m represents an integer of 1 or 2.

Compound (A) is a compound capable of generating an acid upon irradiation with actinic ray or radiation.

The (m+1)-valent linking group represented by A in formula (I) is a linking group for linking $S^+$ and L.

When m is 1, A represents a divalent linking group for linking $S^+$ and L, and divalent groups, e.g., an arylene group, an alkylene group, a cycloalkylene group, an alkenylene group, an ether group, an ester group, etc., and divalent groups obtained by combining these groups can be exemplified, and these groups may have a substituent.

As the arylene group, an arylene group having from 6 to 15 carbon atoms is preferred, e.g., a phenylene group, a naphthylene group, etc., can be exemplified.

As the alkylene group, a straight chain or branched alkylene group having from 1 to 8 carbon atoms is preferred, e.g., a methylene group, an ethylene group, a propylene group, a butylene group, a hexylene group, an octylene group, etc., can be exemplified.

As the cycloalkylene group, a cycloalkylene group having from 5 to 12 carbon atoms is preferred, e.g., a monocyclic residue such as a cyclopentylene group, a cyclohexylene group, etc., and a polycyclic residue such as a normornane skeleton, an adamantane skeleton, etc., can be exemplified.

As the alkenylene group, an alkenylene group having from 2 to 6 carbon atoms is preferred, e.g., an ethenylene group, a propenylene group, a butenylene group, etc., can be exemplified.

When m is 2, A is a group using an arbitrary hydrogen atom in the divalent linking group of the time of m being 1 as a hand for bonding to another L.

The (m+1)-valent linking group represented by A has preferably 20 or less carbon atoms, and more preferably 15 or less carbon atoms.

It is preferred for the (m+1)-valent linking group represented by A to have an aromatic ring, by which stability is improved, and the preservation stability of the composition using this is improved. The aromatic ring may be or may not be directly bonded to the sulfur atom ($S^+$). As the aromatic ring, an aromatic ring having from 1 to 30 carbon atoms is preferred, e.g., a benzene ring, a naphthalene ring, an anthracene ring, a phenanthrene ring, a biphenylene ring, a fluorene ring, a pyrene ring, etc., are exemplified. One or more aromatic rings may be bonded to one and the same A. As the aromatic ring, a benzene ring, a naphthalene ring, and an anthracene ring are especially preferred, and the solubility in a solvent is improved by using these aromatic rings.

The arylene group, alkylene group, cycloalkylene group, and alkenylene group as the (m+1)-valent linking group represented by A may be substituted with one or more organic groups (B).

As the examples of organic groups (B), e.g., an alkyl group, a cycloalkyl group, an aryl group, an aralkyl group, an alkenyl group, an alkoxyl group, an alkoxycarbonylamino group, an alkylthio group, an alkyliminosulfonyl group, a cycloalkylaryloxysulfonyl group, a cyano group, etc., can be exemplified. When a plurality of organic groups (B) are present, the plurality of organic groups (B) may be the same or different.

The alkyl group as organic group (B) may have a substituent. The alkyl group is preferably a straight chain or branched alkyl group having from 1 to 30 carbon atoms, and an oxygen atom, a sulfur atom or a nitrogen atom may be contained in the alkyl chain. Specifically, a straight chain alkyl group, e.g., a methyl group, an ethyl group, an n-propyl group, an n-butyl group, an n-pentyl group, an n-hexyl group, an n-octyl group, an n-dodecyl group, an n-tetradecyl group, an n-octadecyl group, etc., and a branched alkyl group, e.g., an isopropyl group, an isobutyl group, a t-butyl group, a neopentyl group, a 2-ethylhexyl group, etc., can be exemplified.

The cycloalkyl group as organic group (B) may have a substituent. The cycloalkyl group is preferably a cycloalkyl group having from 3 to 20 carbon atoms, and an oxygen atom may be contained in the ring. Specifically, a cyclopropyl group, a cyclopentyl group, a cyclohexyl group, a norbornyl group, an adamantyl group, etc., can be exemplified.

The aryl group as organic group (B) may have a substituent. The aryl group is preferably an aryl group having from 6 to 14 carbon atoms, e.g., a phenyl group, a naphthyl group, etc., can be exemplified.

The aralkyl group as organic group (B) may have a substituent. The aralkyl group is preferably an aralkyl group having from 7 to 20 carbon atoms, e.g., a benzyl group, a phenethyl group, a naphthylmethyl group, and a naphthylethyl group can be exemplified.

As the alkenyl group as organic group (B), a group having a double bond on an arbitrary position of the above alkyl group can be exemplified.

The alkoxyl group, and the alkoxyl group in the alkoxycarbonylamino group as organic group (B) is preferably an alkoxyl group having from 1 to 30 carbon atoms, e.g., a methoxy group, an ethoxy group, a propoxy group, an n-butoxy group, a pentyloxy group, a hexyloxy group, a heptyloxy group, etc., can be exemplified.

As the alkyl group in the alkylthio group and the alkyliminosulfonyl group as organic group (B), the above alkyl group can be exemplified.

As the cycloalkyl group and the aryl group in the cycloalkylaryloxysulfonyl group as organic group (B), the above cycloalkyl group and the aryl group can be exemplified.

As further substituents that each of the above organic groups (B) may have, e.g., a halogen atom, a hydroxyl group, a nitro group, a cyano group, a carboxyl group, a carbonyl group, a cycloalkyl group (preferably having from 3 to 10 carbon atoms), an aryl group (preferably having from 6 to 14 carbon atoms), an alkoxyl group (preferably having from 1 to 10 carbon atoms), an acyl group (preferably having from 2 to 20 carbon atoms), an acyloxy group (preferably having from 2 to 10 carbon atoms), an alkoxycarbonyl group (preferably having from 2 to 20 carbon atoms), an aminoacyl group (preferably having from 2 to 10 carbon atoms), etc., can be exemplified. As a further substituent in connection with the cyclic structure in the aryl group and the cycloalkyl group, an alkyl group (preferably having from 1 to 10 carbon atoms) can be exemplified. As a further substituent in regard to the aminoacyl group, an alkyl group having 1 or 2 carbon atoms (preferably from 1 to 10) can be exemplified.

The (m+1)-valent linking group represented by A may further be substituted with a halogen atom (preferably a fluorine atom), etc.

As the monovalent organic group represented by R, e.g., an alkyl group, a cycloalkyl group, an aryl group, an aralkyl group, an alkenyl group, etc., can be exemplified.

The alkyl group as the monovalent organic group represented by R may have a substituent. The alkyl group is preferably a straight chain or branched alkyl group having from 1 to 30 carbon atoms, and an oxygen atom, a sulfur atom, or a nitrogen atom may be contained in the alkyl chain. Specifically, a straight chain alkyl group, e.g., a methyl group, an ethyl group, an n-propyl group, an n-butyl group, an n-pentyl group, an n-hexyl group, an n-octyl group, an n-dodecyl group, an n-tetradecyl group, an n-octadecyl group, etc., and a branched alkyl group, e.g., an isopropyl group, an isobutyl group, a t-butyl group, a neopentyl group, a 2-ethylhexyl group, etc., can be exemplified.

The cycloalkyl group as the monovalent organic group represented by R may have a substituent. The cycloalkyl group is preferably a cycloalkyl group having from 3 to 20 carbon atoms, and an oxygen atom may be contained in the ring. Specifically, a cyclopropyl group, a cyclopentyl group, a cyclohexyl group, a norbornyl group, an adamantyl group, etc., can be exemplified.

The aryl group as the monovalent organic group represented by R may have a substituent. The aryl group is preferably an aryl group having from 6 to 14 carbon atoms and, e.g., a phenyl group, a naphthyl group, etc., can be exemplified.

The aralkyl group as the monovalent organic group represented by R may have a substituent. The aralkyl group is preferably an aralkyl group having from 7 to 20 carbon atoms and, e.g., a benzyl group, a phenethyl group, a naphthylmethyl group, and a naphthylethyl group can be exemplified.

As the alkenyl group as the monovalent organic group represented by R, a group having a double bond on an arbitrary position of the above alkyl group can be exemplified.

As further substituents that the monovalent organic groups represented by R may have, e.g., a halogen atom, a hydroxyl group, a nitro group, a cyano group, a carboxyl group, a carbonyl group, a cycloalkyl group (preferably having from 3 to 10 carbon atoms), an aryl group (preferably having from 6 to 14 carbon atoms), an alkoxyl group (preferably having from 1 to 10 carbon atoms), an acyl group (preferably having from 2 to 20 carbon atoms), an acyloxy group (preferably having from 2 to 10 carbon atoms), an alkoxycarbonyl group (preferably having from 2 to 20 carbon atoms), an aminoacyl group (preferably having from 2 to 10 carbon atoms), etc., can be exemplified. As a further substituent in connection with the cyclic structure in the aryl group and cycloalkyl group, an alkyl group (preferably having from 1 to 10 carbon atoms) can be exemplified. As a further substituent in regard to the aminoacyl group, an alkyl group having 1 or 2 carbon atoms (preferably from 1 to 10) can be exemplified.

The number of carbon atoms constituting the lactone ring structure represented by L is preferably from 4 to 20, and more preferably from 4 to 10. The lactone ring structure represented by L may be substituted with one or more organic groups (B).

The lactone ring structure represented by L is preferably a 5- to 7-membered lactone structure, and other ring structures may be condensed with the 5- to 7-membered lactone structure to form a bicyclo structure or Spiro structure. The lactone ring structures represented by any of the following formulae (LC1-1) to (LC1-16) are more preferred. Especially preferred lactone ring structures are (LC1-1), (LC1-4), (LC1-5), (LC1-6), (LC1-13) and (LC1-14). By the use of a specific lactone ring structure, development defect is bettered.

LC1-1 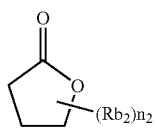

LC1-2 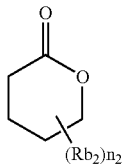

LC1-3 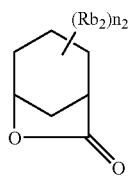

LC1-4 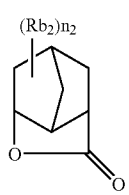

LC1-5 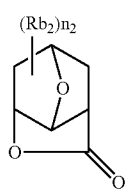

LC1-6 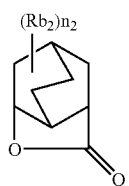

LC1-7 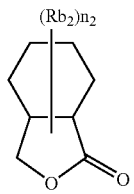

LC1-8 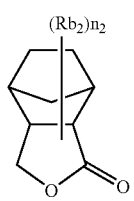

LC1-9 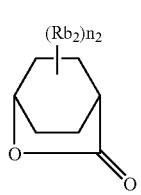

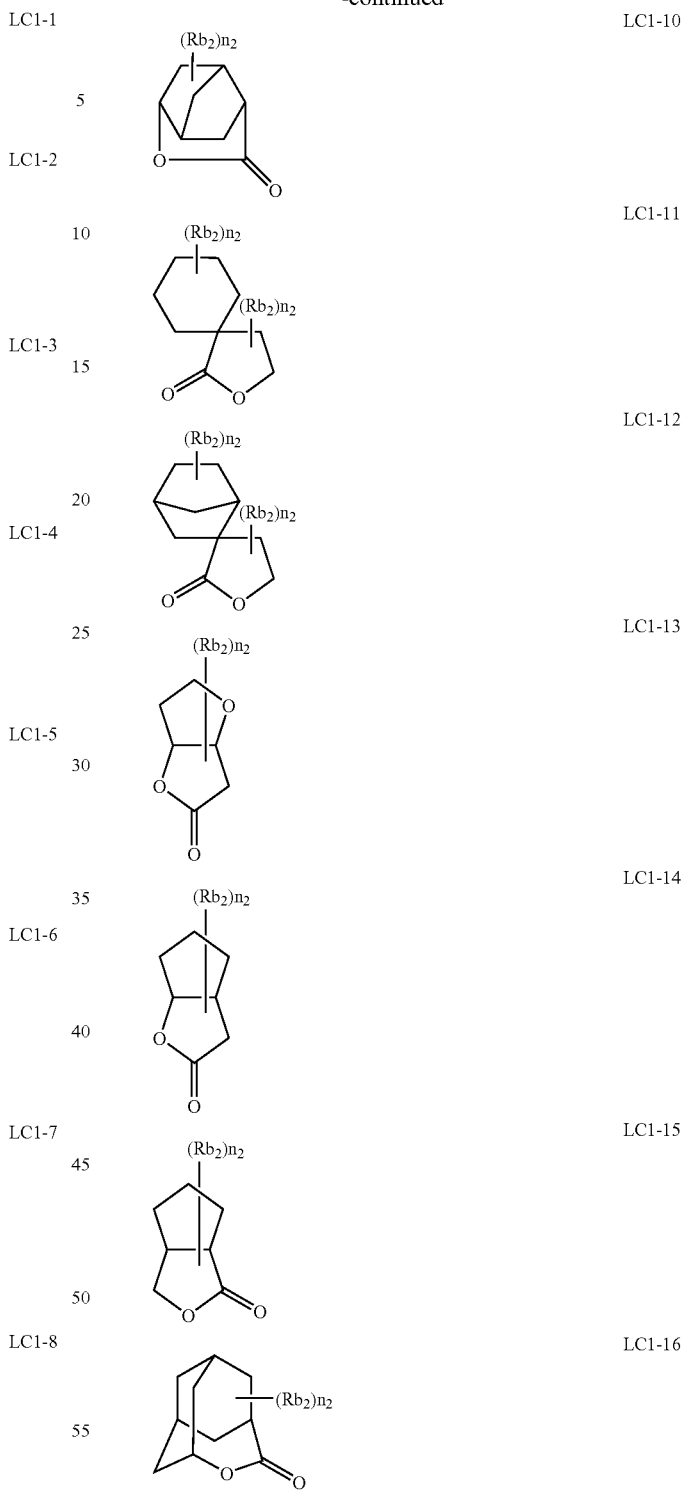

The lactone ring structure may have or may not have a substituent ($Rb_2$). As preferred substituent ($Rb_2$), an alkyl group having from 1 to 8 carbon atoms, a cycloalkyl group having from 3 to 7 carbon atoms, an alkoxyl group having from 1 to 8 carbon atoms, an alkoxycarbonyl group having from 1 to 8 carbon atoms, a carboxyl group, a halogen atom, a hydroxyl group, a cyano group, and an acid-decomposable group are exemplified. $n_2$ represents an integer of from 0 to 4.

When $n_2$ is 2 or more, a plurality of $Rb_2$ may be the same or different, and the plurality of $Rb_2$ may be bonded to each other to form a ring.

It is sufficient for the lactone ring structure represented by L to be bonded to the linking group represented by A on an arbitrary position of the ring.

The specific examples of the cationic parts in compound (A) are shown below, but the invention is not restricted thereto.

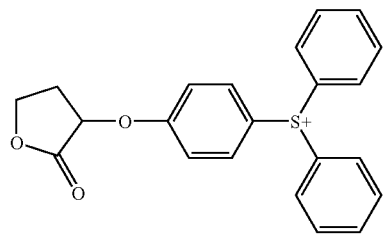

(I-1)

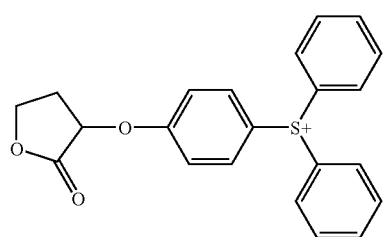

(I-2)

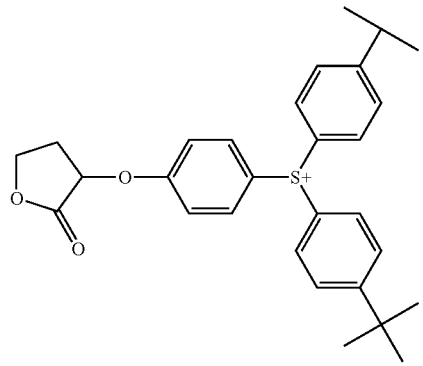

(I-3)

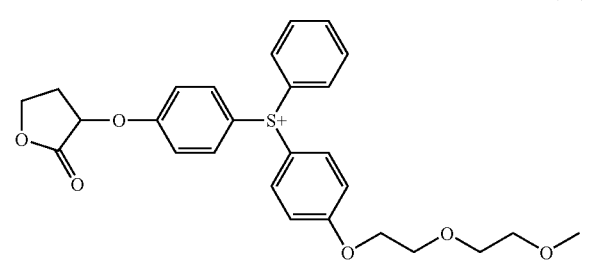

(I-4)

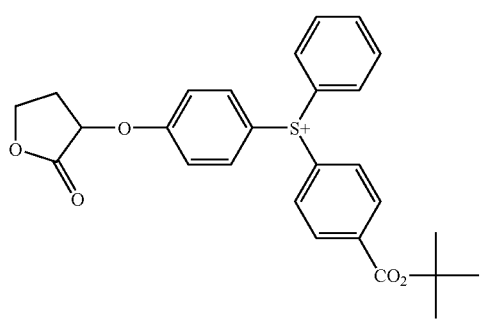

(I-5)

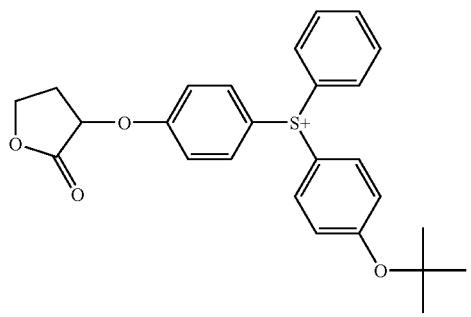

(I-6)

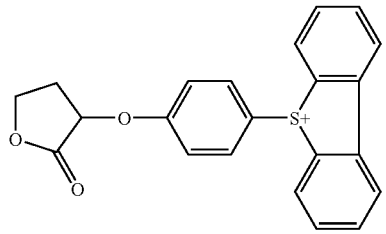

(I-7)

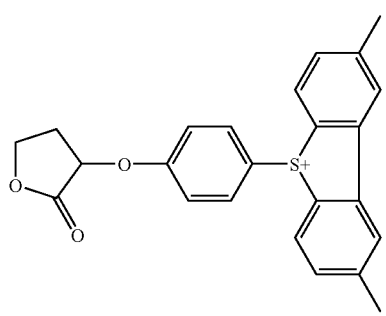

(I-8)

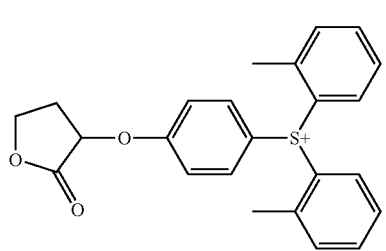

(I-9)

(I-10)
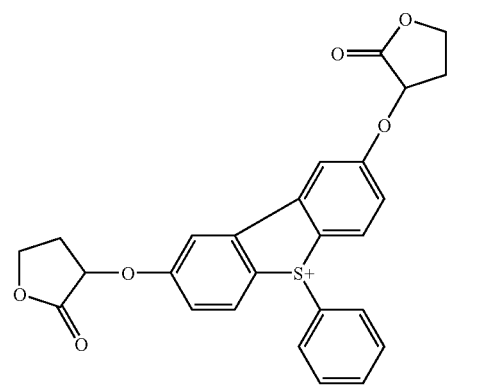
(I-11)
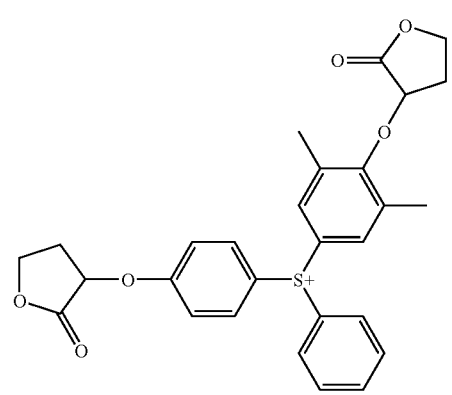
(I-12)
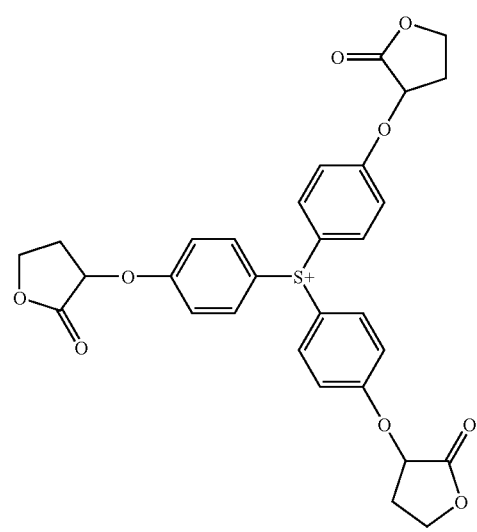
(I-13)
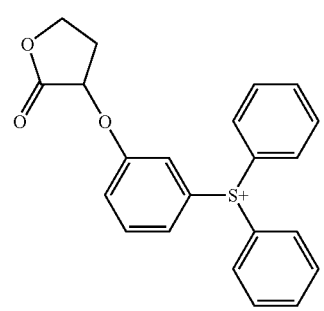
(I-14)
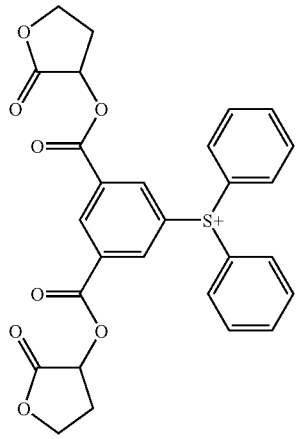
(I-15)
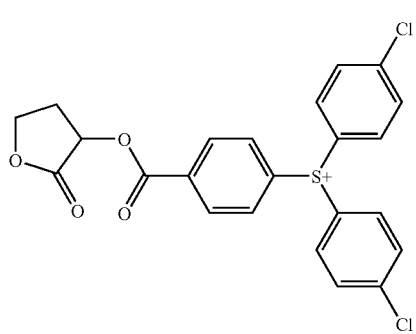
(I-16)
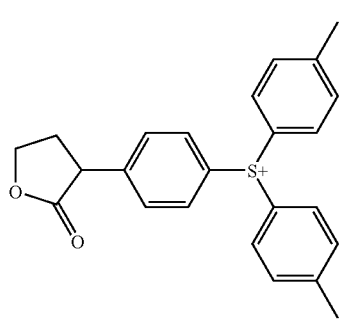
(I-17)
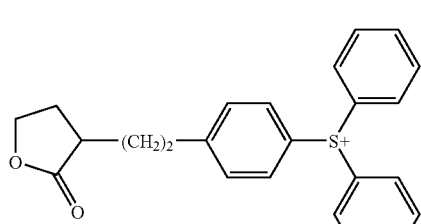
(I-18)
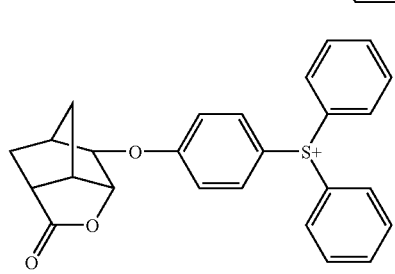

(I-19)
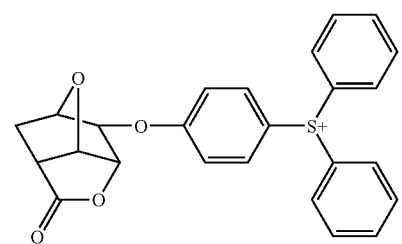
(I-20)
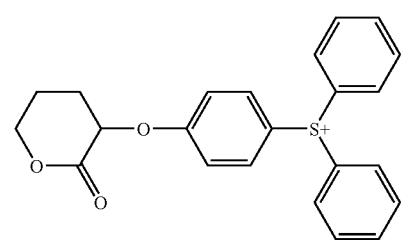
(I-21)
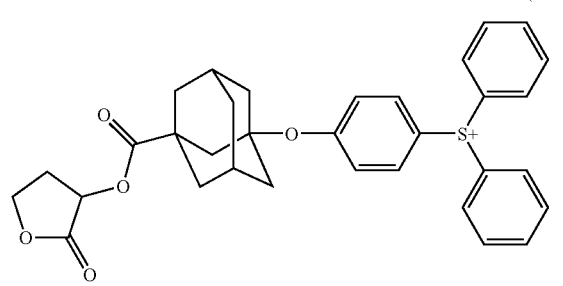
(I-22)
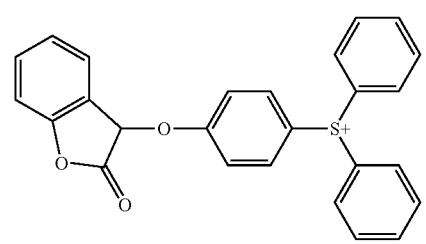
(I-23)
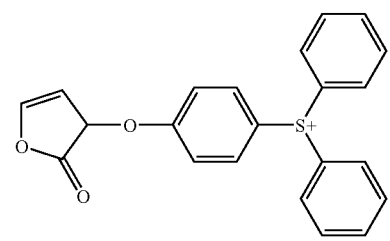
(I-24)
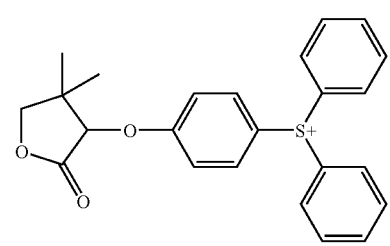
(I-25)
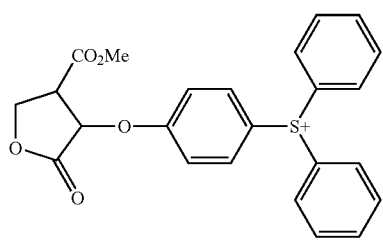
(I-26)
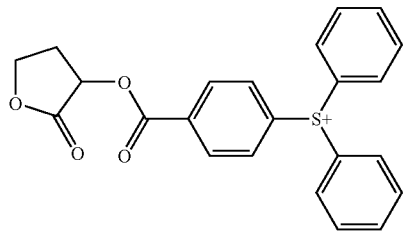
(I-27)
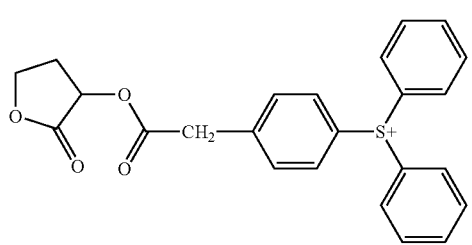
(I-28)
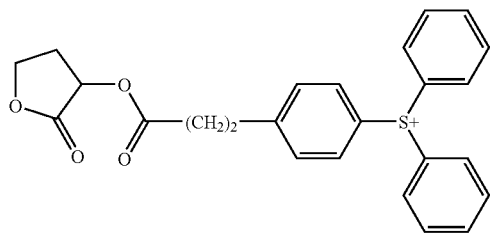
(I-29)
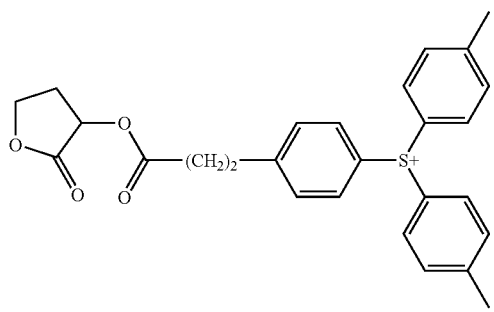
(I-30)
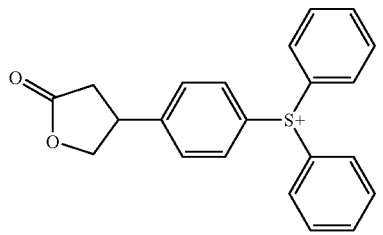

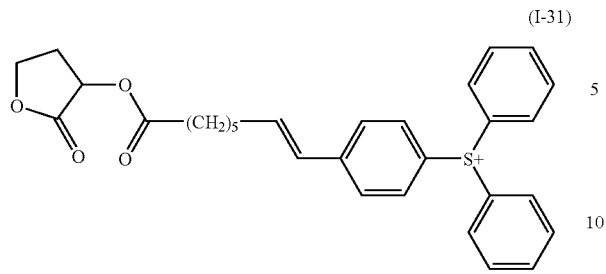 (I-31)
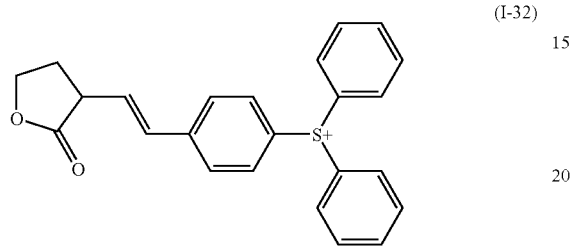 (I-32)
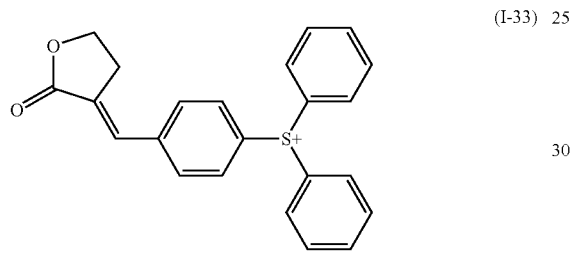 (I-33)
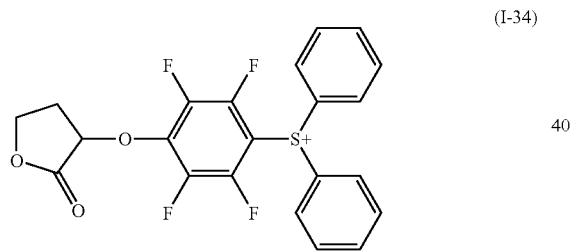 (I-34)
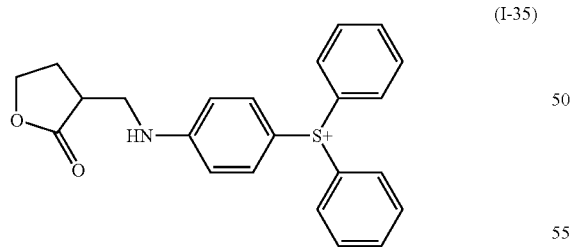 (I-35)
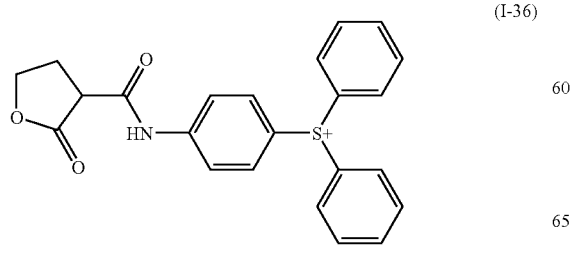 (I-36)
 (I-37)
 (I-38)
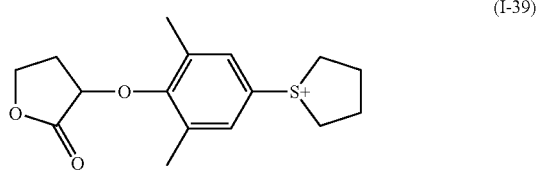 (I-39)
 (I-40)
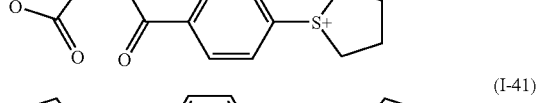 (I-41)
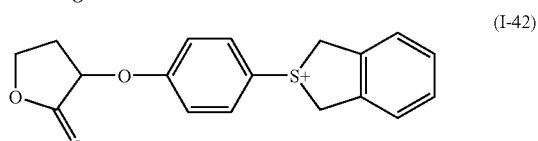 (I-42)
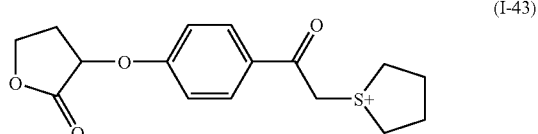 (I-43)
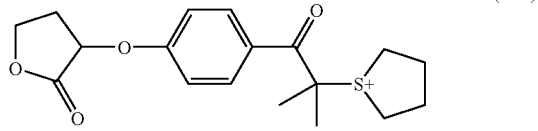 (I-44)
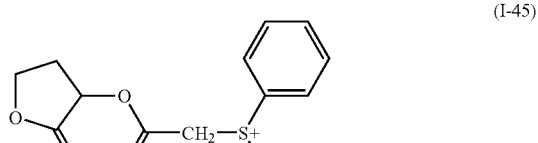 (I-45)
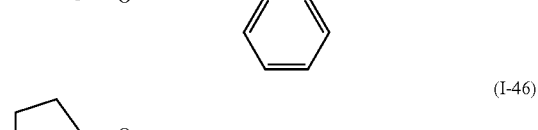 (I-46)

-continued (I-47) 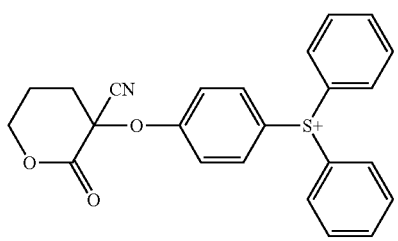

(I-48) 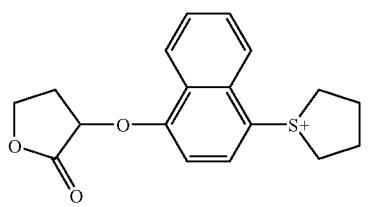

(I-49) 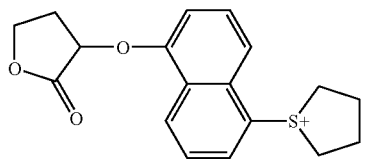

(I-50) 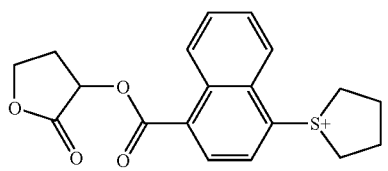

(I-51) 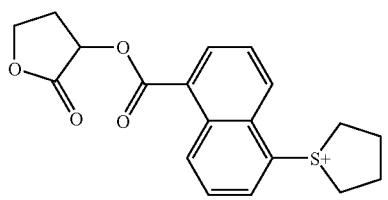

(I-52) 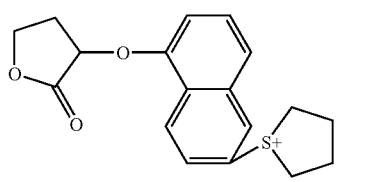

(I-53) 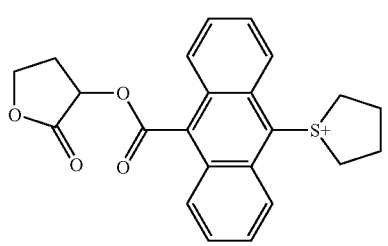

-continued (I-54) 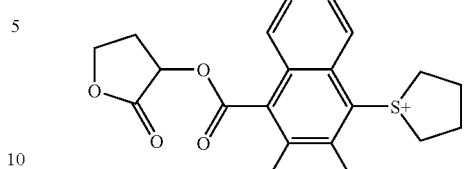

(I-55) 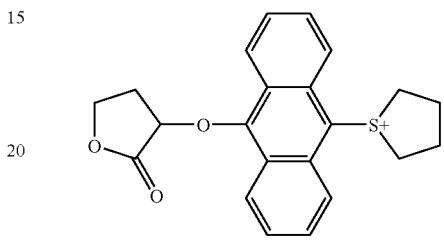

(I-56) 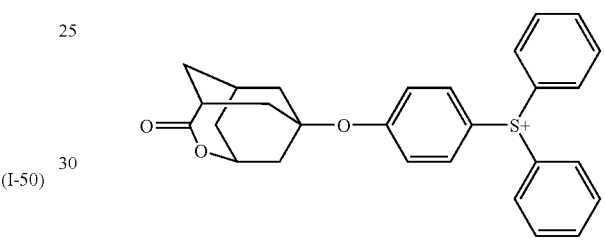

(I-57) 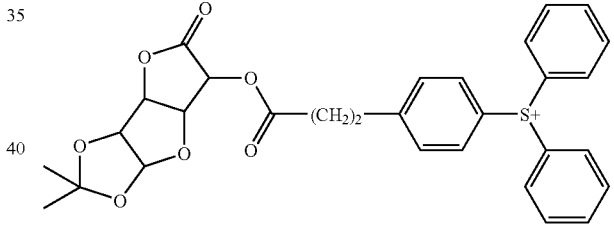

As the anions represented by $X^-$ in formula (I), for example, an organic sulfonate anion ($R^1$—$SO_3^-$), an organic carboxylate anion ($R^1$—$CO_2^-$), an organic imidate anion ($N^-$($SO_2$—$R^1$)$_2$, $N^-$($SO_2$—$R^1$)(CO—$R^1$)), an organic methidate anion ($C^-$($SO_2$—$CO_2^-$), a halogen anion ($Br^-$, $Cl^-$), $BF_4^-$, and $PF_6^-$ are exemplified. As the anions represented by $X^-$, an organic sulfonate anion ($R^1$—$SO_3^-$), an organic carboxylate anion ($R^1$—$CO_2^-$), an organic imidate anion ($N^-$($SO_2$—$R^1$)$_2$, $N^-$($SO_2$—$R^1$)—(CO—$R^1$)), an organic methidate anion ($C^-$($SO_2$—$R^1$)$_3$) are especially preferred. Here, $R^1$ represents a monovalent organic group.

The monovalent organic group represented by $R^1$ preferably has from 1 to 40 carbon atoms and, e.g., an alkyl group, an aryl group and a camphor residue can be exemplified. A plurality of $R^1$ may be the same or different, may be bonded to each other to form a ring, or may be substituted with a halogen atom (preferably a fluorine atom) or the above organic group (B).

The alkyl group represented by $R^1$ is preferably a straight chain or branched alkyl group having from 1 to 30 carbon atoms, and two or more of an oxygen atom, a sulfur atom, a sulfur atom added with an oxygen atom, and nitrogen atom may be contained in the alkyl chain. Specifically as $R^1$, a straight chain alkyl group, e.g., a methyl group, an ethyl group, an n-propyl group, an n-butyl group, an n-pentyl group, an n-hexyl group, an n-octyl group, an n-dodecyl group, an n-tetradecyl group, an n-octadecyl group, etc., and a branched alkyl group, e.g., an isopropyl group, an isobutyl group, a t-butyl group, a neopentyl group, a 2-ethylhexyl group, etc., can be exemplified. By substituting from 30 to 100% of the hydrogen atoms of the alkyl group with fluorine atoms, heat stability is improved, so that more preferred. As the alkyl groups substituted with a fluorine atom, perfluoroalkyl groups, e.g., a perfluoro-methyl group, a perfluoroethyl group, a perfluoropropyl group, a perfluorobutyl group, etc., can be exemplified.

The aryl group represented by $R^1$ may have a substituent. The aryl group is preferably an aryl group having from 6 to 14 carbon atoms and, e.g., a phenyl group, a naphthyl group, etc., can be exemplified. It is preferred that the aryl group is substituted with a fluorine atom. As the aryl group substituted with a fluorine atom, a perfluorophenyl group can be exemplified.

The specific examples of the anionic parts in compound (A) are shown below, but the invention is not restricted thereto.

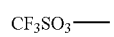 (X1)

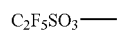 (X2)

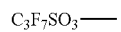 (X3)

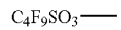 (X4)

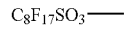 (X5)

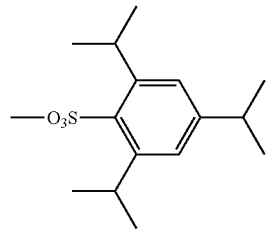 (X6)

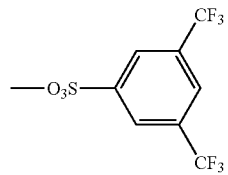 (X7)

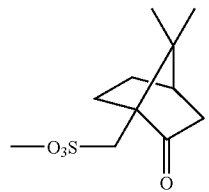 (X8)

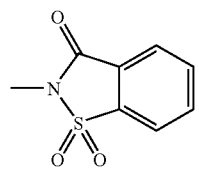 (X9)

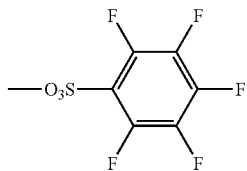 (X10)

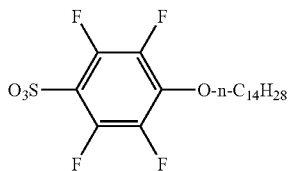 (X11)

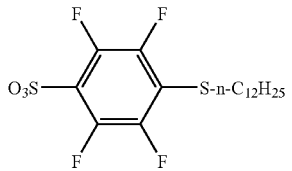 (X12)

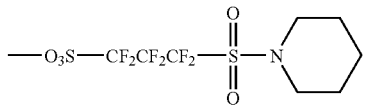 (X10)

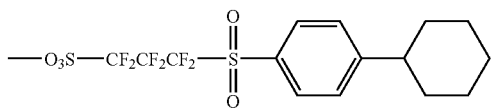 (X11)

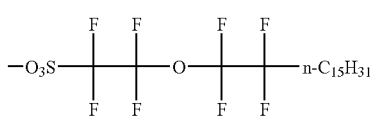 (X12)

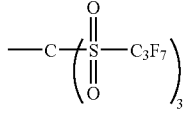 (X13)

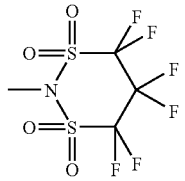 (X14)

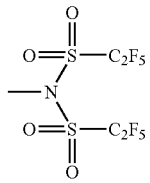 (X15)

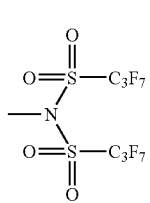 (X16)

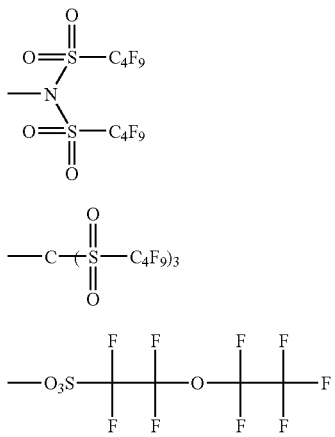

(X17)

(X18)

(X19)

The specific examples of compound (A) are shown in Table 1 below, but the invention is not restricted thereto.

TABLE 1

| Compound (A) | Cationic Part | Anionic Part (X⁻) |
|---|---|---|
| A-1 | I-1 | X4 |
| A-2 | I-1 | X3 |
| A-3 | I-1 | X2 |
| A-4 | I-2 | X4 |
| A-5 | I-3 | X4 |
| A-6 | I-3 | X3 |
| A-7 | I-3 | X2 |
| A-8 | I-4 | X5 |
| A-9 | I-5 | X4 |
| A-10 | I-6 | X4 |
| A-11 | I-7 | X3 |
| A-12 | I-8 | X4 |
| A-13 | I-9 | X16 |
| A-14 | I-10 | X4 |
| A-15 | I-11 | X6 |
| A-16 | I-12 | X7 |
| A-17 | I-13 | X4 |
| A-18 | I-14 | X4 |
| A-19 | I-15 | X12 |
| A-20 | I-16 | X4 |
| A-21 | I-17 | X3 |
| A-22 | I-18 | X4 |
| A-23 | I-19 | X4 |
| A-24 | I-20 | X11 |
| A-25 | I-21 | X4 |
| A-26 | I-22 | X3 |
| A-27 | I-23 | X4 |
| A-28 | I-24 | X3 |
| A-29 | I-25 | X4 |
| A-30 | I-26 | X3 |
| A-31 | I-26 | X3 |
| A-32 | I-27 | X4 |
| A-33 | I-27 | X14 |
| A-34 | I-28 | X4 |
| A-35 | I-28 | X17 |
| A-36 | I-28 | X3 |
| A-37 | I-28 | X15 |
| A-38 | I-28 | X13 |
| A-39 | I-29 | X4 |
| A-40 | I-30 | X4 |
| A-41 | I-31 | X4 |
| A-42 | I-32 | X10 |
| A-43 | I-33 | X4 |
| A-44 | I-34 | X15 |
| A-45 | I-35 | X4 |
| A-46 | I-36 | X4 |
| A-47 | I-37 | X3 |
| A-48 | I-38 | X4 |
| A-49 | I-39 | X4 |
| A-50 | I-40 | X3 |

TABLE 1-continued

| Compound (A) | Cationic Part | Anionic Part (X⁻) |
|---|---|---|
| A-51 | I-41 | X4 |
| A-52 | I-42 | X3 |
| A-53 | I-43 | X4 |
| A-54 | I-44 | X9 |
| A-55 | I-45 | X4 |
| A-56 | I-46 | X3 |
| A-57 | I-47 | X4 |
| A-58 | I-48 | X14 |
| A-59 | I-49 | X11 |
| A-60 | I-50 | X4 |
| A-61 | I-51 | X16 |
| A-62 | I-52 | X4 |
| A-63 | I-53 | X4 |
| A-64 | I-54 | X3 |
| A-65 | I-55 | X3 |
| A-66 | I-56 | X16 |
| A-67 | I-57 | X2 |

Compound (A) is a novel compound.

Compound (A) can be synthesized by the reaction of a sulfonium compound having a hydroxyl group that is easily available and capable of being synthesized and a compound having a lactone structure to which a separable group (e.g., a halogen atom) is introduced according to Williamson's synthesis method (the following scheme 1).

A sulfonium skeleton can be formed by the reaction of a diphenyl sulfoxide derivative and an aryl compound having a lactone structure under an acidic condition or in the presence of an activating agent such as an acid anhydride (refer to JP-A-2002-193925, the following scheme 2).

Scheme 1

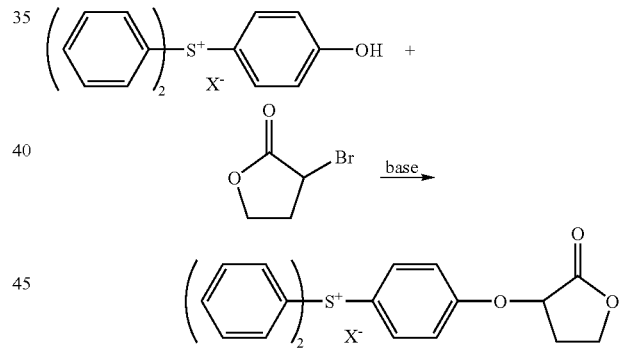

Scheme 2

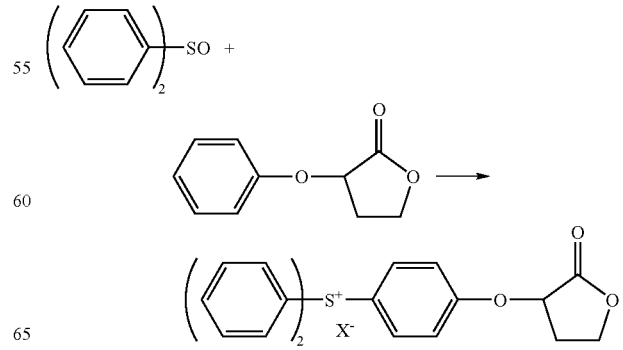

The content of compound (A) in the photosensitive composition of the invention is preferably from 0.1 to 20 mass % based on the solids content of the composition, and more preferably from 0.1 to 10 mass %. (In this specification, mass ratio is equal to weight ratio.)

[2] (B) A compound capable of generating an acid upon irradiation with actinic ray or radiation It is preferred for the photosensitive composition in the invention to further contain a compound capable of generating an acid upon irradiation with actinic ray or radiation (hereinafter also referred to as "an acid generator usable in combination") besides compound (A).

As acid generators usable in combination, photocationic polymerization photoinitiators, photoradical polymerization photoinitiators, photo-decoloring agents, photo-discoloring agents of dyestuffs, known compounds capable of generating an acid upon irradiation with actinic ray or radiation that are used in micro-resists and the like, and the mixtures of these compounds can be optionally selected and used.

For example, diazonium salt, phosphonium salt, sulfonium salt, iodonium salt, imidosulfonate, oximesulfonate, diazodisulfone, disulfone, and o-nitrobenzylsulfonate are exemplified as acid generators usable in combination.

Further, compounds obtained by introducing a group or a compound capable of generating an acid upon irradiation with actinic ray or radiation to the main chain or side chain of polymers, for example, the compounds disclosed in U.S. Pat. No. 3,849,137, German Patent 3,914,407, JP-A-63-26653, JP-A-55-164824, JP-A-62-69263, JP-A-63-146038, JP-A-63-163452, JP-A-62-153853, JP-A-63-146029, etc., can be used.

The compounds capable of generating an acid by the action of lights as disclosed in U.S. Pat. No. 3,779,778, EP 126712, etc., can also be used.

As preferred acid generators usable in combination, compounds represented by the following formula (ZI), (ZII) or (ZIII) can be exemplified.

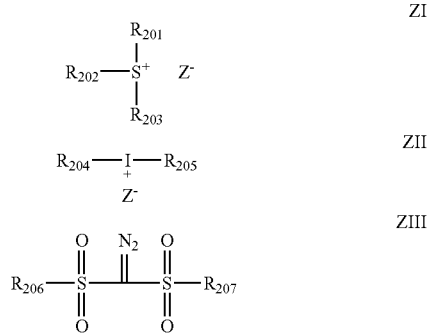

In formula (ZI), $R_{201}$, $R_{202}$ and $R_{203}$ each represents an organic group.

The number of carbon atoms of the organic groups represented by $R_{201}$, $R_{202}$ and $R_{203}$ is generally from 1 to 30, and preferably from 1 to 20.

Two of $R_{201}$, $R_{202}$ and $R_{203}$ may be bonded to each other to form a cyclic structure, and an oxygen atom, a sulfur atom, an ester bond, an amido bond or a carbonyl group may be contained in the ring. As the group formed by bonding two of $R_{201}$, $R_{202}$ and $R_{203}$, an alkylene group (e.g., a butylene group, a pentylene group) can be exemplified.

$Z^-$ represents a non-nucleophilic anion.

The examples of the non-nucleophilic anions represented by $Z^-$ include, e.g., a sulfonate anion, a carboxylate anion, a sulfonylimide anion, a bis(alkylsulfonyl)imide anion, and a tris(alkylsulfonyl)methyl anion.

A non-nucleophilic anion is an anion having extremely low ability of causing a nucleophilic reaction and capable of restraining the aging decomposition due to an intramolecular nucleophilic reaction, so that the aging stability of a resist can be improved with a non-nucleophilic anion.

As the sulfonate anion, e.g., an aliphatic sulfonate anion, an aromatic sulfonate anion and a camphor sulfonate anion are exemplified.

As the carboxylate anion, e.g., an aliphatic carboxylate anion, an aromatic carboxylate anion and an aralkylcarboxylate anion are exemplified.

The aliphatic moiety in the aliphatic sulfonate anion may be an alkyl group or a cycloalkyl group, preferably an alkyl group having from 1 to 30 carbon atoms and a cycloalkyl group having from 3 to 30 carbon atoms, e.g., a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbonyl group, a boronyl group, etc., are exemplified.

The aromatic group in the aromatic sulfonate anion is preferably an aryl group having from 6 to 14 carbon atoms and, e.g., a phenyl group, a tolyl group, a naphthyl group, etc., are exemplified.

The alkyl group, cycloalkyl group and aryl group in the aliphatic sulfonate anion and aromatic sulfonate anion may have a substituent. As the substituents of the alkyl group, cycloalkyl group and aryl group in the aliphatic sulfonate anion and aromatic sulfonate anion, e.g., a nitro group, a halogen atom (a fluorine atom, a chlorine atom, a bromine atom, and an iodine atom), a carboxyl group, a hydroxyl group, an amino group, a cyano group, an alkoxyl group (preferably having from 1 to 15 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms), an alkoxy-carbonyloxy group (preferably having from 2 to 7 carbon atoms), an alkylthio group (preferably having from 1 to 15 carbon atoms), an alkylsulfonyl group (preferably having from 1 to 15 carbon atoms), an alkyliminosulfonyl group (preferably having from 2 to 15 carbon atoms), an aryloxysulfonyl group (preferably having from 6 to 20 carbon atoms), an alkylaryloxysulfonyl group (preferably having from 7 to 20 carbon atoms), a cycloalkylaryloxysulfonyl group (preferably having from 10 to 20 carbon atoms), an alkyloxyalkyloxy group (preferably having from 5 to 20 carbon atoms), a cycloalkylalkyloxyalkyloxy group (preferably having from 8 to 20 carbon atoms), etc., are exemplified. As for the aryl group and the cyclic structure of each group, an alkyl group (preferably having from 1 to 15 carbon atoms) can be further exemplified as the substituent.

As the aliphatic moiety in the aliphatic carboxylate anion, the same alkyl group and cycloalkyl group as in the aliphatic sulfonate anion can be exemplified.

As the aromatic group in an aromatic carboxylate anion, the same aryl group as in the aromatic sulfonate anion can be exemplified.

As the aralkyl group in the aralkylcarboxylate anion, preferably an aralkyl group having from 6 to 12 carbon atoms, e.g., a benzyl group, a phenethyl group, a naphthylmethyl group, a naphthylethyl group, a naphthylmethyl group, etc., can be exemplified.

The alkyl group, cycloalkyl group, aryl group and aralkyl group in the aliphatic carboxylate anion, aromatic carboxylate anion and aralkylcarboxylate anion may have a substituent. As the substituents of the alkyl group, cycloalkyl group, aryl group and aralkyl group in the aliphatic carboxylate anion, aromatic carboxylate anion and aralkylcarboxylate anion, e.g., the same halogen atom, alkyl group, cycloalkyl group, alkoxyl group, alkylthio group, etc., as in the aromatic sulfonate anion can be exemplified.

As the sulfonylimide anion, e.g., a saccharin anion can be exemplified.

The alkyl group in the bis(alkylsulfonyl)imide anion and tris(alkylsulfonyl)methyl anion is preferably an alkyl group having from 1 to 5 carbon atoms and, e.g., a methyl group, an ethyl group, a propyl group, an isopropyl group, an n-butyl group, an isobutyl group, a sec-butyl group, a pentyl group a neopentyl group, etc., are exemplified. As the substituents on these alkyl groups, a halogen atom, an alkyl group substituted with a halogen atom, an alkoxyl group, an alkylthio group, an alkyloxysulfonyl group, an aryloxysulfonyl group, a cycloalkylaryloxysulfonyl group, etc., can be exemplified, and an alkyl group substituted with a fluorine atom is preferred.

As other non-nucleophilic anions, e.g., fluorinated phosphorus, fluorinated boron and fluorinated antimony can be exemplified.

As the non-nucleophilic anions represented by $Z^-$, an aliphatic sulfonate anion in which the α-position of the sulfonic acid is substituted with a fluorine atom, an aromatic sulfonate anion substituted with a fluorine atom or a group having a fluorine atom, a bis(alkylsulfonyl)imide anion in which the alkyl group is substituted with a fluorine atom, and a tris (alkylsulfonyl)methide anion in which the alkyl group is substituted with a fluorine atom are preferred. Especially preferred non-nucleophilic anions are an aliphatic perfluorosulfonate anion having from 4 to 8 carbon atoms, and a benzenesulfonate anion having a fluorine atom, and still more preferred non-nucleophilic anions are a nonafluorobutanesulfonate anion, a perfluorooctanesulfonate anion, a pentafluorobenzenesulfonate anion, and a 3,5-bis(trifluoro-methyl)benzenesulfonate anion.

As the examples of the organic groups represented by $R_{201}$, $R_{202}$ and $R_{203}$, the corresponding groups in the later-described compounds represented by formula (ZI-1), (ZI-2) or (ZI-3) can be exemplified.

The compound represented by formula (ZI) may be a compound having a plurality of structures represented by formula (ZI). For instance, compound (ZI) may be a compound having a structure that at least one of $R_{201}$, $R_{202}$ and $R_{203}$ of the compound represented by formula (ZI) is bonded to at least one of $R_{201}$, $R_{202}$ and $R_{203}$ of another compound represented by formula (ZI).

The following compounds (ZI-1), (ZI-2) and (ZI-3) can be exemplified as more preferred components (ZI).

Compound (ZI-1) is an arylsulfonium compound in the case where at least one of $R_{201}$ to $R_{203}$ in formula (ZI) represents an aryl group, i.e., a compound having arylsulfonium as a cation.

All of $R_{201}$ to $R_{203}$ of the arylsulfonium compound may be aryl groups, or a part of $R_{201}$ to $R_{203}$ is an aryl group and the remainder may be an alkyl group or a cycloalkyl group.

As the arylsulfonium compounds, e.g., a triarylsulfonium compound, a diarylalkylsulfonium compound, an aryldialkyl-sulfonium compound, a diarylcycloalkylsulfonium compound, and an aryldicycloalkylsulfonium compound are exemplified.

As the aryl groups of the arylsulfonium compound, a phenyl group and a naphthyl group are preferred, and the more preferred aryl group is a phenyl group. The aryl group may be an aryl group having a heterocyclic structure having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), and a benzothiophene residue (a group formed by eliminating one hydrogen atom from benzothiophene) can be exemplified. When the arylsulfonium compound has two or more aryl groups, these two or more aryl groups may be the same or different.

As the alkyl group or cycloalkyl group that the arylsulfonium compound has according to necessity, a straight chain or branched alkyl group having from 1 to 15 carbon atoms and a cycloalkyl group having from 3 to 15 carbon atoms are preferred, e.g., a methyl group, an ethyl group, a propyl group, an n-butyl group, a sec-butyl group, a t-butyl group, a cyclopropyl group, a cyclobutyl group, a cyclohexyl group, etc., can be exemplified.

The aryl group, alkyl group and cycloalkyl group represented by $R_{201}$, $R_{202}$ and $R_{203}$ may have a substituent and, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified as the substituents. The preferred substituents are a straight chain or branched alkyl group having from 1 to 12 carbon atoms, a cycloalkyl group having from 3 to 12 carbon atoms, and a straight chain, branched or cyclic alkoxyl group having from 1 to 12 carbon atoms, and more preferred substituents are an alkyl group having from 1 to 4 carbon atoms and an alkoxyl group having from 1 to 4 carbon atoms. The substituent may be substituted on any one of three of $R_{201}$ to $R_{203}$, or may be substituted on all of the three. When $R_{201}$, $R_{202}$ and $R_{203}$ each represents an aryl group, it is preferred that the substituent be substituted on the p-position of the aryl group.

Compound (ZI-2) is described below.

Compound (ZI-2) is a compound in the case where $R_{201}$, $R_{202}$ and $R_{203}$ in formula (ZI) each represents an organic group not containing an aromatic ring. The aromatic ring also includes an aromatic ring containing a hetero atom.

The organic groups not containing an aromatic ring represented by $R_{201}$ to $R_{203}$ generally have from 1 to 30 carbon atoms, and preferably from 1 to 20 carbon atoms.

$R_{201}$, $R_{202}$ and $R_{203}$ each preferably represents an alkyl group, a cycloalkyl group, an allyl group, or a vinyl group, more preferably a straight chain or branched 2-oxoalkyl group, a 2-oxocycloalkyl group or an alkoxycarbonylmethyl group, and especially preferably a straight or branched 2-oxoalkyl group.

The alkyl group and cycloalkyl group represented by $R_{201}$ to $R_{203}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group). The alkyl group is more preferably a 2-oxoalkyl group or an alkoxycarbonylmethyl group. The cycloalkyl group is more preferably a 2-oxocycloalkyl group.

The 2-oxoalkyl group may be either a straight chain or branched group, and a group having >C=O on the 2-position of the above alkyl group can be exemplified as a preferred group.

The 2-oxocycloalkyl group is preferably a group having >C=O on the 2-position of the above cycloalkyl group.

As the alkoxyl group in the alkoxycarbonylmethyl group, an alkoxyl group preferably having from 1 to 5 carbon atoms (e.g., a methoxy group, an ethoxy group, a propoxy group, a butoxy group, a pentoxy group) can be exemplified.

$R_{201}$ to $R_{203}$ may further be substituted with a halogen atom, an alkoxyl group (e.g., having from 1 to 5 carbon atoms), a hydroxyl group, a cyano group, or a nitro group.

Compound (ZI-3) is a compound represented by the following formula (ZI-3), which compound has a phenacylsulfonium salt structure.

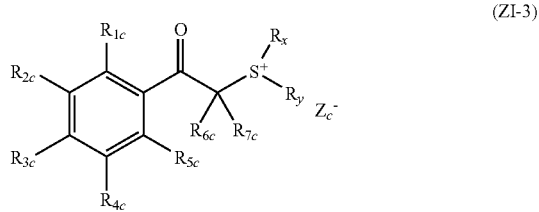

(ZI-3)

In formula (ZI-3), $R_{1c}$, $R_{2c}$, $R_{3c}$, $R_{4c}$ and $R_{5c}$ each represents a hydrogen atom, an alkyl group, a cycloalkyl group, an alkoxy group, or a halogen atom.

$R_{6c}$ and $R_{7c}$ each represents a hydrogen atom, an alkyl group or a cycloalkyl group.

$R_x$ and $R_y$ each represents an alkyl group, a cycloalkyl group, an allyl group, or a vinyl group.

Any two or more of $R_{1c}$ to $R_{5c}$, $R_{6c}$ and $R_{7c}$, and $R_x$ and $R_y$ may be bonded to each other to form cyclic structures, respectively, and the cyclic structures may contain an oxygen atom, a sulfur atom, an ester bond, or an amido bond. As the groups formed by any two or more of $R_{1c}$ to $R_{5c}$, $R_{6c}$ and $R_{7c}$, and $R_x$ and $R_y$, a butylene group, a pentylene group, etc., can be exemplified.

$Z_c^-$ represents a non-nucleophilic anion, and the same non-nucleophilic anions as represented by $Z^-$ in formula (ZI) can be exemplified.

The alkyl groups represented by $R_{1c}$ to $R_{7c}$ may be either straight chain or branched, e.g., an alkyl group having from 1 to 20 carbon atoms, preferably a straight chain or branched alkyl group having from 1 to 12 carbon atoms (e.g., a methyl group, an ethyl group, a straight chain or branched propyl group, a straight chain or branched butyl group, a straight chain or branched pentyl group) can be exemplified. As the cycloalkyl groups represented by $R_{1c}$ to $R_{7c}$, a cycloalkyl group having from 3 to 8 carbon atoms (e.g., a cyclopentyl group and a cyclohexyl group) can be exemplified.

The alkoxyl groups represented by $R_{1c}$ to $R_{5c}$ may be any of straight chain, branched and cyclic, e.g., an alkoxyl group having from 1 to 10 carbon atoms, preferably a straight chain or branched alkoxyl group having from 1 to 5 carbon atoms (e.g., a methoxy group, an ethoxy group, a straight chain or branched propoxy group, a straight chain or branched butoxy group, a straight chain or branched pentoxy group), a cyclic alkoxyl group having from 3 to 8 carbon atoms (e.g., a cyclopentyloxy group, a cyclohexyloxy group) can be exemplified.

It is preferred that any of $R_{1c}$ to $R_{5c}$ represents a straight chain or branched alkyl group, a cycloalkyl group, or a straight chain, branched or cyclic alkoxyl group, it is more preferred that the sum total of the carbon atoms of $R_{1c}$ to $R_{5c}$ is from 2 to 15, by which the solubility in a solvent increases and generation of particles during preservation can be restrained.

As the alkyl group and cycloalkyl group represented by $R_x$ and $R_y$, the same alkyl groups and cycloalkyl groups as represented by $R_{1c}$ to $R_{7c}$ can be exemplified, and a 2-oxoalkyl group, a 2-oxocycloalkyl group, and an alkoxycarbonylmethyl group are more preferred.

As the 2-oxoalkyl group and 2-oxocycloalkyl group, groups having >C=O on the 2-position of the alkyl group and cycloalkyl group represented by $R_{1c}$ to $R_{7c}$ can be exemplified.

As the alkoxyl group in the alkoxycarbonylmethyl group, the same alkoxyl groups as those represented by $R_{1c}$ to $R_{5c}$ can be exemplified.

$R_x$ and $R_y$ each preferably represents an alkyl group or a cycloalkyl group having 4 or more carbon atoms, more preferably 6 or more carbon atoms, and still more preferably an alkyl group or a cycloalkyl group having 8 or more carbon atoms.

In formulae (ZII) and (ZIII), $R_{204}$, $R_{205}$, $R_{206}$ and $R_{207}$ each represents an aryl group, an alkyl group, or a cycloalkyl group.

The aryl group represented by $R_{204}$ to $R_{207}$ is preferably a phenyl group or a naphthyl group, and more preferably a phenyl group. The aryl group represented by $R_{204}$ to $R_{207}$ may be an aryl group having a heterocyclic structure having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), a benzothiophene residue (a group formed by eliminating one hydrogen atom from benzothiophene), etc., can be exemplified.

The alkyl group and cycloalkyl group represented by $R_{204}$ to $R_{207}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group).

The aryl group, alkyl group and cycloalkyl group represented by $R_{204}$ to $R_{207}$ may have a substituent. As the substituents that the aryl group, alkyl group and cycloalkyl group represented by $R_{204}$ to $R_{207}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group, and a phenylthio group can be exemplified.

$Z^-$ represents a non-nucleophilic anion, and the same non-nucleophilic anions as those represented by $Z^-$ in formula (ZI) can be exemplified.

As the acid generators usable in combination, the compounds represented by the following formula (ZIV), (ZV) or (ZVI) can further be exemplified.

Ar$_3$—SO$_2$—SO$_2$—Ar$_4$ (ZIV)

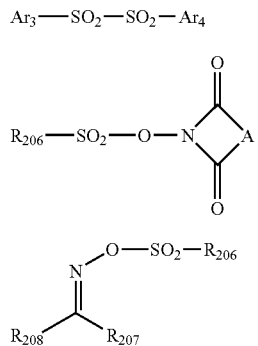
(ZV)

(ZVI)

In formulae (ZIV), (ZV) and (ZVI), Ar$_3$ and Ar$_4$ each represents an aryl group.

R$_{206}$, R$_{207}$ and R$_{208}$ each represents an alkyl group, a cycloalkyl group or an aryl group.

A represents an alkylene group, an alkenylene group or an arylene group.

Of the acid generators usable in combination, more preferred compounds are the compounds represented by formulae (ZI), (ZII) and (ZIII).

Further, as the acid generators usable in combination, a compound generating an acid having one sulfonic acid group or an imido group is preferred, a compound generating a monovalent perfluoroalkanesulfonic acid, a compound generating an aromatic sulfonic acid substituted with a monovalent fluorine atom or a group containing a fluorine atom, and a compound generating an imidic acid substituted with a monovalent fluorine atom or a group containing a fluorine atom are more preferred, and a sulfonium salt of a fluorine-substituted alkanesulfonic acid, a fluorine-substituted benzenesulfonic acid, or a fluorine-substituted imidic acid is still more preferred. As the acid generators usable in combination, a fluorine-substituted alkanesulfonic acid, a fluorine-substituted benzenesulfonic acid, and fluorine-substituted imidic acid each having pKa of −1 or less of generated acid are especially preferred, by which sensitivity is improved.

The examples of especially preferred acid generators usable in combination are shown below.

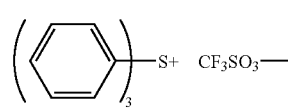
(z1)

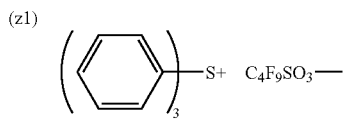
(z2)

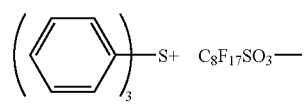
(z3)

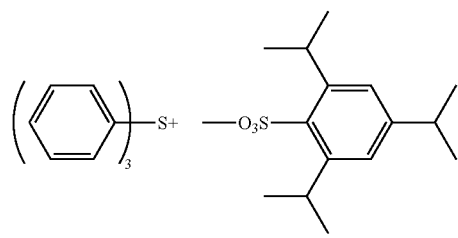
(z4)

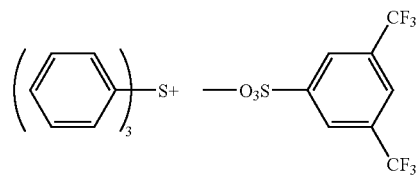
(z5)

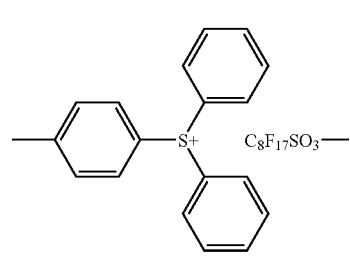
(z6)

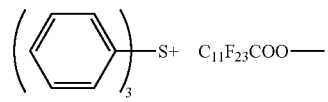
(z7)

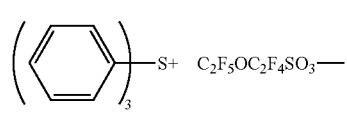
(z8)

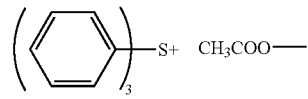
(z9)

-continued
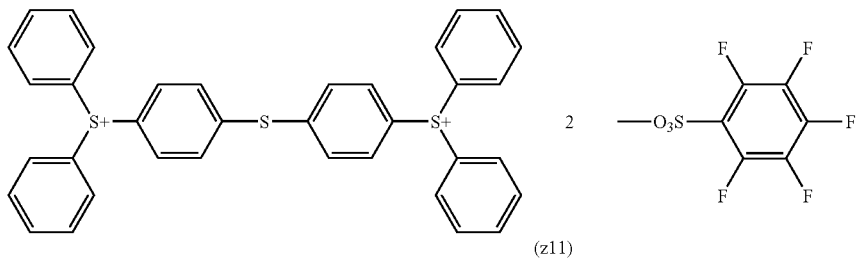
(z10)
(z11)
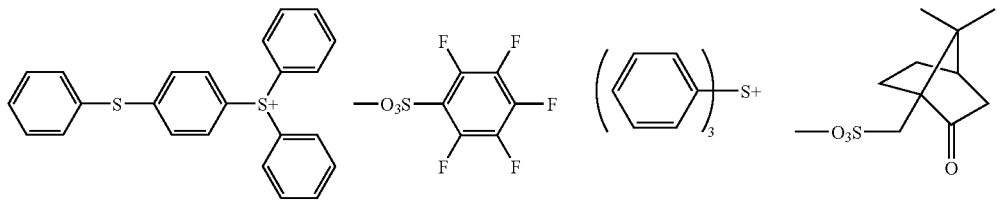
(z12)
(z13)
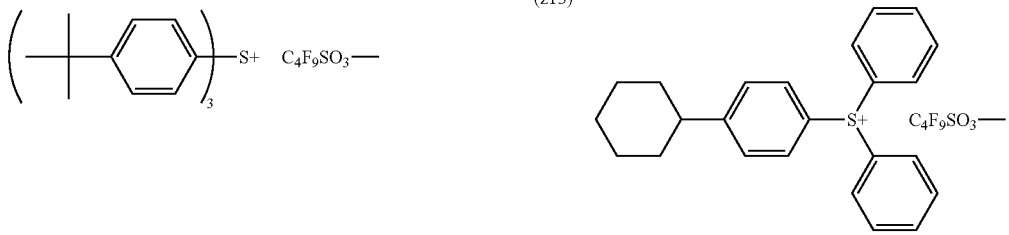
(z14)
(z15)
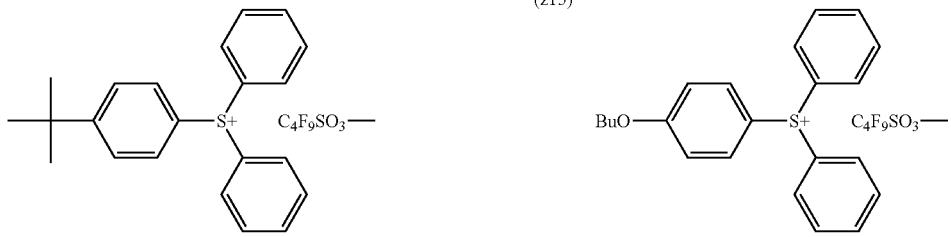
(z16)
(z17)
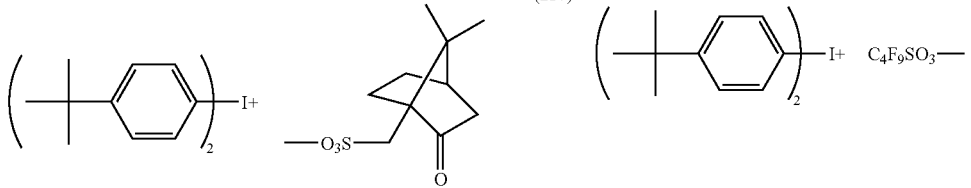
(z18)
(z19)
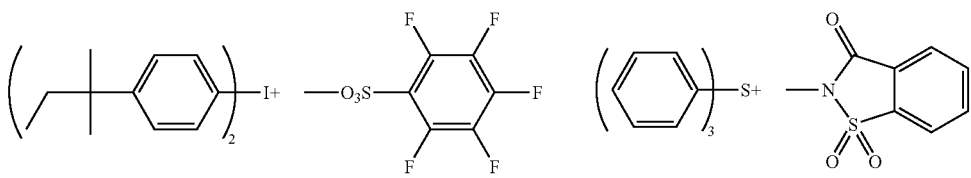
(z20)
(z21)
(z22)
(z23)
(z24)

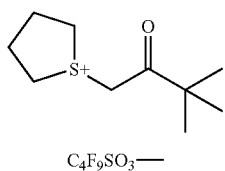
(z25)
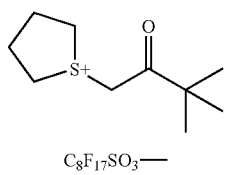
(z26)
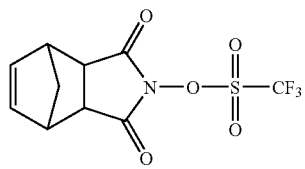
(z27)
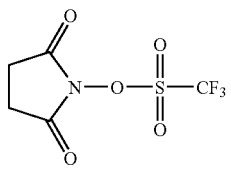
(z28)
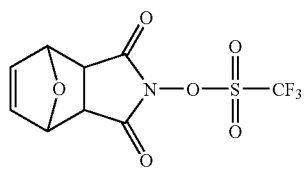
(z29)
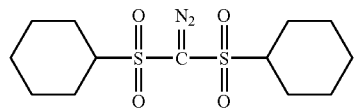
(z30)
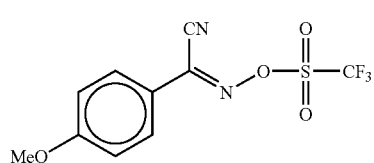
(z31)
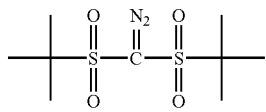
(z32)
(z33)
(z34)
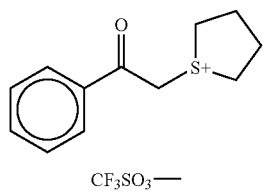
(z35)
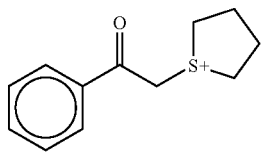
(z36)
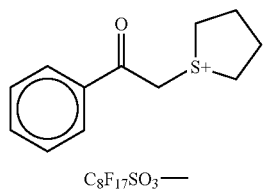
(z37)
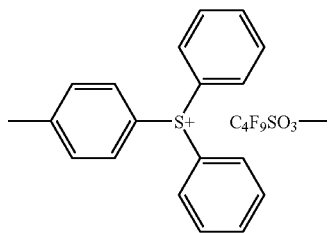
(z38)

-continued
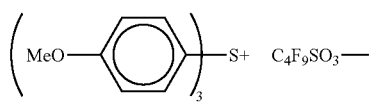 (z38)
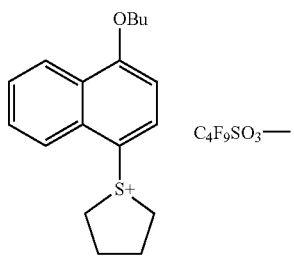 (z40)
 (z41)
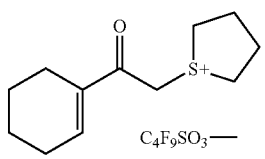 (z42)
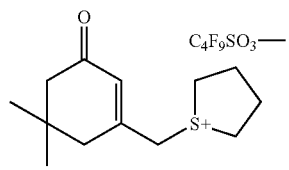 (z43)
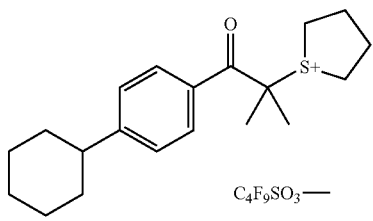 (z44)
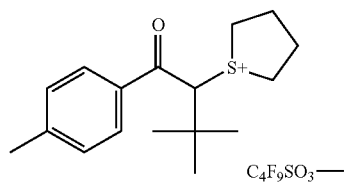 (z45)
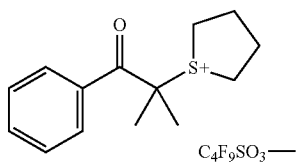 (z46)
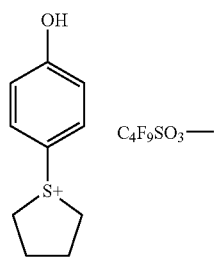 (z47)
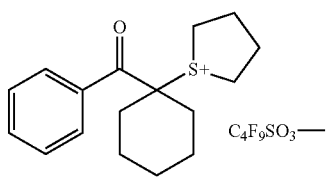 (z48)
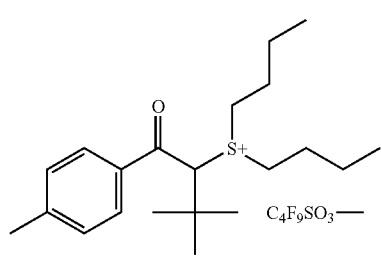 (z49)
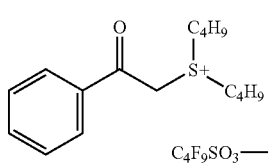 (z50)
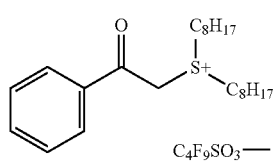 (z51)
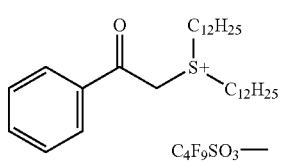 (z52)

-continued
(z53) 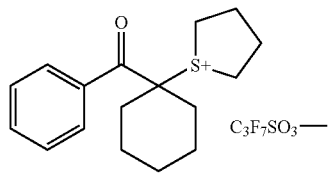
(z54) 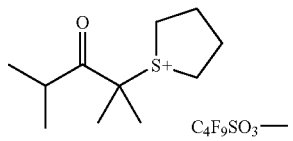
(z55) 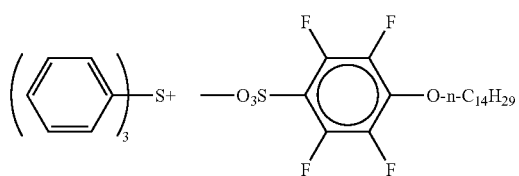
(z56) 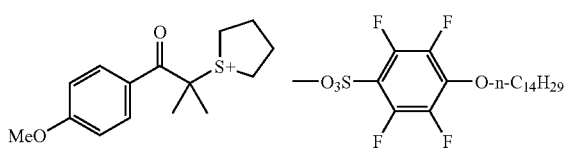
(z57) 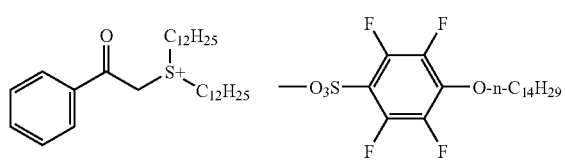
(z58) 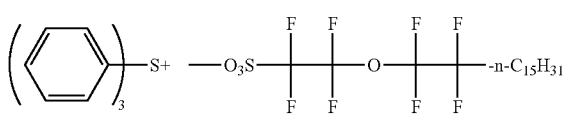
(z59) 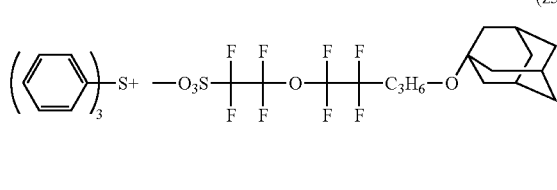
(z60) 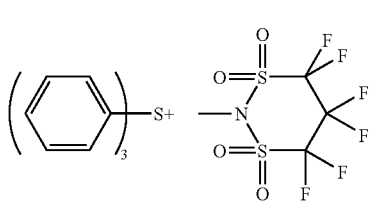
(z61) 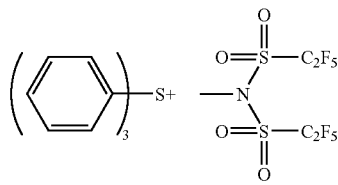
(z62) 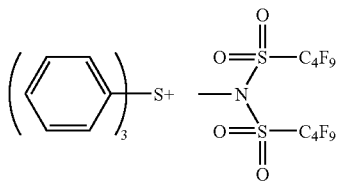
(z63) 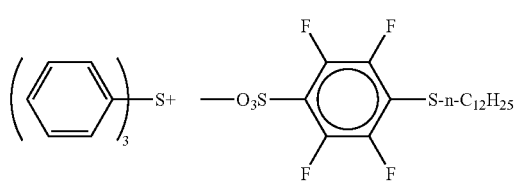
(z64) 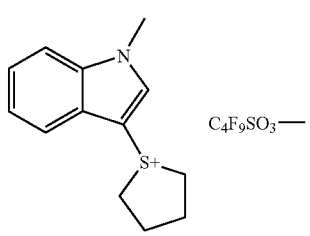
(z65) 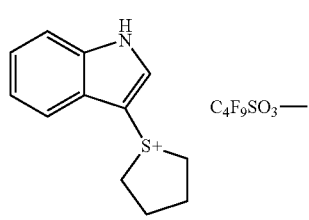
(z66) 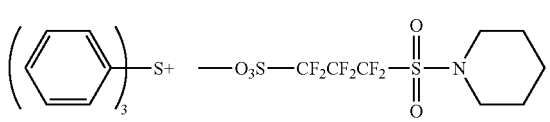
(z67) 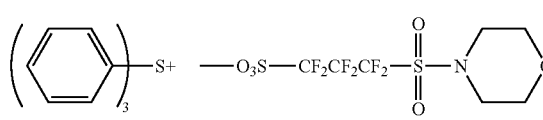
(z68) 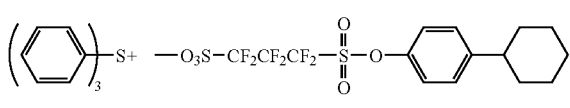

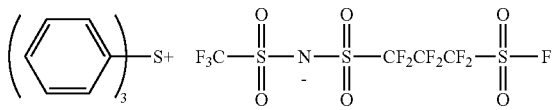 (z69)

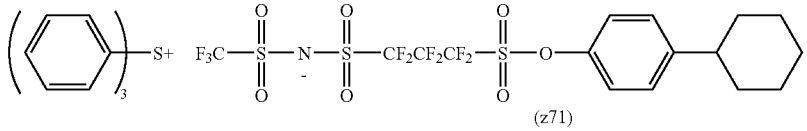 (z70)

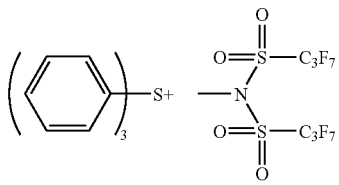 (z71)

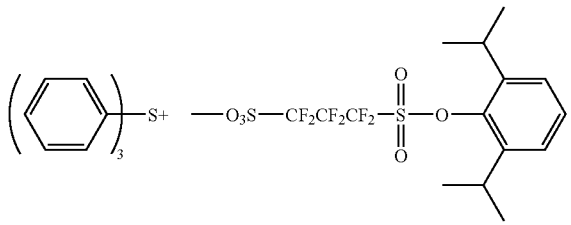 (z72)

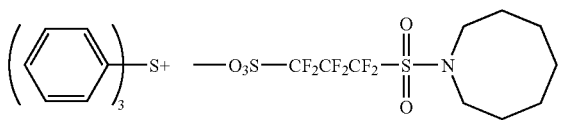 (z73)

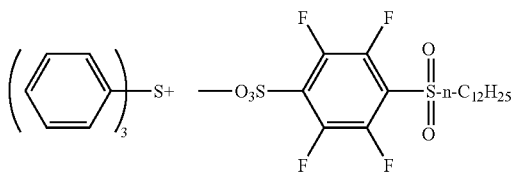 (z74)

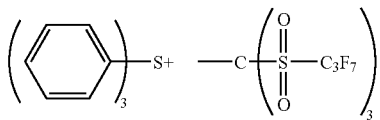 (z75)

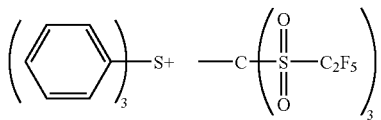 (z76)

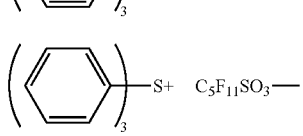 (z79)

The acid generators usable in combination can be used alone, or two or more in combination.

The content of the acid generators usable in combination in a photosensitive composition is preferably from 0.1 to 20 mass % based on the total solids content of the photosensitive composition, more preferably from 0.5 to 10 mass %, and still more preferably from 1 to 7 mass %.

[3] (C) A resin capable of decomposing by the action of an acid to increase solubility in an alkali developing solution (referred to as also component (C)):

A resin capable of decomposing by the action of an acid to increase solubility in an alkali developing solution for use in the positive photosensitive composition in the invention is a resin having a group decomposable by the action of an acid (hereinafter referred to as "an acid-decomposable group") on the main chain or side chain of the resin, or on both the main chain and side chain. A resin having a group decomposable by the action of an acid on the side chain is more preferred.

A preferred acid-decomposable group is a group obtained by substituting the hydrogen atom of a —COOH group or an —OH group with a group capable of being desorbed by an acid.

An especially preferred acid-decomposable group in the invention is an acetal group or a tertiary ester group.

The parent resin in the case where the acid-decomposable group is bonded as the side chain is an alkali-soluble resin having an —OH group or a —COOH group on the side chain. For example, the later-described alkali-soluble resins can be exemplified.

The alkali dissolution rate of these alkali-soluble resins is preferably 170 Å/sec or more when measured using 0.261N tetramethylammonium hydroxide (TMAH) at 23° C., especially preferably 330 Å/sec or more.

From this point of view, particularly preferred alkali-soluble resins are o-, m-, p-poly(hydroxystyrene) and copolymers thereof, hydrogenated poly(hydroxystyrene), halogen- or alkyl-substituted poly(hydroxystyrene), a partially O-alkylated or O-acylated product of poly-(hydroxystyrene), styrene-hydroxystyrene copolymers, α-methylstyrene-hydroxystyrene copolymers, alkali-soluble resins having a hydroxystyrene structure unit such as hydrogenated novolak resins, (meth)acrylic acid, and alkali-soluble resins containing a repeating unit having a carboxyl group such as norbornenecarboxylic acid.

As repeating units having a preferred acid-decomposable group, e.g., t-butoxycarbonyloxystyrene, 1-alkoxyethoxystyrene, and (meth)acrylic acid tertiary alkyl ester are exemplified, and 2-alkyl-2-adamantyl(meth)acrylate and dialkyl (1-adamantyl)methyl(meth)acrylate are more preferred.

Components (C) for use in the invention can be obtained, as disclosed in EP 254853, JP-A-2-25850, JP-A-3-223860 and JP-A-4-251259, by reacting an alkali-soluble resin with the precursor of an acid-decomposable group, or copolymerizing an alkali-soluble resin monomer to which an acid-decomposable group is bonded with various monomers.

When the positive photosensitive composition of the invention is irradiated with KrF excimer laser beams, electron beams, X-rays, or high energy rays of wavelength of 50 nm or lower (e.g., EUV), it is preferred for a resin of component (C) to have a hydroxystyrene repeating unit, more preferably a copolymer of hydroxystyrene/hydroxystyrene protected with an acid-decomposable group, or hydroxystyrene/(meth) acrylic acid tertiary alkyl ester.

The specific examples of component (C) for use in the invention are shown below, but the invention is not restricted thereto.

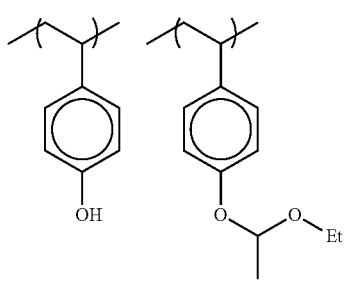
(R-1)

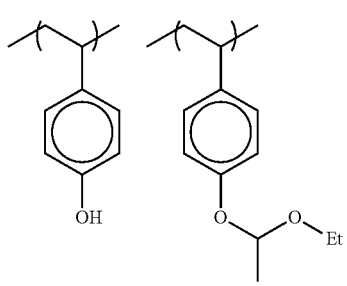
(R-2)

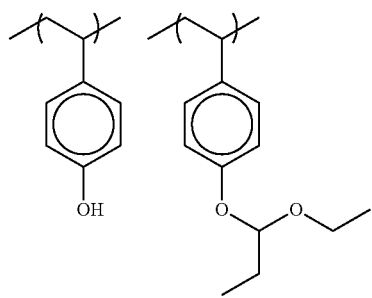
(R-3)

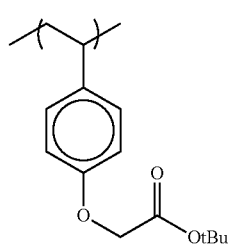

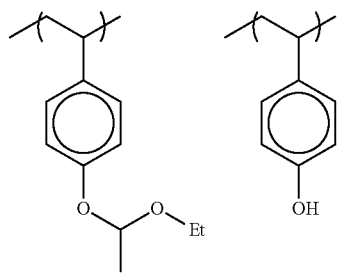
(R-4)

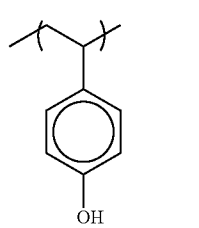

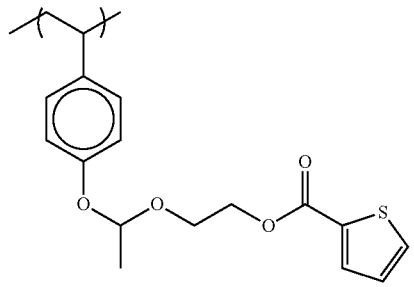
(R-5)

(R-6)
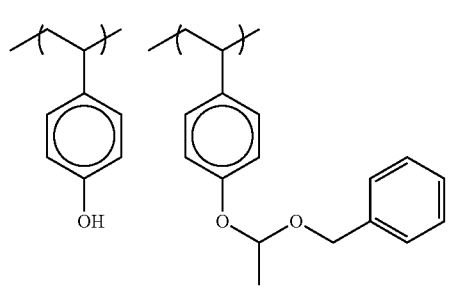
(R-7)
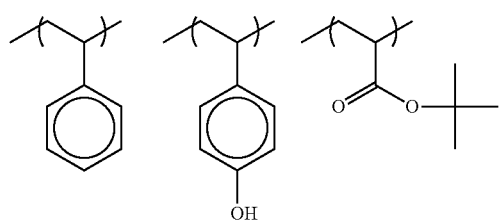
(R-8)
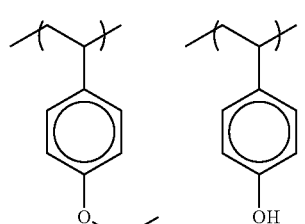
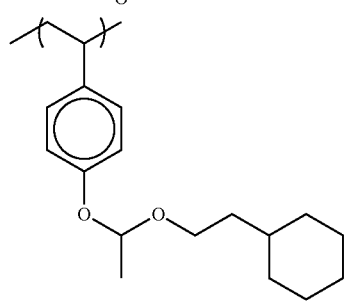
(R-9)
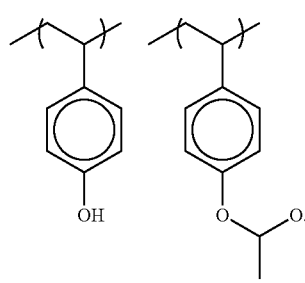
(R-10)
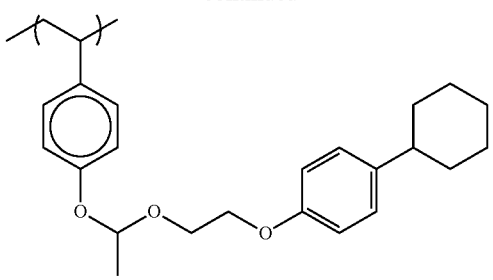
(R-11)
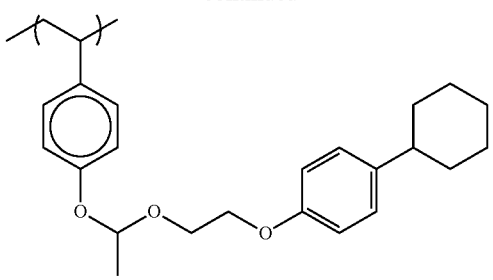
(R-12)
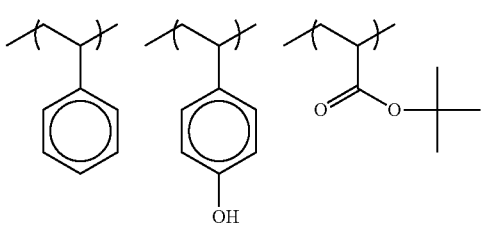
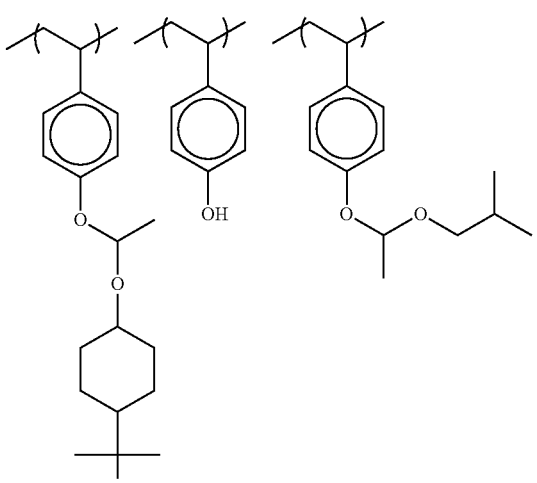
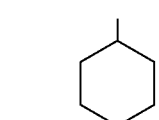
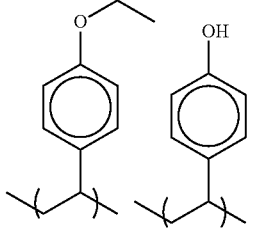
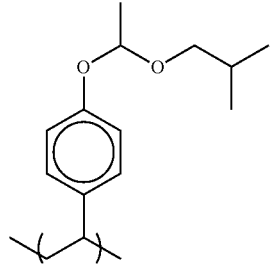

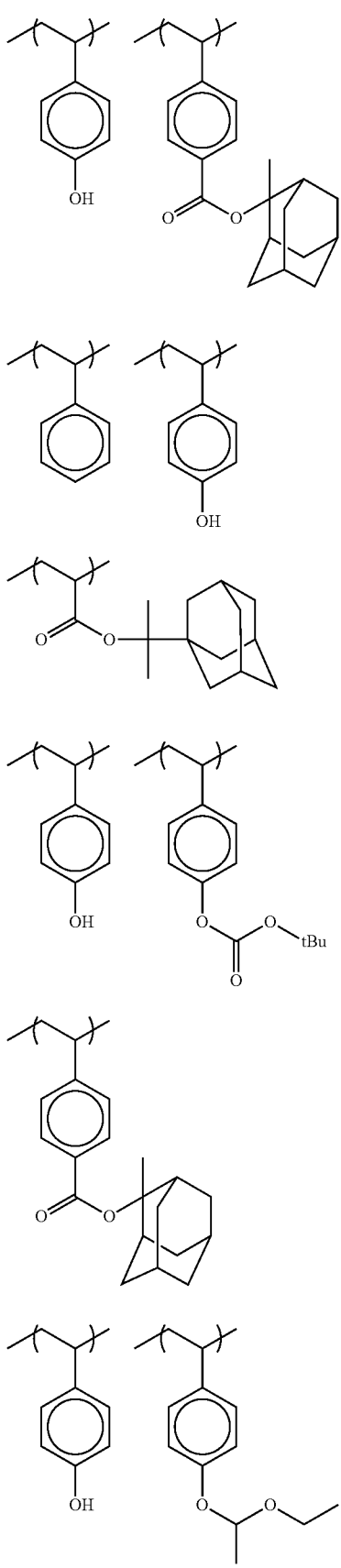
(R-13)
(R-14)
(R-15)
(R-16)

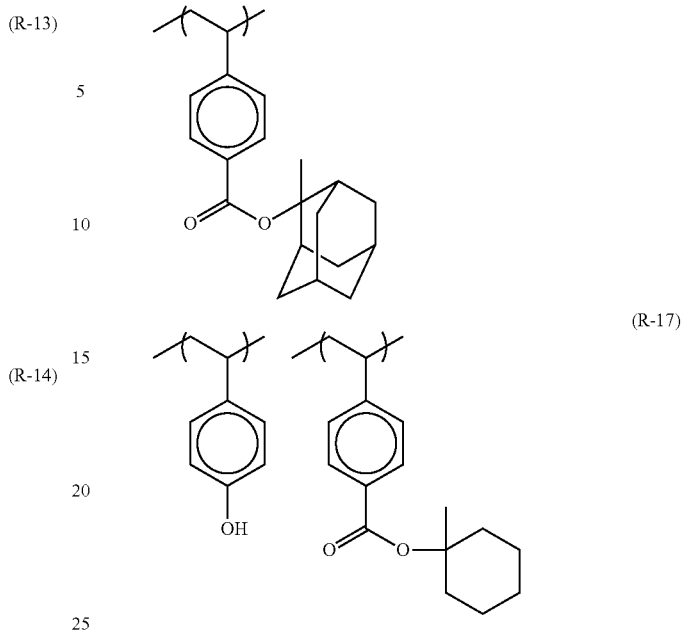
(R-17)

In the above specific examples, tBu means a t-butyl group.

The content of an acid-decomposable group is expressed by B/(B+S), taking the number of the acid-decomposable groups in a resin as (B), and the number of alkali-soluble groups not protected with acid-eliminable groups as (S). The content is preferably from 0.01 to 0.7, more preferably from 0.05 to 0.50, and still more preferably from 0.05 to 0.40.

When the positive photosensitive composition in the invention is irradiated with ArF excimer laser beams, it is preferred that the resin of component (C) is a resin having a monocyclic or polycyclic alicyclic hydrocarbon structure and capable of decomposing by the action of an acid to thereby increase the solubility in an alkali developing solution.

As a resin having a monocyclic or polycyclic alicyclic hydrocarbon structure and capable of decomposing by the action of an acid to thereby increase the solubility in an alkali developing solution (hereinafter also referred to as "an alicyclic hydrocarbon acid-decomposable resin"), a resin containing at least one repeating unit selected from the group consisting of a repeating unit having a partial structure containing alicyclic hydrocarbon represented by any of the following formulae (pI) to (pV), and a repeating unit represented by the following formula (II-AB) is preferred.

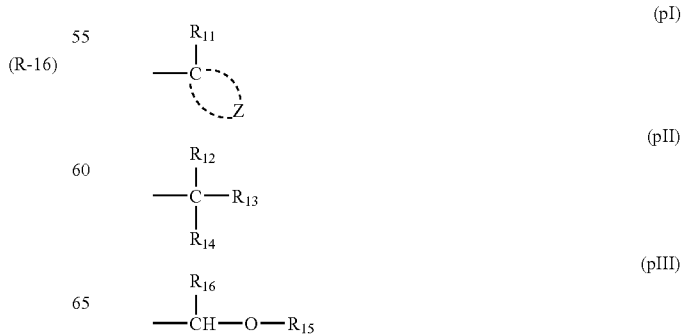

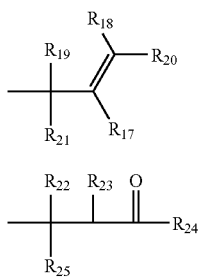

(pIV)

(pV)

In formulae (pI) to (pV), $R_{11}$ represents a methyl group, an ethyl group, an n-propyl group, an isopropyl group, an n-butyl group, an isobutyl group, or a sec-butyl group; and Z represents an atomic group necessary to form a cycloalkyl group together with a carbon atom.

$R_{12}$, $R_{13}$, $R_{14}$, $R_{15}$ and $R_{16}$ each represents a straight chain or branched alkyl group, or a cycloalkyl group, provided that at least one of $R_{12}$ to $R_{14}$, or either $R_{15}$ or $R_{16}$ represents a cycloalkyl group.

$R_{17}$, $R_{18}$, $R_{19}$, $R_{20}$ and $R_{21}$ each represents a hydrogen atom, a straight chain or branched alkyl group or a cycloalkyl group, provided that at least one of $R_{17}$ to $R_{21}$ represents a cycloalkyl group, and either $R_{19}$ or $R_{21}$ represents a straight chain or branched alkyl group or a cycloalkyl group.

$R_{22}$, $R_{23}$, $R_{24}$ and $R_{25}$ each represents a hydrogen atom, a straight chain or branched alkyl group or a cycloalkyl group, provided that at least one of $R_{22}$ to $R_{25}$ represents a cycloalkyl group, and $R_{23}$ and $R_{24}$ may be bonded to each other to form a ring.

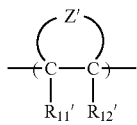

(II-AB)

In formula (II-AB), $R_{11}'$ and $R_{12}'$ each represents a hydrogen atom, a cyano group, a halogen atom, or an alkyl group.

Z' contains bonded two carbon atoms (C—C) and represents an atomic group to form an alicyclic structure.

Formula (II-AB) is more preferably represented by the following formula (II-AB1) or (II-AB2).

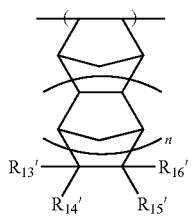

(II-AB1)

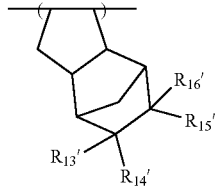

(II-AB2)

In formulae (II-AB1) and (II-AB2), $R_{13}'$, $R_{14}'$, $R_{15}'$ and $R_{16}'$ each represents a hydrogen atom, a halogen atom, a cyano group, —COOH, —COOR$_5$, a group decomposable by the action of an acid, —C(=O)—X-A'—R$_{17}'$, an alkyl group, or a cycloalkyl group. At least two of $R_{13}'$ to $R_{16}'$ may be bonded to form a ring.

$R_5$ represents an alkyl group, a cycloalkyl group, or a group having a lactone structure.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxyl group, —CO—NH—R$_6$, —CO—NH—SO$_2$—R$_6$, or a group having a lactone structure.

$R_6$ represents an alkyl group or a cycloalkyl group.

n represents 0 or 1.

The alkyl group represented by $R_{12}$ to $R_{25}$ in formulae (pI) to (pV) is preferably a straight chain or branched alkyl group having from 1 to 4 carbon atoms, e.g., a methyl group, an ethyl group, an n-propyl group, an isopropyl group, an n-butyl group, an isobutyl group, and a sec-butyl group are exemplified.

The cycloalkyl groups represented by $R_{11}$ to $R_{25}$ or the cycloalkyl group formed by Z and carbon atoms may be monocyclic or polycyclic. Specifically, groups having a monocyclic, bicyclic, tricyclic or tetracyclic structure having 5 or more carbon atoms can be exemplified. The number of carbon atoms of the groups is preferably from 6 to 30, and particularly preferably from 7 to 25.

As preferred cycloalkyl groups, an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group, and a cyclododecanyl group can be exemplified. More preferred cycloalkyl groups are an adamantyl group, a norbornyl group, a cyclohexyl group, a cyclopentyl group, a tetracyclododecanyl group, and a tricyclodecanyl group.

These alkyl groups and cycloalkyl groups may have further substituents. As further substituents of these alkyl groups and cycloalkyl groups, an alkyl group (having from 1 to 4 carbon atoms), a halogen atom, a hydroxyl group, an alkoxyl group (having from 1 to 4 carbon atoms), a carboxyl group, and an alkoxycarbonyl group (having from 2 to 6 carbon atoms) can be exemplified. As substituents that these alkyl group, alkoxyl group and alkoxycarbonyl group may further have, a hydroxyl group, a halogen atom and an alkoxyl group can be exemplified.

The structures represented by formulae (pI) to (pV) in the resin can be used for the protection of alkali-soluble groups. As the alkali-soluble groups, various groups well known in this technical field can be exemplified.

Specifically, the structures in which the hydrogen atoms of carboxylic acid group, a sulfonic acid group, a phenol group and a thiol group are substituted with the structures represented by formulae (pI) to (pV) are exemplified, and preferably the structures in which the hydrogen atoms of carboxylic acid group and a sulfonic acid group are substituted with the structures represented by formulae (pI) to (pV) are exemplified.

As the repeating unit having the alkali-soluble group protected with the structure represented by any of the above formulae (pI) to (pV), a repeating unit represented by the following formula (pA) is preferred.

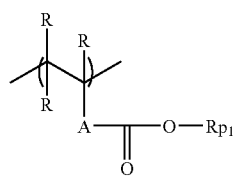

(pA)

In formula (pA), R represents a hydrogen atom, a halogen atom, or a straight chain or branched alkyl group having from 1 to 4 carbon atoms, and a plurality of R's may be the same or different.

A represents a single group or the combination of two or more groups selected from the group consisting of a single bond, an alkylene group, an ether group, a thioether group, a carbonyl group, an ester group, an amido group, a sulfonamido group, a urethane group, and a urea group. A single bond is preferred.

$R_{p1}$ represents a group represented by any of formulae (pI) to (pVI).

The repeating unit represented by (pA) is most preferably a repeating unit by 2-alkyl-2-adamantyl(meth)acrylate and dialkyl(1-adamantyl)methyl(meth)acrylate.

The specific examples of the repeating units represented by formula (pA) are shown below, but the invention is not restricted thereto.
(In the formulae, Rx represents H, $CH_3$, $CF_3$, $CH_2OH$, Rxa, and Rxb each represents an alkyl group having from 1 to 4 carbon atoms.)

1

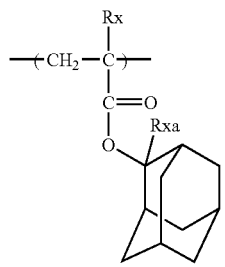

2

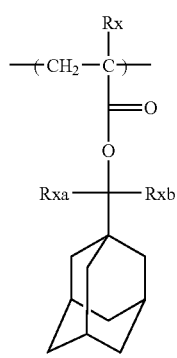

3

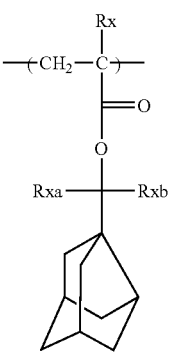

4

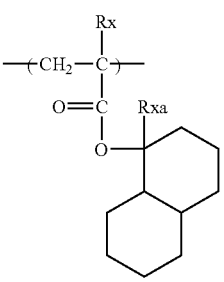

5

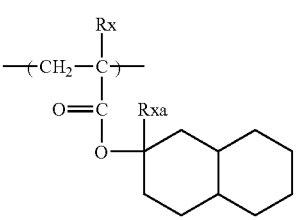

6

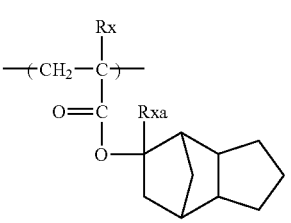

7

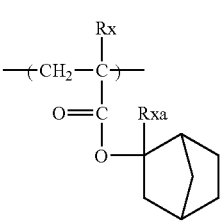

8

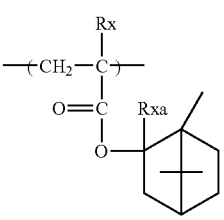

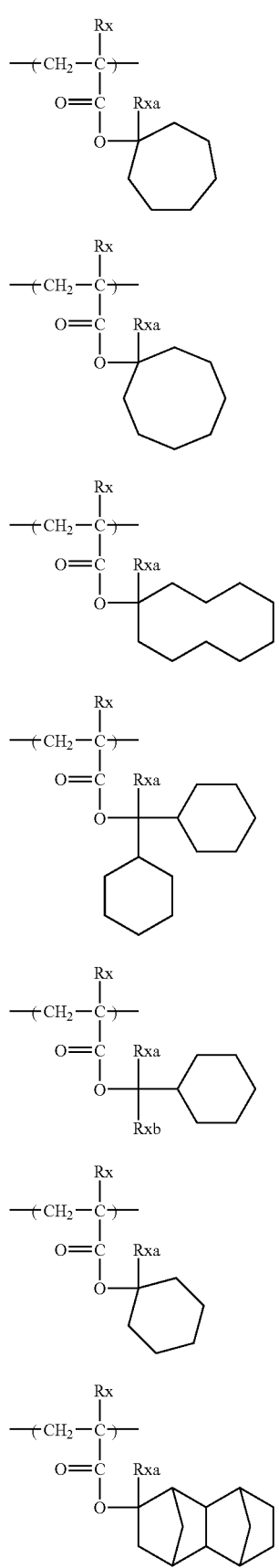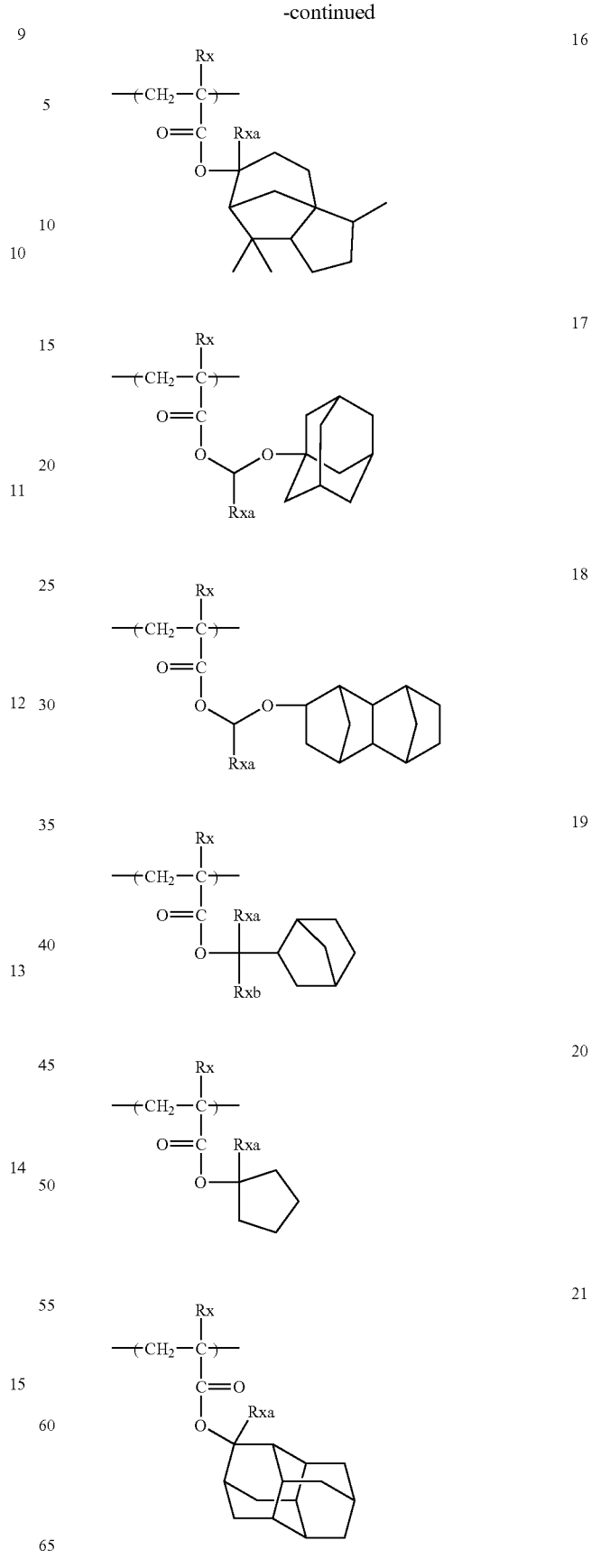

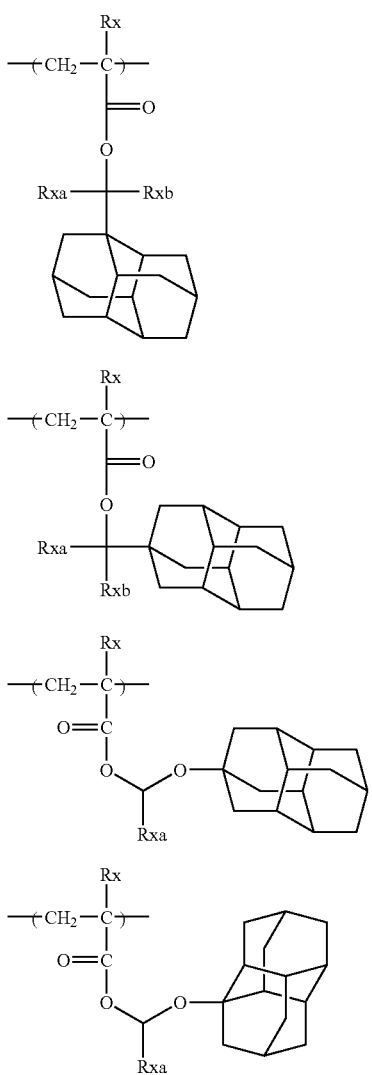

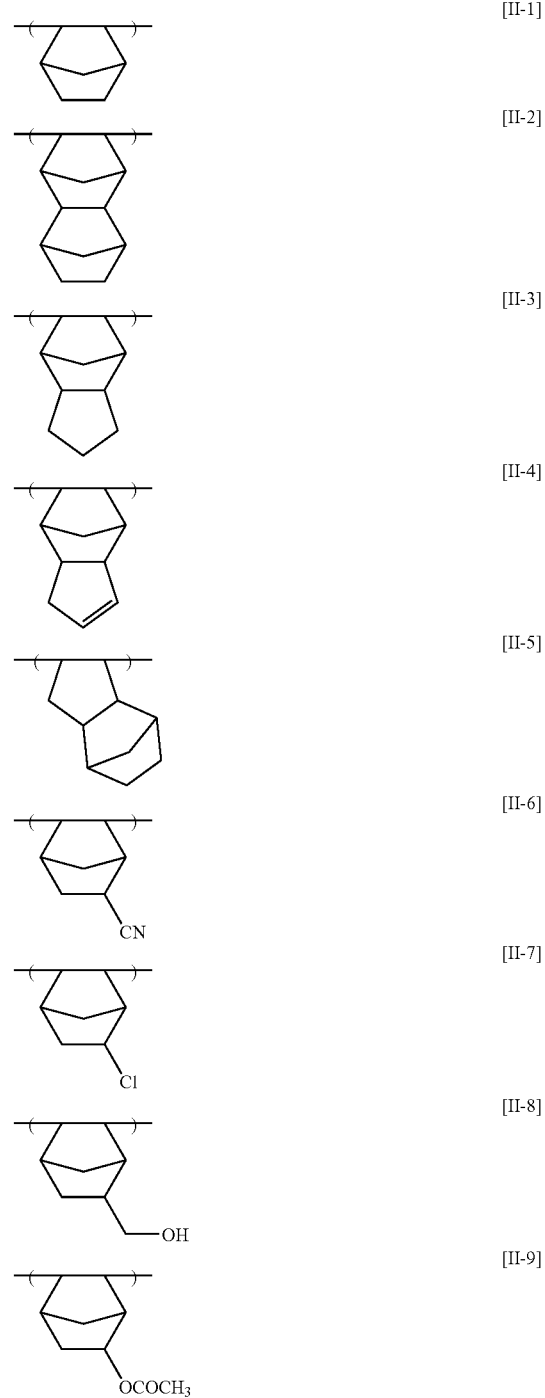

As the halogen atoms represented by $R_{11}'$ and $R_{12}'$ in formula (II-AB), a chlorine atom, a bromine atom, a fluorine atom and an iodine atom are exemplified.

As the alkyl groups represented by $R_n'$ and $R_{12}'$, straight chain or branched alkyl groups having from 1 to 10 carbon atoms are exemplified.

The atomic group represented by Z' to form an alicyclic structure is an atomic group to form a repeating unit having an alicyclic hydrocarbon structure, which may have a substituent, and an atomic group to form a repeating unit having a bridged alicyclic hydrocarbon structure is preferred above all.

As the skeleton of alicyclic hydrocarbon formed, the same alicyclic hydrocarbon groups as represented by $R_{12}$ to $R_{25}$ in formulae (pI) to (pV) are exemplified.

The skeleton of the alicyclic hydrocarbon structure may have a substituent, and as the substituents, the groups represented by $R_{13}'$ to $R_{16}'$ in formula (II-AB1) or (II-AB2) can be exemplified.

In the alicyclic hydrocarbon-based acid-decomposable resin in the invention, a group capable of decomposing by the action of an acid can be contained in at least one repeating unit of a repeating unit having a partial structure containing alicyclic hydrocarbon represented by any of formulae (pI) to (pV), a repeating unit represented by formula (II-AB), and a repeating unit of the later-described copolymer component.

Various substituents of $R_{13}'$ to $R_{16}'$ in formula (II-AB1) or (II-AB2) can also be used as the substituents of the atomic group to form an alicyclic hydrocarbon structure in formula (II-AB), or atomic group Z to form a bridged alicyclic hydrocarbon structure.

The specific examples of the repeating units represented by formula (II-AB1) or (II-AB2) are shown below, but the invention is not restricted thereto.

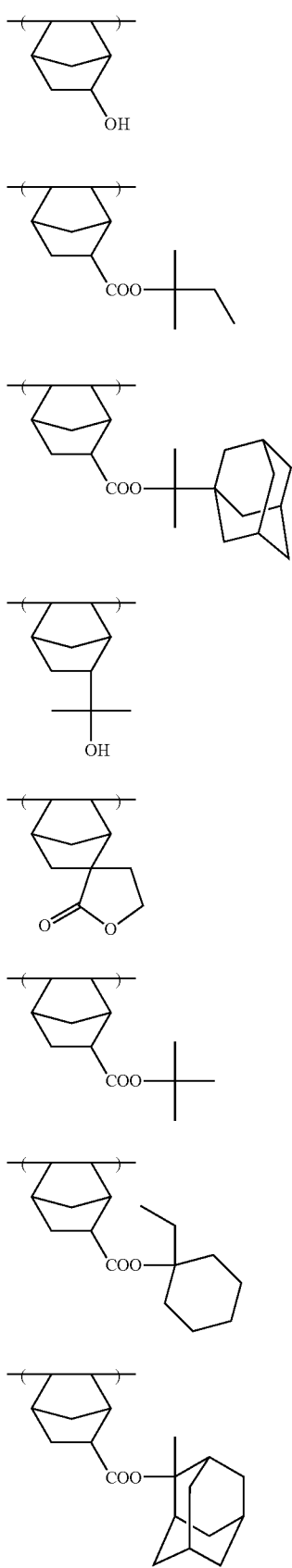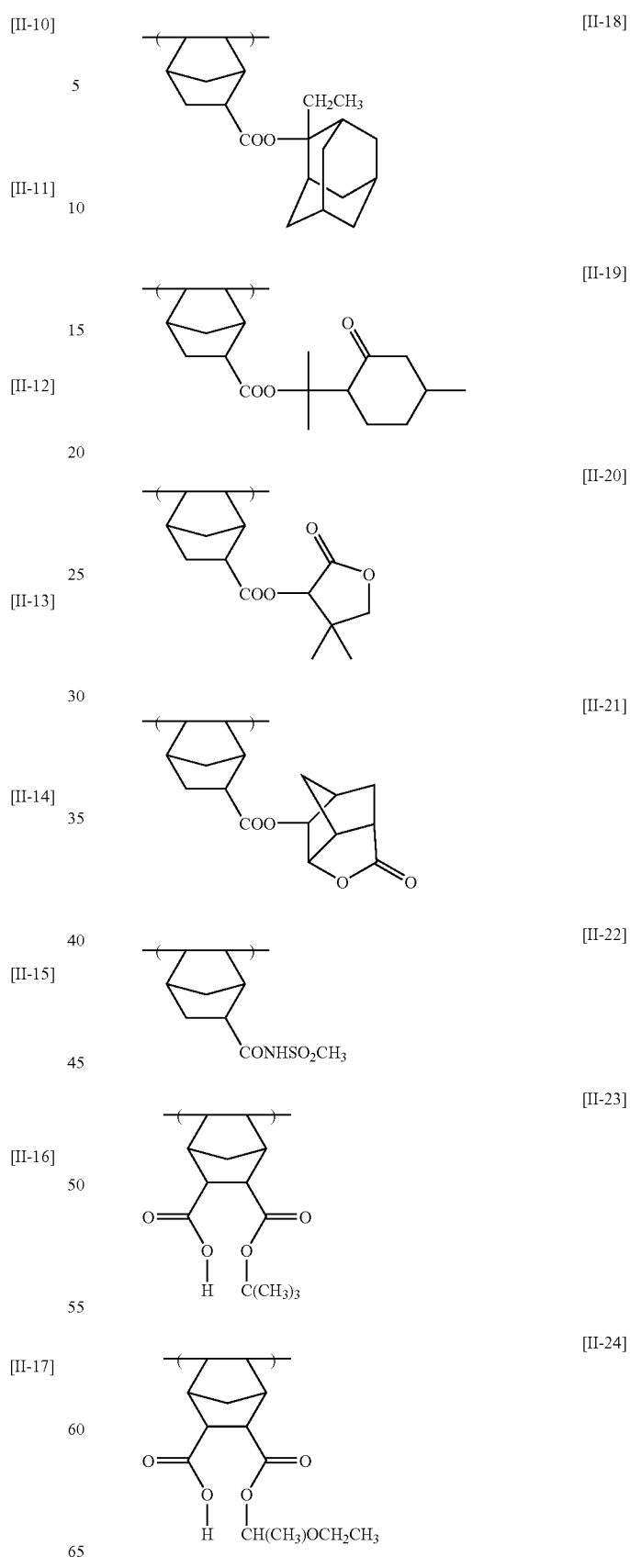

[II-25] 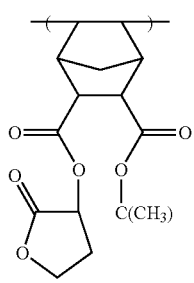

[II-26] 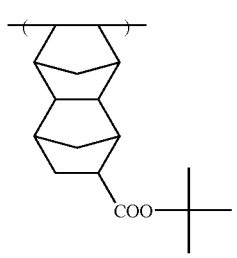

[II-27] 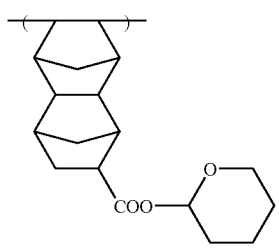

[II-28] 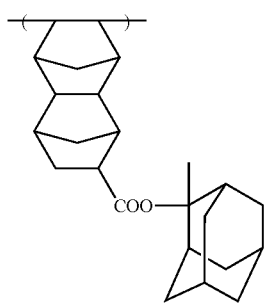

[II-29] 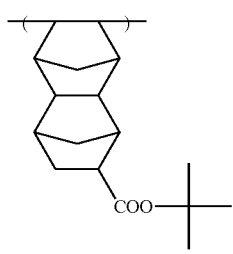

[II-30] 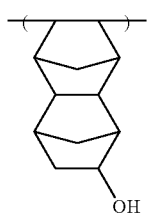

[II-31] 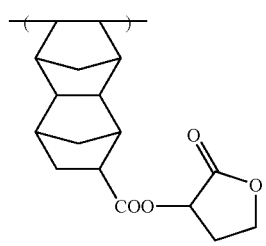

[II-32] 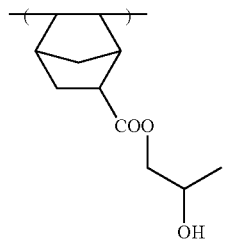

The alicyclic hydrocarbon-based acid-decomposable resin in the invention preferably contains a repeating unit having a group having a lactone structure. As the group having a lactone structure, any group having a lactone structure can be used, but preferably groups having 5- to 7-membered ring lactone structures, and 5- to 7-membered ring lactone structures condensed with other ring structures in the form of forming a bicyclo structure or a Spiro structure are preferred. As the group having a lactone structure, a group having a lactone structure represented by any of the following formulae (LC1-1) to (LC1-16) is more preferred. A group having a lactone structure may be directly bonded to the main chain of a repeating unit. Preferred lactone structures are (LC1-1), (LC1-4) (LC1-5), (LC1-6), (LC1-13) and (LC1-14). By the use of a specific lactone structure, line edge roughness and development defect are bettered.

LC1-1
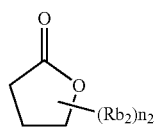

LC1-2
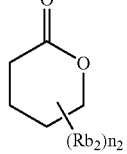

LC1-3
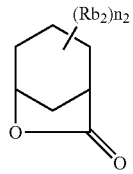

LC1-4
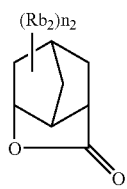

LC1-5
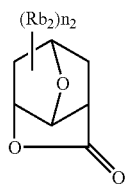

LC1-6
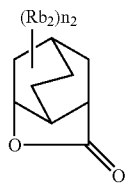

LC1-7
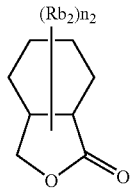

LC1-8
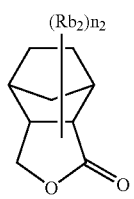

LC1-9
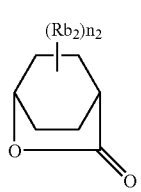

LC1-10
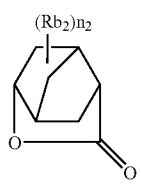

LC1-11
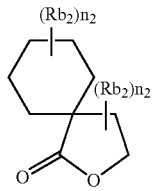

LC1-12
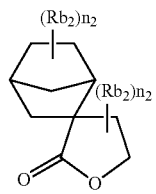

LC1-13
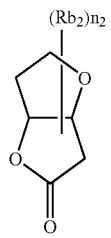

LC1-14
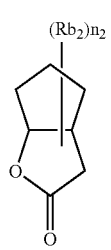

LC1-15
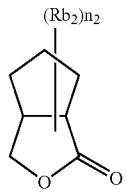

LC1-16
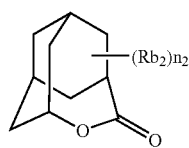

A lactone structure moiety may have or may not have a substituent (Rb$_2$). As preferred substituent (Rb$_2$), an alkyl group having from 1 to 8 carbon atoms, a cycloalkyl group having from 3 to 7 carbon atoms, an alkoxyl group having from 1 to 8 carbon atoms, an alkoxycarbonyl group having from 1 to 8 carbon atoms, a carboxyl group, a halogen atom, a hydroxyl group, a cyano group, and an acid-decomposable group are exemplified. n$_2$ represents an integer of from 0 to 4. When n$_2$ is 2 or more, a plurality of Rb$_2$ may be the same or different, and a plurality of Rb$_2$ may be bonded to each other to form a ring.

As the repeating units having a group having a lactone structure represented by any of formulae (LC1-1) to (LC1-16), a repeating unit in which at least one of R$_{13}$' to R$_{16}$' in formula (II-AB1) or (II-AB2) is a group having a lactone structure represented by any of formulae (LC1-1) to (LC1-16) (for example, R$_5$ of —COOR$_5$ is a group having a lactone structure represented by any of formulae (LC1-1) to (LC1-16)), or a repeating unit represented by the following formula (AI) can be exemplified.

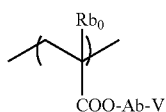 (AI)

In formula (AI), $Rb_0$ represents a hydrogen atom, a halogen atom, or an alkyl group having from 1 to 4 carbon atoms. As the preferred substituents that the alkyl group represented by $Rb_0$ may have, a hydroxyl group and a halogen atom are exemplified.

As the halogen atom represented by $Rb_0$, a fluorine atom, a chlorine atom, a bromine atom and an iodine atom can be exemplified.

$Rb_0$ preferably represents a hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent linking group combining these groups.

Ab preferably represents a single bond or a linking group represented by $-Ab_1-CO_2-$. $Ab_1$ represents a straight chain or branched alkylene group, or a monocyclic or polycyclic cycloalkylene group, and preferably a methylene group, an ethylene group, a cyclohexyl group, an adamantyl group, or a norbornyl group.

V represents a group having a lactone structure represented by any of formulae (LC1-1) to (LC1-16).

Repeating units having a lactone structure generally have optical isomers, and any optical isomer may be used. One kind of optical isomer may be used alone, or a plurality of optical isomers may be used as mixture. When one kind of optical isomer is mainly used, the optical purity (ee) of the optical isomer is preferably 90 or more, and more preferably 95 or more.

The specific examples of repeating units having a group having a lactone structure are shown below, but the invention is not limited thereto.

(In the formulae, $R^x$ represents H, $CH_3$, $CH_2OH$ or $CF_3$.)

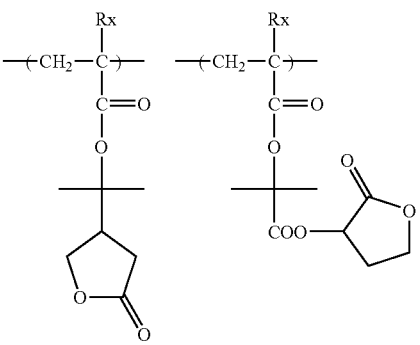

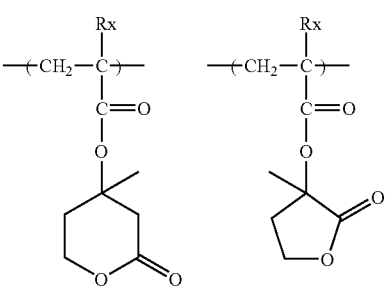

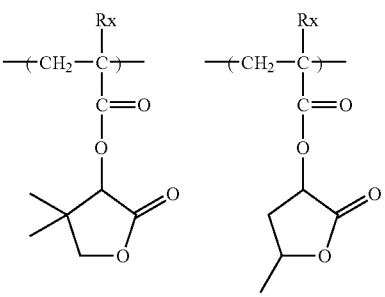

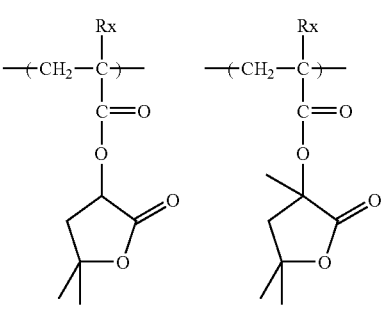

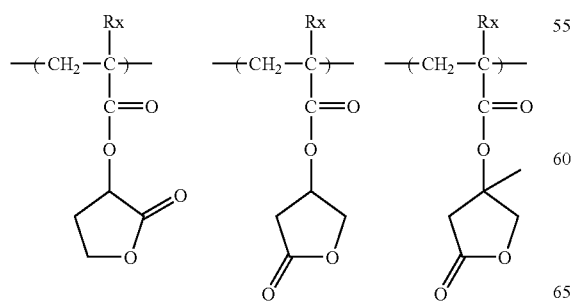

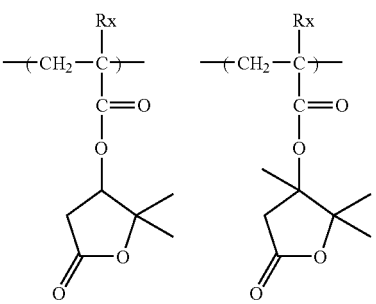

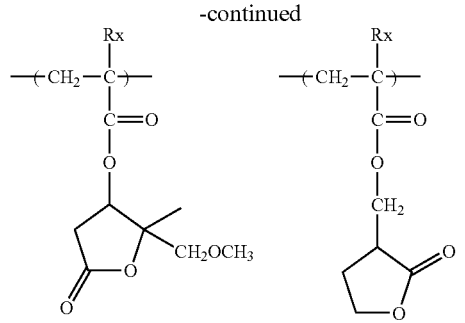
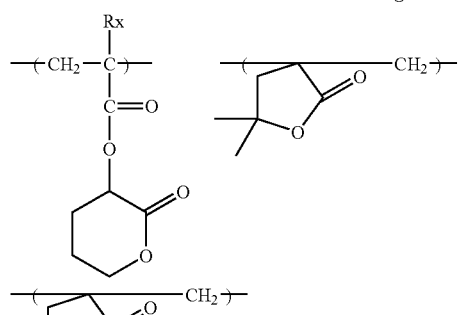
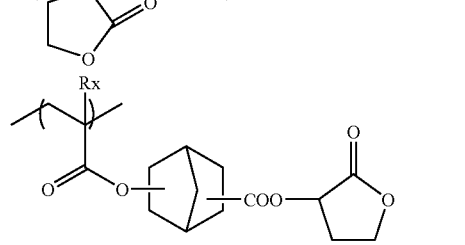
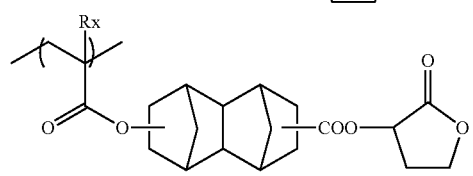
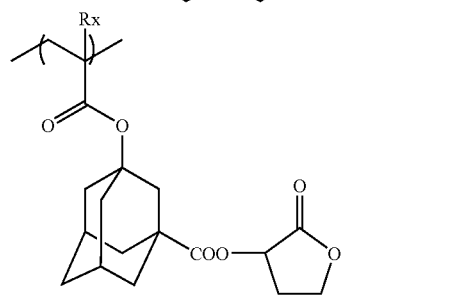
(In the formulae, $R^x$ represents H, $CH_3$, $CH_2OH$ or $CF_3$.)
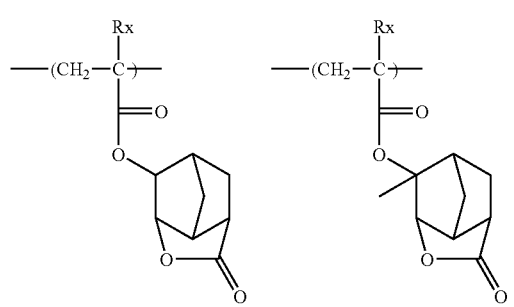
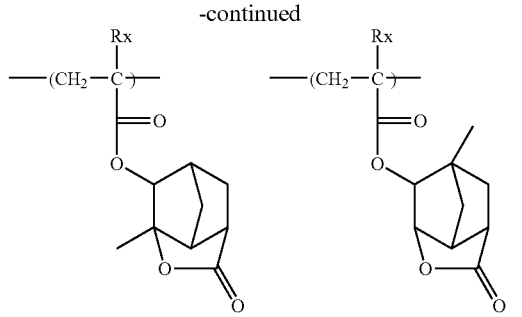
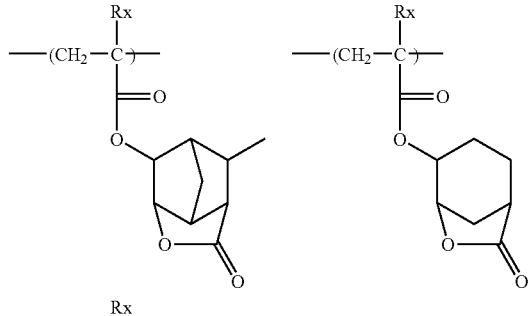
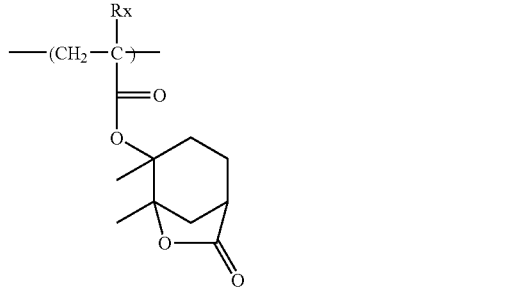
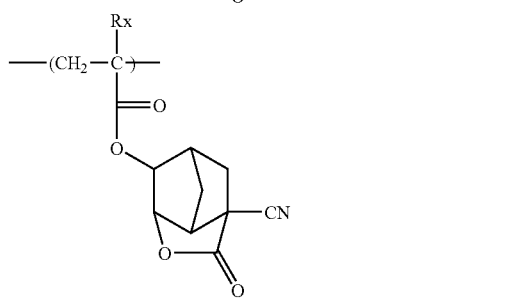
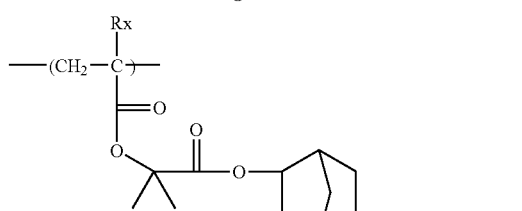
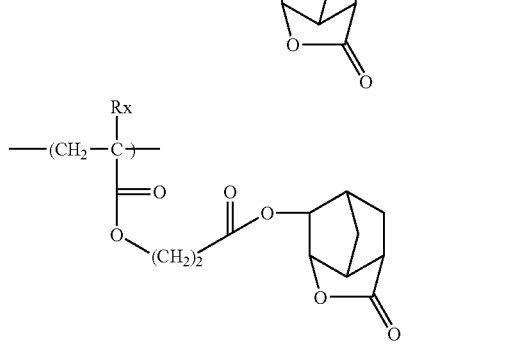

67
-continued
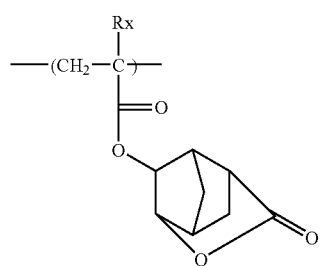
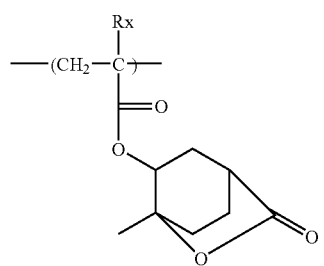
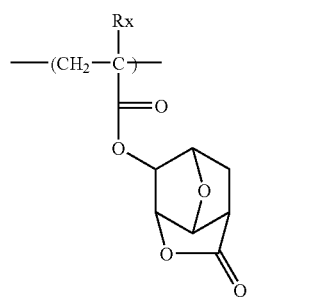
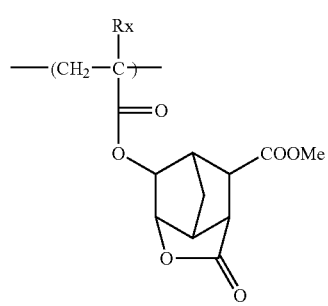
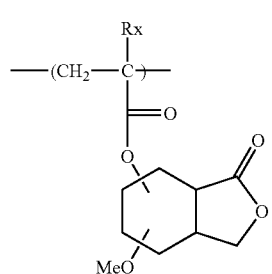
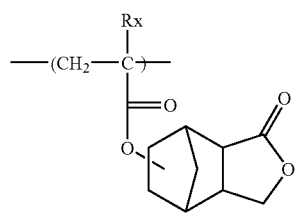
68
-continued
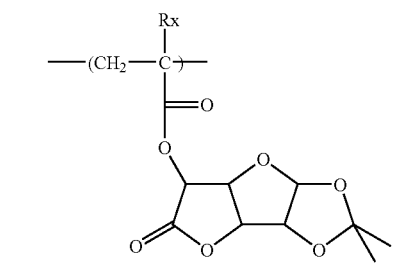
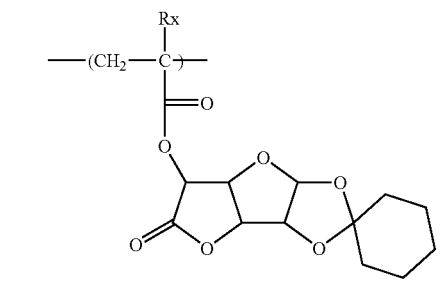
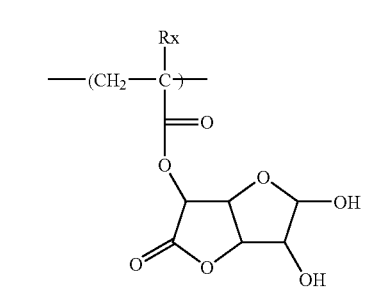
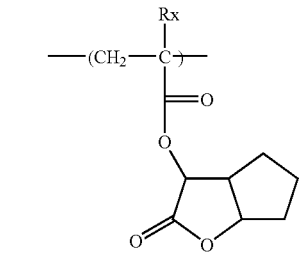
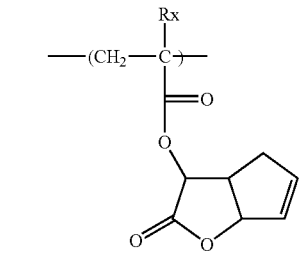
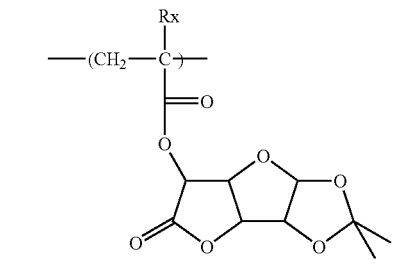

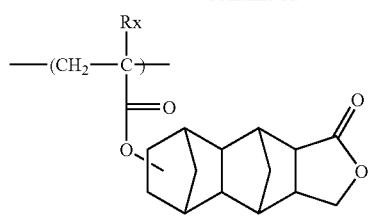

(In the formulae, Rx represents H, CH₃, CH₂OH or CF₃.)

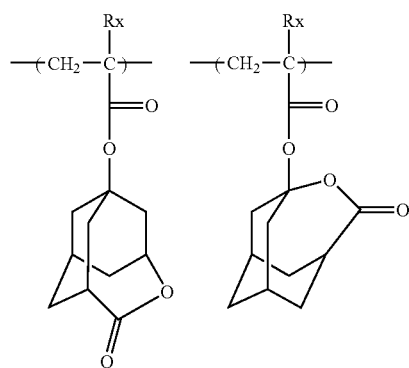

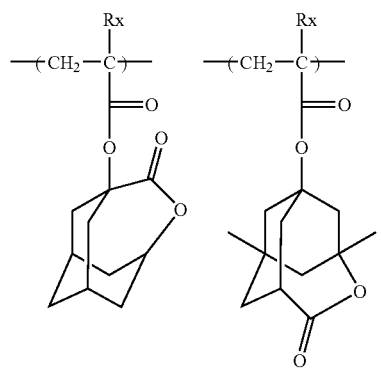

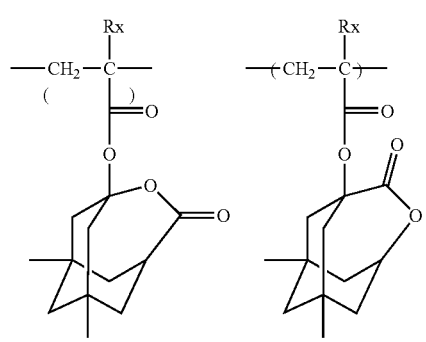

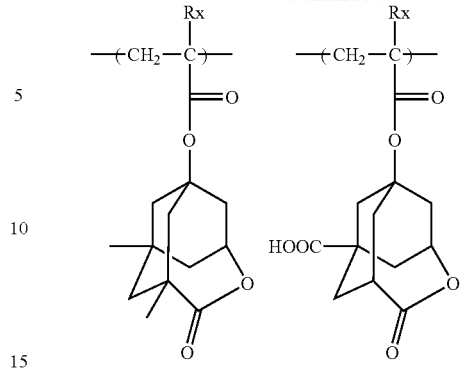

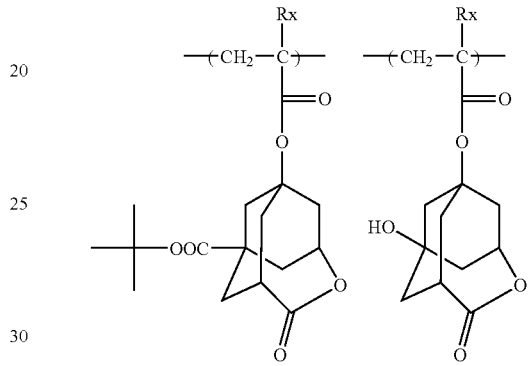

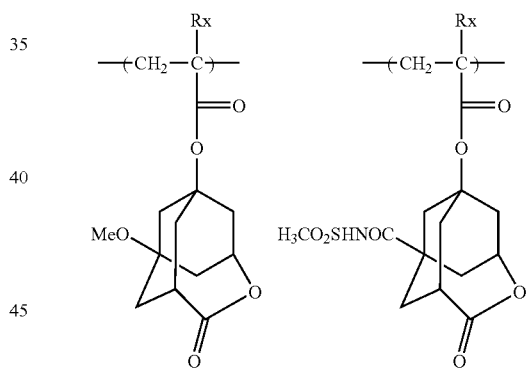

It is preferred for the alicyclic hydrocarbon-based acid-decomposable resin of the invention to have a repeating unit having a group having an alicyclic hydrocarbon structure substituted with a polar group, by which adhesion with a substrate and affinity with a developing solution are improved. As the alicyclic hydrocarbon structure of the alicyclic hydrocarbon structure substituted with a polar group, an adamantyl group, a diamantyl group, and a norbornane group are preferred. As the polar group, a hydroxyl group and a cyano group are preferred. As the group having the alicyclic hydrocarbon structure substituted with a polar group, a group represented by any of the following formulae (VIIa) to (VIId) is preferred.

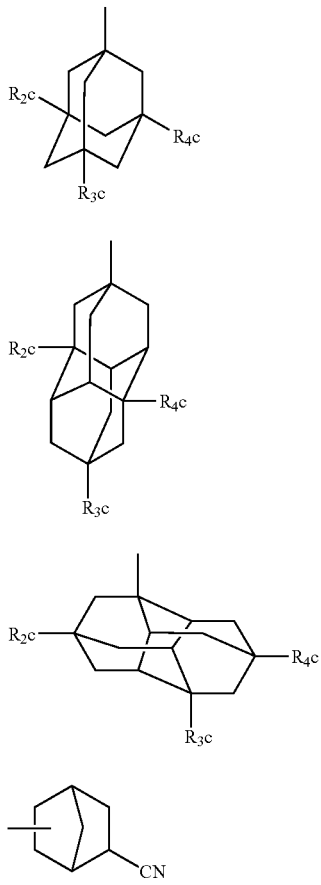

(VIIa)

(VIIb)

(VIIc)

(VIId)

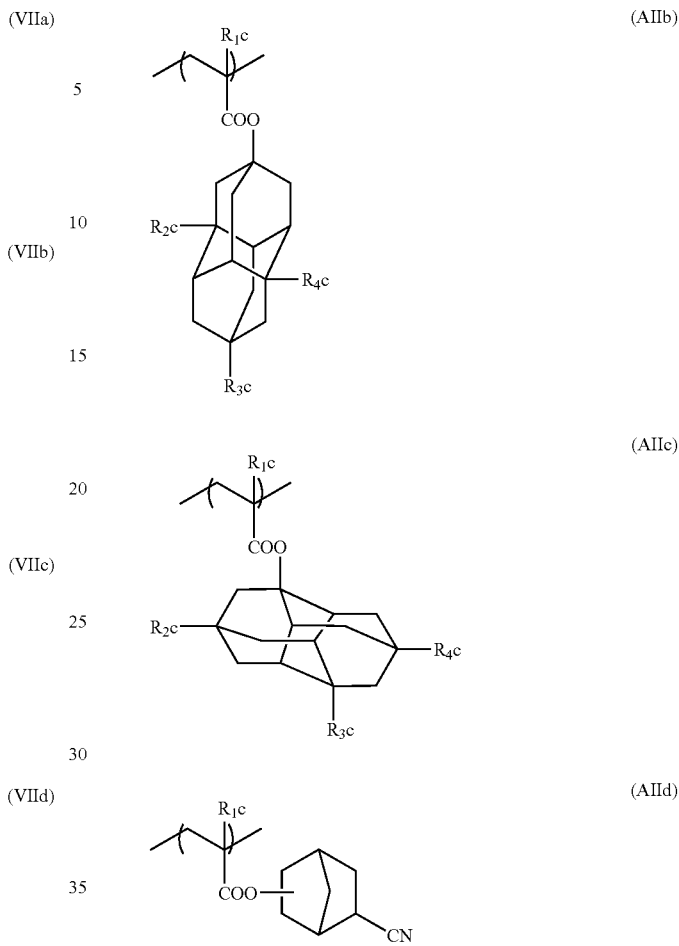

(AIIb)

(AIIc)

(AIId)

In formula (VIIa) to (VIIc), $R_{2c}$, $R_{3c}$ and $R_{4c}$ each represents a hydrogen atom, a hydroxyl group, or a cyano group, provided that at least one of $R_{2c}$, $R_{3c}$ and $R_{4c}$ represents a hydroxyl group or a cyano group. Preferably one or two of $R_{2c}$, $R_{3c}$ and $R_{4c}$ represent a hydroxyl group and the remainder represent a hydrogen atom. In formula (VIIa), more preferably two of $R_{2c}$, $R_{3c}$ and $R_{4c}$ represent a hydroxyl group and the remainder represents a hydrogen atom.

As the repeating unit having a group represented by any of formulae (VIIa) to (VIId), a repeating unit in which at least one of $R_{13}'$ to $R_{16}'$ in formula (II-AB1) or (II-AB2) is a group represented by any of formulae (VIIa) to (VIId) (for example, $R_5$ of —COOR$_5$ is a group represented by any of formulae (VIIa) to (VIId)), or a repeating unit represented by any of the following formulae (AIIa) to (AIId) can be exemplified.

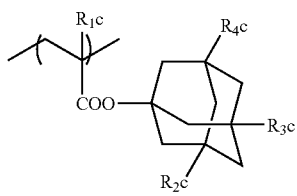

(AIIa)

In formulae (AIIa) to (AIId),), $R_{1c}$ represents a hydrogen atom, a methyl group, a trifluoromethyl group, or a hydroxymethyl group.

The specific examples of the repeating units represented by formulae (AIIa) to (AIId) are shown below, but the invention is not restricted thereto.

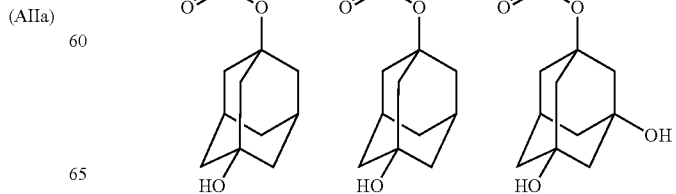

-continued

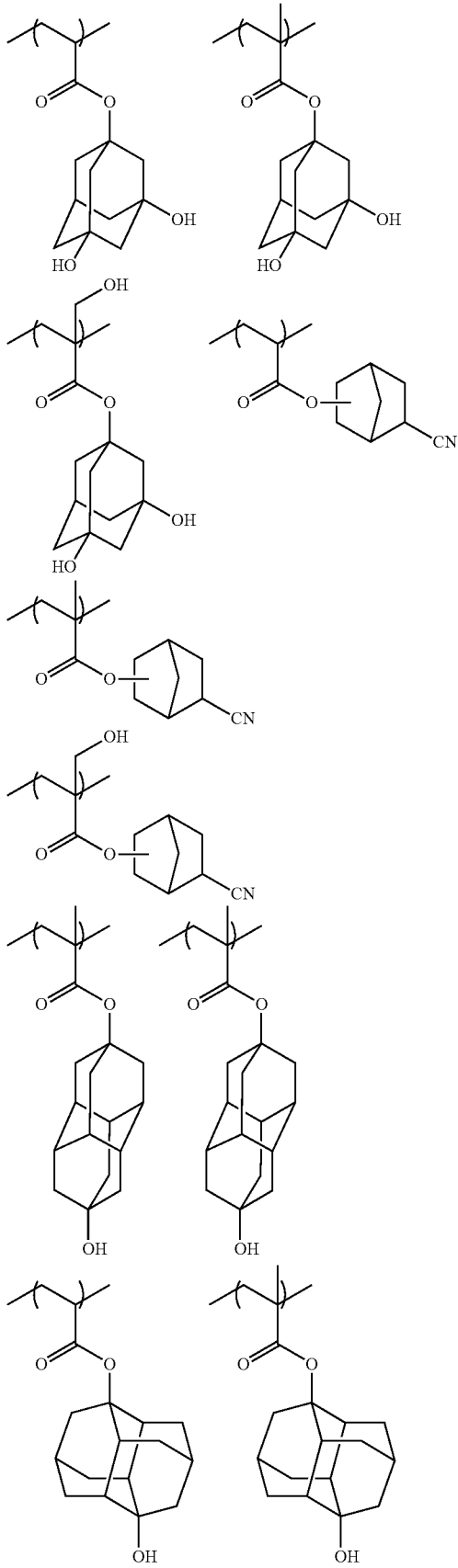

The alicyclic hydrocarbon-based acid-decomposable resin in the invention may have a repeating unit represented by the following formula (VIII).

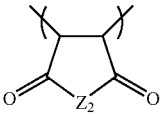

(VIII)

In formula (VIII), $Z_2$ represents —O— or —N($R_{41}$)—. $R_{41}$ represents a hydrogen atom, a hydroxyl group, an alkyl group, or —OSO$_2$—$R_{42}$. $R_{42}$ represents an alkyl group, a cycloalkyl group, or a camphor residue. The alkyl group represented by $R_{41}$ and $R_{42}$ may be substituted with a halogen atom (preferably a fluorine atom) and the like.

As the specific examples of the repeating units represented by formula (VIII), the following compounds are exemplified, but the invention is not restricted thereto.

It is preferred for the alicyclic hydrocarbon-based acid-decomposable resin in the invention to have a repeating unit having an alkali-soluble group, and it is more preferred to have a repeating unit having a carboxyl group, by which the resolution in the use for contact hole is enhanced. As the repeating units having a carboxyl group, a repeating unit having a carboxyl group directly bonded to the main chain of a resin such as a repeating unit by acrylic acid or methacrylic acid, a repeating unit having a carboxyl group bonded to the main chain of a resin via a linking group, and a repeating unit having a carboxyl group introduced to the terminals of a polymer chain by polymerization with a polymerization initiator having an alkali-soluble group and a chain transfer agent are exemplified, and any of these repeating units is preferably used. Linking groups may have a monocyclic or polycyclic hydrocarbon structure. The repeating unit by acrylic acid or methacrylic acid is especially preferred.

The alicyclic hydrocarbon-based acid-decomposable resin in the invention may further have a repeating unit having one to three groups represented by the following formula (F1), by which line edge roughness property is improved.

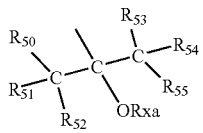
(F1)

In formula (F1), $R_{50}$, $R_{51}$, $R_{52}$, $R_{53}$, $R_{54}$ and $R_{55}$ each represents a hydrogen atom, a fluorine atom, or an alkyl group, provided that at least one of $R_{50}$ to $R_{55}$ represents a fluorine atom, or an alkyl group in which at least one hydrogen atom is substituted with a fluorine atom.

Rxa represents a hydrogen atom or an organic group (preferably an acid-decomposable protective group, an alkyl group, a cycloalkyl group, an acyl group, or an alkoxycarbonyl group).

The alkyl group represented by $R_{50}$ to $R_{55}$ may be substituted with a halogen atom, e.g., a fluorine atom, or a cyano group, and preferably an alkyl group having from 1 to 3 carbon atoms, e.g., a methyl group and a trifluoromethyl group can be exemplified.

It is preferred that all of $R_{50}$ to $R_{55}$ represent a fluorine atom.

As the organic group represented by Rxa, an acid-decomposable protective group, and an alkyl group, a cycloalkyl group, an acyl group, an alkylcarbonyl group, an alkoxycarbonyl group, an alkoxycarbonylmethyl group, an alkoxymethyl group, and a 1-alkoxyethyl group, each of which may have a substituent, are preferred.

The repeating unit having the group represented by formula (F1) is preferably a repeating unit represented by the following formula (F2).

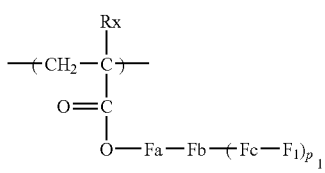
(F2)

In formula (F2), $R^x$ represents a hydrogen atom, a halogen atom, or an alkyl group having from 1 to 4 carbon atoms. As preferred substituents that the alkyl group represented by $R^x$ may have, a hydroxyl group and a halogen atom are exemplified.

Fa represents a single bond or a straight chain or branched alkylene group, and preferably a single bond.

Fb represents a monocyclic or polycyclic hydrocarbon group.

Fc represents a single bond or a straight chain or branched alkylene group, and preferably a single bond or a methylene group.

$F_1$ represents a group represented by formula (F1).

$P_1$ is from 1 to 3.

As the cyclic hydrocarbon group represented by Fb, a cyclopentyl group, a cyclohexyl group, or a norbornyl group is preferred.

The specific examples of the repeating units having the group represented by formula (F1) are shown below, but the invention is not restricted thereto.

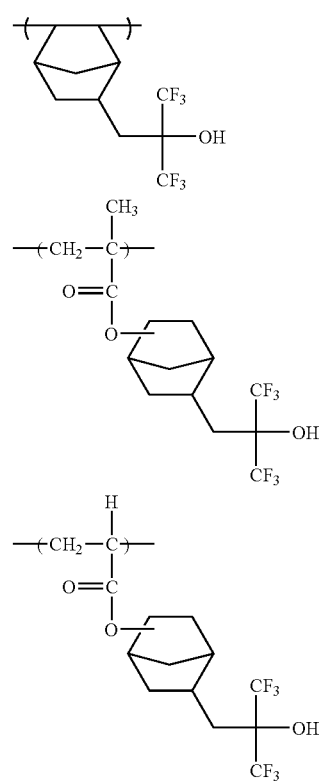

The alicyclic hydrocarbon-based acid-decomposable resin in the invention may further contain a repeating unit having an alicyclic hydrocarbon structure and not showing acid decomposability, by containing such a repeating unit, the elution of low molecular weight components from a resist film into an immersion liquid can be reduced at the time of immersion exposure. As such repeating units, e.g., 1-adamantyl(meth)acrylate, tricyclodecanyl(meth)acrylate, and cyclohexyl(meth)acrylate, are exemplified.

The alicyclic hydrocarbon-based acid-decomposable resin in the invention can contain various kinds of repeating structural units, besides the above repeating structural units, for the purpose of the adjustments of dry etching resistance, aptitude for standard developing solutions, adhesion to a substrate, resist profile, and further, general requisite characteristics of resists, e.g., resolution, heat resistance and sensitivity.

As these repeating structural units, the repeating structural units corresponding to the monomers shown below can be exemplified, but the invention is not restricted thereto.

By containing such various repeating structural units, fine adjustment of performances required of the alicyclic hydrocarbon-based acid-decomposable resin, in particular the following performances, becomes possible, that is, (1) Solubility in a coating solvent,
(2) A film-forming property (a glass transition point),
(3) Alkali developability,
(4) Decrease of layer thickness (hydrophobic-hydrophilic property, selection of an alkali-soluble group),
(5) Adhesion of an unexposed area to a substrate, and
(6) Dry etching resistance.

The examples of such monomers include compounds having one addition polymerizable unsaturated bond selected from acrylic esters, methacrylic esters, acrylamides, methacryl-amides, allyl compounds, vinyl ethers, vinyl esters, etc.

In addition to the aforementioned compounds, addition polymerizable unsaturated compounds copolymerizable with the monomers corresponding to the above various repeating structural units may be used for copolymerization.

In the alicyclic hydrocarbon-based acid-decomposable resin, the molar ratio of the content of each repeating structural unit is arbitrarily set to adjust dry etching resistance and aptitude for standard developing solutions of a resist, adhesion to a substrate, and resist profile, in addition, general requisite characteristics of a resist, e.g., resolution, heat resistance and sensitivity.

As preferred embodiments of the alicyclic hydrocarbon-based acid-decomposable resin in the invention, the following resins are exemplified.

(1) A resin containing a repeating unit having a partial structure containing the alicyclic hydrocarbon represented by any of formulae (pI) to (pV) (a side chain type), preferably a resin containing a (meth)acrylate repeating unit having the structure of any of formulae (pI) to (pV);
(2) A resin containing a repeating unit represented by formula (II-AB) (a main chain type); however, the following is further exemplified as embodiment (2):
(3) A resin containing a repeating unit represented by formula (II-AB), a maleic anhydride derivative and a (meth)acrylate structure (a hybrid type).

In the alicyclic hydrocarbon-based acid-decomposable resin, the content of a repeating unit having an acid-decomposable group is preferably from 10 to 60 mol % in the total repeating structural units, more preferably from 20 to 50 mol %, and still more preferably from 25 to 40 mol %.

In the alicyclic hydrocarbon-based acid-decomposable resin, the content of a repeating unit having a partial structure containing the alicyclic hydrocarbon represented by any of formulae (pI) to (pV) is preferably from 20 to 70 mol % in the total repeating structural units, more preferably from 20 to 50 mol %, and still more preferably from 25 to 40 mol %.

In the alicyclic hydrocarbon-based acid-decomposable resin, the content of a repeating unit represented by formula (II-AB) is preferably from 10 to 60 mol % in the total repeating structural units, more preferably from 15 to 55 mol %, and still more preferably from 20 to 50 mol %.

The content of the repeating structural units on the basis of the monomers of further copolymerization components in the resin can also be optionally set according to the desired resist performances, and the content is generally preferably 99 mol % or less to the total mol number of the repeating structural units having a partial structure containing the alicyclic hydrocarbon represented by any of formulae (pI) to (pV) and the repeating units represented by formula (II-AB), more preferably 90 mol % or less, and still more preferably 80 mol % or less.

When the composition in the invention is for ArF exposure, it is preferred that the resin does not have an aromatic group from the aspect of the transparency to ArF rays.

The alicyclic hydrocarbon-based acid-decomposable resin for use in the invention is preferably such that all the repeating units consist of (meth)acrylate repeating units. In this case, any of the following cases can be used, that is, a case where all the repeating units consist of methacrylate, a case where all the repeating units consist of acrylate, and a case where the repeating units consist of mixture of methacrylate and acrylate, but it is preferred that acrylate repeating units account for 50 mol % or less of all the repeating units. More preferred resins are ternary copolymers comprising from 20 to 50 mol % of repeating units having a partial structure containing the alicyclic hydrocarbon represented by any of formulae (pI) to (pV), from 20 to 50 mol % of repeating units having a lactone structure, and from 5 to 30 mol % of repeating units having an alicyclic hydrocarbon structure substituted with a polar group, and quaternary copolymers further containing from 0 to 20 mol % of other repeating units.

Especially preferred resins are ternary copolymers comprising from 20 to 50 mol % of a repeating unit having an acid-decomposable group represented by any of the following formulae (ARA-1) to (ARA-5), from 20 to 50 mol % of a repeating unit having a lactone group represented by any of the following formulae (ARL-1) to (ARL-6), and from 5 to 30 mol % of a repeating unit having an alicyclic hydrocarbon structure substituted with a polar group represented by any of the following formulae (ARH-1) to (ARH-3), and quaternary copolymers further containing from 5 to 20 mol % of a repeating unit having a carboxyl group or a structure represented by formula (F1), and a repeating unit having an alicyclic hydrocarbon structure and not showing acid decomposability.

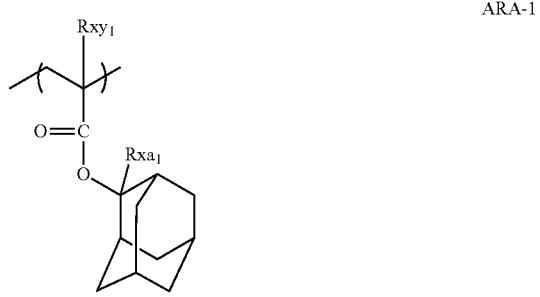

ARA-1

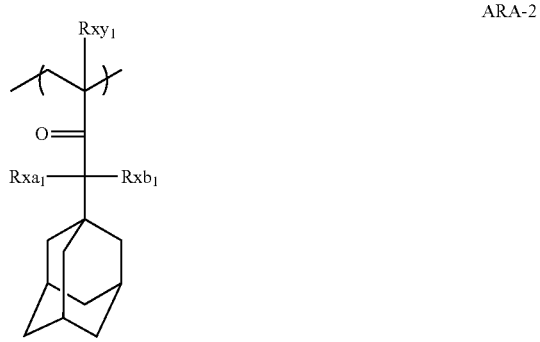

ARA-2

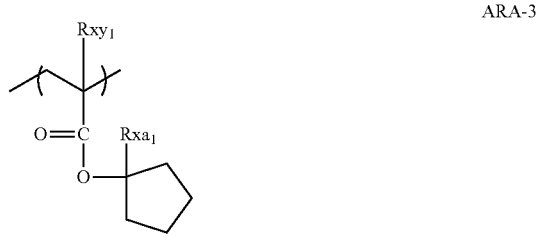

ARA-3

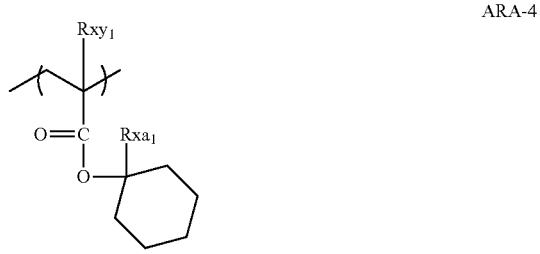

ARA-4

-continued

ARA-5
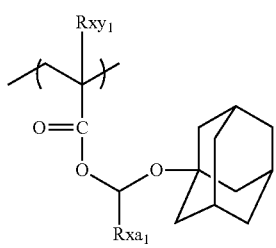

ARL-1
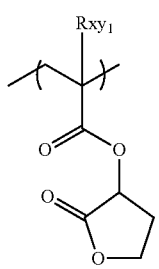

ARL-2
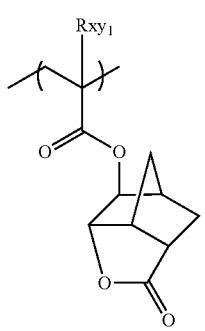

ARL-3
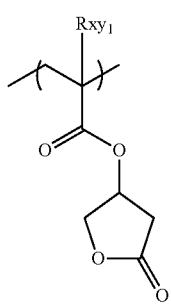

ARL-4
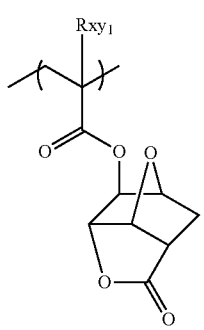

-continued

ARL-5
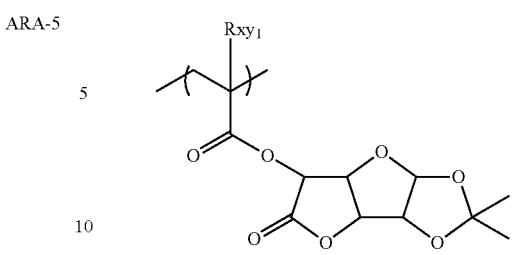

ARL-6
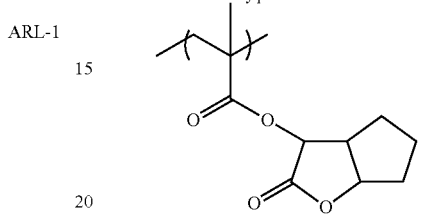

ARH-1
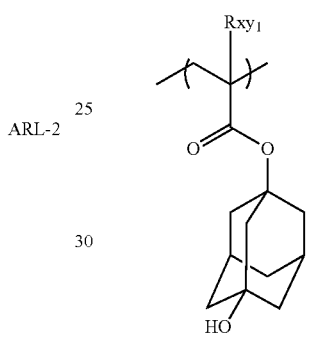

ARH-2
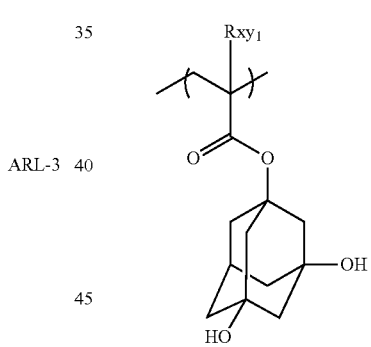

ARH-3
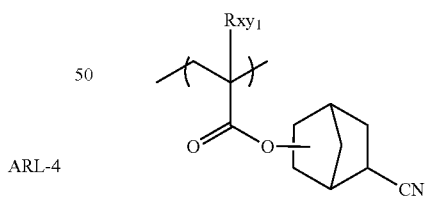

In the above formulae, $Rxy_1$ represents a hydrogen atom or a methyl group.

$Rxa_1$ and $Rxb_1$ each represents a methyl group or an ethyl group.

The alicyclic hydrocarbon-based acid-decomposable resins for use in the invention can be synthesized according to ordinary methods (e.g., radical polymerization). For instance, as ordinary methods, a batch polymerization method of dissolving a monomer and an initiator in a solvent and heating the solution to perform polymerization, and a dropping polymerization method of adding a solution of a monomer and an initiator to a heated solvent over 1 to 10 hours by dropping are exemplified, and dropping polymerization is preferred. As reaction solvents, ethers, e.g., tetrahydrofuran, 1,4-dioxane, and diisopropyl ether, ketones, e.g., methyl ethyl ketone and methyl isobutyl ketone, an ester solvent, e.g., ethyl acetate, amide solvents, e.g., dimethylformamide and dimethyacetamide, and the later-described solvents capable of dissolving the composition of the invention, e.g., propylene glycol monomethyl ether acetate, propylene glycol monomethyl ether, and cyclohexanone are exemplified. It is more preferred to use the same solvent in polymerization as the solvent used in the resist composition in the invention, by which the generation of particles during preservation can be restrained.

It is preferred to perform polymerization reaction in the atmosphere of inert gas such as nitrogen or argon. Polymerization is initiated with commercially available radical polymerization initiators (e.g., azo initiators, peroxide and the like). As radical polymerization initiators, azo initiators are preferred, and azo initiators having an ester group, a cyano group, or a carboxyl group are preferred. As preferred initiators, azobisisobutyronitrile, azobis-dimethylvaleronitrile, dimethyl-2,2'-azibis(2-methyl-propionate), etc., are exemplified. Initiators are added additionally or dividedly, if desired, and after termination of the reaction, the reaction product is put into a solvent and an objective polymer is recovered as powder or a solid state. The reaction concentration is from 5 to 50 mass %, and preferably from 10 to 30 mass %. The reaction temperature is generally from 10 to 150° C., preferably from 30 to 120° C., and more preferably from 60 to 100° C.

When the photosensitive composition according to the invention is used in the upper layer resist of a multilayer resist, it is preferred that the resin of component (C) should have a silicon atom.

As resins having a silicon atom and capable of decomposing by the action of an acid to thereby increase the solubility in an alkali developing solution, resins having a silicon atom at least on one side of the main chain and the side chain can be used. As resins having a siloxane structure on the side chain of resins, copolymer of e.g., an olefin monomer having a silicon atom on the side chain, and a (meth)acrylic acid monomer having maleic anhydride and an acid decomposable group on the side chain.

As resins having a silicon atom, resins having a trialkylsilyl structure and a monocyclic or polycyclic siloxane structure are preferred, resins having repeating units having the structures represented by any of the following formulae (SS-1) to (SS-4) are more preferred, and (meth)acrylic ester repeating units having the structures represented by any of formulae (SS-1) to (SS-4), vinyl repeating units, and allyl repeating units are still more preferred.

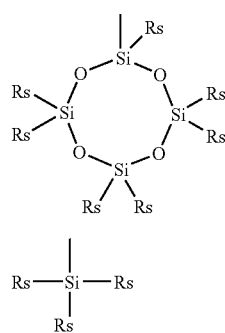

SS-1

SS-2

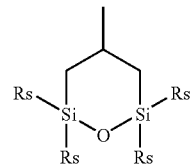

SS-3

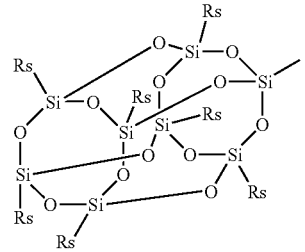

SS-4

In formulae (SS-1) to (SS-4), Rs represents an alkyl group having from 1 to 5 carbon atoms, preferably a methyl group or an ethyl group.

It is preferred that resins having silicon atoms have two or more kinds of different repeating units having silicon atoms, resins having both (Sa) repeating unit having from 1 to 4 silicon atoms and (Sb) repeating unit having from 5 to 10 silicon atoms are more preferred, and resins having at least one repeating unit having a structure represented by any of formulae (SS-1) to (SS-3) and a repeating unit having a structure represented by formula (SS-4) are still more preferred.

When the positive photosensitive composition of the invention is irradiated with $F_2$ excimer laser beams, the resin of component (C) is preferably a resin having a structure wherein the main chain and/or side chain of the polymer skeleton are substituted with fluorine atoms and capable of decomposing by the action of an acid to increase the solubility in an alkali developing solution (hereinafter also referred to as "a fluorine-based acid-decomposable resin), the resin is more preferably a resin having a hydroxyl group the 1-position of which is substituted with a fluorine atom or a fluoroalkyl group, or having a group obtained by protecting a hydroxyl group the 1-position of which is substituted with a fluorine atom or a fluoroalkyl group with an acid-decomposable group. The especially preferred resin is a resin having a hexafluoro-2-propanol structure, or a resin having a structure that the hydroxyl group of hexafluoro-2-propanol is protected with an acid-decomposable group. By the incorporation of fluorine atoms, the transparency to the far ultraviolet rays, in particular to $F_2$ ray (157 nm) can be improved.

As the fluorine-based acid-decomposable resin, resins having at least one repeating unit represented by any of the following formulae (FA) to (FG) are preferably exemplified.

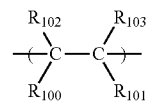

(FA)

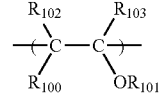

(FB)

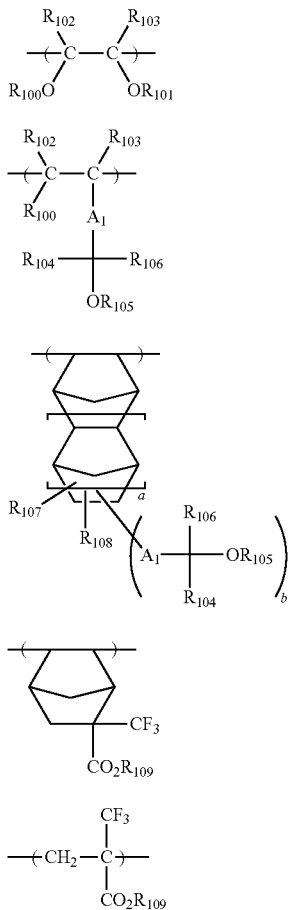

(FC)

(FD)

(FE)

(FF)

(FG)

In the above formulae, $R_{100}$, $R_{101}$, $R_{102}$ and $R_{103}$ each represents a hydrogen atom, a fluorine atom, an alkyl group, or an aryl group.

$R_{104}$ and $R_{106}$ each represents a hydrogen atom, a fluorine atom, or an alkyl group, and at least one of $R_{104}$ and $R_{106}$ represents a fluorine atom or a fluoroalkyl group. Preferably both $R_{104}$ and $R_{106}$ represent a trifluoromethyl group.

$R_{105}$ represents a hydrogen atom, an alkyl group, a cycloalkyl group, an acyl group, an alkoxycarbonyl group, or a group decomposable by the action of an acid.

$A_1$ represents a single bond, a divalent linking group, e.g., an alkylene group, a cycloalkylene group, an alkenylene group, an arylene group, —OCO—, —COO—, —CON($R_{24}$)—, or a linking group containing a plurality of these groups. $R_{24}$ represents a hydrogen atom or an alkyl group.

$R_{107}$ and $R_{108}$ each represents a hydrogen atom, a halogen atom, an alkyl group, an alkoxyl group, an alkoxycarbonyl group, or a group decomposable by the action of an acid.

$R_{109}$ represents a hydrogen atom, an alkyl group, a cycloalkyl group, or a group decomposable by the action of an acid.

b represents 0, 1 or 2.

Further, $R_{100}$ and $R_{101}$ in formulae (FA) and (FC) may form a ring through an alkylene group (having from 1 to 5 carbon atoms) which may be substituted with a fluorine atom.

The repeating units represented by formulae (FA) to (FG) have at least 1, preferably 3 or more, fluorine atoms per one repeating unit.

In formulae (FA) to (FG), the alkyl group is an alkyl group having from 1 to 8 carbon atoms, specifically, a methyl group, an ethyl group, a propyl group, an n-butyl group, a sec-butyl group, a hexyl group, a 2-ethylhexyl group, and an octyl group are preferably exemplified.

The cycloalkyl group may be monocyclic or polycyclic. As the monocyclic cycloalkyl groups, those having from 3 to 8 carbon atoms, e.g., a cyclopropyl group, a cyclopentyl group, a cyclohexyl group, a cycloheptyl group, and a cyclooctyl group are preferably exemplified. As the polycyclic groups, preferably those having from 6 to 20 carbon atoms, e.g., an adamantyl group, a norbornyl group, an isoboronyl group, a camphanyl group, a dicyclopentyl group, an α-pinel group, a tricyclodecanyl group, a tetracyclododecyl group, and an androstanyl group are exemplified. However, the carbon atoms in the monocyclic or polycyclic cycloalkyl groups may be substituted with hetero atoms such as an oxygen atom, etc.

The fluoroalkyl group is a fluoroalkyl group having from 1 to 12 carbon atoms, and specifically a trifluoromethyl group, a perfluoroethyl group, a perfluoropropyl group, a perfluorobutyl group, a perfluorohexyl group, a perfluorooctyl group, a perfluorooctylethyl group, and a perfluorododecyl group are preferably exemplified.

The aryl group is an aryl group having from 6 to 15 carbon atoms, and specifically a phenyl group, a tolyl group, a dimethylphenyl group, a 2,4,6-trimethylphenyl group, a naphthyl group, an anthryl group and a 9,10-dimethoxyanthryl group are preferably exemplified.

The alkoxyl group is an alkoxyl group having from 1 to 8 carbon atoms, and specifically a methoxy group, an ethoxy group, an n-propoxy group, an isopropoxy group, a butoxy group, a pentoxy group, an allyloxy group, and an octoxy group are preferably exemplified.

The acyl group is an acyl group having from 1 to 10 carbon atoms, and specifically a formyl group, an acetyl group, a propanoyl group, a butanoyl group, a pivaloyl group, an octanoyl group, and a benzoyl group are preferably exemplified.

As the alkoxycarbonyl group, an i-propoxycarbonyl group, a t-butoxycarbonyl group, a t-amyloxycarbonyl group, and a 1-methyl-1-cyclohexyloxycarbonyl group, preferably a secondary, and more preferably a tertiary alkoxycarbonyl group are exemplified.

As the halogen atom, e.g., a fluorine atom, a chlorine atom, a bromine atom and an iodine atom are exemplified.

As the alkylene group, preferably an alkylene group having from 1 to 8 carbon atoms, e.g., a methylene group, an ethylene group, a propylene group, a butylene group, a hexylene group, and an octylene group are exemplified.

As the alkenylene group, preferably an alkenylene group having from 2 to 6 carbon atoms, e.g., an ethenylene group, a propenylene group and a butenylene group are exemplified.

As the cycloalkylene group, preferably a cycloalkylene group having from 5 to 8 carbon atoms, e.g., a cyclopentylene group and a cyclohexylene group are exemplified.

As the arylene group, preferably an arylene group having from 6 to 15 carbon atoms, e.g., a phenylene group, a tolylene group and a naphthylene group are exemplified.

These groups may have a substituent, and the examples of the substituents include groups having active hydrogen, e.g., an alkyl group, a cycloalkyl group, an aryl group, an amino group, an amido group, a ureido group, a urethane group, a hydroxyl group, and a carboxyl group, a halogen atom (e.g., a fluorine atom, a chlorine atom, a bromine atom, and an iodine atom), an alkoxyl group (e.g., a methoxy group, an ethoxy group, a propoxy group, a butoxy group), a thioether group, an acyl group (e.g., an acetyl group, a propanoyl group, a benzoyl group), an acyloxy group (e.g., an acetoxy group, a propanoyloxy group, a benzoyloxy group), an alkoxycarbonyl group (e.g., a methoxycarbonyl group, an ethoxycarbonyl group, a propoxycarbonyl group), a cyano group, and a nitro group are exemplified.

Here, as the alkyl, cycloalkyl and aryl groups, those described above are exemplified, but the alkyl group may further be substituted with a fluorine atom or a cycloalkyl group.

As the groups capable of decomposing by the action of an acid to increase the solubility in an alkali developing solution contained in the fluorine-based acid-decomposable resins, e.g., $-O-C(R_{36})(R_{37})(R_{38})$, $-O-C(R_{36})(R_{37})(OR_{39})$, $-O-COO-C(R_{36})(R_{37})(R_{38})$, $-O-C(R_{01})(R_{02})COO-C(R_{36})(R_{37})(R_{38})$, $-COO-C(R_{36})(R_{37})(R_{38})$, and $-COO-C(R_{36})(R_{37})(OR_{39})$ can be exemplified.

$R_{36}$, $R_{37}$, $R_{38}$ and $R_{39}$ each represents an alkyl group, a cycloalkyl group, an aryl group, an aralkyl group, or an alkenyl group; $R_{01}$ and $R_{02}$ each represents a hydrogen atom, an alkyl group, a cycloalkyl group, an alkenyl group (e.g., a vinyl group, an allyl group, a butenyl group, a cyclohexenyl group), an aralkyl group (e.g., a benzyl group, a phenethyl group, a naphthylmethyl group), or an aryl group.

The preferred specific examples of the groups include the ether groups or the ester groups of tertiary alkyl groups such as a t-butyl group, a t-amyl group, a 1-alkyl-1-cyclohexyl group, a 2-alkyl-2-adamantyl group, a 2-adamantyl-2-propyl group, and a 2-(4-methylcyclohexyl)-2-propyl group, acetal groups or acetal ester groups such as a 1-alkoxy-1-ethoxy group and a tetrahydropyranyl group, a t-alkylcarbonate group and a t-alkylcarbonylmethoxy group.

The specific examples of the repeating units represented by formulae (FA) to (FG) are shown below, but the invention is not restricted thereto.

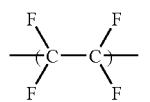

(F-1)

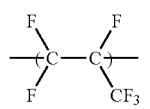

(F-2)

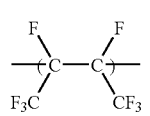

(F-3)

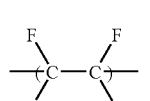

(F-4)

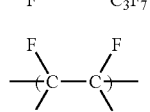

(F-5)

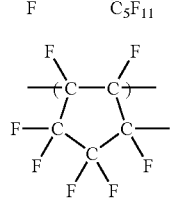

(F-6)

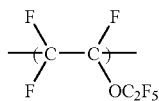

(F-7)

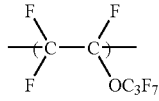

(F-8)

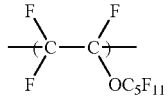

(F-9)

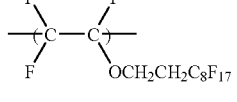

(F-10)

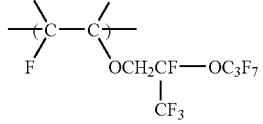

(F-11)

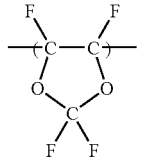

(F-12)

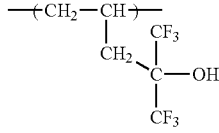

(F-13)

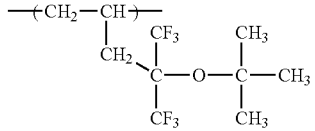

(F-14)

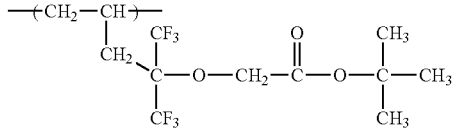

(F-15)

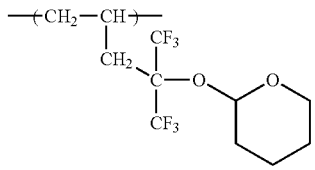

(F-16)

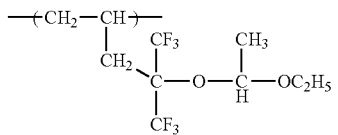

(F-17)

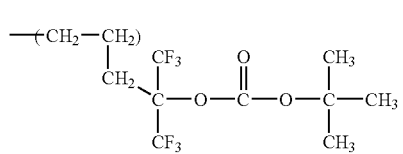 (F-18)
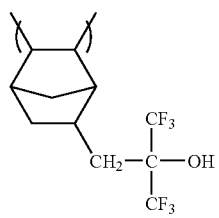 (F-19)
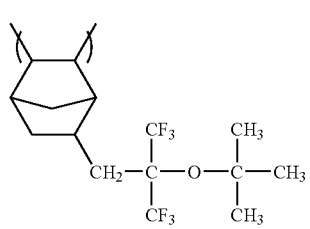 (F-20)
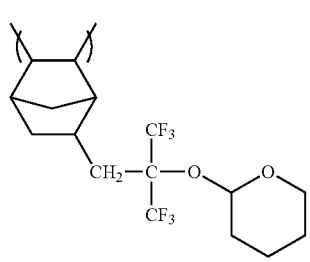 (F-21)
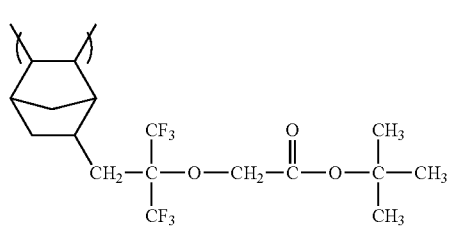 (F-22)
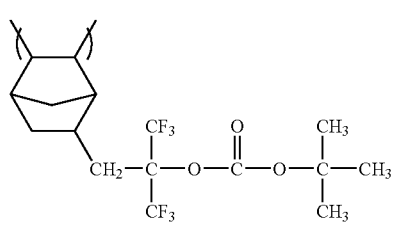 (F-23)
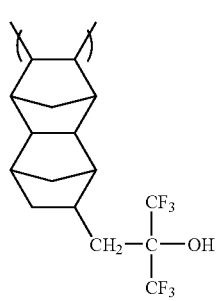 (F-24)
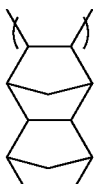 (F-25)
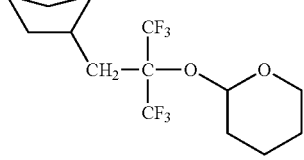 (F-26)
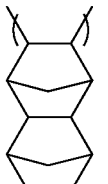 (F-27)
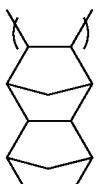 (F-28)
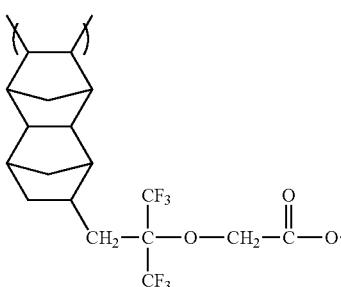 (F-29)
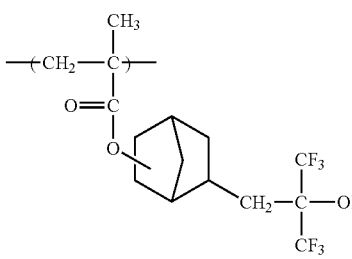

(F-30) 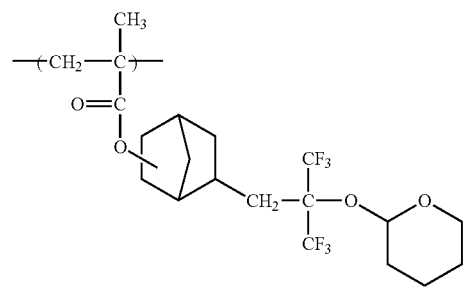
(F-31) 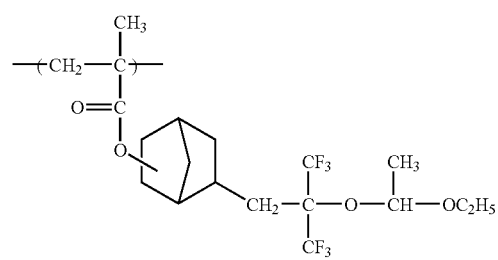
(F-32)
(F-33)
(F-34)
(F-35) 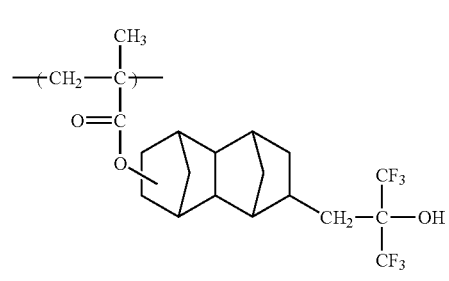
(F-36) 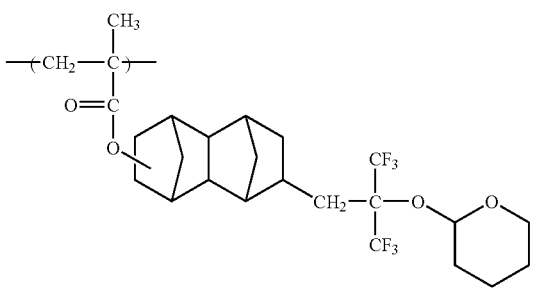
(F-37) 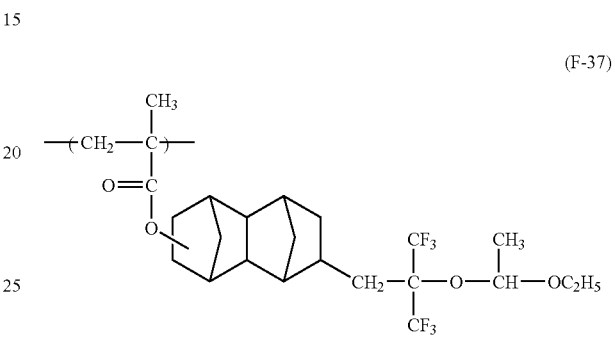
(F-38) 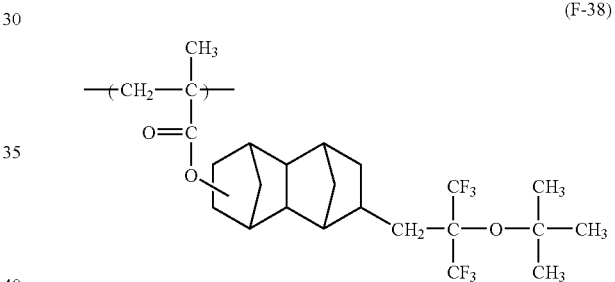
(F-39) 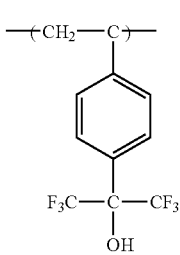
(F-40) 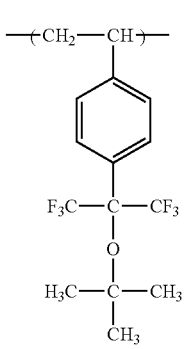

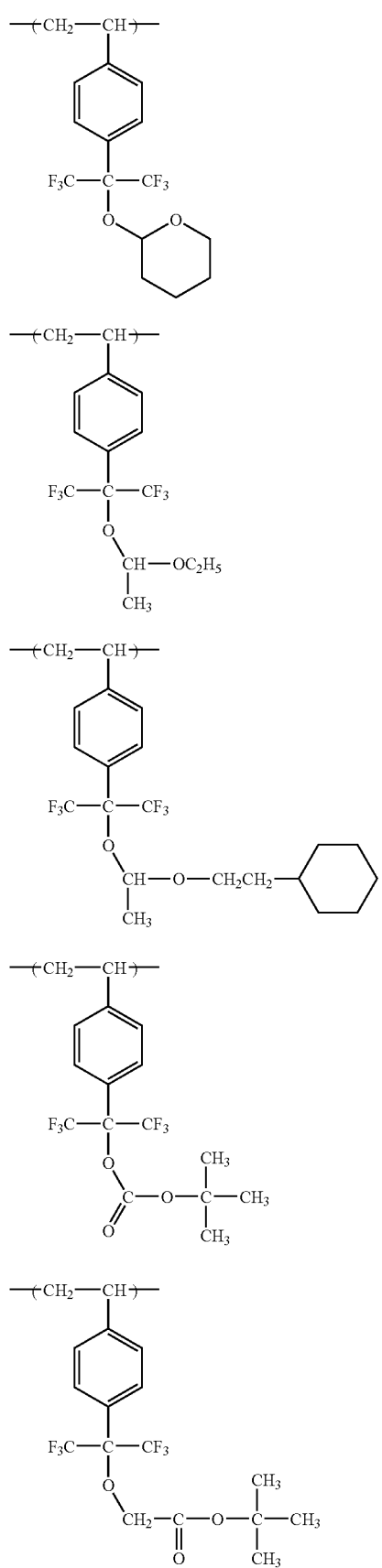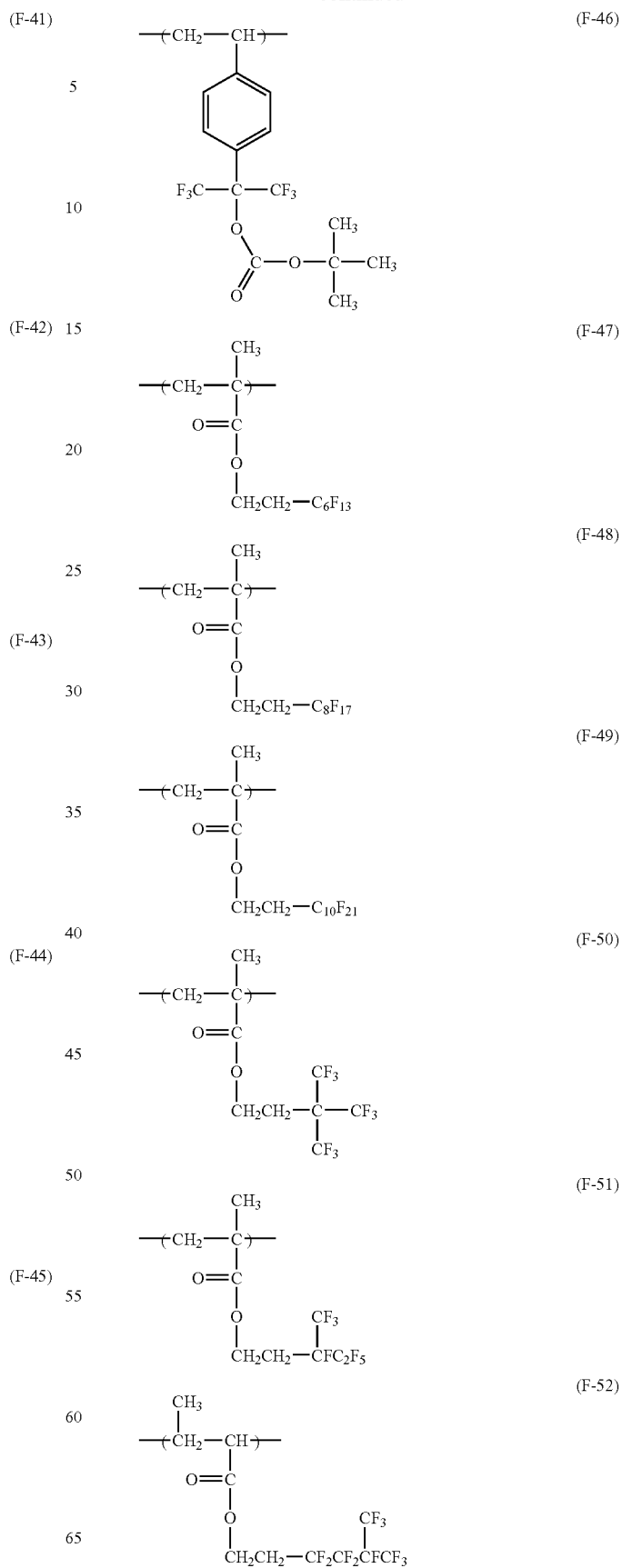

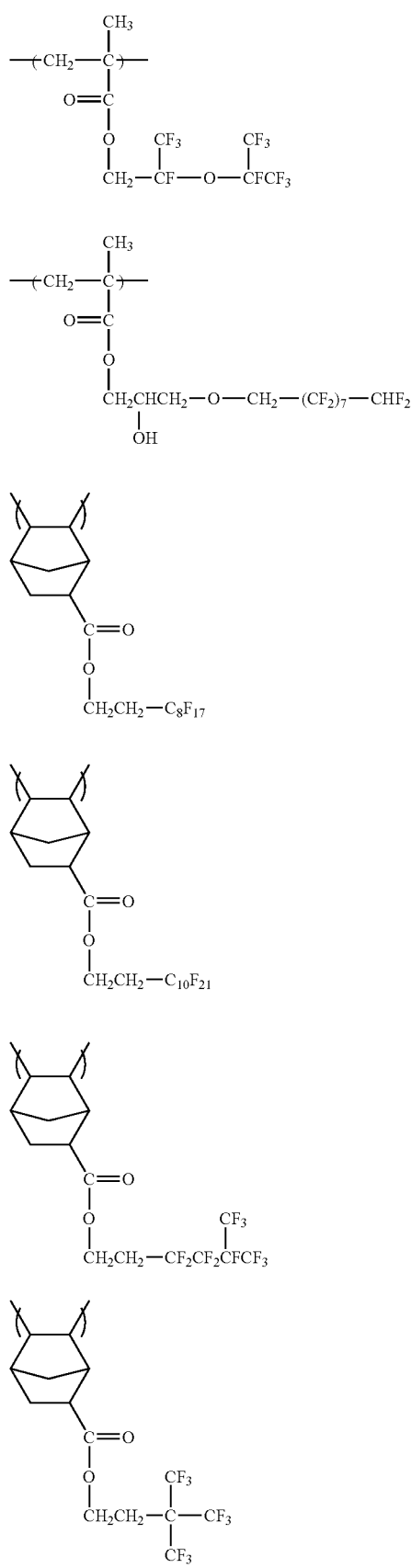
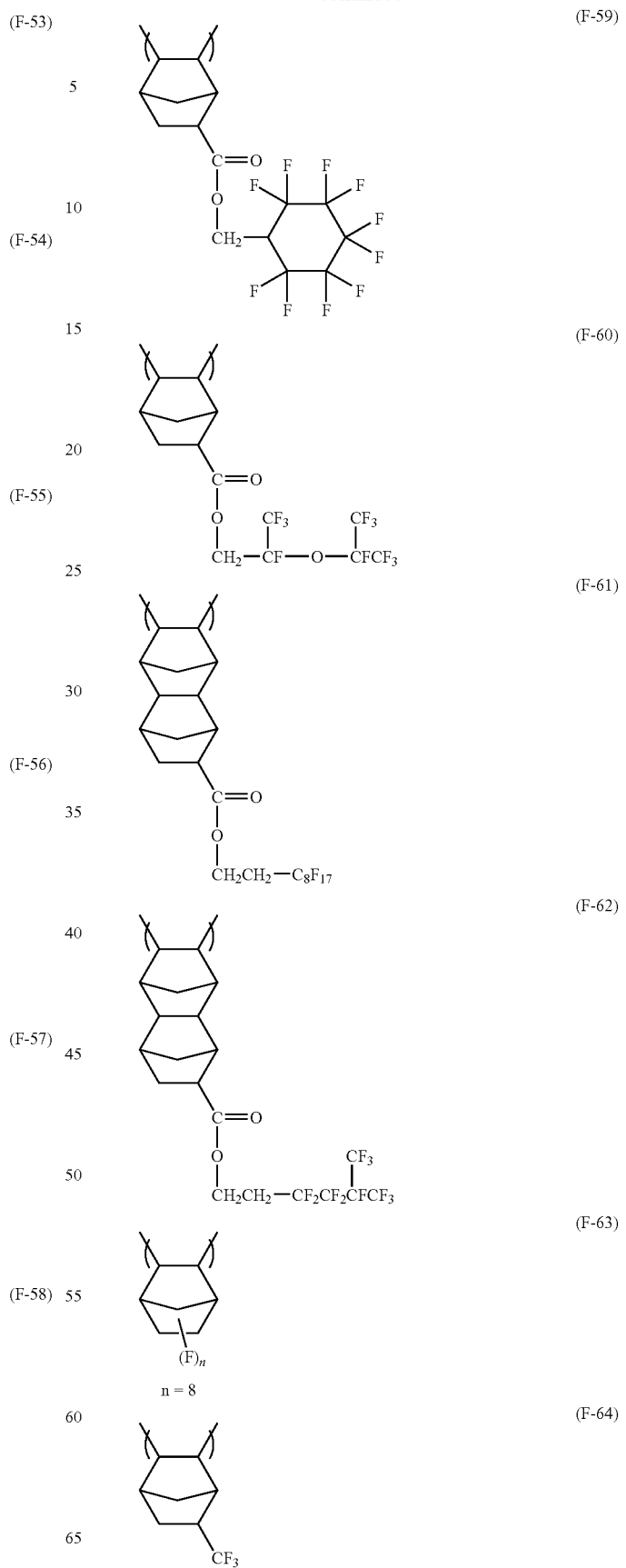

(F-65)

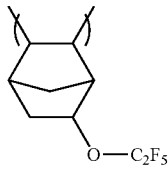

The total content of the repeating units represented by formulae (FA) to (FG) is generally from 10 to 80 mol % to all the repeating units constituting the resin, preferably from 30 to 70 mol %, and more preferably from 35 to 65 mol %.

For the purpose of further improving the performances of the resist of the invention, the fluorine-based acid-decomposable resins may further be copolymerized with other polymerizable monomers in addition to the above repeating structural units.

As the usable copolymerizable monomers, compounds having one addition polymerizable unsaturated bond selected from acrylic esters, acrylamides, methacrylic esters, methacryl-amides, allyl compounds, vinyl ethers, vinyl esters, styrens, and crotonic esters other than described above are exemplified.

It is preferred that these fluorine-based acid-decomposable resins contain other repeating units as the copolymerization components besides the above repeating units having fluorine atoms from the points of improving dry etching resistance, adjusting alkali solubility, and improving adhesion with substrates. Preferred other repeating units are as follows.

1) The repeating units having an alicyclic hydrocarbon structure represented by any of formulae (pI) to (pVI) and formula (II-AB). Specifically the above exemplified repeating units 1 to 23 and repeating units [II-1] to [II-32] shown above. Preferably repeating units 1 to 23, wherein $R^x$ represents $CF_3$.

2) The repeating units having a lactone structure represented by formula (Lc) and any of formulae (V-1) to (V-5). Specifically the above-exemplified repeating units, in particular, the above-exemplified repeating units represented by formula (Lc) and formulae (V-1) to (V-4).

3) The repeating units derived from the vinyl compounds having maleic anhydride, vinyl ether or a cyano group represented by the following formula (XV), (XVI) or (XVII). Specifically repeating units (C-1) to (C-15) shown below. These repeating units may or may not contain a fluorine atom.

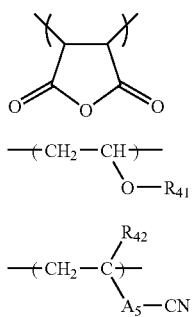

In the above formulae, $R_{41}$ represents an alkyl group, a cycloalkyl group, an aralkyl group, or an aryl group, and the alkyl group represented by $R_{41}$ may be substituted with an aryl group.

$R_{42}$ represents a hydrogen atom, a halogen atom, a cyano group, or an alkyl group.

$A_5$ represents a single bond, a divalent alkylene group, alkenylene group, cycloalkylene group, or arylene group, or —O—CO—$R_{22}$—, —CO—O—$R_{23}$—, or —CO—N($R_{24}$)—$R_{25}$—.

$R_{22}$, $R_{23}$ and $R_{25}$, which may be the same or different, each represents a single bond, or a divalent alkylene group, alkenylene group, cycloalkylene group or arylene group which may have an ether group, an ester group, an amido group, a urethane group or a ureido group.

$R_{24}$ represents a hydrogen atom, an alkyl group, a cycloalkyl group, an aralkyl group, or an aryl group.

Here, as the examples of the substituents, the same groups as the substituents in formulae (FA) to (FG) can be exemplified.

The specific examples of the repeating structural units represented by formulae (XV) to (XVII) are shown below, but the invention is not restricted thereto.

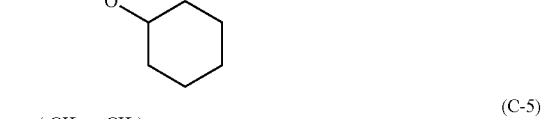

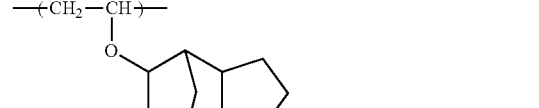

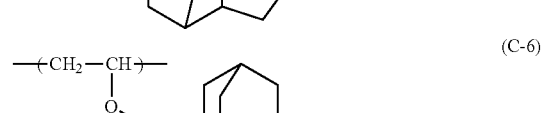

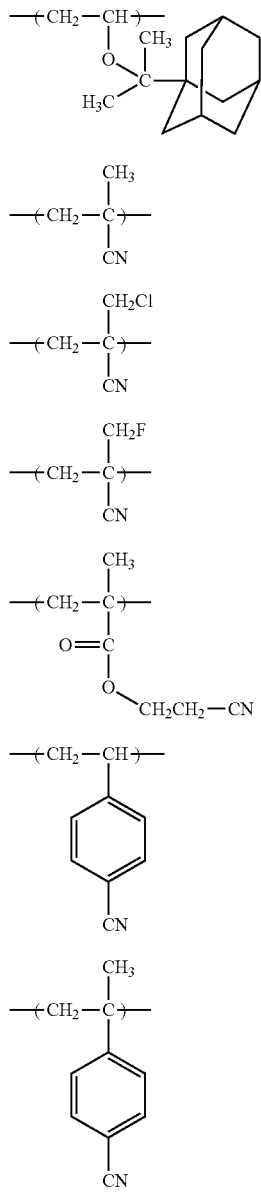

(C-9)
(C-10)
(C-11)
(C-12)
(C-13)
(C-14)
(C-15)

The total amount of the repeating units represented by any of formulae (XV) to (XVII) and other repeating units is generally from 0 to 70 mol % to the total repeating units constituting the resin, preferably from 10 to 60 mol %, and more preferably from 20 to 50 mol %.

The fluorine-based acid-decomposable resins may contain an acid-decomposable group in any repeating unit.

The content of a repeating unit having an acid decomposable group is preferably from 10 to 70 mol % to the total repeating units, more preferably from 20 to 60 mol %, and still more preferably from 30 to 60 mol %.

The fluorine-based acid-decomposable resins can be synthesized by radical polymerization almost similar to the synthesis of alicyclic hydrocarbon-based acid-decomposable resins.

The weight average molecular weight of the resin of component (C) is preferably from 2,000 to 200,000 as the polystyrene equivalent by the GPC method. By making the weight average molecular weight 2,000 or more, heat resistance and dry etching resistance can be improved, and by making the weight average molecular weight 200,000 or less, developability can be improved, and film-forming property can be heightened, since the viscosity becomes low. The weight average molecular weight is more preferably from 5,000 to 50,000, and still more preferably from 7,000 to 30,000. By the adjustment of the molecular weight, it is possible to reconcile the heat resistance of the composition, resolution, development failure and the like. The degree of dispersion of molecular weight (Mw/Mn) of the resin of component (C) is preferably from 1.0 to 3.0, more preferably from 1.2 to 2.5, and still more preferably from 1.2 to 1.6. By the adjustment of the degree of dispersion to a proper range, the performance of line edge roughness can be increased.

In the positive photosensitive composition in the invention, the proportion of the resin of component (C) of the invention in the entire composition is preferably from 40 to 99.99 mass % in the total solids content, more preferably from 50 to 99 mass %, and still more preferably from 80 to 96 mass %.

[4] (D) A dissolution inhibiting compound capable of decomposing by the action of an acid to increase solubility in an alkali developing solution having a molecular weight of 3,000 or less (hereinafter also referred to as "component (D)" or "dissolution inhibiting compound"):

As (D) the dissolution inhibiting compound capable of decomposing by the action of an acid to thereby increase the solubility in an alkali developing solution having a molecular weight of 3,000 or less, alicyclic or aliphatic compounds containing an acid-decomposable group, such as cholic acid derivatives containing an acid-decomposable group described in Proceeding of SPIE, 2724, 355 (1996) are preferred so as not to reduce the permeability to lights of 220 nm or less. As acid-decomposable groups and alicyclic structures, the same as those described above in the alicyclic hydrocarbon-based acid-decomposable resin are exemplified.

When the photosensitive composition of the invention is exposed with a KrF excimer laser or irradiated with electron beams, a phenolic compound having a structure that the phenolic hydroxyl group is substituted with an acid-decomposable group is preferably used. As the phenolic compounds, compounds having from 1 to 9 phenolic skeletons are preferred, and those having from 2 to 6 are more preferred.

The molecular weight of the dissolution-inhibiting compound in the invention is 3,000 or less, preferably from 300 to 3,000, and more preferably from 500 to 2,500.

The addition amount of the dissolution-inhibiting compound is preferably from 3 to 50 mass % based on the solids content of the photosensitive composition, and more preferably from 5 to 40 mass %.

The specific examples of the dissolution-inhibiting compounds are shown below, but the invention is not restricted thereto.

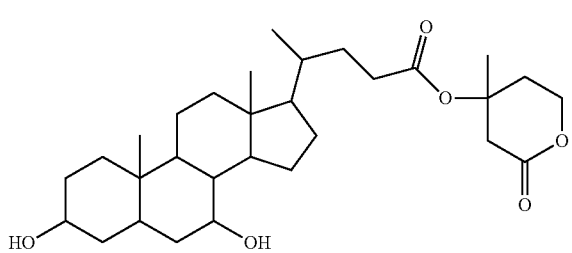

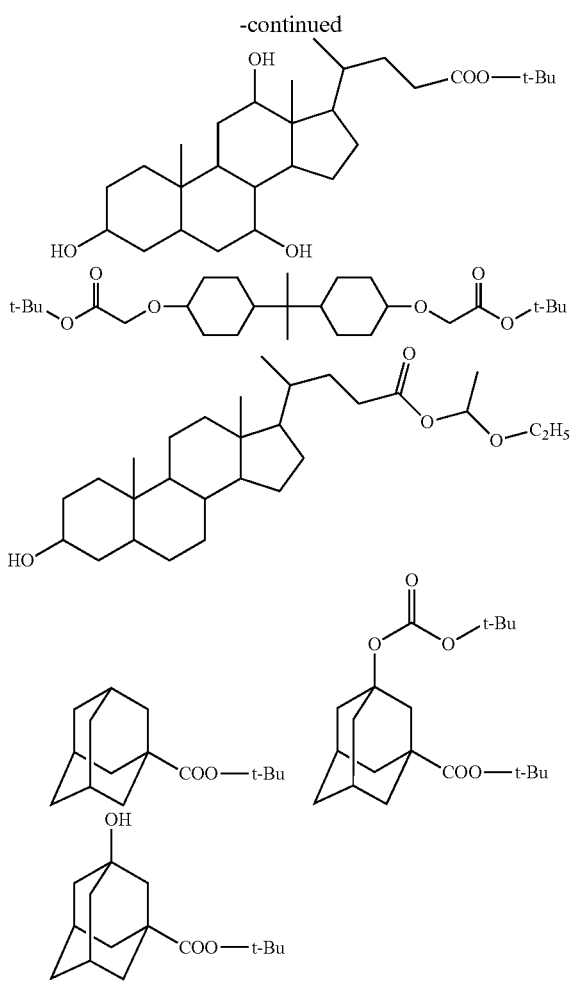

[5] (E) A resin soluble in an alkali developing solution (hereinafter also referred to as "component (E)" or "alkali-soluble resin"):

The alkali dissolution rate of alkali-soluble resins is preferably 20 Å/sec or more when measured with 0.261 N tetramethylammonium hydroxide (TMAH) at 23° C., and especially preferably 200 Å/sec or more.

As alkali-soluble resins for use in the invention, e.g., novolak resins, hydrogenated novolak resins, acetone-pyrogallol resins, o-polyhydroxystyrene, m-polyhydroxy-styrene, p-polyhydroxystyrene, hydrogenated polyhydroxy-styrene, halogen- or alkyl-substituted polyhydroxystyrene, hydroxystyrene-N-substituted maleimide copolymers, o/p- and m/p-hydroxystyrene copolymers, partially O-alkylated products of the hydroxyl group of polyhydroxystyrene (e.g., from 5 to 30 mol % O-methylated, O-(1-methoxy)ethylated, O-(1-ethoxy)ethylated, O-2-tetrahydropyranylated, and O-(t-butoxycarbonyl)methylated products), or partially O-acylated products (e.g., from 5 to 30 mol % o-acetylated and O-(t-butoxy)carbonylated products), styrene-maleic anhydride copolymers, styrene-hydroxystyrene copolymers, α-methylstyrene-hydroxystyrene copolymers, carboxyl group-containing methacrylic resins and derivatives thereof, and polyvinyl alcohol derivatives can be exemplified, but the invention is not limited to these resins.

Particularly preferred alkali-soluble resins are novolak resins, o-polyhydroxystyrene, m-polyhydroxystyrene p-polyhydroxystyrene, copolymers of them, alkyl-substituted polyhydroxystyrene, partially O-alkylated or O-acylated products of polyhydroxystyrene, styrene-hydroxystyrene copolymers, and α-methylstyrene-hydroxystyrene copolymers.

The novolak resins can be obtained by addition condensation to aldehydes with the prescribed monomers as main components in the presence of acid catalysts.

The weight average molecular weight of alkali-soluble resins is 2,000 or more, preferably from 5,000 to 200,000, and more preferably from 5,000 to 100,000.

Here, the weight average molecular weight is defined as the polystyrene equivalent by gel permeation chromatography.

Alkali-soluble resins (E) in the invention may be used in combination of two kinds or more.

The use amount of alkali-soluble resins is from 40 to 97 mass % based on the total solids content of the photosensitive composition, and preferably from 60 to 90 mass %.

[6] (F) An acid crosslinking agent capable of crosslinking with the alkali-soluble resin by the action of an acid (hereinafter also referred to as "component (F)" or "a crosslinking agent"):

A crosslinking agent is used in the negative photosensitive composition of the invention.

Every compound capable of crosslinking the resins soluble in an alkali developing solution by the action of an acid can be used as crosslinking agents, but the following (1) to (3) are preferably used.

(1) Hydroxymethyl body, alkoxymethyl body and acyloxymethyl body of phenol derivatives (2) Compounds having an N-hydroxymethyl group, an N-alkoxy-methyl group or an N-acyloxymethyl group (3) Compounds having an epoxy group As the alkoxymethyl groups, those having 6 or less carbon atoms, and as the acyloxymethyl groups, those having 6 or less carbon atoms are preferred.

Of these crosslinking agents, particularly preferred compounds are shown below.

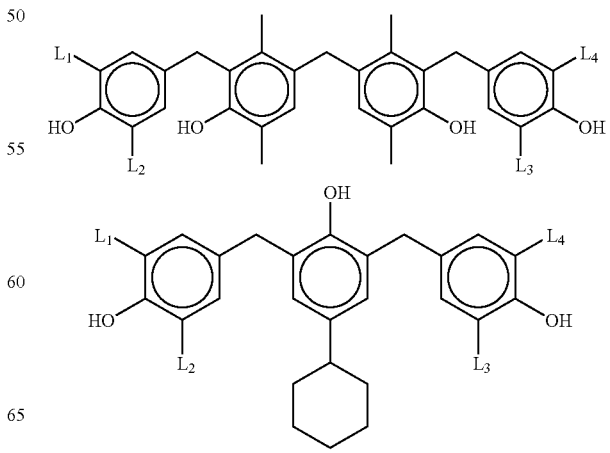

-continued

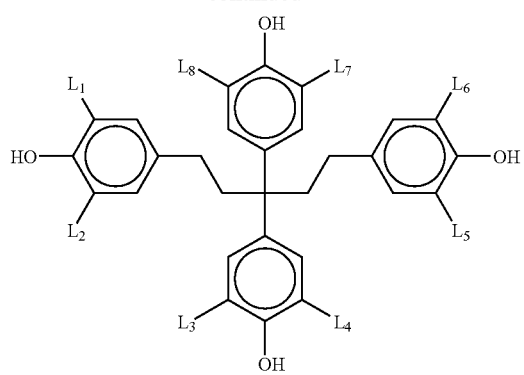
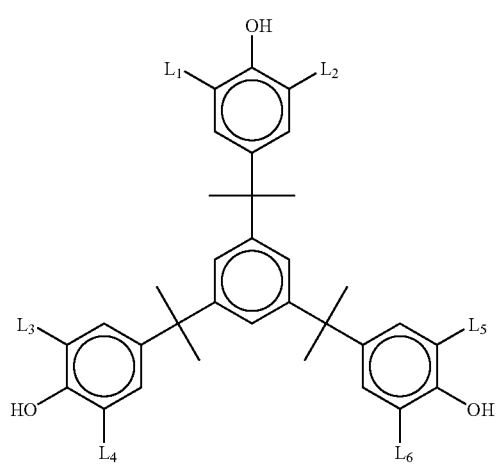
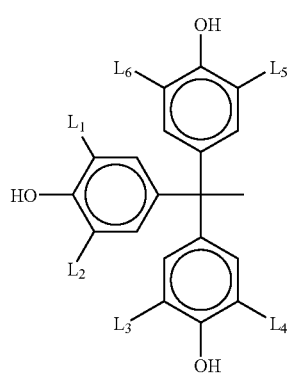
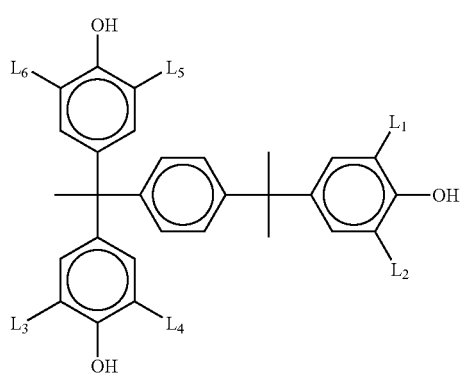

-continued

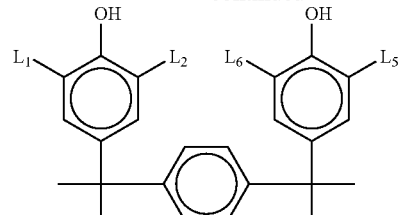
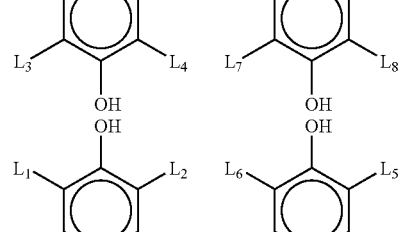
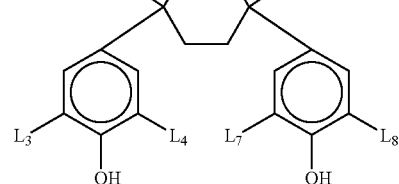
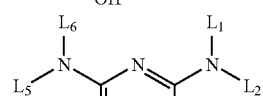
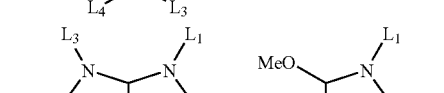
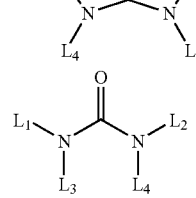
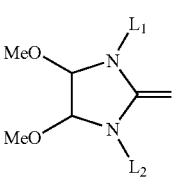
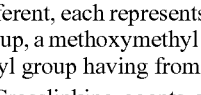

In the above formulae, $L_1$ to $L_8$, which may be the same or different, each represents a hydrogen atom, a hydroxymethyl group, a methoxymethyl group, an ethoxymethyl group, or an alkyl group having from 1 to 6 carbon atoms.

Crosslinking agents are used generally in proportion of from 3 to 70 mass % in the solids content of the photosensitive composition, and preferably from 5 to 50 mass %.

Other Components:

[7] (G) A basic compound

For decreasing the fluctuation of performances during the period of time from exposure to heating, it is preferred for the photosensitive composition of the invention to contain (G) a basic compound.

As the preferred structures of basic compounds, the structures represented by any of the following formulae (A) to (E) can be exemplified.

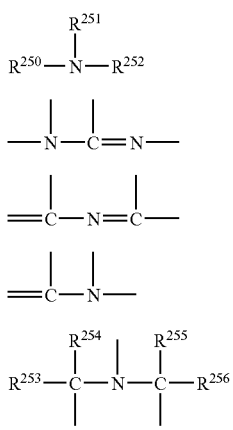

(A)

(B)

(C)

(D)

(E)

In formula (A), $R_{250}$, $R_{251}$ and $R_{252}$ each represents a hydrogen atom, an alkyl group having from 1 to 20 carbon atoms, a cycloalkyl group having from 3 to 20 carbon atoms, or an aryl group having from 6 to 20 carbon atoms, and $R_{250}$ and $R_{251}$ may be bonded to each other to form a ring. These groups may have a substituent, and as the alkyl group and cycloalkyl group having a substituent, an aminoalkyl group having from 1 to 20 carbon atoms or an aminocycloalkyl group having from 3 to 20 carbon atoms, a hydroxyalkyl group having from 1 to 20 carbon atoms or a hydroxycycloalkyl group having from 3 to 20 carbon atoms are preferred.

These groups may contain an oxygen atom, a sulfur atom or a nitrogen atom in the alkyl chain.

In formula (E), $R_{253}$, $R_{254}$, $R_{255}$ and $R_{256}$ each represents an alkyl group having from 1 to 6 carbon atoms, or a cycloalkyl group having from 3 to 6 carbon atoms.

As the preferred examples of basic compounds, guanidine, aminopyrrolidine, pyrazole, pyrazoline, piperazine, aminomorpholine, aminoalkylmorpholine, and piperidine can be exemplified, and these compounds may have a substituent. As further preferred compounds, compounds having an imidazole structure, a diazabicyclo structure, an onium hydroxide structure, an onium carboxylate structure, a trialkylamine structure, an aniline structure, or a pyridine structure, alkylamine derivatives having a hydroxyl group and/or an ether bond, and aniline derivatives having a hydroxyl group and/or an ether bond can be exemplified.

As the compounds having an imidazole structure, imidazole, 2,4,5-triphenylimidazole, and benzimidazole can be exemplified. As the compounds having a diazabicyclo structure, 1,4-diazabicyclo[2.2.2]octane, 1,5-diazabicyclo[4.3.0] non-5-ane, and 1,8-diazabicyclo[5.4.0]undeca-7-ene can be exemplified. As the compounds having an onium hydroxide structure, triarylsulfonium hydroxide, phenacylsulfonium hydroxide, sulfonium hydroxide having a 2-oxoalkyl group, specifically triphenylsulfonium hydroxide, tris(t-butyl-phenyl)sulfonium hydroxide, bis(t-butylphenyl)iodonium hydroxide, phenacylthiophenium hydroxide, and 2-oxopropyl-thiophenium hydroxide can be exemplified. The compounds having an onium carboxylate structure are compounds having an onium hydroxide structure in which the anionic part is carboxylated, e.g., acetate, adamantane-1-carboxylate, and perfluoroalkyl carboxylate are exemplified. As the compounds having a trialkylamine structure, tri(n-butyl) amine and tri(n-octyl)amine can be exemplified. As the aniline compounds, 2,6-diisopropylaniline and N,N-dimethylaniline can be exemplified. As the alkylamine derivatives having a hydroxyl group and/or an ether bond, ethanolamine, diethanol-amine, triethanolamine, and tris (methoxyethoxyethyl)amine can be exemplified. As the aniline derivatives having a hydroxyl group and/or an ether bond, N,N-bis(hydroxyethyl)-aniline can be exemplified.

These basic compounds are used alone or in combination of two or more. However, when the use amount of component (B) is 0.05 mass % or more, a basic compound may not be used. When a basic compound is used, the use amount of the basic compound is generally from 0.001 to 10 mass % based on the solids content of the photosensitive composition, and preferably from 0.01 to 5 mass %. For obtaining a sufficient addition effect, the addition amount is preferably 0.001 mass % or more, and in view of sensitivity and the developability of a non-exposed area, the addition amount is preferably 10 mass % or less.

[8] (J) Low molecular compound containing a nitrogen atom and having a group capable of leaving by the action of an acid The composition of the present invention may contain a low molecular compound containing a nitrogen atom and having a group capable of leaving by the action of an acid (hereinafter, sometimes referred to as a "low molecular compound (J)" or a "component (J)").

The group capable of leaving by the action of an acid is not particularly limited but is preferably an acetal group, a carbonate group, a carbamate group, a tertiary ester group, a tertiary hydroxyl group or a hemiaminal ether group, more preferably a carbamate group or a hemiaminal ether group.

The molecular weight of the low molecular compound (J) having a group capable of leaving by the action of an acid is preferably from 100 to 1,000, more preferably from 100 to 700, still more preferably from 100 to 500.

The compound (J) is preferably an amine derivative having on the nitrogen atom a group capable of leaving by the action of an acid.

The component (J) may have a protective group-containing carbamate group on the nitrogen atom. The protective group constituting the carbamate group can be represented by the following formula (J-1):

(J-1)

In formula (J-1), each R' independently represents a hydrogen atom, a linear or branched alkyl group, a cycloalkyl group, an aryl group, an aralkyl group or an alkoxyalkyl group. Each R' may combine with every other R' to form a ring.

R' is preferably a linear or branched alkyl group, a cycloalkyl group or an aryl group, more preferably a linear or branched alkyl group or a cycloalkyl group.

Specific structures of the group are set forth below.

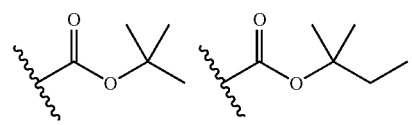

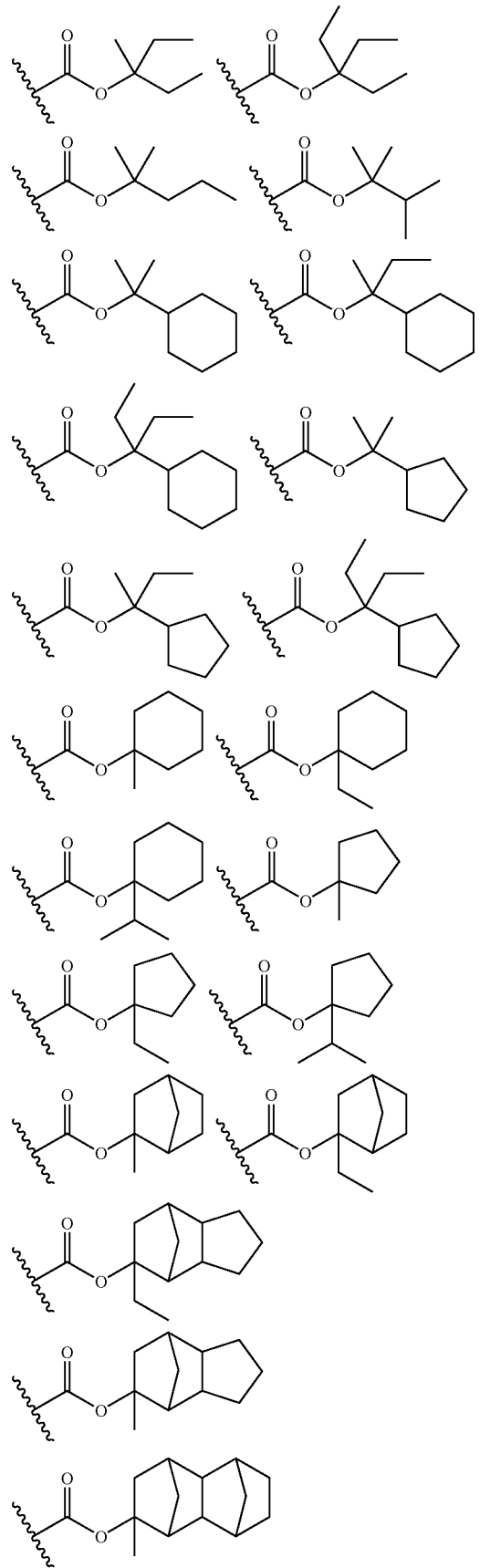
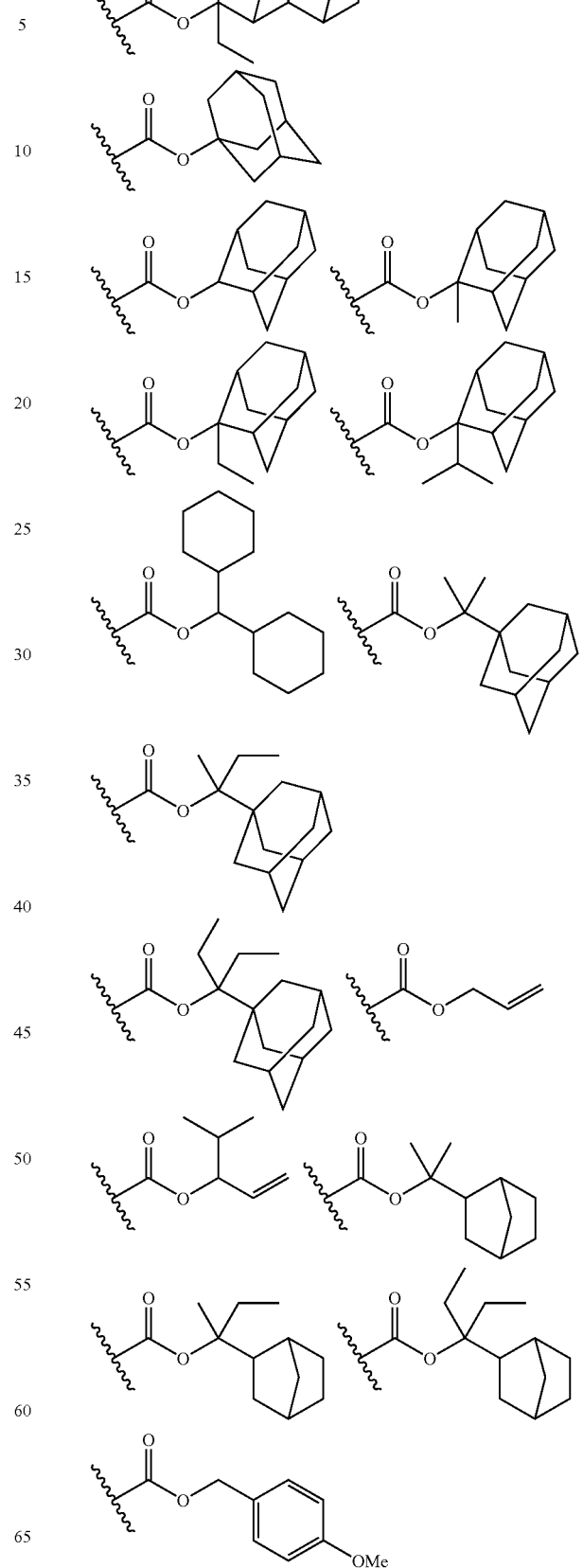

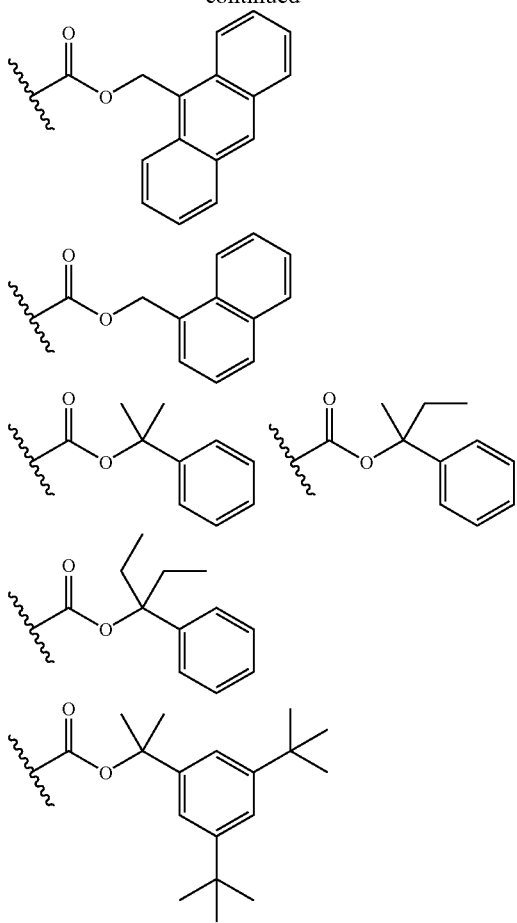

The compound (J) may also be composed by arbitrarily combining the later-described basic compound and the structure represented by formula (J-1).

The compound (J) is more preferably a compound having a structure represented by the following formula (A).

Incidentally, the compound (J) may be a compound corresponding to the above-described basic compound as long as it is a low molecular compound having a group capable of leaving by the action of an acid.

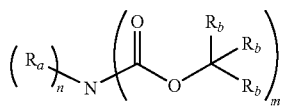

(A)

In formula (A), Ra represents a hydrogen atom, an alkyl group, a cycloalkyl group, an aryl group or an aralkyl group. Also, when n=2, two Ra's may be the same or different, and two Ra's may combine with each other to form a divalent heterocyclic hydrocarbon group (preferably having a carbon number of 20 or less) or a derivative thereof.

Each Rb independently represents a hydrogen atom, an alkyl group, a cycloalkyl group, an aryl group, an aralkyl group or an alkoxyalkyl group, provided that in —C(Rb)(Rb)(Rb), when one or more Rb's are a hydrogen atom, at least one of remaining Rb's is a cyclopropyl group, a 1-alkoxyalkyl group or an aryl group.

At least two Rb's may combine to form an alicyclic hydrocarbon group, an aromatic hydrocarbon group, a heterocyclic hydrocarbon group or a derivative thereof.

n represents an integer of 0 to 2, m represents an integer of 1 to 3, and n+m=3.

In formula (A), each of the alkyl group, cycloalkyl group, aryl group and aralkyl group of Ra and Rb may be substitute with a functional group such as hydroxyl group, cyano group, amino group, pyrrolidino group, piperidino group, morpholino group and oxo group, an alkoxy group or a halogen atom. The same applies to the alkoxyalkyl group of Rb.

Examples of the alkyl group, cycloalkyl group, aryl group and aralkyl group (each of these alkyl, cycloalkyl, aryl and aralkyl groups may be substituted with the above-described functional group, an alkoxy group or a halogen atom) of Ra and/or Rb include:

a group derived from a linear or branched alkane such as methane, ethane, propane, butane, pentane, hexane, heptane, octane, nonane, decane, undecane and dodecane, and a group where the group derived from an alkane is substituted with one or more in kind or number of cycloalkyl groups such as cyclobutyl group, cyclopentyl group and cyclohexyl group;

a group derived from a cycloalkane such as cyclobutane, cyclopentane, cyclohexane, cycloheptane, cyclooctane, norbornane, adamantane and noradamantane, and a group where the group derived from a cycloalkane is substituted with one or more in kind or number of linear or branched alkyl groups such as methyl group, ethyl group, n-propyl group, i-propyl group, n-butyl group, 2-methylpropyl group, 1-methylpropyl group and tert-butyl group;

a group derived from an aromatic compound such as benzene, naphthalene and anthracene, and a group where the group derived from an aromatic compound is substituted with one or more in kind or number of linear or branched alkyl groups such as methyl group, ethyl group, n-propyl group, i-propyl group, n-butyl group, 2-methylpropyl group, 1-methylpropyl group and tert-butyl group;

a group derived from a heterocyclic compound such as pyrrolidine, piperidine, morpholine, tetrahydrofuran, tetrahydropyran, indole, indoline, quinoline, perhydroquinoline, indazole and benzimidazole, and a group where the group derived from a heterocyclic compound is substituted with one or more in kind or number of linear or branched alkyl groups and aromatic compound-derived groups; a group where the group derived from a linear or branched alkane or the group derived from a cycloalkane is substituted with one or more in kind or number of aromatic compound-derived groups such as phenyl group, naphthyl group and anthracenyl group; and a group where the substituent above is substituted with a functional group such as hydroxyl group, cyano group, amino group, pyrrolidino group, piperidino group, morpholino group and oxo group.

Examples of the divalent heterocyclic hydrocarbon group (preferably having a carbon number of 1 to 20) formed by combining Ra's with each other or a derivative thereof include a group derived from a heterocyclic compound such as pyrrolidine, piperidine, morpholine, 1,4,5,6-tetrahydropyrimidine, 1,2,3,4-tetrahydro quinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted with one or more in kind or number of linear or branched alkane-derived groups, cycloalkane-derived groups, aromatic compound-derived groups, heterocyclic compound-derived groups and functional groups such as hydroxyl group, cyano group, amino group, pyrrolidino group, piperidino group, morpholino group and oxo group.

Specific examples of the compound (J) particularly preferred in the present invention are set forth below, but the present invention is not limited thereto.

(D-1)
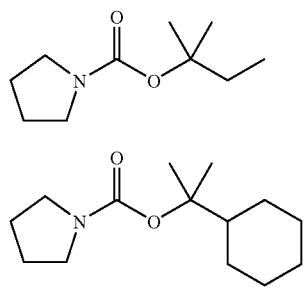

(D-2)
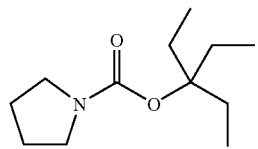

(D-3)
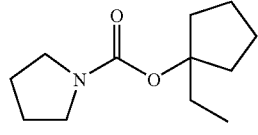

(D-4)
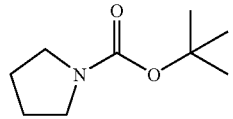

(D-5)
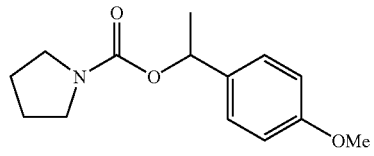

(D-6)
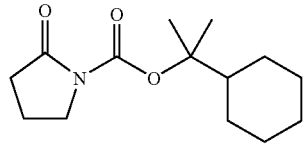

(D-7)
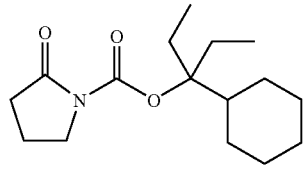

(D-8)
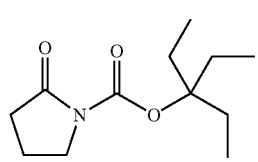

(D-9)

(D-10)
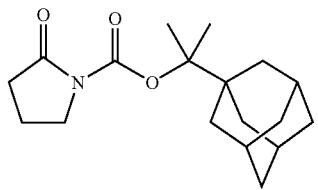

(D-11)
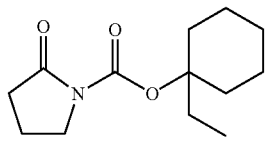

(D-12)
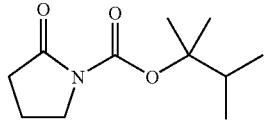

(D-13)
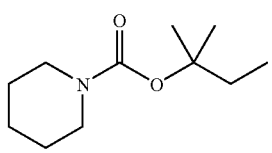

(D-14)
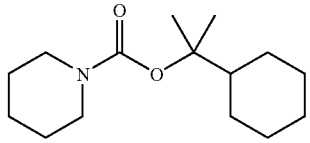

(D-15)
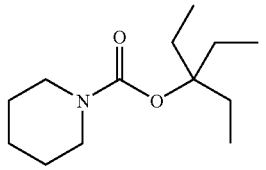

(D-16)
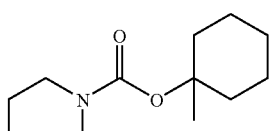

(D-17)
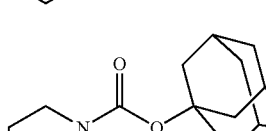
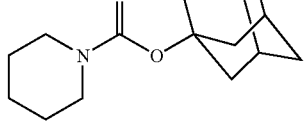

(D-18)
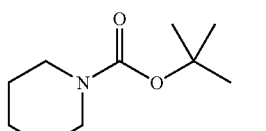

(D-19)
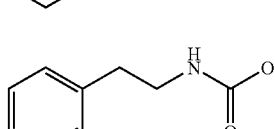

(D-20)
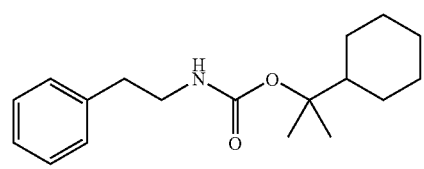
(D-21)
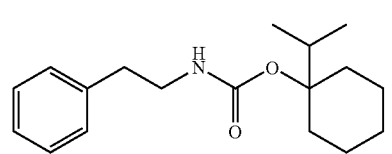
(D-22)
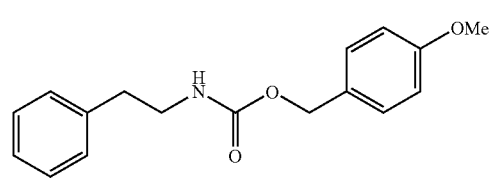
(D-23)
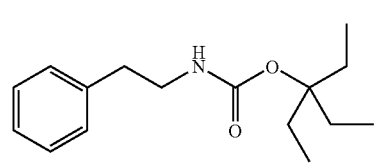
(D-24)
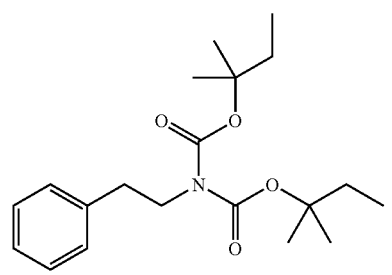
(D-25)
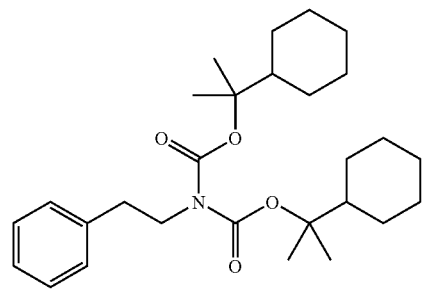
(D-26)
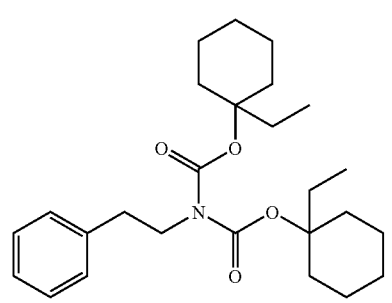
(D-27)
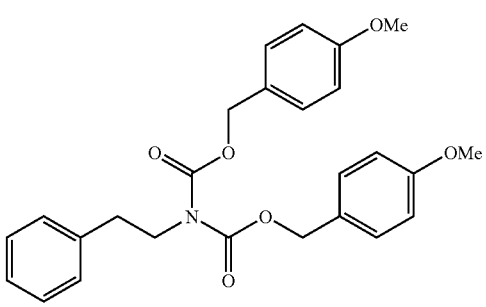
(D-28)
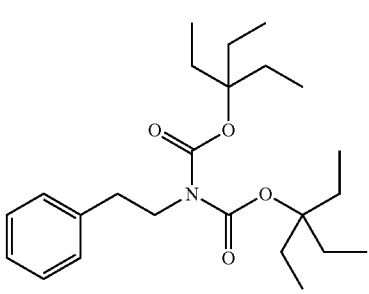
(D-29)
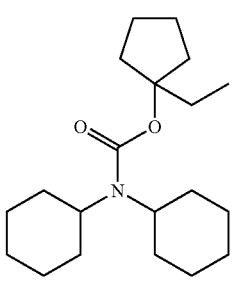
(D-30)
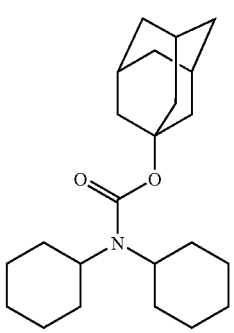
(D-31)
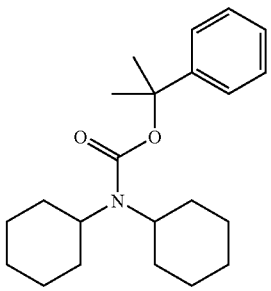

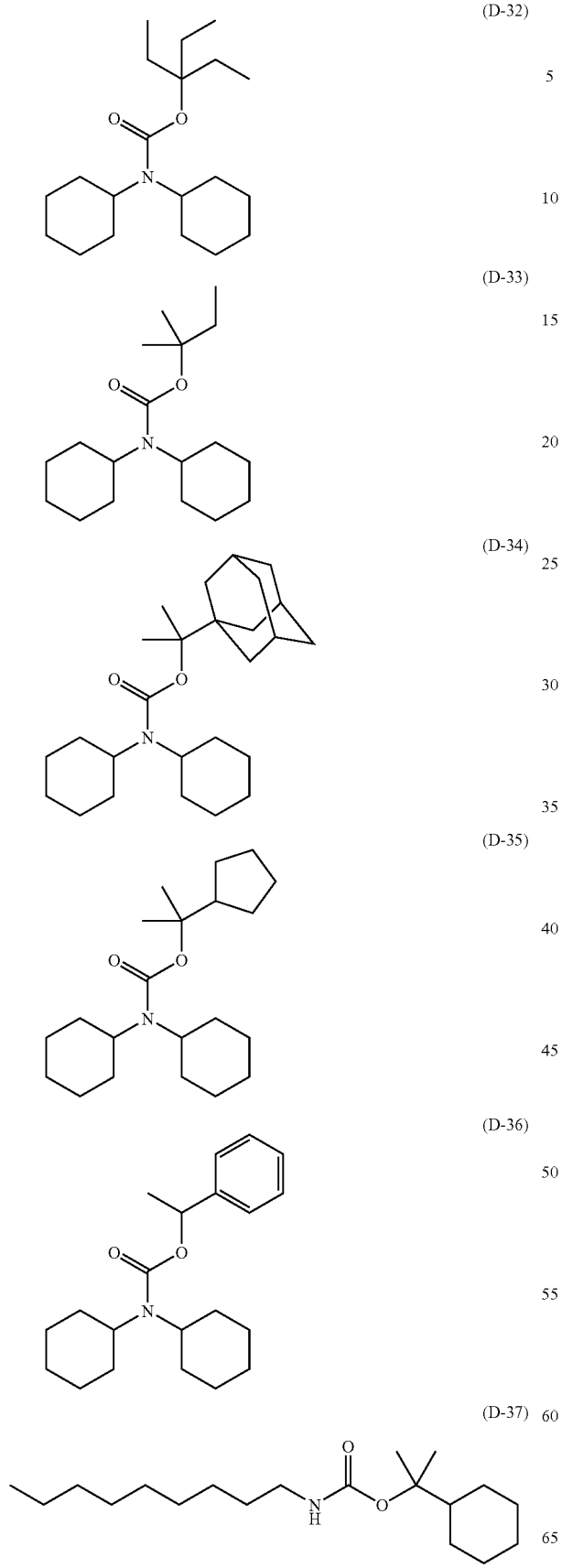

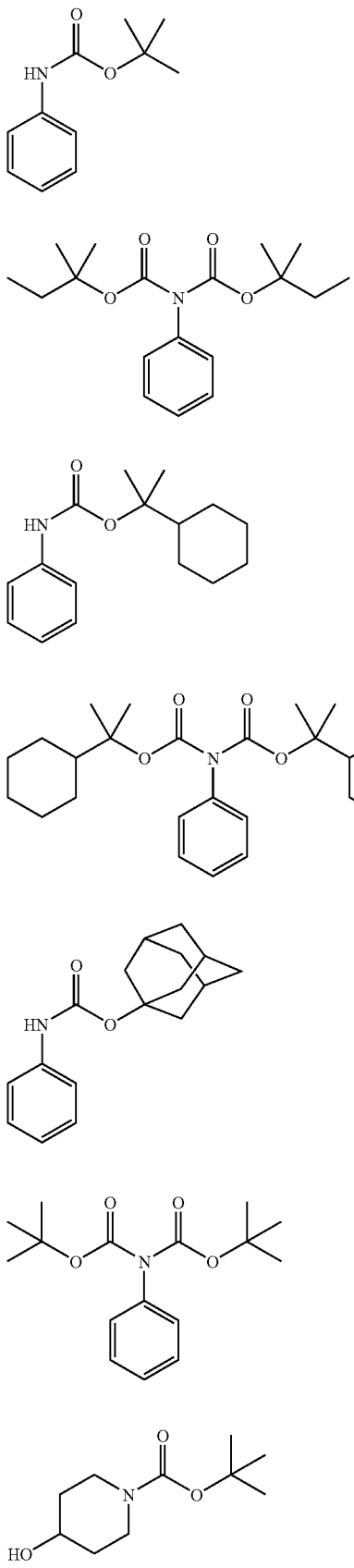

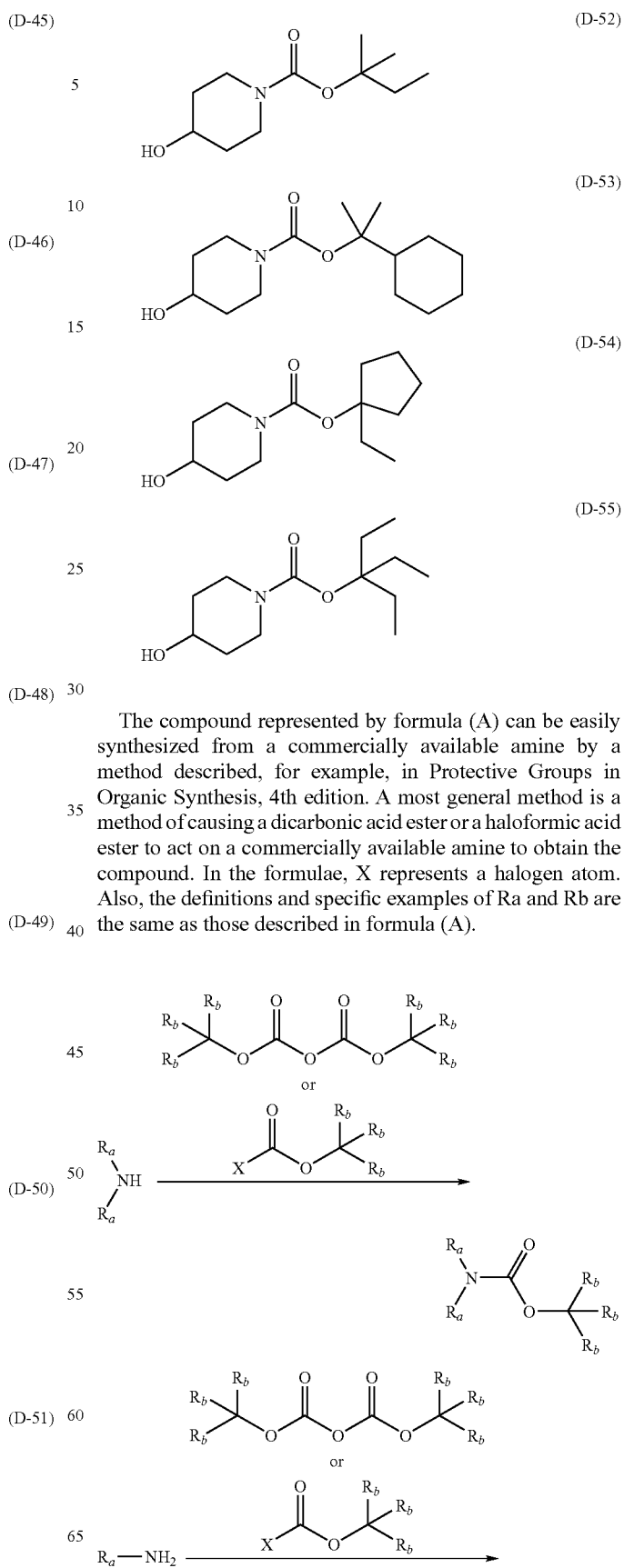

The compound represented by formula (A) can be easily synthesized from a commercially available amine by a method described, for example, in Protective Groups in Organic Synthesis, 4th edition. A most general method is a method of causing a dicarbonic acid ester or a haloformic acid ester to act on a commercially available amine to obtain the compound. In the formulae, X represents a halogen atom. Also, the definitions and specific examples of $R_a$ and $R_b$ are the same as those described in formula (A).

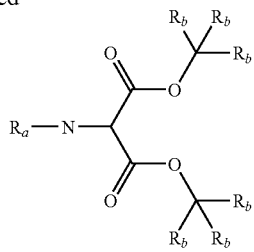

In the present invention, one kind of (J) a low molecular compound containing a nitrogen atom and having a group capable of leaving by the action of an acid may be used alone, or two or more kinds of the compounds may be mixed and used.

The composition of the present invention may not contain (J) a low molecular compound containing a nitrogen atom and having a group capable of leaving by the action of an acid, but in the case of containing the low molecular compound, the content of the compound (J) is usually from 0.001 to 20 mass %, preferably from 0.001 to 10 mass %, more preferably from 0.01 to 5 mass %, based on the entire solid compound of the composition combined with the basic compound described later.

The ratio between the acid generator and the compound (J), which are used in the composition, is preferably acid generator/[compound (J)+above-described basic compound] (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure until heat treatment. The acid generator/[compound (J)+above-described basic compound] (by mol) is more preferably from 5.0 to 200, still more preferably from 7.0 to 150.

[9] (H) Surfactant:

It is preferred for the photosensitive composition in the invention to further contain a surfactant, and it is more preferred to contain either one, or two or more, of fluorine and/or silicon surfactants (a fluorine surfactant, a silicon surfactant, a surfactant containing both a fluorine atom and a silicon atom).

By containing a surfactant, it becomes possible for the photosensitive composition in the invention to provide a resist pattern excellent in sensitivity and resolution, and low in defects in adhesion and development in using an exposure light source of 250 nm or lower, in particular, 220 nm or lower.

These fluorine and/or silicon surfactants are disclosed, e.g., in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862, U.S. Pat. Nos. 5,405,720, 5,360,692, 5,529,881, 5,296,330, 5,436,098, 5,576,143, 5,294,511 and 5,824,451. The commercially available surfactants shown below can also be used as they are.

As the commercially available fluorine or silicon surfactants usable in the invention, e.g., Eftop EF301 and EF303 (manufactured by Shin-Akita Kasei Co., Ltd.), Fluorad FC 430, 431 and 4430 (manufactured by Sumitomo 3M Limited), Megafac F171, F173, F176, F189, F113, F110, F177, F120, and R08 (manufactured by Dainippon Ink and Chemicals Inc.), Sarfron S-382, SC 101, 102, 103, 104, 105 and 106 (manufactured by ASAHI GLASS CO., LTD.), Troy Sol S-366 (manufactured by Troy Chemical Co., Ltd.), GF-300 and GF-150 (manufactured by TOAGOSEI CO., LTD.), Sarfron S-393 (manufactured by SEIMI CHEMICAL CO., LTD.), Eftop EF121, EF122A, EF122B, RF122C, EF125M, EF135M, EF351, 352, EF801, EF802, and EF601 (manufactured by JEMCO INC.), PF636, PF656, PF6320 and PF6520 (manufactured by OMNOVA), and FTX-204D, 2086, 218G, 230G, 204D, 208D, 212D, 218, and 222D (manufactured by NEOS) are exemplified. In addition, polysiloxane polymer KP-341 (manufactured by Shin-Etsu Chemical Co., Ltd.) can also be used as a silicon surfactant.

In addition to these known surfactants as exemplified above, surfactants using polymers having fluoro-aliphatic groups derived from fluoro-aliphatic compounds manufactured by a telomerization method (also called a telomer method) or an oligomerization method (also called an oligomer method) can be used. The fluoro-aliphatic compounds can be synthesized by the method disclosed in JP-A-2002-90991.

As the polymers having fluoro-aliphatic groups, copolymers of monomers having fluoro-aliphatic groups and (poly(oxyalkylene)) acrylate and/or (poly(oxyalkylene)) methacrylate are preferred, and they may be distributed at random or block copolymerized. As the poly(oxyalkylene) groups, a poly(oxyethylene) group, a poly(oxypropylene) group, and a poly(oxybutylene) group are exemplified. Further, the polymers may be units having alkylenes different in chain length in the same chain length, such as a block combination of poly(oxyethylene and oxypropylene and oxyethylene), and a block combination of poly(oxyethylene and oxypropylene). In addition, copolymers of monomers having fluoro-aliphatic groups and poly(oxyalkylene) acrylate (or methacrylate) may be not only bipolymers but also terpolymers or higher polymers obtained by copolymerization of monomers having different two or more kinds of fluoro-aliphatic groups or different two or more kinds of poly(oxyalkylene) acrylates (or methacrylates) at the same time.

For example, as commercially available surfactants, Megafac F178, F470, F473, F475, F476 and F472 (manufactured by Dainippon Ink and Chemicals Inc.) can be exemplified. Further, copolymers of acrylate (or methacrylate) having a $C_6F_{13}$ group and poly(oxyalkylene) acrylate (or methacrylate), and copolymers of acrylate (or methacrylate) having a $C_3F_7$ group, poly(oxyethylene) acrylate (or methacrylate), and poly(oxy-propylene) acrylate (or methacrylate) are exemplified.

In the invention, surfactants other than fluorine and/or silicon surfactants can also be used. Specifically, nonionic surfactants, such as polyoxyethylene alkyl ethers, e.g., polyoxyethylene lauryl ether, polyoxyethylene stearyl ether, polyoxyethylene cetyl ether, polyoxyethylene oleyl ether, etc., polyoxyethylene alkylallyl ether, e.g., polyoxyethylene octylphenol ether, polyoxyethylene nonylphenol ether, etc., polyoxyethylene-polyoxypropylene block copolymers, sorbitan fatty acid esters, e.g., sorbitan monolaurate, sorbitan monopalmitate, sorbitan monostearate, sorbitan monooleate, sorbitan trioleate, sorbitan tristearate, etc., and polyoxyethylene sorbitan fatty acid esters, e.g., polyoxy-ethylene sorbitan monolaurate, polyoxyethylene sorbitan monopalmitate, polyoxyethylene sorbitan monostearate, polyoxyethylene sorbitan trioleate, polyoxyethylene sorbitan tristearate, etc., can be exemplified.

These surfactants may be used alone or may be used in combination of some kinds.

The use amount of surfactants is preferably in proportion of from 0.01 to 10 mass % to the total amount of the positive resist composition (excluding solvents), and more preferably from 0.1 to 5 mass %.

[10] (I) Organic solvent:

The above components of the photosensitive composition of the invention are dissolved in a prescribed organic solvent.

As the organic solvents usable in the invention, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran are exemplified.

(Ia) Ketone Solvents:

Solvents containing at least a ketone structure are preferably used in the invention.

As the solvents containing a ketone structure, chain-like ketone solvents and cyclic ketone solvents are exemplified, and those having from 5 to 8 carbon atoms are preferred for capable of obtaining good coating property.

As the chain-like ketone solvents, e.g., 2-heptanone, methyl ethyl ketone, methyl isobutyl ketone, etc., are exemplified, and 2-heptanone is preferred.

As the cyclic ketone solvents, e.g., cyclopentanone, 3-methyl-2-cyclopentanone, cyclohexanone, 2-methylcyclohexanone, 2,6-dimethylcyclohexanone, cycloheptanone, cyclooctanone, isophorone, etc., are exemplified, and cyclohexanone and cycloheptanone are preferred.

It is preferred that the solvents having a ketone structure are used alone, or as mixed solvents with other solvents. As the solvents to be mixed (combined use solvents), propylene glycol monoalkyl ether carboxylate, alkyl lactate, propylene glycol monoalkyl ether, alkyl alkoxypropionate, lactone compounds, etc., can be exemplified.

As the propylene glycol monoalkyl ether carboxylate, e.g., propylene glycol monomethyl ether acetate, propylene glycol monomethyl ether propionate, propylene glycol monoethyl ether acetate, etc., can be exemplified.

As the alkyl lactate, e.g., methyl lactate, ethyl lactate, etc., can be exemplified.

As the propylene glycol monoalkyl ether, e.g., propylene glycol monomethyl ether and propylene glycol monoethyl ether, etc., can be exemplified.

As the alkyl alkoxypropionate, e.g., methyl methoxy-propionate, ethyl methoxypropionate, methyl ethoxypropionate, ethyl ethoxypropionate, etc., can be exemplified.

As the lactone compounds, e.g., γ-butyrolactone, etc., can be exemplified.

As preferred combined use solvent, propylene glycol monoalkyl ether carboxylate, alkyl lactate and propylene glycol monoalkyl ether can be exemplified, and as more preferred combined use solvent, propylene glycol monomethyl ether acetate can be exemplified.

By the use of mixed solvents of ketone solvents and combined use solvents, substrate adhesion, developability and DOF are improved.

The ratio of the ketone solvent and the combined use solvent (mass ratio) is preferably from 10/90 to 95/5, more preferably from 20/80 to 80/20, and still more preferably from 30/70 to 70/30.

In view of heightening uniform film thickness and resistance to development failure, high boiling point solvents having a boiling point of 200° C. or higher, e.g., ethylene carbonate, propylene carbonate, etc., may be mixed.

The addition amount of these high boiling point solvents is generally from 0.1 to 15 mass % in all the solvents, preferably from 0.5 to 10 mass %, and more preferably from 1 to 5 mass %.

In the invention, a photosensitive composition having solids content concentration of generally from 3 to 25 mass %, preferably from 5 to 22 mass %, and more preferably from to 15 mass % is prepared with a single solvent, preferably two or more solvents.

[11] Hydrophobic Resin (HR)

The actinic ray-sensitive or radiation-sensitive resin composition (also called as photosensitive composition) of the present invention, particularly when applied to immersion exposure, may contain a hydrophobic resin having at least either a fluorine atom or a silicon atom (hereinafter referred to as a "hydrophobic resin (HR)" or simply as a "resin (HR)"). The hydrophobic resin (HR) is unevenly distributed to the surface layer of the film and when the immersion medium is water, can enhance the static/dynamic contact angle on the resist film surface for water as well as the followability of the immersion liquid.

The hydrophobic resin (HR) is, as described above, unevenly distributed to the interface but unlike a surfactant, need not have necessarily a hydrophilic group in the molecule and may not contribute to uniform mixing of polar/nonpolar substances.

The hydrophobic resin typically contains a fluorine atom and/or a silicon atom. The fluorine atom and/or silicon atom in the hydrophobic resin (HR) may be contained in the main chain of the resin or may be contained in the side chain.

In the case of containing a fluorine atom, the hydrophobic resin (HR) is preferably a resin having a fluorine atom-containing alkyl group, a fluorine atom-containing cycloalkyl group or a fluorine atom-containing aryl group, as a fluorine atom-containing partial structure.

The fluorine atom-containing alkyl group (preferably having a carbon number of 1 to 10, more preferably from 1 to 4) is a linear or branched alkyl group with at least one hydrogen atom being substituted for by a fluorine atom and may further have a substituent other than a fluorine atom.

The fluorine atom-containing cycloalkyl group is a monocyclic or polycyclic cycloalkyl group with at least one hydrogen atom being substituted for by a fluorine atom and may further have a substituent other than a fluorine atom.

The fluorine atom-containing aryl group is an aryl group (e.g., phenyl, naphthyl) with at least one hydrogen atom being substituted for by a fluorine atom and may further have a substituent other than a fluorine atom.

Preferred examples of the fluorine atom-containing alkyl group, fluorine atom-containing cycloalkyl group and fluorine atom-containing aryl group include groups represented by the following formulae (F2) to (F4), but the present invention is not limited thereto.

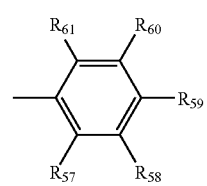

(F2)

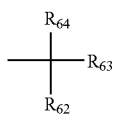

(F3)

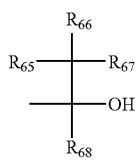

(F4)

In formulae (F2) to (F4), each of $R_{57}$ to $R_{68}$ independently represents a hydrogen atom, a fluorine atom or a (linear or branched) alkyl group, provided that at least one of $R_{57}$ to $R_{61}$, at least one of $R_{62}$ to $R_{64}$ and at least one of $R_{65}$ to $R_{68}$ are independently a fluorine atom or an alkyl group (preferably having a carbon number of 1 to 4) with at least one hydrogen atom being substituted for by a fluorine atom.

It is preferred that all of $R_{57}$ to $R_{61}$ and $R_{65}$ to $R_{67}$ are a fluorine atom. Each of $R_{62}$, $R_{63}$ and $R_{68}$ is preferably an alkyl group (preferably having a carbon number of 1 to 4) with at least one hydrogen atom being substituted for by a fluorine atom, more preferably a perfluoroalkyl group having a carbon number of 1 to 4. $R_{62}$ and $R_{63}$ may combine together to form a ring.

Specific examples of the group represented by formula (F2) include p-fluorophenyl group, pentafluorophenyl group and 3,5-di(trifluoromethyl)phenyl group.

Specific examples of the group represented by formula (F3) include trifluoromethyl group, pentafluoropropyl group, pentafluoroethyl group, heptafluorobutyl group, hexafluoroisopropyl group, heptafluoroisopropyl group, hexafluoro(2-methyl)isopropyl group, nonafluorobutyl group, octafluoroisobutyl group, nonafluorohexyl group, nonafluoro-tert-butyl group, perfluoroisopentyl group, perfluorooctyl group, perfluoro(trimethyl)hexyl group, 2,2,3,3-tetrafluorocyclobutyl group and perfluorocyclohexyl group. Among these, hexafluoroisopropyl group, heptafluoroisopropyl group, hexafluoro(2-methyl)isopropyl group, octafluoroisobutyl group, nonafluoro-tert-butyl group and perfluoroisopentyl group are preferred, and hexafluoroisopropyl group and heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

The fluorine atom-containing partial structure may be directly bonded to the main chain or may be bonded to the main chain through a group selected from the group consisting of an alkylene group, a phenylene group, an ether bond, a thioether bond, a carbonyl group, an ester bond, an amide bond, a urethane bond and a ureylene bond, or a group composed of a combination of two or more thereof.

As for the repeating unit having a fluorine atom, those shown below are preferred.

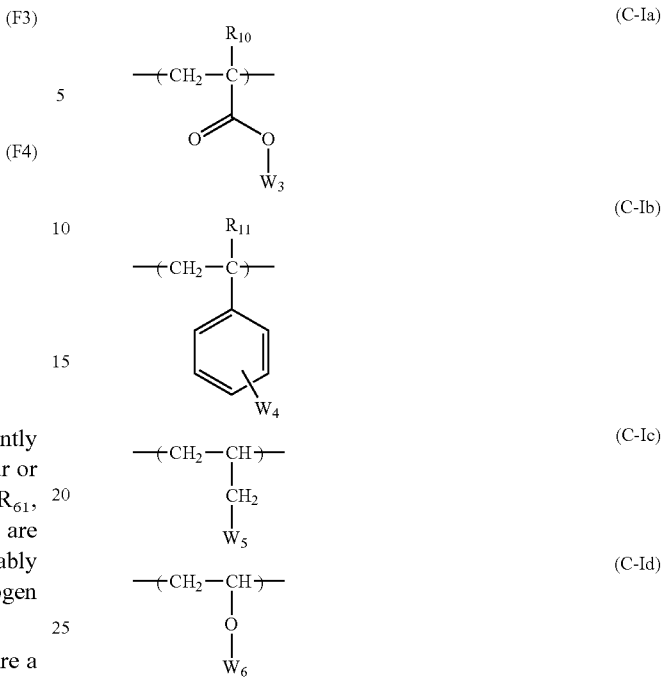

In the formulae, each of $R_{10}$ and $R_{11}$ independently represents a hydrogen atom, a fluorine atom or an alkyl group. The alkyl group is preferably a linear or branched alkyl group having a carbon number of 1 to 4 and may have a substituent, and the alkyl group having a substituent includes, in particular, a fluorinated alkyl group.

Each of $W_3$ to $W_6$ independently represents an organic group having at least one or more fluorine atoms. Specific examples thereof include the atomic groups of (F2) to (F4).

Other than these, the hydrophobic resin (HR) may contain a unit shown below, as the repeating unit having a fluorine atom.

In the formulae, each of $R_4$ to $R_7$ independently represents a hydrogen atom, a fluorine atom or an alkyl group. The alkyl group is preferably a linear or branched alkyl group having a carbon number of 1 to 4 and may have a substituent, and the alkyl group having a substituent includes, in particular, a fluorinated alkyl group.

However, at least one of $R_4$ to $R_7$ represents a fluorine atom. $R_4$ and $R_5$, or $R_6$ and $R_7$ may form a ring.

$W_2$ represents an organic group having at least one fluorine atom. Specific examples thereof include the atomic groups of (F2) to (F4).

$L_2$ represents a single bond or a divalent linking group. The divalent linking group is a substituted or unsubstituted arylene group, a substituted or unsubstituted alkylene group, a substituted or unsubstituted cycloalkylene group, —O—, —SO$_2$—, —CO—, —N(R)— (wherein R represents a hydrogen atom or an alkyl group), —NHSO$_2$—, or a divalent linking group formed by combining a plurality of these groups.

Q represents an alicyclic structure. The alicyclic structure may have a substituent, may be monocyclic or polycyclic, and in the case of polycyclic, may be crosslinked. The monocyclic structure is preferably a cycloalkyl group having a carbon number of 3 to 8, and examples thereof include a cyclopentyl group, a cyclohexyl group, a cyclobutyl group and a cyclooctyl group. Examples of the polycyclic structure include a group containing a bicyclo, tricyclo or tetracyclo structure having a carbon number of 5 or more. A cycloalkyl group having a carbon number of 6 to 20 is preferred, and examples thereof include an adamantyl group, a norbornyl group, a dicyclopentyl group, a tricyclodecanyl group and a tetracyclododecyl group. A part of carbon atoms in the cycloalkyl group may be substituted with a heteroatom such as oxygen atom. In particular, Q is preferably, for example, a norbornyl group, a tricyclodecanyl group, a tetracyclododecyl group, Specific examples of the repeating unit having a fluorine atom are set forth below, but the present invention is not limited thereto.

In specific examples, $X_1$ represents a hydrogen atom, —CH$_3$, —F or —CF$_3$. $X_2$ represents —F or —CF$_3$.

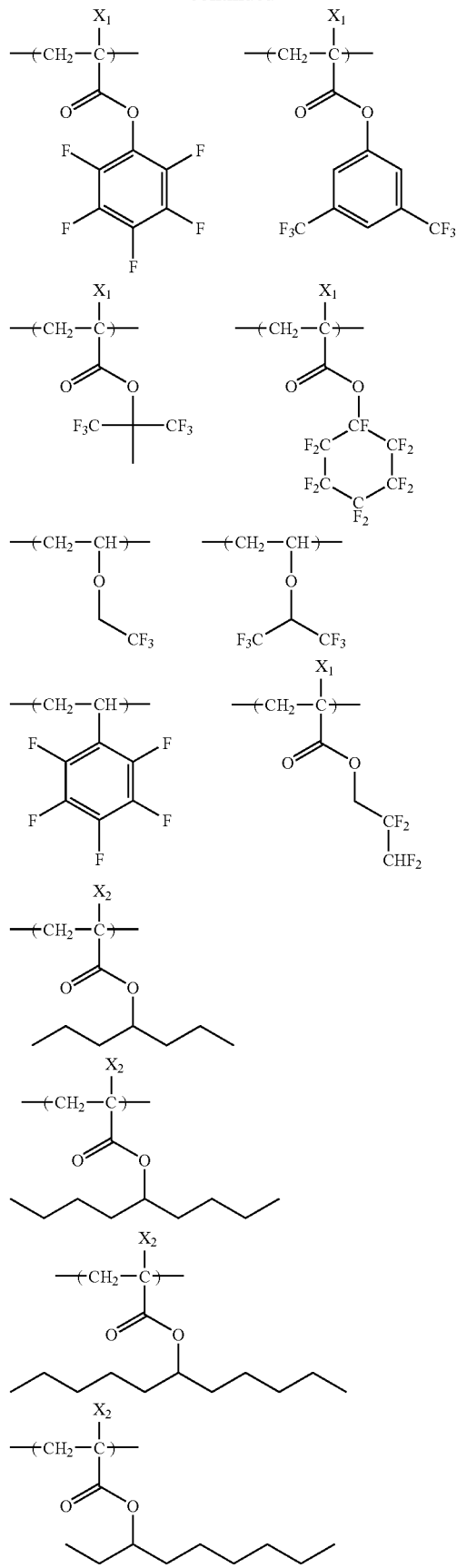

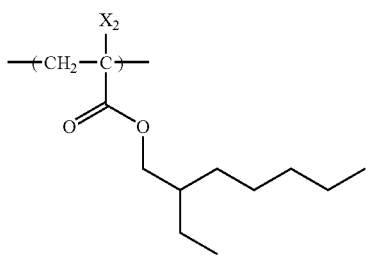
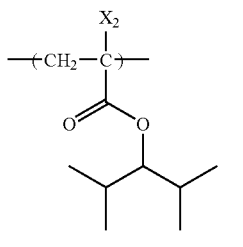
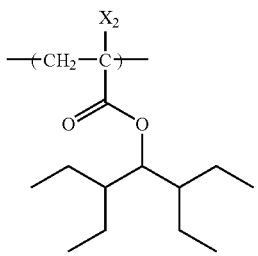
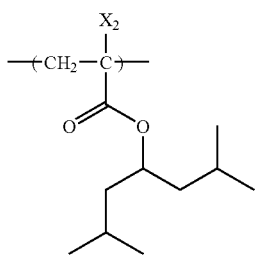
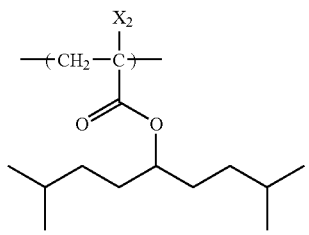
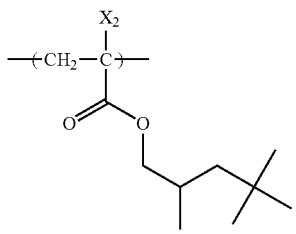
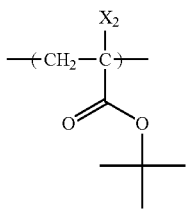
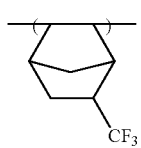
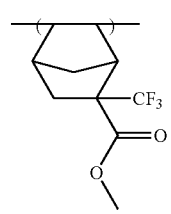
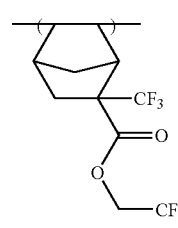

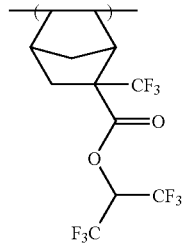

The hydrophobic resin (HR) may contain a silicon atom. The hydrophobic resin is preferably a resin having an alkylsilyl structure (preferably a trialkylsilyl group) or a cyclic siloxane structure, as a silicon atom-containing partial structure.

Specific examples of the alkylsilyl structure and cyclic siloxane structure include groups represented by the following formulae (CS-1) to (CS-3):

(CS-1)

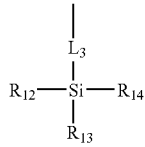

(CS-2)

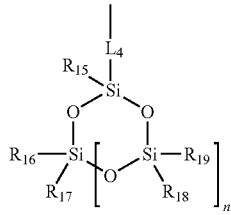

(CS-3)

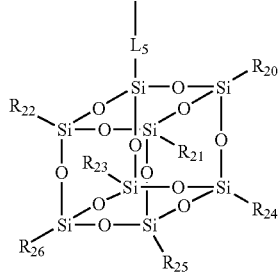

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. The divalent linking group is a sole group or a combination of two or more groups (preferably with a total carbon number of 12 or less) selected from the group consisting of an alkylene group, a phenylene group, an ether bond, a thioether bond, a carbonyl group, an ester bond, an amide bond, a urethane bond and a urea bond.

n represents an integer of 1 to 5. n is preferably an integer of 2 to 4.

Specific examples of the repeating unit having a group represented by formulae (CS-1) to (CS-3) are set forth below, but the present invention is not limited thereto. In specific examples, $X_1$ represents a hydrogen atom, —$CH_3$, —F or —$CF_3$.

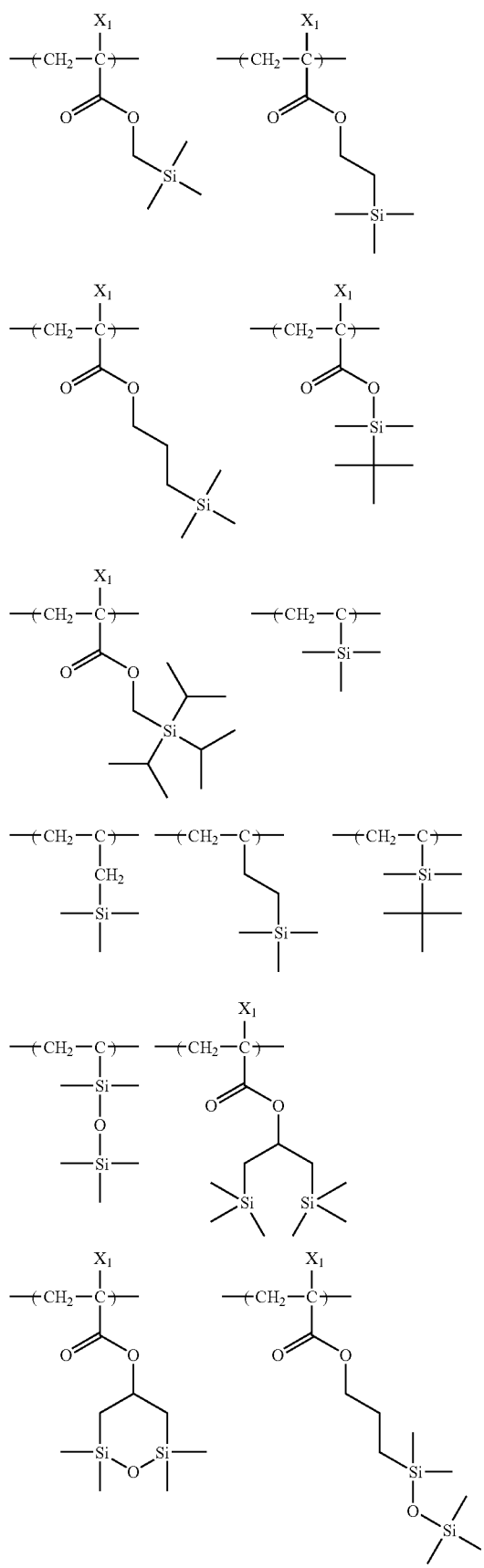

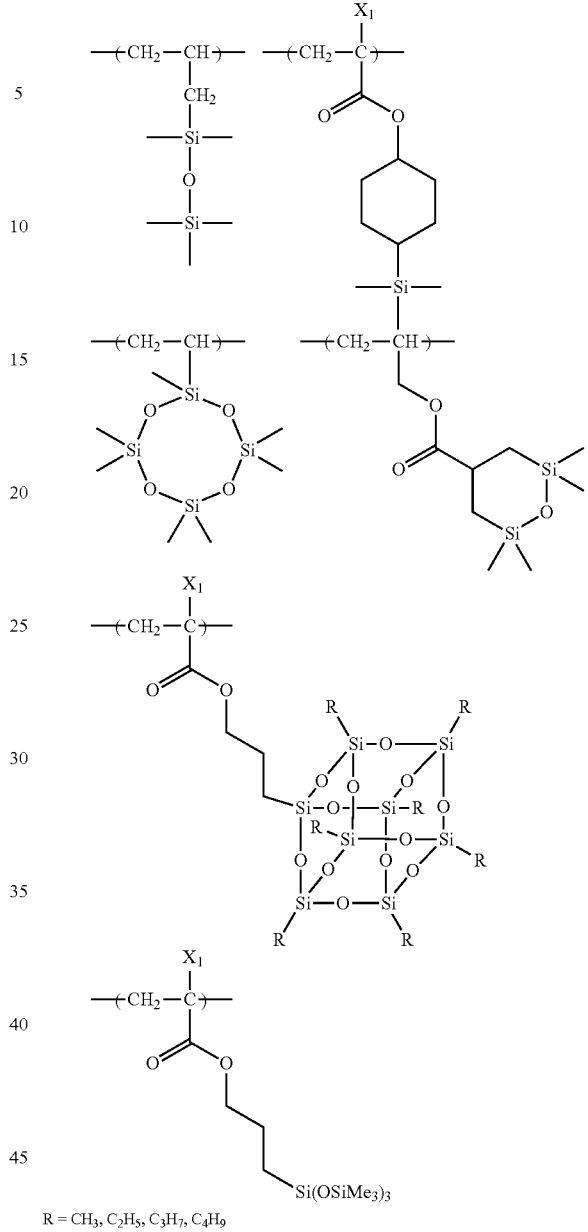

R = CH$_3$, C$_2$H$_5$, C$_3$H$_7$, C$_4$H$_9$

Furthermore, the hydrophobic resin (HR) may contain at least one group selected from the group consisting of the following (x) to (z):

(x) an alkali-soluble group, (y) a group capable of decomposing by the action of an alkali developing solution to increase the solubility in an alkali developing solution (hereinafter sometimes referred to as a "polarity converting group"), and (z) a group capable of decomposing by the action of an acid.

Examples of the alkali-soluble group (x) include a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkyl sulfonyl)imide group, a tris(alkylcarbonyl)methylene group and a tris(alkylsulfonyl)methylene group.

Preferred alkali-soluble groups are a fluorinated alcohol group (preferably hexafluoroisopropanol), a sulfonimide group and a bis(carbonyl)methylene group.

Examples of the repeating unit having (x) an alkali-soluble group include a repeating unit where an alkali-soluble group is directly bonded to the resin main chain, such as repeating unit by an acrylic acid or a methacrylic acid, and a repeating unit where an alkali-soluble group is bonded to the resin main chain through a linking group, and an alkali-soluble group may also be introduced into the polymer chain terminal by using an alkali-soluble group-containing polymerization initiator or chain transfer agent at the polymerization. All of these cases are preferred. The repeating unit having (x) an alkali-soluble group may contain at least either a fluorine atom or a silicon atom.

The content of the repeating unit having (x) an alkali-soluble group is preferably from 1 to 50 mol %, more preferably from 3 to 35 mol %, still more preferably from 5 to 20 mol %, based on all repeating units in the hydrophobic resin (HR).

Specific examples of the repeating unit having (x) an alkali-soluble group are set forth below, but the present invention is not limited thereto. In the formulae, $R^x$ represents hydrogen atom, $CH_3$, $CF_3$ or $CH_2OH$.

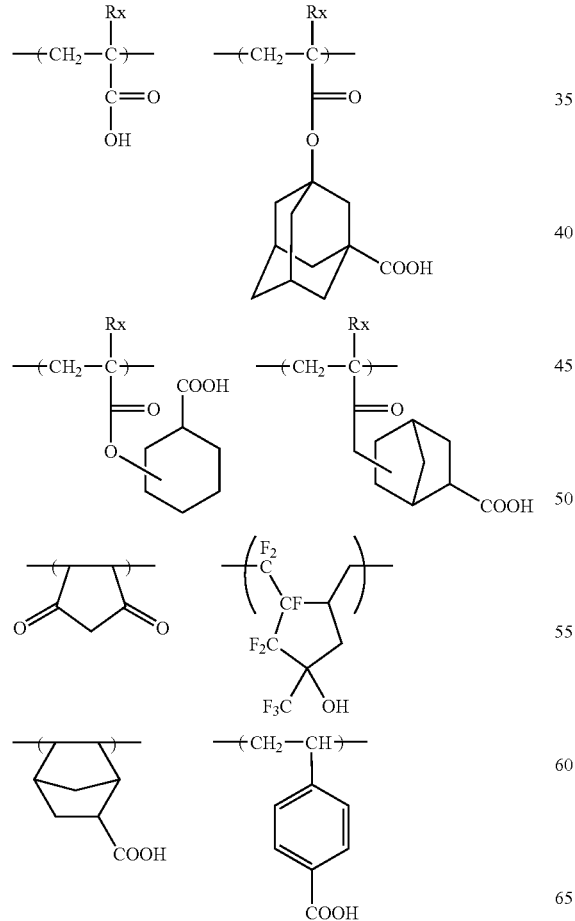

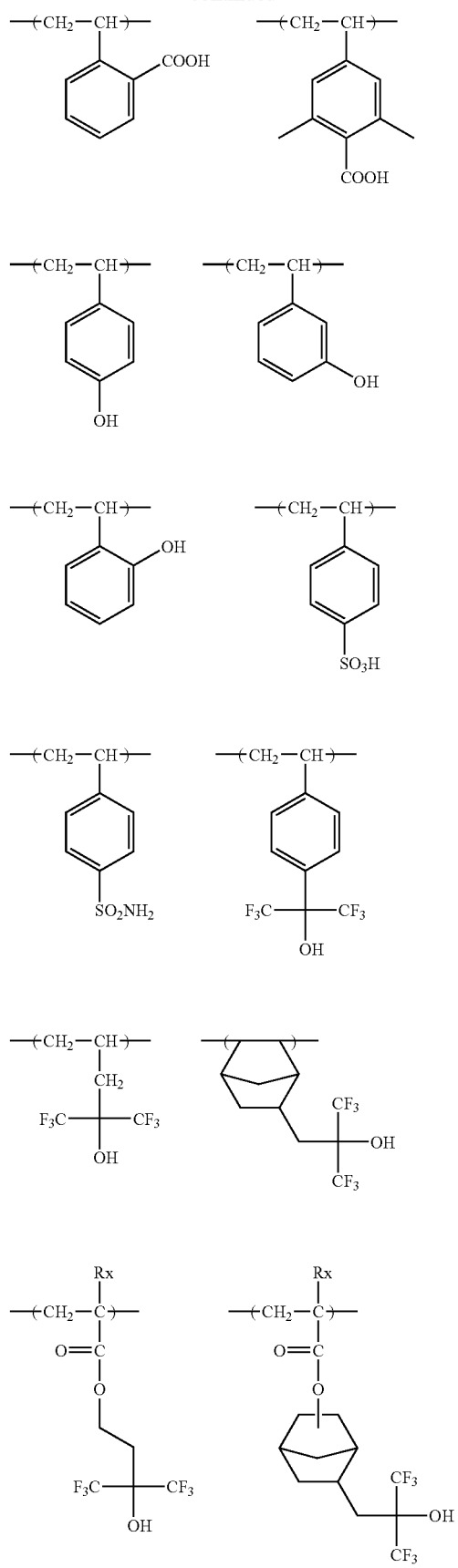

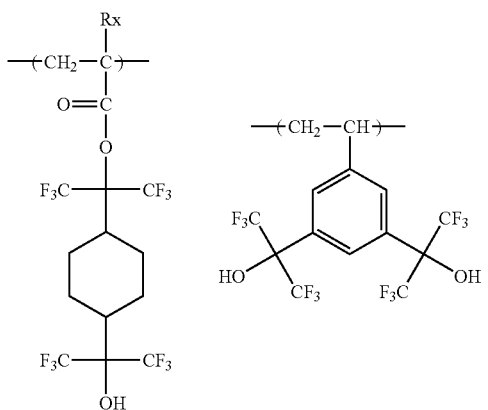
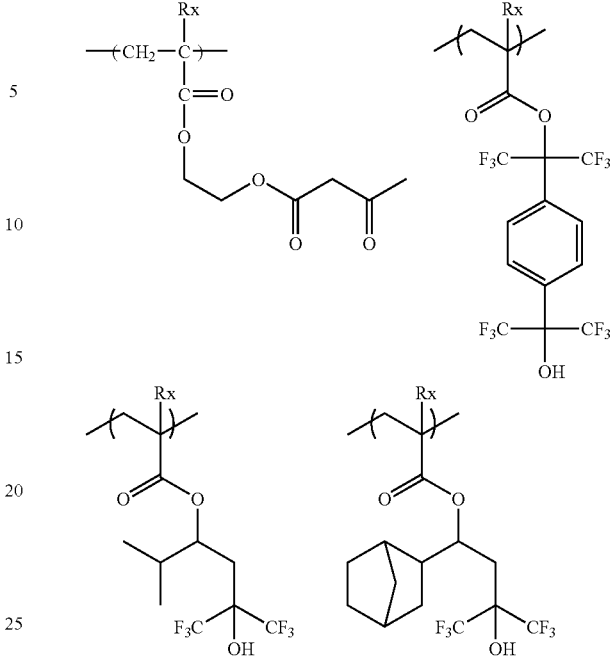
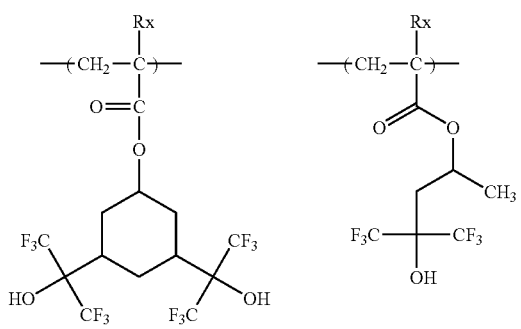
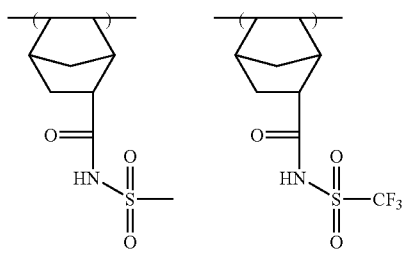
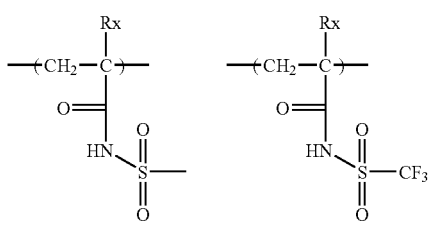
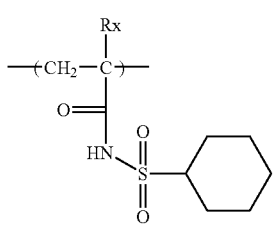

Examples of the group (y) capable of decomposing by the action of an alkali developing solution to increase the solubility in an alkali developing solution (polarity converting group (y)) include a lactone group, a carboxylic acid ester group (—COO—), an acid anhydride group (—C(O)OC(O)—), an acid imide group (—NHCONH—), a carboxylic acid thioester group (—COS—), a carbonic acid ester group (—OC(O)O—), a sulfuric acid ester group (—OSO$_2$O—) and a sulfonic acid ester group (—SO$_2$O—), with a lactone group being preferred.

The actinic ray-sensitive or radiation-sensitive resin composition of the present invention preferably contains (Cy) a resin having at least either a fluorine atom or a silicon atom and containing (cy) a repeating unit having at least one polarity converting group (y). The resin (Cy) has hydrophobicity and addition of the resin (Cy) is preferred particularly from the standpoint of reducing the development defect. Incidentally, an ester group directly bonded to the main chain of the repeating unit as in an acrylate is poor in the function of decomposing by the action of an alkali developing solution to increase the solubility in an alkali developing solution and is not included in the polarity converting group of the present invention.

As for the polarity converting group (y), both a configuration where the polarity converting group is contained in a repeating unit composed of an acrylic acid ester or a methacrylic acid ester and thereby is introduced into the side chain of the resin, and a configuration where the polarity converting group (y) is introduced into the polymer chain terminal by using a polymerization initiator or chain transfer agent containing the polarity converging group at the polymerization, are preferred.

Specific examples of the repeating unit (cy) having (y) a polarity converting group include the specific examples of the repeating unit having a group having a lactone structure (for example, a repeating unit represented by formula (AI)), which are described with respect to the resin (C).

The repeating unit (cy) includes, for example, a repeating unit represented by formula (K0):

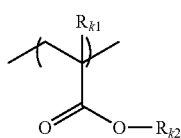
(K0)

In the formula, $R_{k1}$ represents a hydrogen atom, a halogen atom, a hydroxyl group, an alkyl group, a cycloalkyl group, an aryl group, or a polarity converting group-containing group.

$R_{k2}$ represents an alkyl group, a cycloalkyl group, an aryl group, or a polarity converting group-containing group, provided that at least either one of $R_{k1}$ and $R_{k2}$ represents a polarity converting group-containing group.

The polarity converting group is, as described above, a group capable of decomposing by the action of an alkali developing solution to increase the solubility in an alkali developing solution. The polarity converting group is preferably a group X in a partial structure represented by formula (KA-1) or (KB-1):

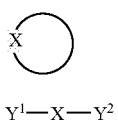
(KA-1)

$Y^1—X—Y^2$ (KB-1)

In formulae (KA-1) and (KB-1), X represents a carboxylic acid ester group: —COO—, an acid anhydride group: —C(O)OC(O)—, an acid imide group: —NHCONH—, a carboxylic acid thioester group: —COS—, a carbonic acid ester group: —OC(O)O—, a sulfuric acid ester group: —OSO$_2$O—, or a sulfonic acid ester group: —SO$_2$O—.

Each of $Y^1$ and $Y^2$, which may be the same or different, represents an electron-withdrawing group.

Incidentally, the repeating unit (cy) has a preferred group capable of increasing the solubility in an alkali developing solution by containing a group having a partial structure represented by formula (KA-1) or (KB-1), but as in the case of the partial structure represented by formula (KA-1) or the partial structure represented by formula (KB-1) where $Y^1$ and $Y^2$ are monovalent, when the partial structure does not have a bond, the group having the partial structure is a group having a monovalent or greater valent group formed by removing at least one arbitrary hydrogen atom in the partial structure.

The partial structure represented by formula (KA-1) or (KB-1) is connected to the main chain of the resin (Cy) at an arbitrary position through a substituent.

The partial structure represented by formula (KA-1) is a structure forming a ring structure together with the group as X.

In formula (KA-1), X is preferably a carboxylic acid ester group (that is, a case of forming a lactone ring structure as KA-1), an acid anhydride group or a carbonic acid ester group, more preferably a carboxylic acid ester group.

The ring structure represented by formula (KA-1) may have a substituent and, for example, may have nka substituents $Z_{ka1}$.

$Z_{ka1}$ represents, when a plurality of $Z_{ka1}$'s are present, each independently represents, a halogen atom, an alkyl group, a cycloalkyl group, an ether group, a hydroxyl group, an amide group, an aryl group, a lactone ring group or an electron-withdrawing group.

$Z_{ka1}$'s may combine with each other to form a ring. Examples of the ring formed by combining $Z_{ka1}$'s with each other include a cycloalkyl ring and a heterocycle (e.g., cyclic ether ring, lactone ring).

nka represents an integer of 0 to 10 and is preferably an integer of 0 to 8, more preferably an integer of 0 to 5, still more preferably an integer of 1 to 4, and most preferably an integer of 1 to 3.

The electron-withdrawing group as $Z_{ka1}$ has the same meaning as the electron-withdrawing group of $Y^1$ and $Y^2$ described later. The electron-withdrawing group above may be substituted with another electron-withdrawing group.

$Z_{ka1}$ is preferably an alkyl group, a cycloalkyl group, an ether group, a hydroxyl group or an electron-withdrawing group, more preferably an alkyl group, a cycloalkyl group or an electron-withdrawing group. The ether group is preferably an ether group substituted, for example, with an alkyl group or a cycloalkyl group, that is, an alkyl ether group. The electron-withdrawing group has the same meaning as above.

Examples of the halogen atom as $Z_{ka1}$ include a fluorine atom, a chlorine atom, a bromine atom and an iodine atom, with a fluorine atom being preferred.

The alkyl group as $Z_{ka1}$ may have a substituent and may be either linear or branched. The linear alkyl group is preferably an alkyl group having a carbon number of 1 to 30, more preferably from 1 to 20, and examples thereof include a methyl group, an ethyl group, an n-propyl group, an n-butyl group, a sec-butyl group, a tert-butyl group, an n-pentyl group, an n-hexyl group, an n-heptyl group, an n-octyl group, an n-nonyl group and an n-decanyl group. The branched alkyl group is preferably an alkyl group having a carbon number of 3 to 30, more preferably from 3 to 20, and examples thereof include an i-propyl group, an i-butyl group, a tert-butyl group, an i-pentyl group, a tert-pentyl group, an i-hexyl group, a tert-hexyl group, an i-heptyl group, a tert-heptyl group, an i-octyl group, a tert-octyl group, an i-nonyl group and a tert-decanoyl group. An alkyl group having a carbon number of 1 to 4, such as methyl group, ethyl group, n-propyl group, i-propyl group, n-butyl group, i-butyl group and tert-butyl group, is preferred.

The cycloalkyl group as $Z_{ka1}$ may have a substituent and may be monocyclic or polycyclic, and in the case of polycyclic, the cycloalkyl group may be crosslinked. That is, in this case, the cycloalkyl group may have a bridged structure.

The monocyclic cycloalkyl group is preferably a cycloalkyl group having a carbon number of 3 to 8, and examples thereof include a cyclopropyl group, a cyclopentyl group, a cyclohexyl group, a cyclobutyl group and a cyclooctyl group.

Examples of the polycyclic cycloalkyl group include a group having a bicyclo, tricyclo or tetracyclo structure and having a carbon number of 5 or more. A cycloalkyl group having a carbon number of 6 to 20 is preferred, and examples thereof include an adamantyl group, a norbornyl group, an isoboronyl group, a camphanyl group, a dicyclopentyl group, an α-pinel group, a tricyclodecanyl group, a tetracyclododecyl group and an androstanyl group.

These cycloalkyl groups include, for example, those represented by the following formulae. Incidentally, a part of carbon atoms in the cycloalkyl group may be substituted for by a heteroatom such as oxygen atom.

(1)

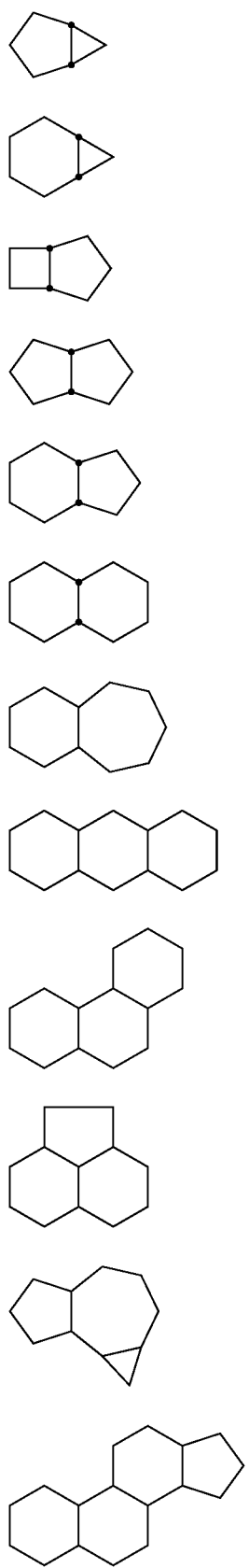
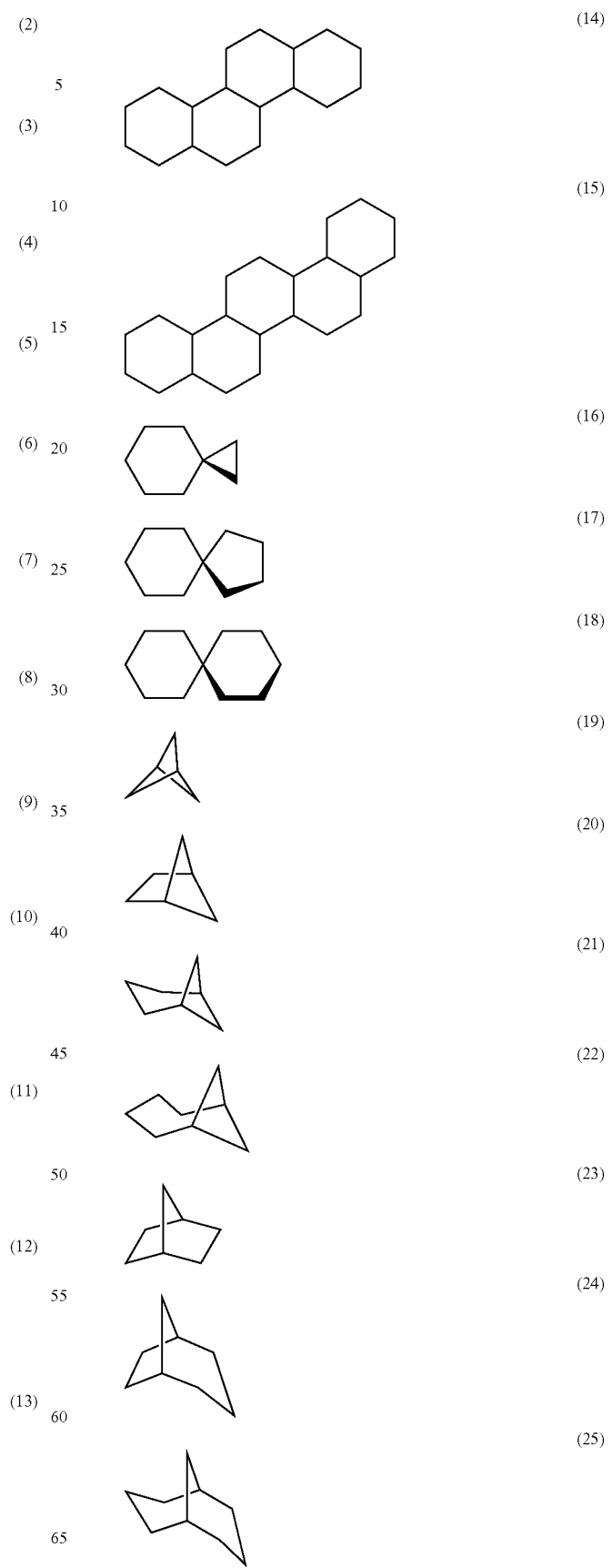

-continued
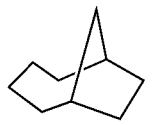
(26)
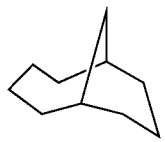
(27)
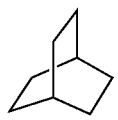
(28)
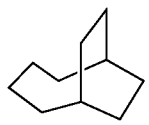
(29)
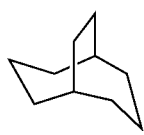
(30)
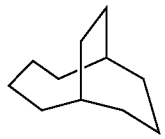
(31)
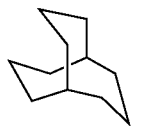
(32)
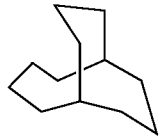
(33)
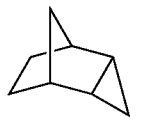
(34)
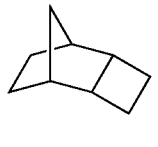
(35)
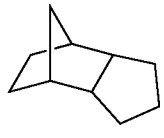
(36)
-continued
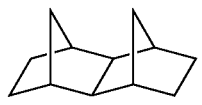
(37)
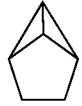
(38)
(39)
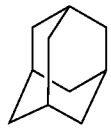
(40)
(41)
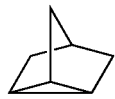
(42)
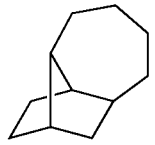
(43)
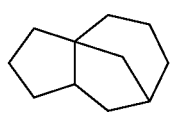
(44)
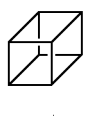
(45)
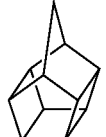
(46)
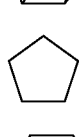
(47)
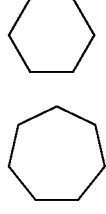
(48)
(49)

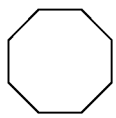

The preferred alicyclic moiety includes an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. An adamantyl group, a decalin group, a norbornyl group, a cedrol group, a cyclohexyl group, a cycloheptyl group, a cyclooctyl group, a cyclodecanyl group, a cyclododecanyl group and a tricyclodecanyl group are more preferred.

The substituent of the alicyclic structure includes an alkyl group, a halogen atom, a hydroxyl group, an alkoxy group, a carboxyl group and an alkoxycarbonyl group. The alkyl group is preferably a lower alkyl group such as methyl group, ethyl group, propyl group, isopropyl group and butyl group, more preferably a methyl group, an ethyl group, a propyl group or an isopropyl group. The alkoxy group is preferably an alkoxy group having a carbon number of 1 to 4, such as methoxy group, ethoxy group, propoxy group and butoxy group. Examples of the substituent which the alkyl group and alkoxy group may have include a hydroxyl group, a halogen atom and an alkoxy group (preferably having a carbon number of 1 to 4).

The groups above may further have a substituent, and examples of the further substituent include a hydroxyl group, a halogen atom (e.g., fluorine, chlorine, bromine, iodine), a nitro group, a cyano group, the above-described alkyl group, an alkoxy group such as methoxy group, ethoxy group, hydroxyethoxy group, propoxy group, hydroxypropoxy group, n-butoxy group, isobutoxy group, sec-butoxy group and tert-butoxy group, an alkoxycarbonyl group such as methoxycarbonyl group and ethoxycarbonyl group, an aralkyl group such as benzyl group, phenethyl group and cumyl group, an aralkyloxy group, an acyl group such as formyl group, acetyl group, butyryl group, benzoyl group, cinnamyl group and valeryl group, an acyloxy group such as butyryloxy group, the above-described alkenyl group, an alkenyloxy group such as vinyloxy group, propenyloxy group, allyloxy group and butenyloxy group, the above-described aryl group, an aryloxy group such as phenoxy group, and an aryloxycarbonyl group such as benzoyloxy group.

It is preferred that X in formula (KA-1) is a carboxylic acid ester group and the partial structure represented by formula (KA-1) is a lactone ring, and the lactone ring is preferably a 5- to 7-membered lactone ring.

In this connection, as in (KA-1-1) to (KA-1-17) shown below, another ring structure is preferably condensed to a 5- to 7-membered lactone ring that is the partial structure represented by formula (KA-1), in the form of forming a bicyclo or Spiro structure.

Examples of the peripheral ring structure with which the ring structure represented by formula (KA-1) may combine include those in (KA-1-1) to (KA-1-17) shown below and structures based on these structures.

The structure containing the lactone ring structure represented by formula (KA-1) is more preferably a structure represented by any one of the following (KA-1-1) to (KA-1-17). The lactone structure may be bonded directly to the main chain. Preferred structures are (KA-1-1), (KA-1-4), (KA-1-5), (KA-1-6), (KA-1-13), (KA-1-14) and (KA-1-17).

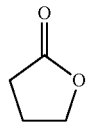
KA-1-1

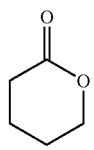
KA-1-2

KA-1-3

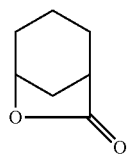
KA-1-4

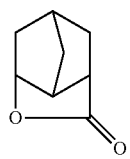
KA-1-5

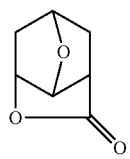
KA-1-6

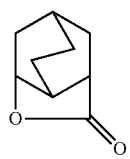
KA-1-7

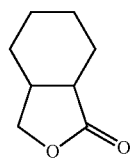
KA-1-8

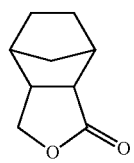
KA-1-9

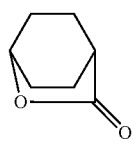

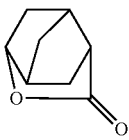
KA-1-10

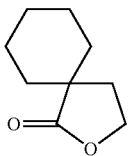
KA-1-11

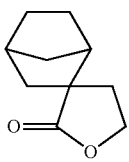
KA-1-12

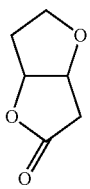
KA-1-13

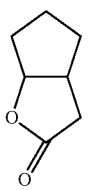
KA-1-14

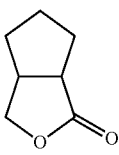
KA-1-15

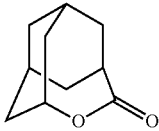
KA-1-16

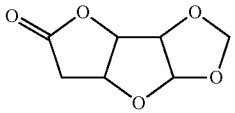
KA-1-17

The structure containing the above-described lactone ring structure may or may not have a substituent. Preferred examples of the substituent are the same as those of the substituent $Z_{ka1}$ which the ring structure represented by formula (KA-1) may have.

In formula (KB-1), X is preferably a carboxylic acid ester group (—COO—).

In formula (KB-1), each of $Y^1$ and $Y^2$ independently represents an electron-withdrawing group.

The electron-withdrawing group is a partial structure represented by the following formula (EW). In formula (EW), * indicates a bond directly bonded to (KA-1) or a bond directly bonded to X of (KB-1).

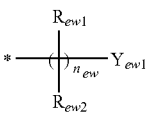
(EW)

In formula (EW), $n_{ew}$ is a repetition number of the linking group represented by —C($R_{ew1}$)($R_{ew2}$)— and represents an integer of 0 or 1. In the case where $n_{ew}$ is 0, this indicates a single bond and means that $Y_{ew1}$ is directly bonded.

$Y_{ew1}$ is a halogen atom, a cyano group, a nitrile group, a nitro group, a halo(cyclo)alkyl or haloaryl group represented by —C($R_{f1}$)($R_{f2}$)—$R_{f3}$ described later, an oxy group, a carbonyl group, a sulfonyl group, a sulfinyl group, or a combination thereof. The electron-withdrawing group may be, for example, a structure shown below. The term "halo(cyclo) alkyl group" indicates an alkyl or cycloalkyl group that is at least partially halogenated, and the "haloaryl group" indicates an aryl group that is at least partially halogenated. In the following structural formulae, each of $R_{ew3}$ and $R_{ew4}$ independently represents an arbitrary structure. The partial structure represented by formula (EW) has an electron-withdrawing group regardless of what structure $R_{ew3}$ or $R_{ew4}$ is, and each of $R_{ew3}$ and $R_{ew4}$ may be connected, for example, to the main chain of the resin but is preferably an alkyl group, a cycloalkyl group or an alkyl fluoride group.

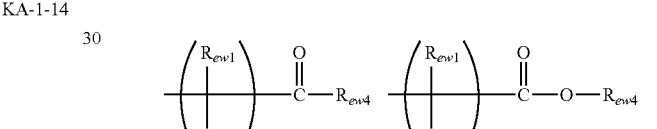

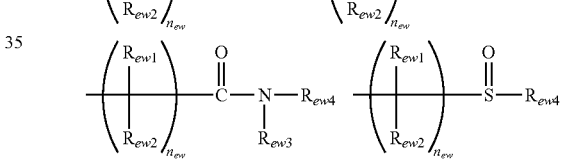

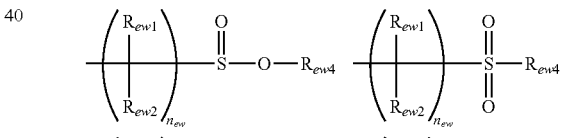

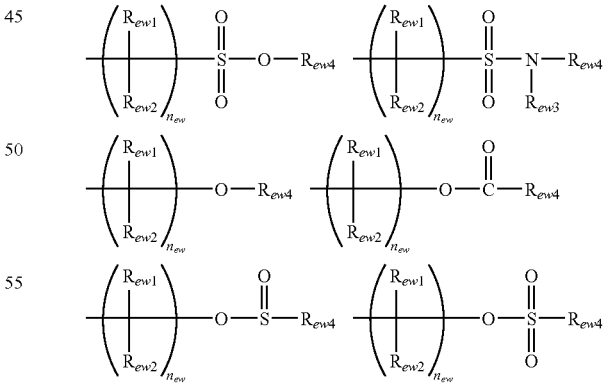

In the case where $Y_{ew1}$ is a divalent or greater valent group, the remaining bond forms bonding with an arbitrary atom or substituent. At least any one group of $Y_{ew1}$, $R_{ew1}$ and $R_{ew2}$ may be connected to the main chain of the resin (Cy) through a further substituent.

$Y_{ew1}$ is preferably a halogen atom or a halo(cyclo)alkyl or haloaryl group represented by —C($R_{f1}$)($R_{f2}$)—$R_{f3}$.

Each of $R_{ew1}$ and $R_{ew2}$ independently represents an arbitrary substituent, for example, represents a hydrogen atom, an alkyl group, a cycloalkyl group or an aryl group.

At least two members out of $R_{ew1}$, $R_{ew2}$ and $Y_{ew1}$ may combine with each other to form a ring.

$R_{f1}$ represents a halogen atom, a perhaloalkyl group, a perhalocycloalkyl group or a perhaloaryl group and is preferably a fluorine atom, a perfluoroalkyl group or a perfluorocycloalkyl group, more preferably a fluorine atom or a trifluoromethyl group.

Each of $R_{f1}$ and $R_{f3}$ independently represents a hydrogen atom, a halogen atom or an organic group, and $R_{f2}$ and $R_{f3}$ may combine to form a ring. Examples of the organic group include an alkyl group, a cycloalkyl group and an alkoxy group. $R_{f2}$ is preferably the same group as $R_{f1}$ or combines with $R_{f3}$ to form a ring.

$R_{f1}$ to $R_{f3}$ may combine to form a ring, and examples of the ring formed include a (halo)cycloalkyl ring and a (halo)aryl ring.

Examples of the (halo)alkyl group in $R_{f1}$ to $R_{f3}$ include the alkyl groups in $Z_{ka1}$ and halogenated structures thereof.

The (per)halocycloalkyl group and (per)haloaryl group in $R_{f1}$ to $R_{f3}$ or in the ring formed by combining $R_{f2}$ and $R_{f3}$ include, for example, structures resulting from halogenation of cycloalkyl groups in $Z_{ka1}$ and are preferably a fluorocycloalkyl group represented by $-C_{(n)}F_{(2n-2)}H$, and a perfluoroaryl group represented by $-C_{(n)}F_{(n-1)}$, wherein the carbon number n is not particularly limited but is preferably from 5 to 13, more preferably 6.

The ring which may be formed by combining at least two members of $R_{ew1}$, $R_{ew2}$ and $Y_{ew1}$ with each other is preferably a cycloalkyl group or a heterocyclic group, and the heterocyclic group is preferably a lactone ring group. Examples of the lactone ring include structures represented by formulae (ω-1) to (KA-1-17).

Incidentally, the repeating unit (cy) may have a plurality of partial structures represented by formula (KA-1), a plurality of partial structures represented by formula (KB-1), or both a partial structure of formula (KA-1) and a partial structure of formula (KB-1).

In this connection, the partial structure of formula (KA-1) may partially or entirely serve also as the electron-withdrawing group of $Y^1$ or $Y^2$ in formula (KB-1). For example, in the case where X in formula (KA-1) is a carboxylic acid ester group, the carboxylic acid ester group may function as an electron-withdrawing group of $Y^1$ or $Y^2$ in formula (KB-1).

The repeating unit (cy) may be (cy') a repeating unit having at least either a fluorine atom or a silicon atom and a polarity converting group on one side chain, (cy*) a repeating unit having a polarity converting group and having neither a fluorine atom nor a silicon atom, or (cy") a repeating unit having a polarity converting group on one side chain and at the same time, having at least either a fluorine atom or a silicon atom on a side chain different from the side chain above in the same repeating unit, but the resin (Cy) preferably contains a repeating unit (cy') as the repeating unit (cy).

In the case where the resin (Cy) contains the repeating unit (cy*), the resin is preferably a copolymer with a repeating unit having at least either a fluorine atom or a silicon atom (a repeating unit (c1) described later). Also, in the repeating unit (cy"), the side chain having a polarity converting group and the side chain having at least either a fluorine atom or a silicon atom are preferably bonded to the same carbon atom in the main chain, that is, have a positional relationship like the following formula (K1).

In the formula, B1 represents a partial structure having a group capable of increasing the solubility in an alkali developing solution, and B2 represents a partial structure having at least either a fluorine atom or a silicon atom.

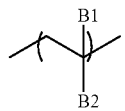

(K1)

Also, in the repeating unit (cy*) and the repeating unit (cy"), the polarity converting group is more preferably a partial structure represented by —COO— in the structure of formula (KA-1).

The repeating unit (cy) may be a repeating unit having a partial structure shown below.

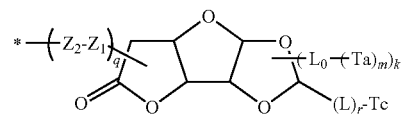

(cc)

In formula (cc), $Z_1$ represents a single bond, an ether bond, an ester bond, an amide bond, a urethane bond or a urea bond, and when a plurality of $Z_1$'s are present, each $Z_1$ may be the same as or different from every other $Z_1$. $Z_1$ is preferably an ester bond.

$Z_2$ represents a chain or cyclic alkylene group and when a plurality of $Z_2$'s are present, each $Z_2$ may be the same as or different from every other $Z_2$. $Z_2$ is preferably an alkylene group having a carbon number of 1 or 2 or a cycloalkylene group having a carbon number of 5 to 10.

Each Ta independently represents an alkyl group, a cycloalkyl group, an alkoxy group, a nitrile group, a hydroxyl group, an amide group, an aryl group or an electron-withdrawing group (having the same meaning as the electron-withdrawing group of $Y^1$ and $Y^2$ in formula (KB-1)) and is preferably an alkyl group, a cycloalkyl group or an electron-withdrawing group, more preferably an electron-withdrawing group. When a plurality of Ta's are present, Ta's may combine with each other to form a ring.

Each $L_0$ independently represents a single bond or an (m+1)-valent hydrocarbon group (preferably having a carbon number of 20 or less) and is preferably a single bond. The single bond as $L_0$ is formed when m is 1. The (m+1)-valent hydrocarbon group as $L_0$ represents an (m+1)-valent hydrocarbon group formed by removing m−1 arbitrary hydrogen atoms from, for example, an alkylene group, a cycloalkylene group, a phenylene group or a combination thereof.

Each L independently represents a carbonyl group, a carbonyloxy group or an ether group.

Tc represents a hydrogen atom, an alkyl group, a cycloalkyl group, a nitrile group, a hydroxyl group, an amide group, an aryl group or an electron-withdrawing group (having the same meaning as the electron-withdrawing group of $Y^1$ and $Y^2$ in formula (KB-1)).

* represents a bond to the main or side chain of the resin. That is, a partial structure represented by formula (cc) may be directly bonded to the main chain, or a partial structure represented by formula (cc) may be bonded to the side chain of the resin. In this connection, the bond to the main chain is a bond to an atom present in the bonding constituting the main chain, and the bond to the side chain is a bond to an atom present in the portion except for the bonding constituting the main chain.

m represents an integer of 1 to 28 and is preferably an integer of 1 to 3, more preferably 1.

k represents an integer of 0 to 2 and is preferably 1.

q is a repetition number of the group ($Z_2$—$Z_1$) and represents an integer of 0 to 5, preferably from 0 to 2.

r represents an integer of 0 to 5.

Incidentally, -(L)$_r$-Tc may be replaced by the above-described -L$_0$-(Ta)$_m$.

It is also preferred to have a fluorine atom at the terminal of sugar lactone or have a fluorine atom on a side chain different from the side chain on the sugar lactone side within the same repeating unit (corresponding to the repeating unit (cy")).

The carbon number of the chain alkylene group as $Z_2$ is, in the case of a linear alkylene group, preferably from 1 to 30, more preferably from 1 to 20, and in the case of a branched alkylene group, preferably from 3 to 30, more preferably from 3 to 20. Specific examples of the chain alkylene group as $R_2$ include groups resulting from removal of one arbitrary hydrogen atom in specific examples of the alkyl group as $Z_{ka1}$ above.

The cyclic alkylene group as $Z_2$ is preferably a cyclic alkylene group having a carbon number of 3 to 8, and specific examples thereof include groups resulting from removal of one arbitrary hydrogen atom in the cycloalkyl group as $Z_{ka1}$ above.

The preferred carbon numbers and specific examples of the alkyl group and cycloalkyl group as Ta and Tc are the same as those described above for the alkyl group and cycloalkyl group as $Z_{ka1}$.

The alkoxy group as Ta is preferably an alkoxy group having a carbon number of 1 to 8, and examples thereof include a methoxy group, an ethoxy group, a propoxy group and a butoxy group.

The aryl group as Ta and Tc is preferably an aryl group having a carbon number of 6 to 12, and examples thereof include a phenyl group and a naphthyl group.

The preferred carbon numbers and specific examples of the alkylene group and cycloalkylene group as $L_0$ are the same as those described above for the chain alkylene group and cyclic alkylene group as $Z_2$.

As for the more specific structure of the repeating unit (cc), repeating units having a partial structure shown below are preferred.

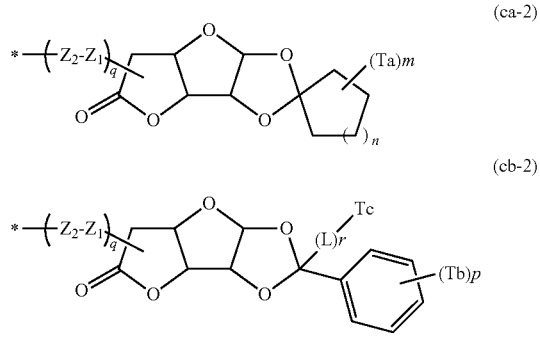

In formulae (ca-2) and (cb-2), n represents an integer of 0 to 11 and is preferably an integer of 0 to 5, more preferably 1 or 2.

p represents an integer of 0 to 5 and is preferably an integer of 0 to 3, more preferably 1 or 2.

Each Tb independently represents an alkyl group, a cycloalkyl group, an alkoxy group, a nitrile group, a hydroxyl group, an amide group, an aryl group or an electron-withdrawing group (having the same meaning as the electron-withdrawing group of $Y^1$ and $Y^2$ in formula (KB-1)) and is preferably an alkyl group, a cycloalkyl group or an electron-withdrawing group. When a plurality of Tb's are present, Tb's may combine with each other to form a ring.

\* represents a bond to the main or side chain of the resin. That is, a partial structure represented by formula (ω-2) or (cb-2) may be directly bonded to the main chain, or a partial structure represented by formula (ca-2) or (cb-2) may be bonded to the side chain of the resin.

$Z_1$, $Z_2$, Ta, Tc, L, \*, m, q and r have the same meanings as those in formula (cc) and preferred embodiments are also the same.

The repeating unit (cy) may be a repeating unit having a partial structure represented by formula (KY-0).

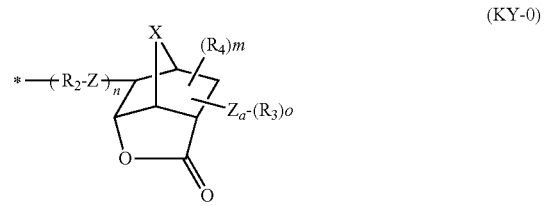

In formula (KY-0), $R_2$ represents a chain or cyclic alkylene group and when a plurality of $R_2$'s are present, each $R_2$ may be the same as or different from every other $R_2$.

$R_3$ represents a linear, branched or cyclic hydrocarbon group where a part or all of hydrogen atoms on the constituent carbons are substituted for by a fluorine atom. When a plurality of $R_3$'s are present, each $R_3$ may be the same as or different from every other $R_3$.

$R_4$ represents a halogen atom, a cyano group, a hydroxy group, an amide group, an alkyl group, a cycloalkyl group, an alkoxy group, a phenyl group, an acyl group, an alkoxycarbonyl group or a group represented by R—C(=O)— or R—C(=O)O— (wherein R represents an alkyl group or a cycloalkyl group). When a plurality of $R_4$'s are present, each $R_4$ may be the same as or different from every other $R_4$, and two or more $R_4$'s may combine to form a ring.

X represents an alkylene group, an oxygen atom or a sulfur atom.

Each of Z and Za represents a single bond, an ether bond, an ester bond, an amide bond, a urethane bond or a urea bond and when a plurality of Z's or Za's are present, each Z or Za may be the same as or different from every other Z or Za.

\* represents a bond to the main or side chain of the resin.

o is the number of substituents and represents an integer of 1 to 7.

m is the number of substituents and represents an integer of 0 to 7.

n is a repetition number and represents an integer of 0 to 5.

The structure of —$R_2$—Z— is preferably a structure represented by —(CH$_2$)$_t$—COO— (wherein 1 represents an integer of 1 to 5).

The preferred carbon number range and specific examples of the chain or cyclic alkylene group as $R_2$ are the same as those described for the chain alkylene group and cyclic alkylene group in $Z_2$ of formula (cc).

The carbon number of the linear, branched or cyclic hydrocarbon group as $R_3$ is, in the case of a linear hydrocarbon group, preferably from 1 to 30, more preferably from 1 to 20; in the case of a branched hydrocarbon group, preferably from 3 to 30, more preferably from 3 to 20; and in the case of a cyclic hydrocarbon group, from 6 to 20. Specific examples of $R_3$ include the specific examples of the alkyl group and cycloalkyl group as $Z_{ka1}$ above.

The preferred carbon numbers and specific examples of the alkyl group and cycloalkyl group as $R_4$ and R are the same as those described above for the alkyl group and cycloalkyl group as $Z_{ka1}$.

The acyl group as $R_4$ is preferably an acyl group having a carbon number of 2 to 6, and examples thereof include a formyl group, an acetyl group, a propionyl group, a butyryl group, an isobutyryl group, a valeryl group and a pivaloyl group.

Examples of the alkyl moiety in the alkoxy group and alkoxycarbonyl group as $R_4$ include a linear, branched or cyclic alkyl moiety, and the preferred carbon number and specific examples of the alkyl moiety are the same as those described above for the alkyl group and cycloalkyl group as $Z_{ka1}$.

Examples of the alkylene group as X include a chain or cyclic alkylene group, and the preferred carbon number and specific examples thereof are the same as those described for the chain alkylene group and cyclic alkylene group as $R_2$.

As for the specific structure, the repeating unit (cy) also includes repeating units having a partial structure shown below.

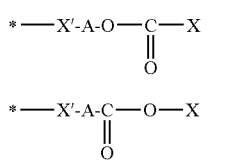

In formulae (rf-1) and (rf-2), X' represents an electron-withdrawing substituent and is preferably a carbonyloxy group, an oxycarbonyl group, a fluorine atom-substituted alkylene group or a fluorine atom-substituted cycloalkylene group.

A represents a single bond or a divalent linking group represented by —C(Rx)(Ry)—, wherein each of Rx and Ry independently represents a hydrogen atom, a fluorine atom, an alkyl group (which preferably has a carbon number of 1 to 6 and may be substituted with a fluorine atom or the like), or a cycloalkyl group (which preferably has a carbon number of 5 to 12 and may be substituted with a fluorine atom or the like). Each of Rx and Ry is preferably a hydrogen atom, an alkyl group or a fluorine atom-substituted alkyl group.

X represents an electron-withdrawing group and specific examples thereof include those electron-withdrawing groups as $Y^1$ and $Y^2$ above. An alkyl fluoride group, a cycloalkyl fluoride group, an aryl group substituted with fluorine or an alkyl fluoride group, and an aralkyl group substituted with fluorine or an alkyl fluoride group are preferred.

* represents a bond to the main or side chain of the resin, that is, a bond which is bonded to the main chain of the resin through a single bond or a linking group.

Incidentally, when X' is a carbonyloxy group or an oxycarbonyl group, A is not a single bond.

The polarity converting group is decomposed by the action of an alkali developing solution to effect polarity conversion, whereby the receding contact angle with water of the resin composition film after alkali development can be decreased. Decrease in the receding contact angle with water of the film after alkali development is preferred from the standpoint of suppressing the development defect.

The receding contact angle with water of the resin composition film after alkali development is preferably 50° or less, more preferably 40° or less, still more preferably 35° or less, and most preferably 30° or less, at a temperature of 23±3° C. and a humidity of 45±5%.

The receding contact angle is a contact angle measured when a contact line recedes on the liquid droplet-substrate interface, and this is generally known to be useful in simulating the mobility of a liquid droplet in the dynamic state. In a simple manner, the receding contact angle can be defined as a contact angle at the time of the liquid droplet interface receding when a liquid droplet ejected from a needle tip is landed on a substrate and then the liquid droplet is again suctioned into the needle. In general, the receding contact angle can be measured by a contact angle measuring method called an expansion/contraction method.

The above-described receding contact angle of the film after alkali development is the contact angle measured by an expansion/contraction method described in Examples later. That is, an organic antireflection film, ARC29A (produced by Nissan Chemical Industries, Ltd.), is coated on a silicon wafer (8 inches in diameter) and baked at 205° C. for 60 seconds to form a 98 nm-thick antireflection film, the composition of the present invention is coated thereon and baked at 120° C. for 60 seconds to form a 120 nm-thick film, this film is developed with an aqueous tetramethylammonium hydroxide solution (2.38 mass %) for 30 seconds, rinsed with pure water and spin-dried, and the contact angle of the obtained film is measured by the expansion/contraction method.

The hydrolysis rate of the resin (Cy) for an alkali developing solution is preferably 0.001 nm/sec or more, more preferably 0.01 nm/sec or more, still more preferably 0.1 nm/sec or more, and most preferably 1 nm/sec or more.

The hydrolysis rate of the resin (Cy) for an alkali developing solution is the rate at which the thickness of a resin film formed of the resin (Cy) alone decreases when treated with TMAH (an aqueous tetramethylammonium hydroxide solution) (2.38 mass %) at 23° C.

The repeating unit (cy) is more preferably a repeating having at least two or more polarity converting groups.

In the case where the repeating unit (cy) has at least two polarity converting groups, the repeating unit preferably has a group containing a partial structure having two polarity converting groups represented by the following formula (KY-1). Incidentally, when the structure represented by formula (KY-1) does not have a bond, this is a group containing a monovalent or greater valent group resulting from removal of at least one arbitrary hydrogen atom in the structure.

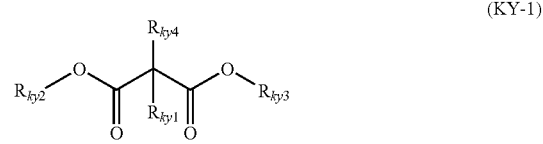

In formula (KY-1), each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group. Alternatively, $R_{ky1}$ and $R_{ky4}$ may be bonded to the same atom to form a double bond. For example, $R_{ky1}$ and $R_{ky4}$ may be bonded to the same oxygen atom to form a part (=O) of a carbonyl group.

Each of $R_{ky2}$ and $R_{ky3}$ independently represents an electron-withdrawing group, or while $R_{ky1}$ and $R_{ky2}$ combine to form a lactone ring, $R_{ky3}$ is an electron-withdrawing group. The lactone ring formed is preferably a structure of (KA-1-1) to (KA-1-17). Examples of the electron-withdrawing group is the same as those for $Y^1$ and $Y^2$ in formula (KB-1), and a halogen atom and a halo(cyclo)alkyl or haloaryl group represented by —C($R_{f1}$)($R_{f2}$)—$R_{f3}$ are preferred. Preferably, $R_{ky3}$ is a halogen atom or a halo(cyclo)alkyl or haloaryl group represented by —C($R_{f1}$)($R_{f2}$)—$R_{f3}$, and $R_{ky2}$ combines with $R_{ky1}$ to form a lactone ring or is an electron-withdrawing group containing no halogen atom.

$R_{ky1}$, $R_{ky2}$ and $R_{ky4}$ may combine with each other to form a monocyclic or polycyclic structure.

Specific examples of $R_{ky1}$ and $R_{ky4}$ include the same groups as those for $Z_{ka1}$ in formula (KA-1).

The lactone ring formed by combining $R_{ky1}$ and $R_{ky2}$ is preferably a structure of (KA-1-1) to (KA-1-17). Examples of the electron-withdrawing group are the same as those for $Y^1$ and $Y^2$ in formula (KB-1).

The structure represented by formula (KY-1) is preferably a structure represented by the following formula (KY-2). Here, the structure represented by formula (KY-2) is a group having a monovalent or greater valent group resulting from removal of at least one arbitrary hydrogen atom in the structure.

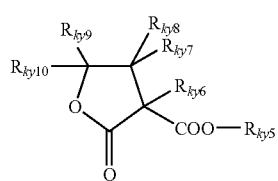
(KY-2)

In formula (KY-2), each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group.

Two or more members of $R_{ky6}$ to $R_{ky10}$ may combine with each other to form a monocyclic or polycyclic structure.

$R_{ky5}$ represents an electron-withdrawing group. Examples of the electron-withdrawing group are the same as those for $Y^1$ and $Y^2$, and a halogen atom and a halo(cyclo)alkyl or haloaryl group represented by —C($R_{f1}$)($R_{f2}$)—$R_{f3}$ are preferred.

Specific examples of $R_{ky5}$ to $R_{ky10}$ include the same groups as those for $Z_{ka1}$ in formula (KA-1).

The structure represented by formula (KY-2) is preferably a partial structure represented by the following formula (KY-3).

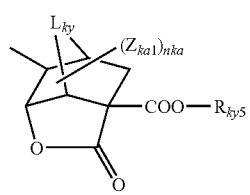
(KY-3)

In formula (KY-3), $Z_{ka1}$ and nka have the same meanings as in formula (KA-1). $R_{ky5}$ has the same meaning as in formula (KY-2).

$L_{ky}$ represents an alkylene group, an oxygen atom or a sulfur atom. Examples of the alkylene group of $L_{ky}$ include a methylene group and an ethylene group. $L_{ky}$ is preferably an oxygen atom or a methylene group, more preferably a methylene group.

The repeating unit (cy) is not limited as long as it is a repeating unit obtained by polymerization such as addition polymerization, condensation polymerization and addition condensation, but a repeating unit obtained by addition polymerization of a carbon-carbon double bond is preferred. Examples thereof include an acrylate-based repeating unit (including a system having a substituent at the α- or β-position), a styrene-based repeating unit (including a system having a substituent at the α- or β-position), a vinyl ether-based repeating unit, a norbornene-based repeating unit, and a maleic acid derivative (e.g., maleic anhydride or a derivative thereof, maleimide) repeating unit. An acrylate-based repeating unit, a styrene-based repeating unit, a vinyl ether-based repeating unit and a norbornene-based repeating unit are preferred, an acrylate-based repeating unit, a vinyl ether-based repeating unit and a norbornene-based repeating unit are more preferred, and an acrylate-based repeating unit is most preferred.

In the case where the repeating unit (cy) is a repeating unit having at least either a fluorine atom or a silicon atom (that is, a repeating unit corresponding to the repeating unit (cy') or (cy")), examples of the fluorine atom-containing partial structure in the repeating unit (cy) are the same as those in the repeating unit (c1) described later, and the groups represented by formula (F2) to (F4) are preferred. Also, examples of the silicon atom-containing partial structure in the repeating unit (cy) are the same as those in the repeating unit (c1) described later, and the groups represented by formulae (CS-1) to (CS-3) are preferred.

In the resin (Cy), the content of the repeating unit (cy) is preferably from 10 to 100 mol %, more preferably from 20 to 99 mol %, still more preferably from 30 to 97 mol %, and most preferably from 40 to 95 mol %, based on all repeating units in the resin (Cy).

The content of the repeating unit (cy') is preferably from 10 to 100 mol %, more preferably from 20 to 100 mol %, still more preferably from 30 to 100 mol %, and most preferably from 40 to 100 mol %, based on all repeating units in the resin (Cy).

The content of the repeating unit (cy*) is preferably from 5 to 70 mol %, more preferably from 5 to 60 mol %, still more preferably from 10 to 50 mol %, and most preferably from 10 to 40 mol %, based on all repeating units in the resin (Cy). The content of the repeating unit having at least either a fluorine atom or a silicon atom, which is used together with the repeating unit (cy*), is preferably from 10 to 95 mol %, more preferably from 15 to 85 mol %, still more preferably from 20 to 80 mol %, and most preferably from 25 to 75 mol %, based on all repeating units in the resin (Cy).

The content of the repeating unit (cy") is preferably from 10 to 100 mol %, more preferably from 20 to 100 mol %, still more preferably from 30 to 100 mol %, and most preferably from 40 to 100 mol %, based on all repeating units in the resin (Cy).

Specific examples of the repeating unit (cy) having a group capable of increasing the solubility in an alkali developing solution are set forth below, but the present invention is not limited thereto.

Ra represents a hydrogen atom, a fluorine atom, a methyl group or a trifluoromethyl group.
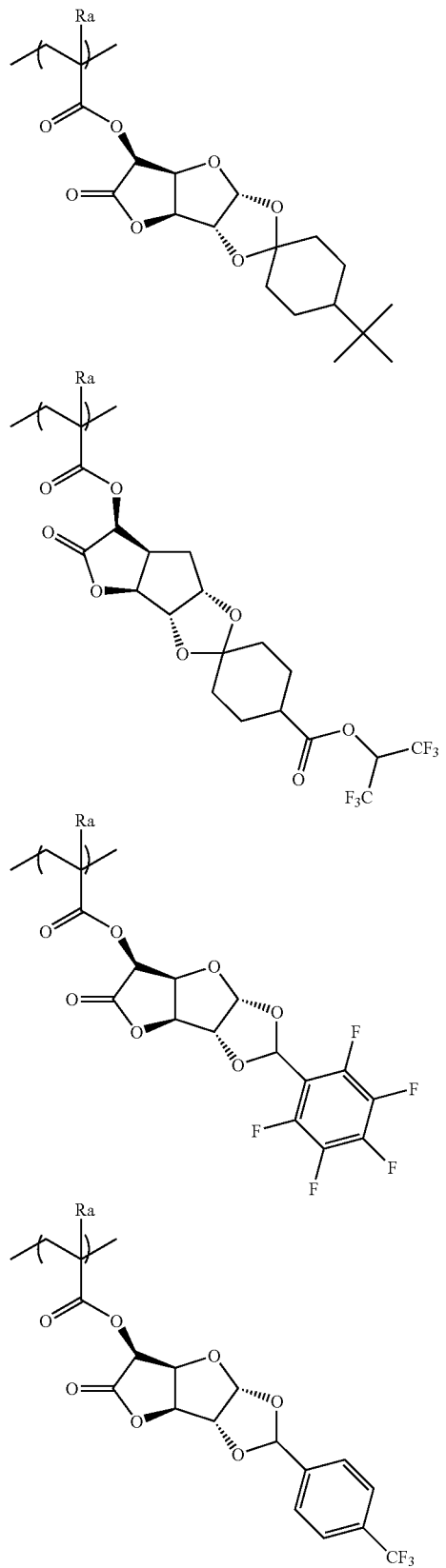
-continued
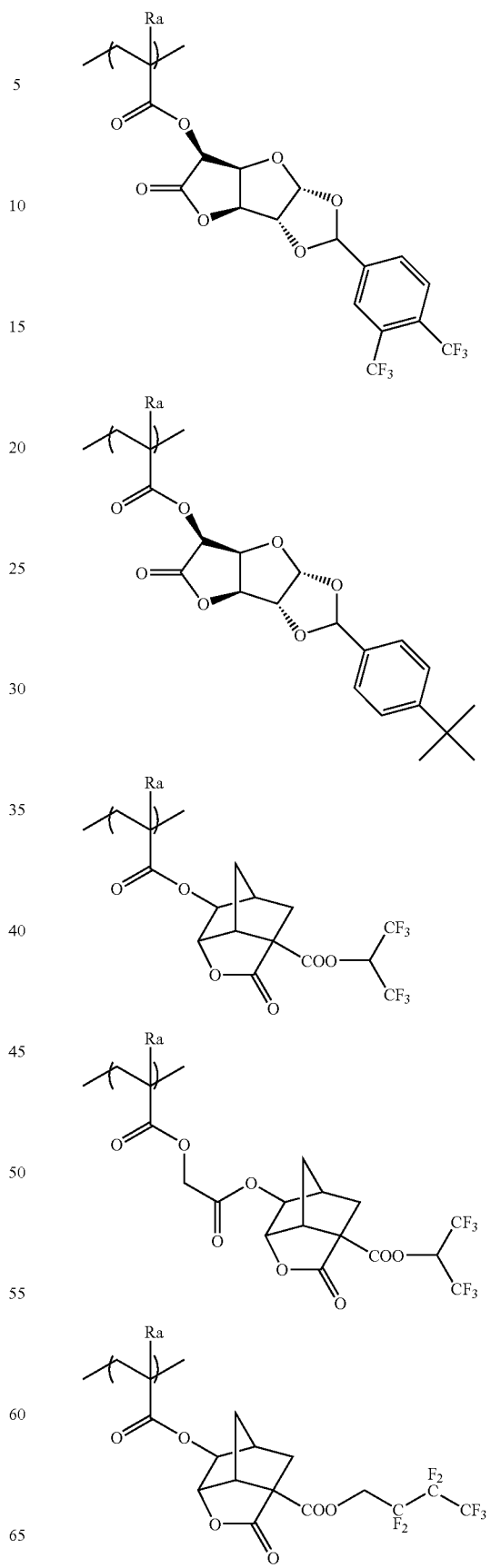

153
-continued
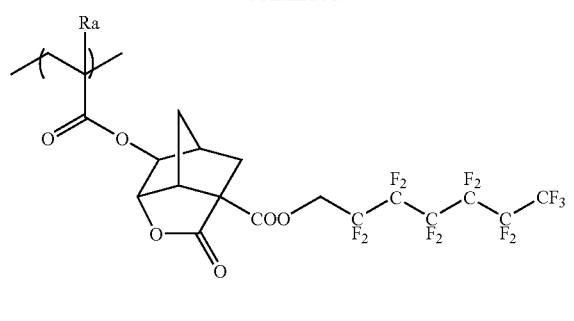
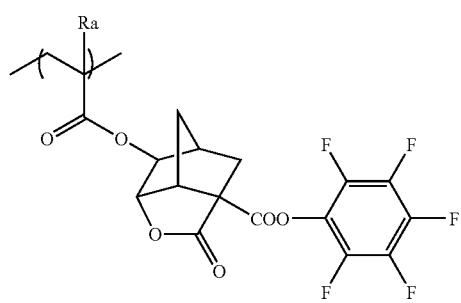
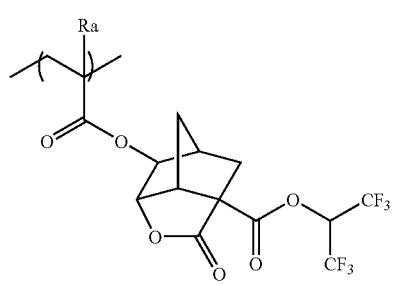
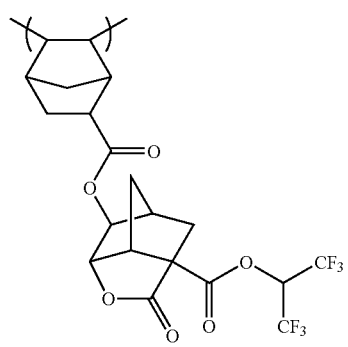
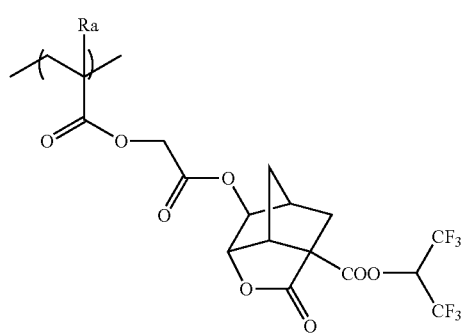
154
-continued
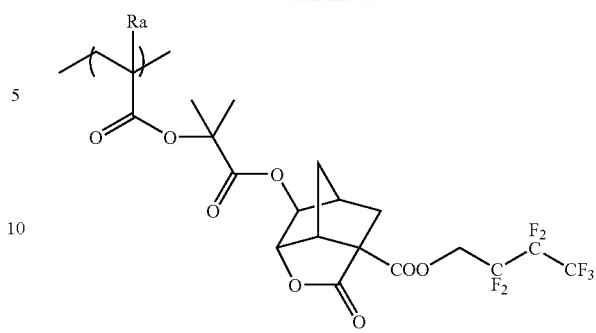
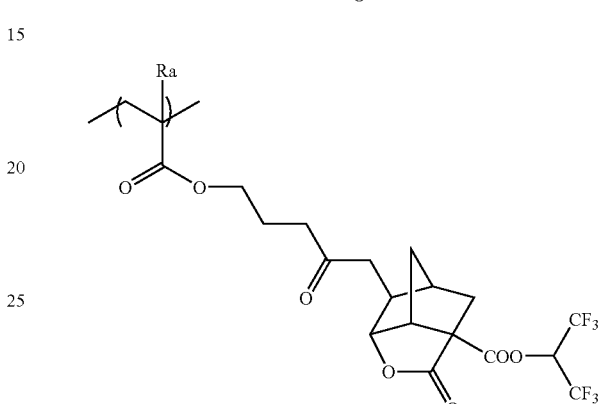
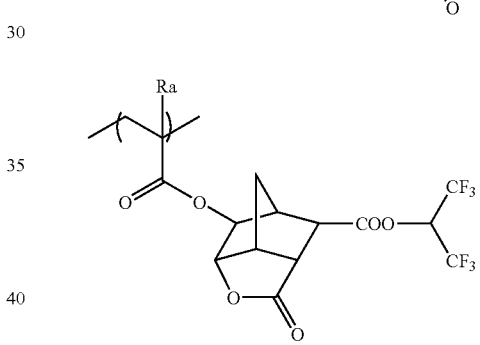
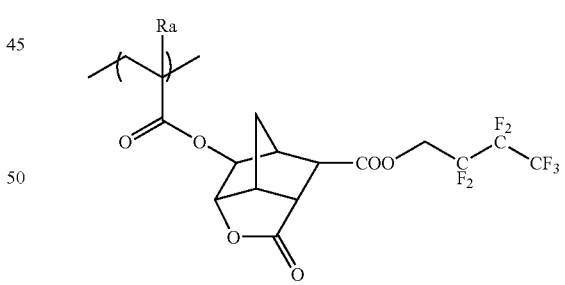
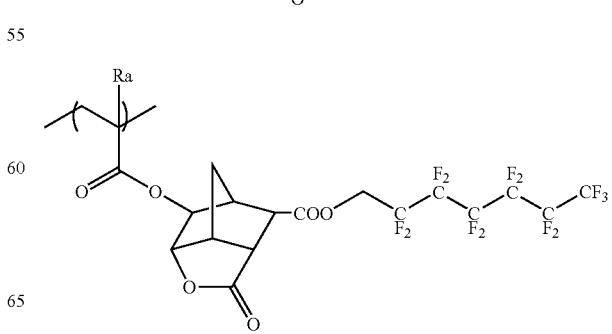

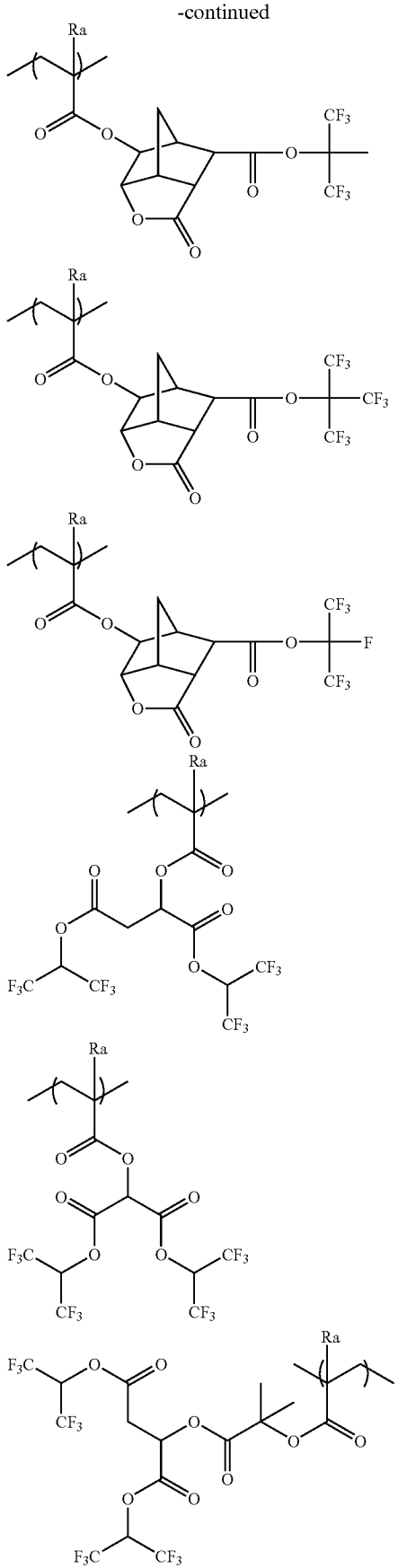
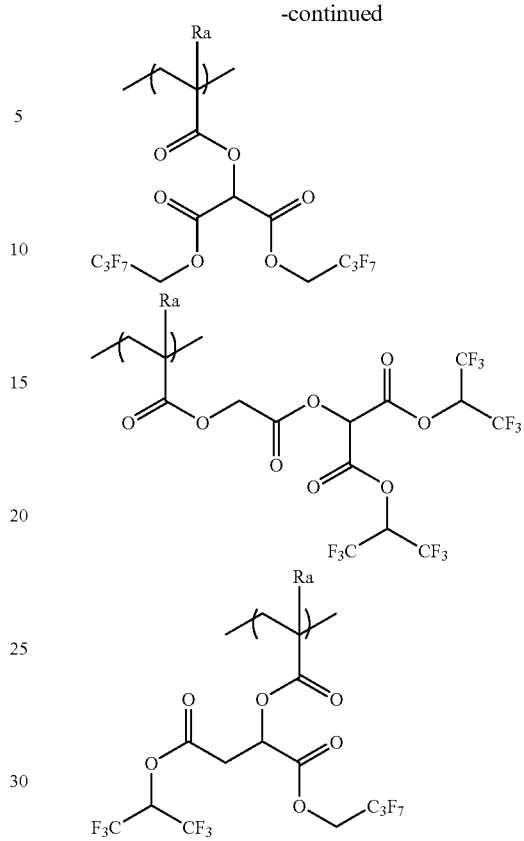

The resin (Cy) may further contain (c1) a repeating unit having at least either a fluorine atom or a silicon atom, which is different from repeating units (cy') and (cy").

Examples of the fluorine atom-containing partial structure in the repeating unit (c1) are the same as those described above, and the groups represented by formulae (F2) to (F4) are preferred.

Examples of the silicon atom-containing partial structure in the repeating unit (c1) are the same as those described above, and the groups represented by formulae (CS-1) to (CS-3) are preferred.

The repeating unit (c1) having at least either a fluorine atom or a silicon atom is preferably a (meth)acrylate-based repeating unit.

Specific examples of the repeating unit (c1) are the same as the above-described specific examples of the repeating unit having a fluorine atom and the repeating unit having a group represented by formulae (CS-1) to (CS-3), but the present invention is not limited thereto.

Examples of the repeating unit having (z) a group capable of decomposing by the action of an acid, contained in the hydrophobic resin (HR), are the same as those of the repeating unit having an acid-decomposable group described for the resin (C). The repeating unit having (z) a group capable of decomposing by the action of an acid may contain at least either a fluorine atom or a silicon atom. In the hydrophobic resin (HR), the content of the repeating unit having (z) a group capable of decomposing by the action of an acid is preferably from 1 to 80 mol %, more preferably from 10 to 80 mol %, still more preferably from 20 to 60 mol %, based on all repeating units in the resin (HR).

The hydrophobic resin (HR) may further contain a repeating unit represented by the following formula (III):

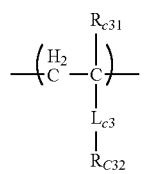
(III)

In formula (III), $R_{c31}$ represents a hydrogen atom, an alkyl group (which may be substituted with fluorine), a cyano group or a —$CH_2$—O—$R_{ac2}$ group, wherein $R_{ac2}$ represents a hydrogen atom, an alkyl group or an acyl group. $R_{c31}$ is preferably a hydrogen atom, a methyl group, a hydroxymethyl group or a trifluoromethyl group, more preferably a hydrogen atom or a methyl group.

$R_{c32}$ represents a group having an alkyl group, a cycloalkyl group, an alkenyl group or a cycloalkenyl group. Each of these groups may be substituted with a fluorine atom- or silicon atom-containing group.

$L_{c3}$ represents a single bond or a divalent linking group.

In formula (III), the alkyl group of $R_{c32}$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The aryl group is preferably an aryl group having a carbon number of 6 to 20, more preferably a phenyl group or a naphthyl group, and each of these groups may have a substituent.

$R_{c32}$ is preferably an unsubstituted alkyl group or a fluorine atom-substituted alkyl group.

The divalent linking group of $L_{c3}$ is preferably an alkylene group (preferably having a carbon number of 1 to 5), an oxy group, a phenylene group or an ester bond (a group represented by —COO—).

The hydrophobic resin (HR) may further contain a repeating unit represented by the following formula (CII-AB):

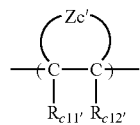
(CII-AB)

In formula (CII-AB), each of $R_{c11}'$ and $R_{c12}'$ independently represents a hydrogen atom, a cyano group, a halogen atom or an alkyl group.

$Z_c'$ represents an atomic group for forming an alicyclic structure containing two bonded carbon atoms (C—C).

In the case where each group in the repeating units represented by formulae (III) and (CII-AB) is substituted with a fluorine atom- or silicon atom-containing group, the repeating unit corresponds also to the repeating unit (c1).

Specific examples of the repeating units represented by formulae (III) and (CII-AB) are set forth below, but the present invention is not limited thereto. In the formulae, Ra represents H, $CH_3$, $CH_2OH$, $CF_3$ or CN. Incidentally, the repeating unit where Ra is $CF_3$ corresponds also to the repeating unit (c1).

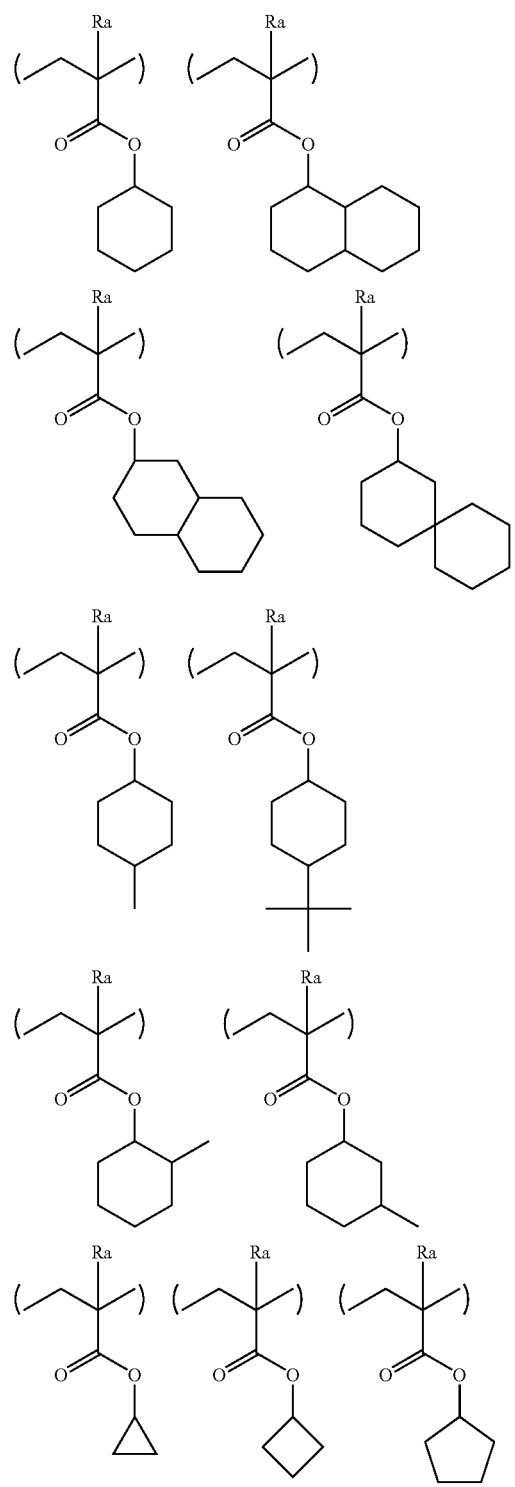

-continued

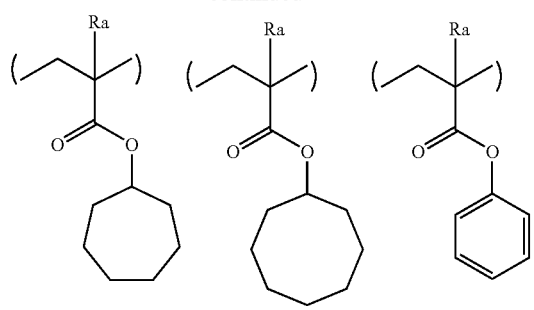
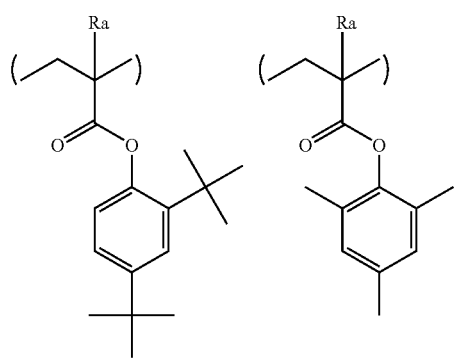
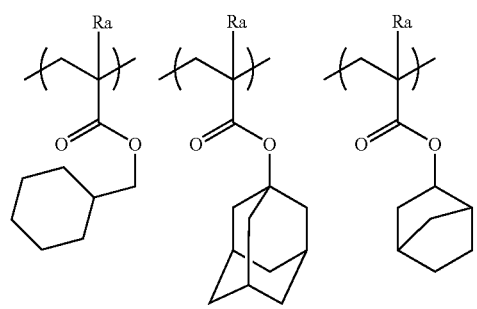
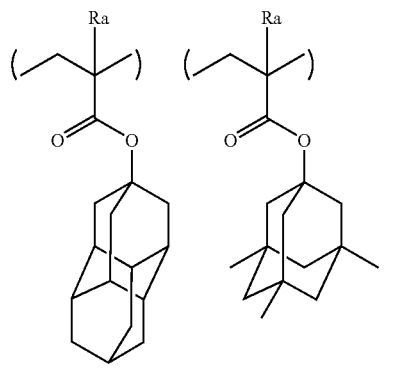
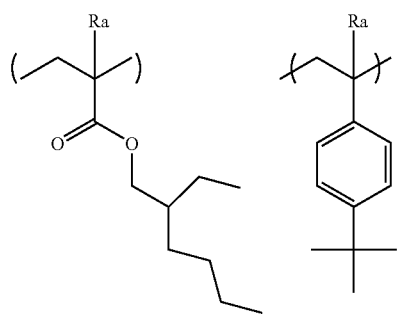

-continued

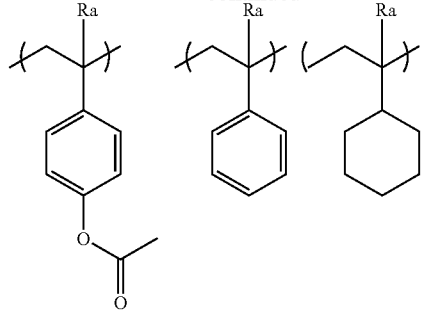
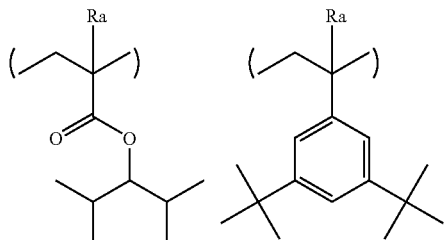
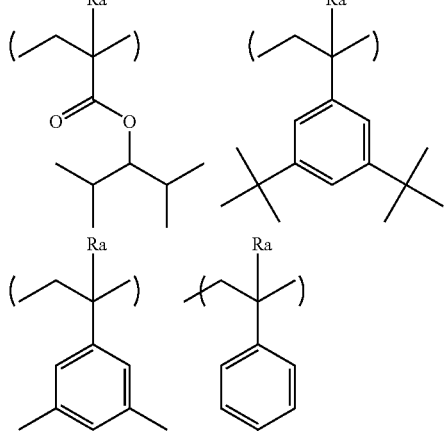
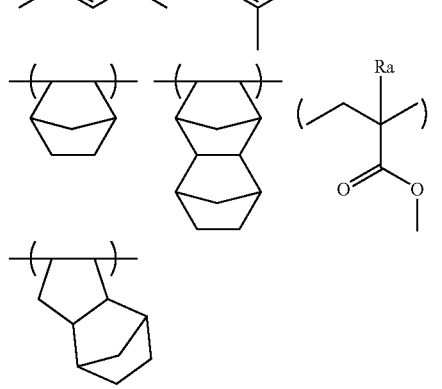

In the case where the hydrophobic resin (HR) contains a fluorine atom, the fluorine atom content is preferably from 5 to 80 mass %, more preferably from 10 to 80 mass %, based on the weight average molecular weight of the hydrophobic resin (HR). Also, the fluorine atom-containing repeating unit preferably occupies from 10 to 100 mol %, more preferably from 30 to 100 mol %, based on all repeating units contained in the hydrophobic resin (HR).

In the case where the hydrophobic resin (HR) contains a silicon atom, the silicon atom content is preferably from 2 to 50 mass %, more preferably from 2 to 30 mass %, based on the weight average molecular weight of the hydrophobic resin (HR). Also, the silicon atom-containing repeating unit preferably occupies from 10 to 100 mol %, more preferably from 20 to 100 mol %, based on all repeating units contained in the hydrophobic resin (HR).

The standard polystyrene-equivalent weight average molecular of the hydrophobic resin (HR) is preferably from 1,000 to 100,000, more preferably from 1,000 to 50,000, still more preferably from 2,000 to 15,000.

One kind of the hydrophobic resin (HR) may be used, or a plurality of kinds thereof may be used in combination.

The content of the hydrophobic resin (HR) in the composition is preferably from 0.01 to 10 mass %, more preferably from 0.05 to 8 mass %, still more preferably from 0.1 to 5 mass %, based on the entire solid content in the composition of the present invention.

In the hydrophobic resin (HR), similarly to the resin (C), it is of course preferred that the content of impurities such as metal is small, but also, the content of residual monomers or oligomer components is preferably from 0.01 to 5 mass %, more preferably from 0.01 to 3 mass %, still more preferably from 0.05 to 1 mass %. When these conditions are satisfied, a resist composition free of extraneous substances in the liquid or change with aging of sensitivity or the like can be obtained. Furthermore, in view of resolution, resist profile, side wall of pattern, roughness and the like, the molecular weight distribution (Mw/Mn, sometimes referred to as "polydispersity") is preferably from 1 to 5, more preferably from 1 to 3, still more preferably from 1 to 2.

As for the hydrophobic resin (HR), various commercially available products may be used, or the resin may be synthesized by a conventional method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred.

The reaction solvent, the polymerization initiator, the reaction conditions (e.g., temperature, concentration) and the purification method after reaction are the same as those described for the resin (C), but in the synthesis of the hydrophobic resin (HR), the concentration in reaction is preferably from 30 to 50 mass %.

Specific examples of the hydrophobic resin (HR) are set forth below. Also, the molar ratio of repeating units (corresponding to repeating units starting from the left), weight average molecular weight and polydispersity of each resin are shown in Tables later.

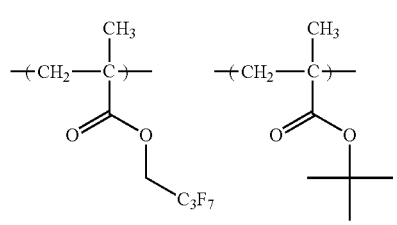
(HR-1)

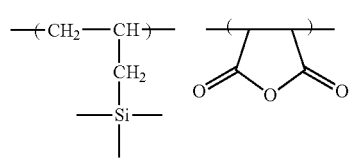
(HR-2)

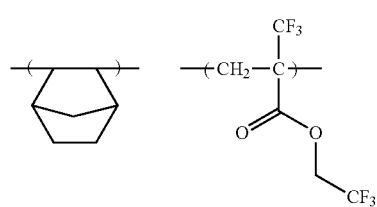
(HR-3)

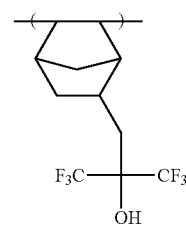
(HR-4)

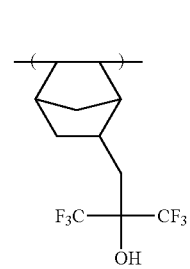
(HR-5)

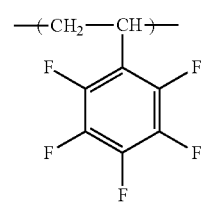
(HR-6)

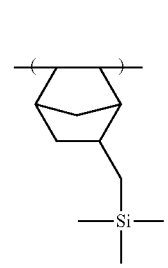
(HR-7)

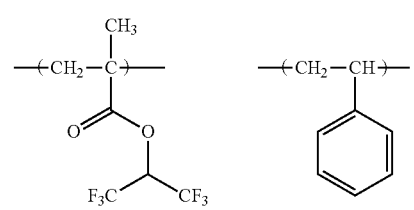
(HR-8)

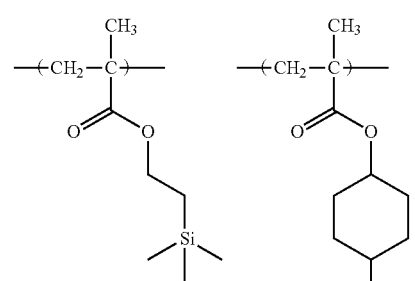
(HR-9)

(HR-10)
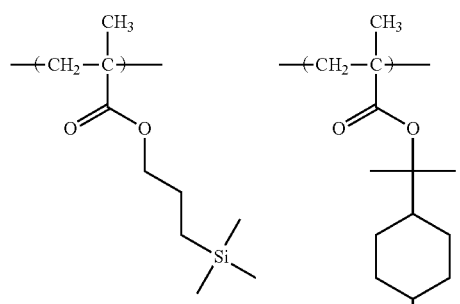
(HR-11)
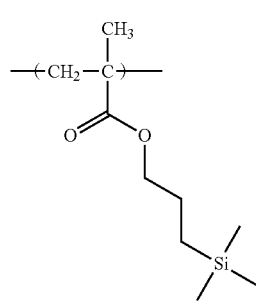
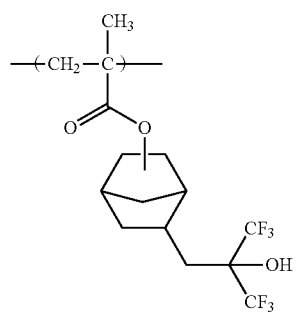
(HR-12)
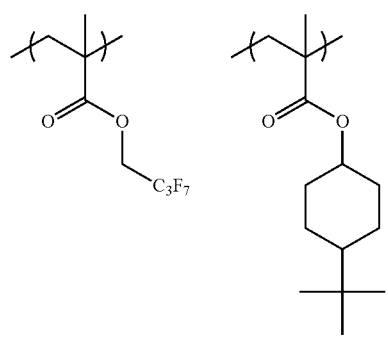
(HR-13)
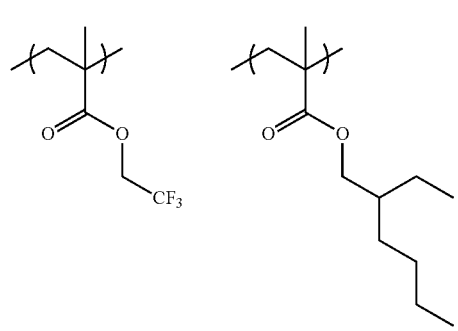
(HR-14)
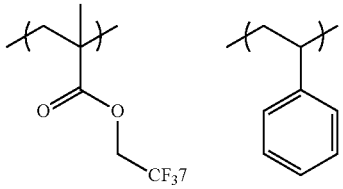
(HR-15)
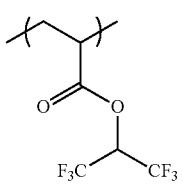
(HR-16)
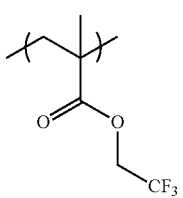
(HR-17)
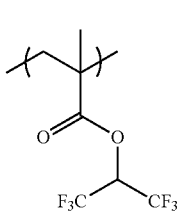
(HR-18)
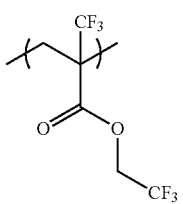
(HR-19)
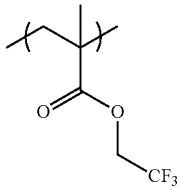

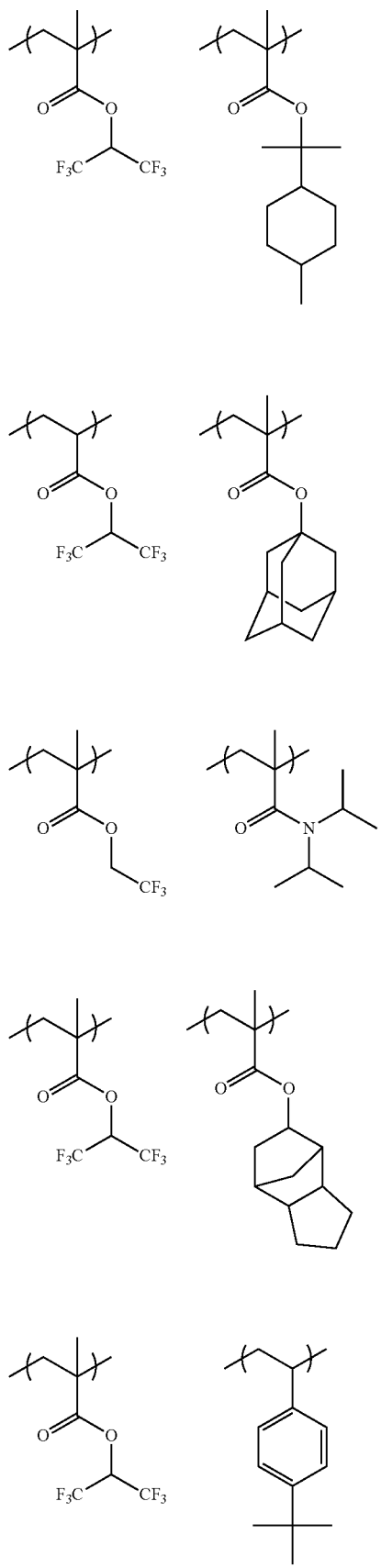
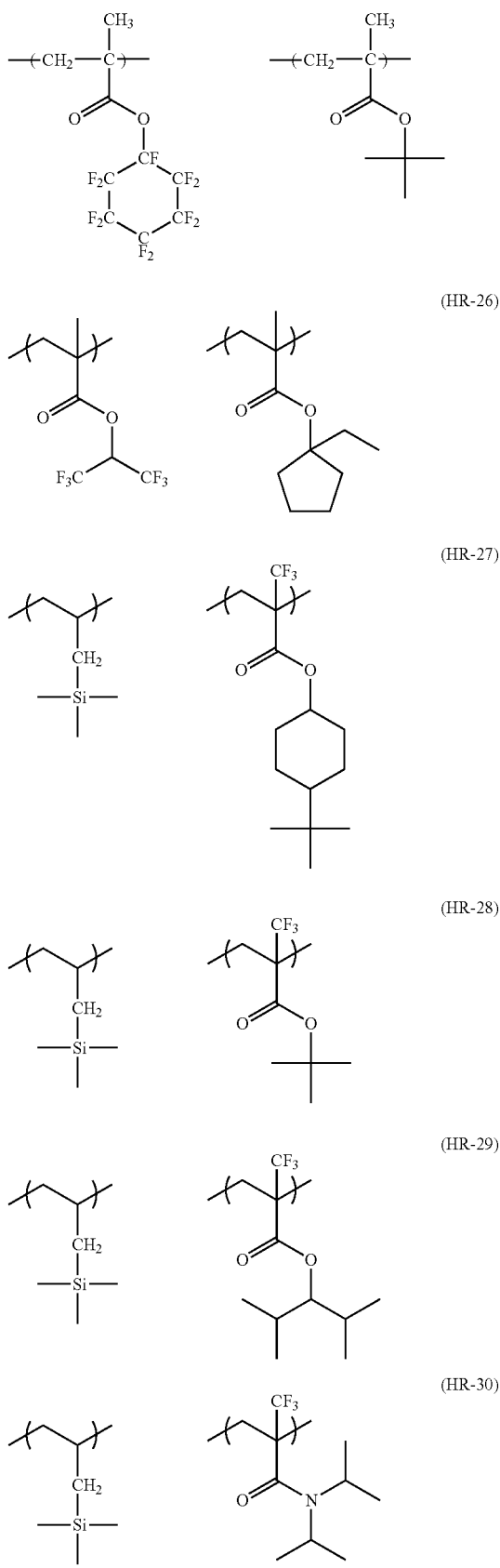

(HR-31) 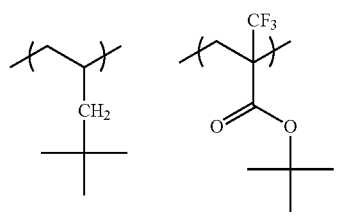 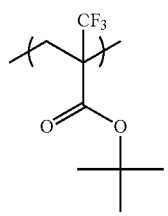
(HR-32) 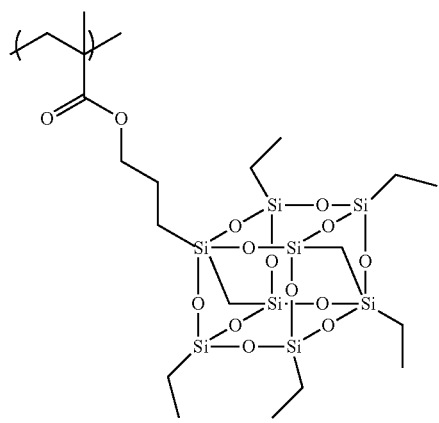
(HR-33) 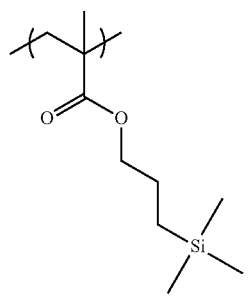 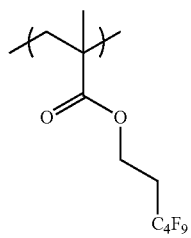
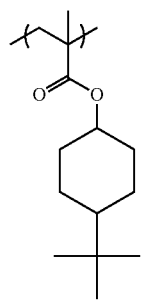
(HR-34) 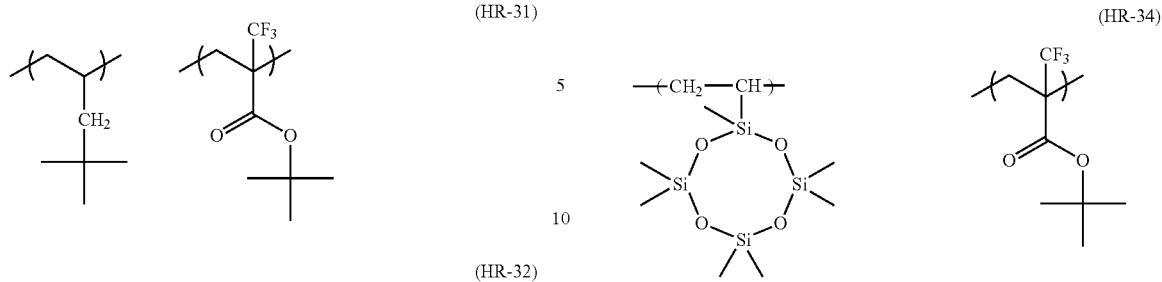 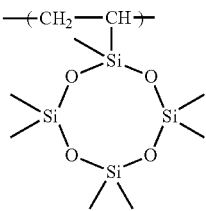
(HR-35) 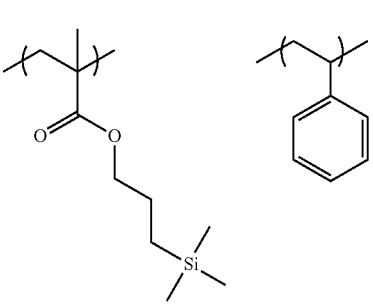
(HR-36) 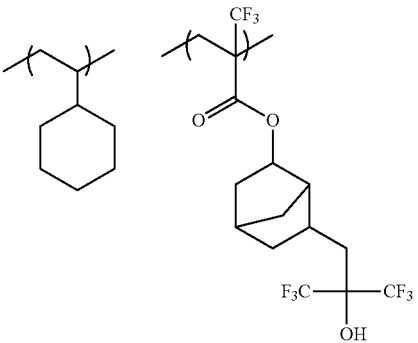
(HR-37) 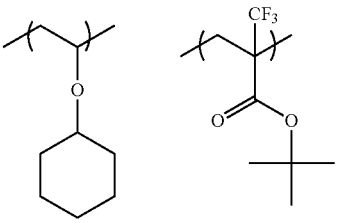
(HR-38) 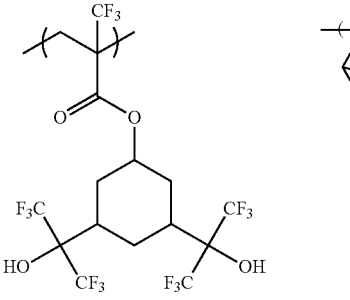 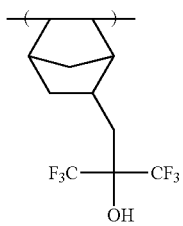

(HR-39) 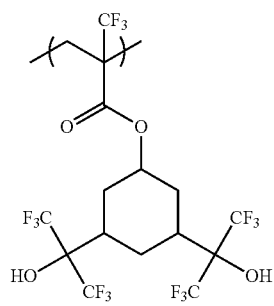 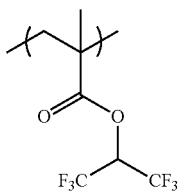
(HR-44) 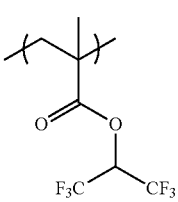 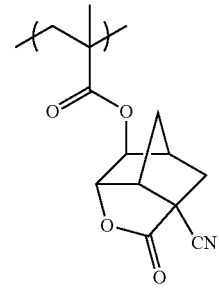
(HR-40) 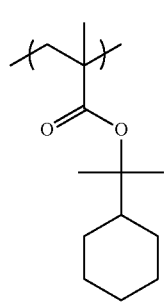 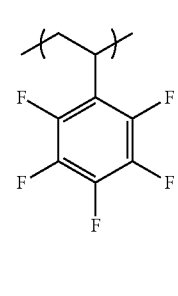
(HR-45) 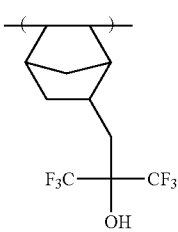
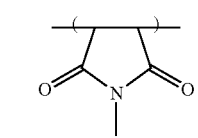
(HR-41) 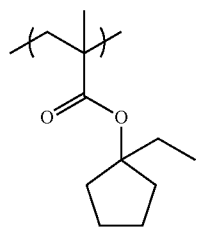 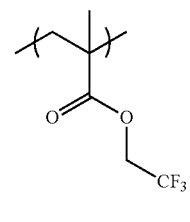
(HR-46) 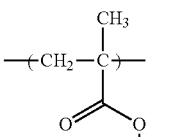 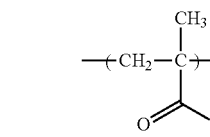
(HR-42) 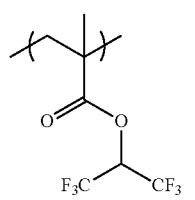 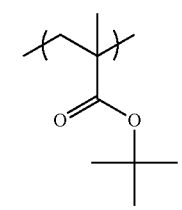
(HR-47) 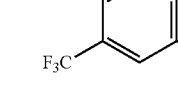 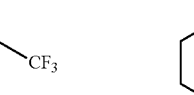
(HR-43) 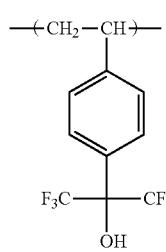 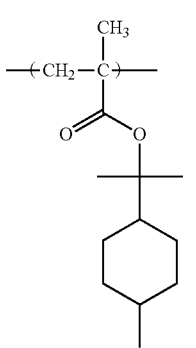
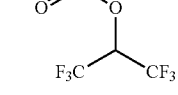 
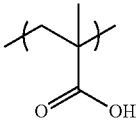

(HR-48)
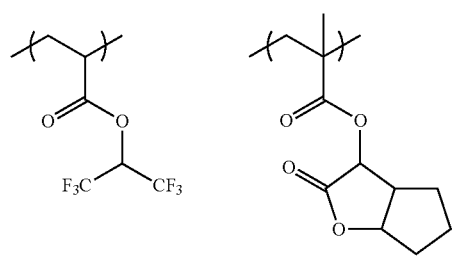
(HR-49)
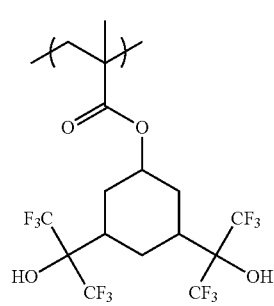
(HR-50)
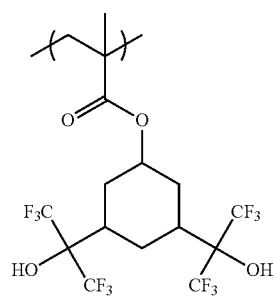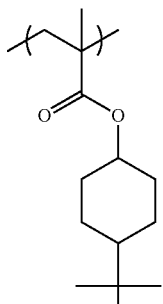
(HR-51)
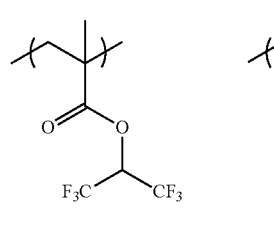
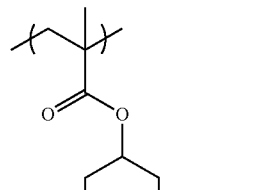
(HR-52)
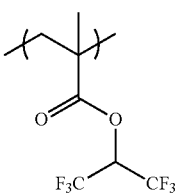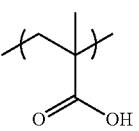
(HR-53)
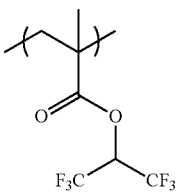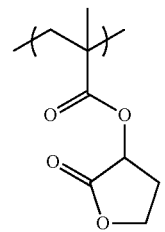
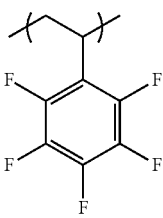
(HR-54)
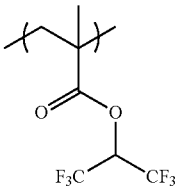
(HR-55)
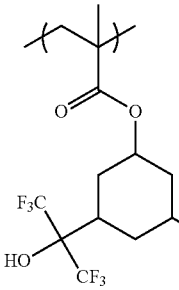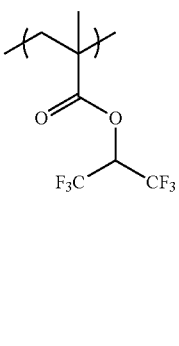

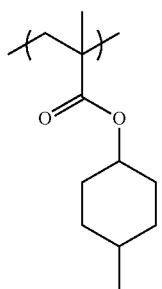
(HR-56)
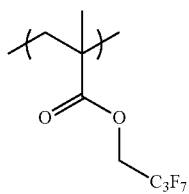
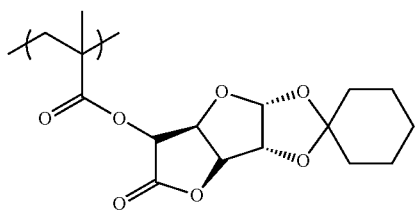
(HR-57)
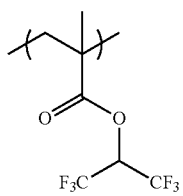
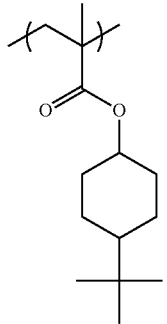
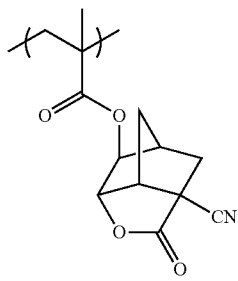
(HR-58)
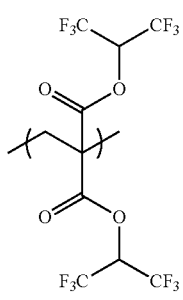
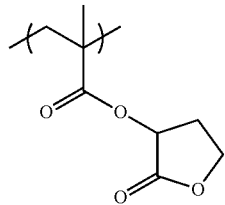
(HR-59)
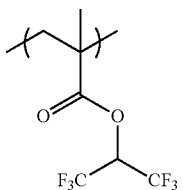
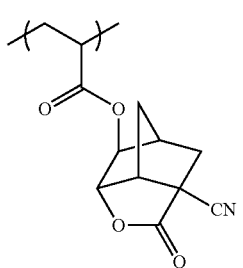
(HR-60)
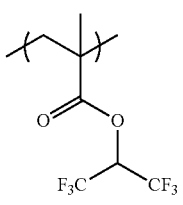
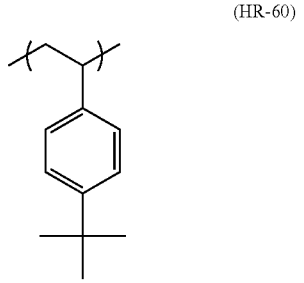
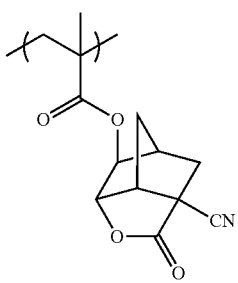
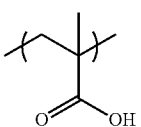
(HR-61)
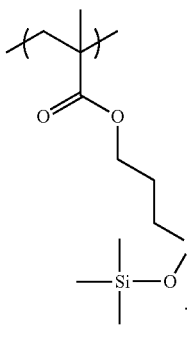
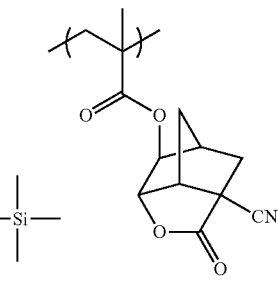
(HR-62)
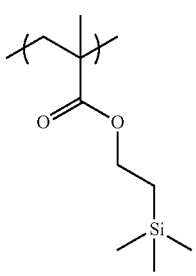
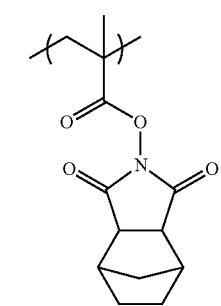

(HR-63)
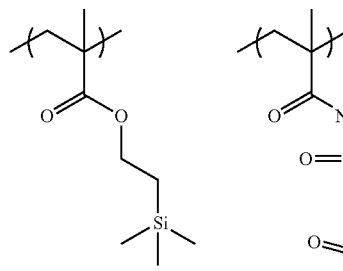
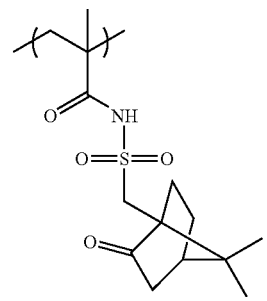
(HR-64)
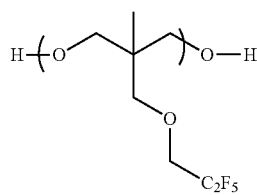
(HR-65)
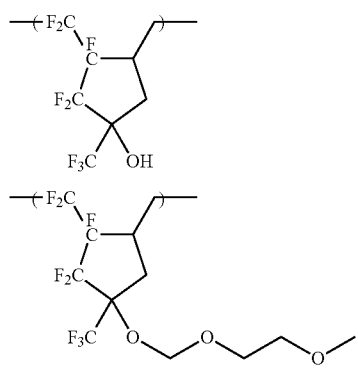
(HR-66)
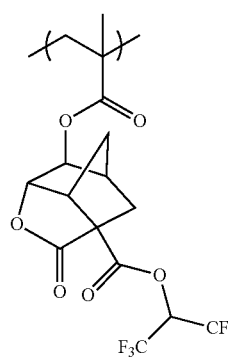
(HR-67)
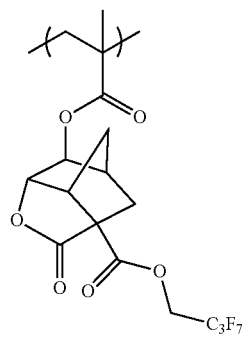
(HR-68)
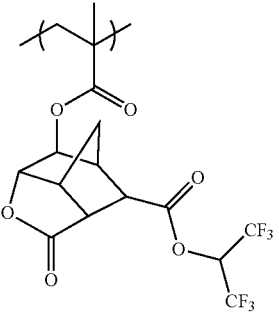
(HR-69)
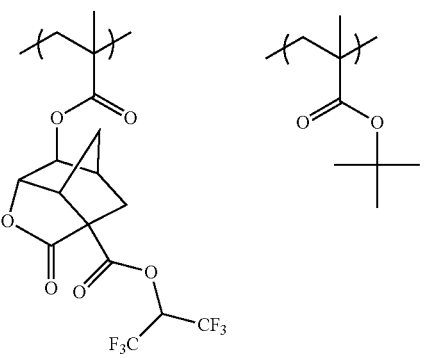
(HR-70)
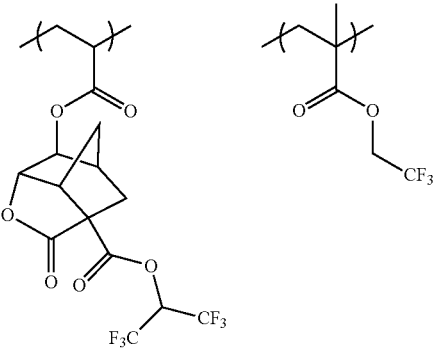
(HR-71)
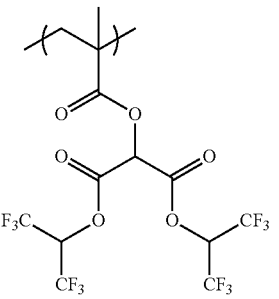
(HR-72)
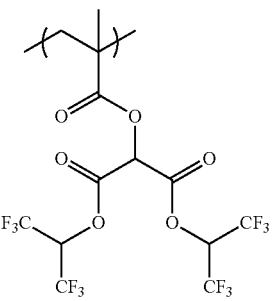

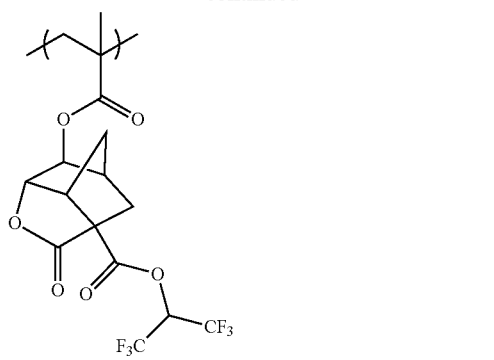
(HR-73)
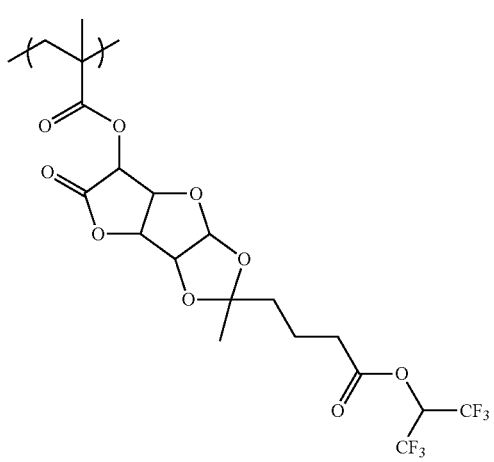
(HR-74)
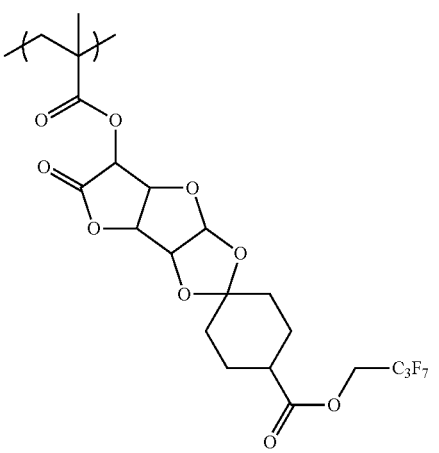
(HR-75)
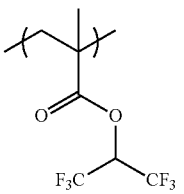
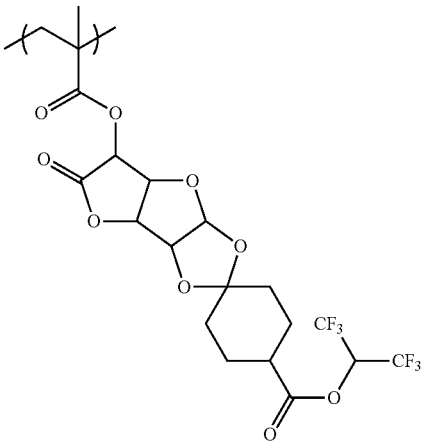
(HR-76)
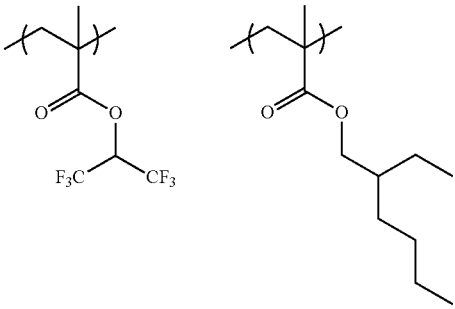

(HR-77)
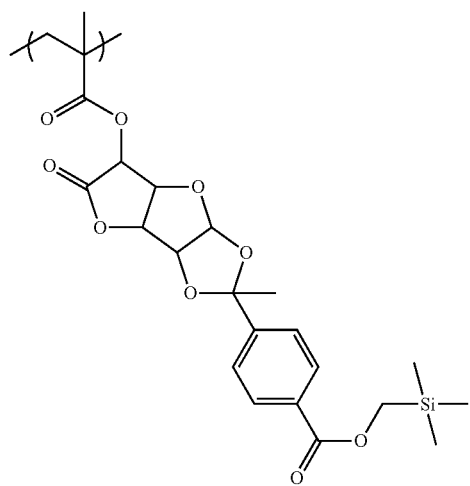
(HR-78)
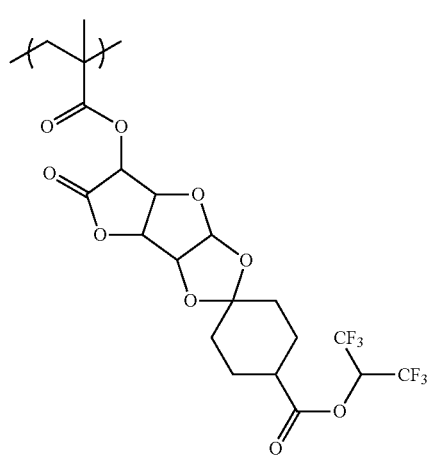
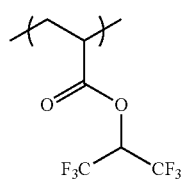
(HR-79)
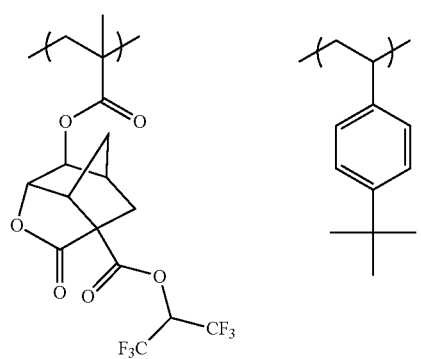
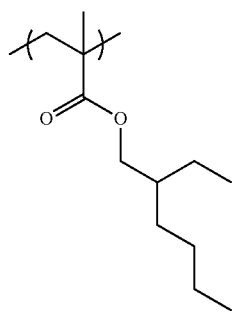
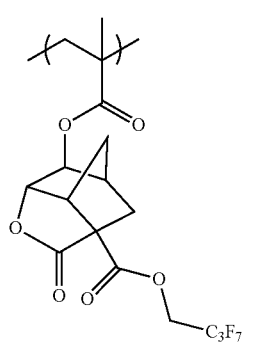
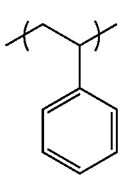
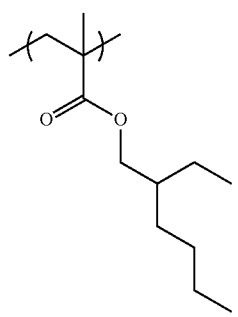
(HR-80)
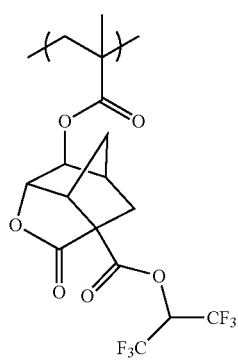
(HR-81)
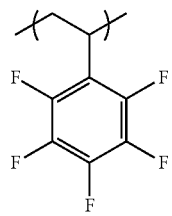
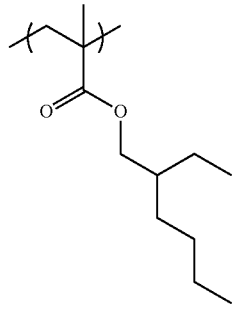

(HR-82)
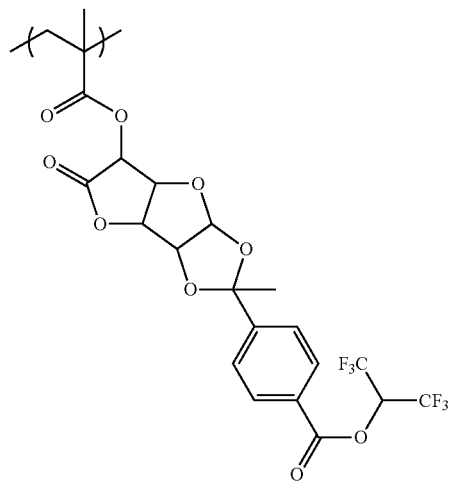
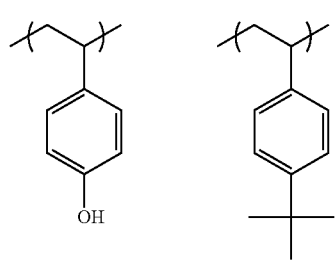
(HR-83)
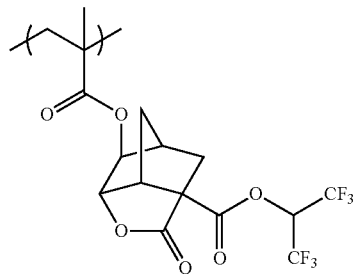
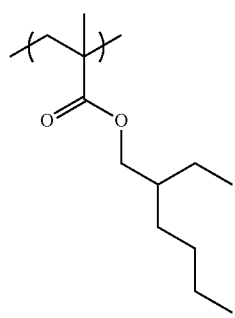
(HR-84)
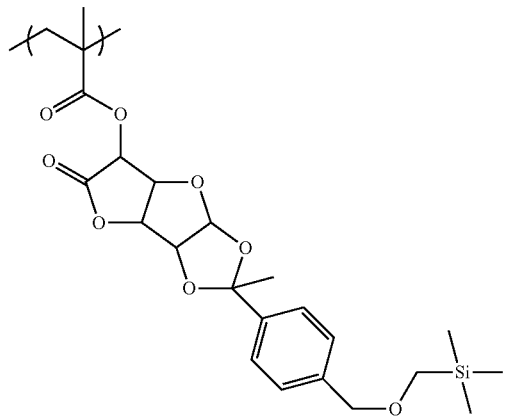
(HR-85)
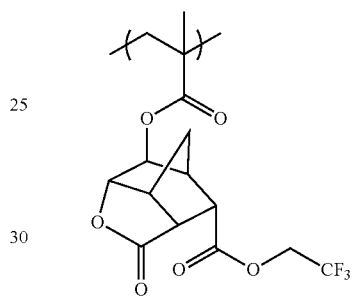
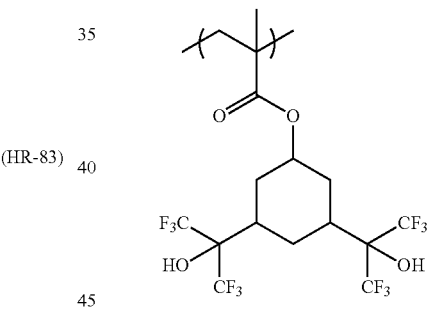
(HR-86)
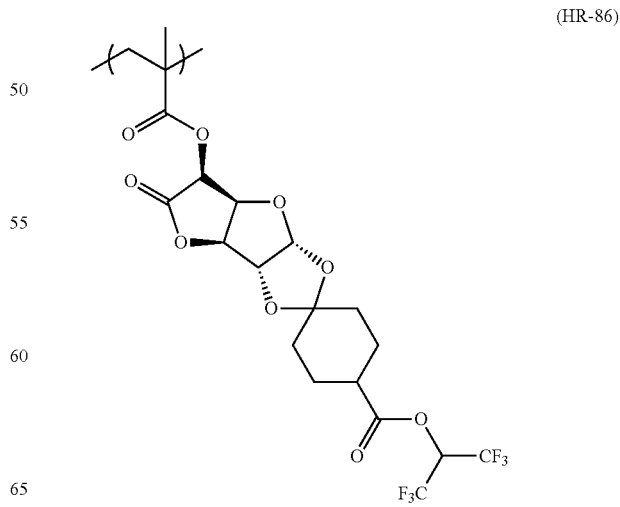

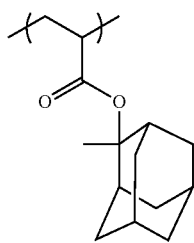
(HR-87)
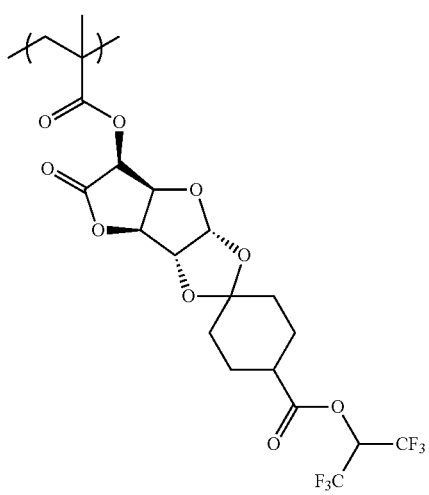
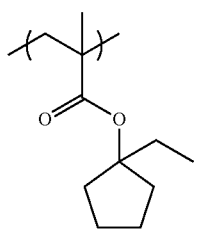
(HR-88)
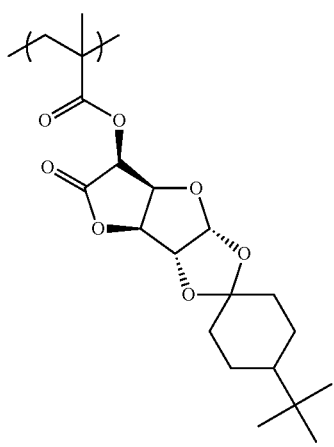
(HR-89)
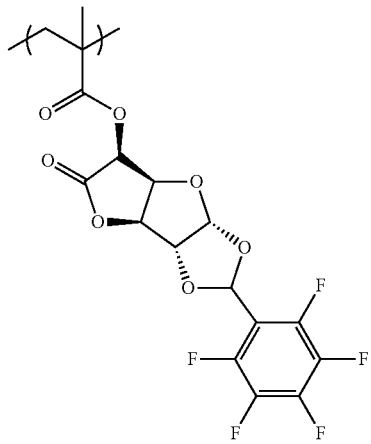
(HR-90)
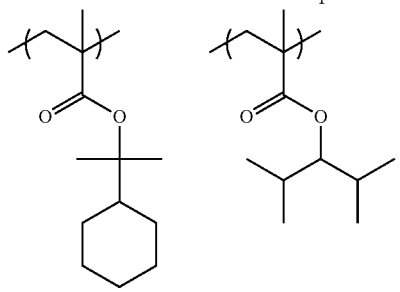
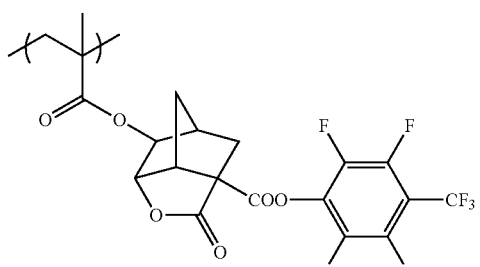
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |

-continued

| Resin | Composition | Mw | Mw/Mn |
|---|---|---|---|
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |
| HR-66 | 100 | 6000 | 1.5 |
| HR-67 | 100 | 6000 | 1.4 |
| HR-68 | 100 | 9000 | 1.5 |
| HR-69 | 60/40 | 8000 | 1.3 |
| HR-70 | 80/20 | 5000 | 1.4 |
| HR-71 | 100 | 9500 | 1.5 |
| HR-72 | 40/60 | 8000 | 1.4 |
| HR-73 | 55/30/5/10 | 8000 | 1.3 |
| HR-74 | 100 | 13000 | 1.4 |
| HR-75 | 70/30 | 8000 | 1.3 |
| HR-76 | 50/40/10 | 9500 | 1.5 |
| HR-77 | 100 | 9000 | 1.6 |
| HR-78 | 80/20 | 3500 | 1.4 |
| HR-79 | 90/8/2 | 13000 | 1.5 |
| HR-80 | 85/10/5 | 5000 | 1.5 |
| HR-81 | 80/18/2 | 6000 | 1.5 |
| HR-82 | 50/20/30 | 5000 | 1.3 |
| HR-83 | 90/10 | 8000 | 1.4 |
| HR-84 | 100 | 9000 | 1.6 |
| HR-85 | 80/20 | 15000 | 1.6 |
| HR-86 | 70/30 | 4000 | 1.42 |
| HR-87 | 60/40 | 8000 | 1.32 |
| HR-88 | 100 | 3800 | 1.29 |
| HR-89 | 100 | 6300 | 1.35 |
| HR-90 | 50/40/10 | 8500 | 1.51 |

Other Additives:

If necessary, dyes, plasticizers, surfactants other than the surfactants of component (H), photosensitizers, and compounds for expediting the dissolution of composition in a developing solution may be further added to the photosensitive composition in the present invention.

Compounds for expediting dissolution in a developing solution that can be used in the invention are low molecular weight compounds having a molecular weight of 1,000 or less and having two or more phenolic OH groups or one or more carboxyl groups. When carboxyl groups are contained, alicyclic or aliphatic compounds are preferred.

The preferred addition amount of these dissolution accelerating compounds is preferably from 2 to 50 mass % based on the resin of component (C) or the resin of component (E), and more preferably from 5 to 30 mass %. The amount is preferably 50 mass % or less in the point of restraint of development residue and prevention of pattern deformation in development.

These phenolic compounds having a molecular weight of 1,000 or less can be easily synthesized with referring to the methods disclosed, e.g., in JP-A-4-122938, JP-A-2-28531, U.S. Pat. No. 4,916,210, and EP 219294.

As the specific examples of the alicyclic or aliphatic compounds having a carboxyl group, carboxylic acid derivatives having a steroid structure, e.g., cholic acid, deoxycholic acid, and lithocholic acid, adamantanecarboxylic acid derivatives, adamantanedicarboxylic acid, cyclohexanecarboxylic acid, and cyclohexanedicarboxylic acid are exemplified, but the invention is not restricted to these compounds.

Pattern Forming Method:

The photosensitive composition in the invention is used by dissolving each of the above components in a prescribed organic solvent, preferably dissolving in a mixed solvent as described above, and coating the solution on a prescribed support as follows.

For example, the photosensitive composition is coated on a substrate such as the one used in the manufacture of precision integrated circuit element (e.g., silicon/silicon dioxide coating) by an appropriate coating method with a spinner or a coater, and dried, to thereby form a photosensitive film (resist film).

The photosensitive film is irradiated with actinic ray or radiation through a prescribed mask, preferably subjected to baking (heating), and then development. Thus, a good pattern can be obtained.

At the time of irradiation with actinic ray or radiation, exposure (immersion exposure) may be performed by filling a liquid (an immersion medium) having higher refractive index than that of air between a photosensitive film and a lens, by which resolution can be raised.

As actinic rays or radiation, infrared rays, visible rays, ultraviolet rays, far ultraviolet rays, X-rays and electron beams can be exemplified, and preferably far ultraviolet rays of wavelengths of 250 nm or less, and more preferably 220 nm or less. Specifically, a KrF excimer laser (248 nm), an ArF excimer laser (193 nm), an $F_2$ excimer laser (157 nm), X-rays and electron beams are exemplified, and ArF excimer lasers, $F_2$ excimer lasers, EUV (13 nm), and electron beams are preferred.

Immersion Exposure:

When the photosensitive composition in the invention is subjected to immersion exposure, it is preferred that the photosensitive composition is used in a thickness of from 30 to 250 nm in view of the improvement of resolution, and more preferably a thickness of from 30 to 100 nm. Such a desired thickness can be realized by setting the concentration of solids content in the photosensitive composition in a proper range and giving appropriate viscosity to thereby improve the coating property and film forming property.

The concentration of all the solids content in the photosensitive composition is generally from 1 to 10 mass %, more preferably from 1 to 8 mass %, and still more preferably from 1.0 to 6.0 mass %.

When the photosensitive composition in the invention is subjected to immersion exposure, the photosensitive composition is used by dissolving each of the above components in a prescribed organic solvent, preferably in a mixed solvent as described above, and coating the solution on a prescribed support as follows. When the photosensitive composition in the invention is subjected to immersion exposure, it is preferred to add the hydrophobic resin (HR) to the photosensitive composition.

That is, the photosensitive composition is coated on a substrate such as the one used in the production of precision integrated circuit elements (e.g., silicon/silicon dioxide coating) by an appropriate coating method with a spinner or a coater in an arbitrary thickness (generally from 30 to 500 nm). After coating, if necessary, a resist film is washed with the immersion liquid. The washing time is generally from 5 seconds to 5 minutes.

Subsequently, the coated resist is dried by spin or bake to form a resist film, and the resist film formed is subjected to exposure (immersion exposure) for pattern formation through a mask via an immersion liquid. For example, exposure is performed in the state of filling an immersion liquid between a resist film and an optical lens. The exposure dose can be optionally set, but is generally from 1 to 100 mJ/cm$^2$. After exposure, if necessary, the resist film is washed with the immersion liquid. The washing time is generally from 5 seconds to 5 minutes. After that, the resist film is preferably subjected to spin or/and bake, development and rinsing, whereby a good pattern can be obtained. It is preferred to perform bake, and the temperature of bake is generally from 30 to 300° C. The time from exposure to bake process is preferably shorter from the viewpoint of PED.

The exposure rays here are far ultraviolet rays of wavelengths of preferably 250 nm or less, and more preferably 220 nm or less. Specifically, a KrF excimer laser (248 nm), an ArF excimer laser (193 nm), an $F_2$ excimer laser (157 nm), and X-rays are exemplified.

Incidentally, the variation of performances of a resist at the time when subjected to immersion exposure is thought to be resulting from the contact of a resist surface with an immersion liquid.

An immersion liquid for use in immersion exposure is described below.

An immersion liquid for use in immersion exposure preferably has a temperature coefficient of refractive index as small as possible so as to be transparent to the exposure wavelength and to hold the distortion of an optical image reflected on the resist at the minimum. In particular, when the exposure light source is an ArF excimer laser (wavelength: 193 nm), it is preferred to use water as the immersion liquid for easiness of availability and capable of handling easily, in addition to the above points.

It is also possible to use a medium having a refractive index of 1.5 or more for capable of improving the refractive index. The medium may be an aqueous solution or an organic solvent.

When water is used as the immersion liquid, to reduce the surface tension of water and to increase the surface activity, a trace amount of additive (a liquid) that does not dissolve the resist layer on a wafer and has a negligible influence on the optical coating of the underside of a lens element may be added. As such additives, aliphatic alcohols having a refractive index almost equal to the refractive index of water are preferred, specifically methyl alcohol, ethyl alcohol and isopropyl alcohol are exemplified. By adding an alcohol having a refractive index almost equal to that of water, even if the alcohol component in water is evaporated and the concentration of the content is changed, the refractive index variation of the liquid as a whole can be made extremely small. On the other hand, when impurities opaque to the light of 193 nm or substances largely different from water in a refractive index are mixed, these substances bring about the distortion of an optical image reflected on the resist. Accordingly the water to be used is preferably distilled water. Further, pure water filtered through an ion exchange filter may be used.

The electric resistance of water is preferably 18.3 MΩ·cm or higher, and TOC (total organic material concentration) is preferably 20 ppb or lower, and it is preferred that water has been subjected to deaeration treatment.

It is possible to heighten lithographic performance by increasing the refractive index of an immersion liquid. From such a point of view, additives capable of increasing the refractive index may be added to water, or heavy water ($D_2O$) may be used in place of water.

A film hardly soluble in an immersion liquid (hereinafter also referred to as "topcoat") may be provided between a resist film by the positive resist composition of the invention and an immersion liquid so as not to bring the resist film into direct contact with the immersion liquid. The necessary functions required of the topcoat are the aptitude for coating on the upper layer of a resist, the transparency to radiation, in particular the transparency to the ray of 193 nm, and the insolubility in an immersion liquid. It is preferred that the topcoat is not mixed with a resist and can be coated uniformly on a resist upper layer.

From the viewpoint of the transparency to 193 nm, a polymer not containing an aromatic group is preferred as the topcoat. Specifically, hydrocarbon polymers, acrylic ester polymers, polymethacrylic acid, polyacrylic acid, polyvinyl ether, silicon-containing polymers, and fluorine-containing polymers are exemplified. The hydrophobic resin (HR) mentioned above is also preferable as the topcoat. Considering that impurities eluting from a topcoat to the immersion liquid contaminate the optical lens, the residual monomer components of the polymer contained in the topcoat is preferably less.

When the topcoat is peeled off, a developing solution may be used, or a remover may be used separately. As the remover, a solvent low in penetration into a resist is preferred. In view of capable of performing a peeling process at the same time with the development process of a resist, it is preferred that the topcoat can be peeled off by an alkali developing solution. From the viewpoint of performing peeling with an alkali developing solution, the topcoat is preferably acidic, but from the viewpoint of non-intermixture with the resist, it may be neutral or alkaline.

Resolution increases when there is no difference in the refractive indexes between the topcoat and the immersion liquid. When water is used as the immersion liquid in ArF excimer laser (wavelength: 193 nm) exposure, it is preferred that the refractive index of the topcoat for ArF immersion exposure is nearer the refractive index of the immersion liquid. For bringing the refractive index of the topcoat nearer to that of the immersion liquid, it is preferred for the topcoat to contain a fluorine atom. Further, from the viewpoint of the transparency and refractive index, the thickness of the topcoat is preferably thinner.

It is preferred that a topcoat should not be mixed with a resist, and further not mixed with an immersion liquid. From this point of view, when water is used as the immersion liquid, the solvent for a topcoat is preferably hardly soluble in the solvent of the resist and a nonaqueous medium. Further, when an immersion liquid is an organic solvent, the topcoat may be aqueous or nonaqueous.

A resist composition in the invention as formed to a resist film has the receding contact angle of water to the resist film of preferably 65° or more. Here, the receding contact angle is the angle under normal temperature and atmospheric pressure. The receding contact angle is the contact angle of going back at the time when a resist film is inclined and a droplet begins to drop.

In a development process, a developing solution is used as follows. As the alkali developing solution of a resist composition, alkaline aqueous solutions of inorganic alkalis, e.g., sodium hydroxide, potassium hydroxide, sodium carbonate, sodium silicate, sodium metasilicate, aqueous ammonia, etc., primary amines, e.g., ethylamine, n-propylamine, etc., secondary amines, e.g., diethylamine, di-n-butylamine, etc., tertiary amines, e.g., triethylamine, methyldiethylamine, etc., alcohol amines, e.g., dimethylethanolamine, triethanolamine, etc., quaternary ammonium salts, e.g., tetramethylammonium hydroxide, tetraethylammonium hydroxide, etc., and cyclic amines, e.g., pyrrole, piperidine, etc., can be used.

An appropriate amount of alcohols and surfactants may be added to these alkali developing solutions.

The alkali concentration of an alkali developing solution is generally from 0.1 to 20 mass %.

The pH of an alkali developing solution is generally from 10.0 to 15.0.

EXAMPLE

The invention will be described with reference to examples, but the invention is not limited thereto.

Synthesis of Compound (A)

Synthesis Example 1

Synthesis of Compound (A-1)

A mixture comprising 4.0 g (6.91 mmol) of 4-hydroxyphenyldiphenylsulfonium 1,1,2,2,3,3,4,4,4-nonafluorobutane-1-sulfonate, 1.71 g (10.37 mmol) of 3-bromo-dihydrofuran-2(3H)-one, 2.87 g of potassium carbonate, and 30 ml of acetone was refluxed under nitrogen current for 7 hours. To the reaction mixture were added 200 ml of water and 200 ml of ethyl acetate, the organic layer was washed with water, a saturated sodium chloride aqueous solution, and water in the order, and the organic layer was dried with sodium sulfate. The solvent was concentrated, and the residue was purified by column chromatography (SiO$_2$, chloroform/methanol: 6/1) to obtain 2.55 g of brown and oily objective compound (A-1).

$^1$H-NMR (400 MHz, CDCl$_3$) δ 2.45 (m, 1H), 2.99 (m, 1H), 4.56 (m, 1H), 5.33 (t, 1H), 7.41 (d, 2H), 7.63-7.77 (m, 15H)

$^{19}$F-NMR (400 MHz, CDCl$_3$) δ –126 (s, 2F), –122 (s, 2F), –115 (s, 2F), –81 (s, 3F)

Synthesis Example 2

Synthesis of Compound (A-34)

A mixture comprising 13.65 g (90.9 mmol) of 3-phenylpropanoic acid, 15.0 g (90.9 mmol) of 3-bromo-dihydrofuran-2(3H)-one, 37.7 g of potassium carbonate, and 150 ml of acetone was refluxed under nitrogen current for 9 hours. To the reaction mixture were added 200 ml of water and 400 ml of ethyl acetate, the organic layer was washed with water, a saturated sodium hydrogencarbonate aqueous solution, a saturated sodium chloride aqueous solution, and water in the order, and the organic layer was dried with sodium sulfate. The solvent was concentrated to obtain 24.3 g of brown and oily tetrahydro-2-oxofuran-3-yl 3-phenylpropanoate. The oily compound (5.00 g) (21.3 mmol), 4.32 g (21.3 mmol) of diphenyl sulfoxide, 6 ml of trifluoroacetic anhydride, and 6.7 g (22.3 mmol) of 1,1,2,2,3,3,4,4,4-nonafluorobutane-1-sulfonic acid were stirred with ice-cooling for 3 hours, and further at room temperature for 2 hours. Chloroform (200 ml) was added to the reaction solution, the organic layer was washed with water, and the residue was purified by column chromatography (SiO$_2$, chloroform/methanol: 10/1) to obtain 8.2 g of oily compound (A-34).

$^1$H-NMR (400 MHz, CDCl$_3$) δ 2.30 (m, 1H), 2.68 (m, 1H), 2.80 (t, 2H), 3.08 (t, 2H), 4.28 (m, 1H), 4.47 (m, 1H), 5.43 (t, 1H), 7.56 (d, 2H), 7.65-7.70 (m, 15H)

$^{19}$F-NMR (400 MHz, CDCl$_3$) δ 126 (s, 2F), –122 (s, 2F), –115 (s, 2F), –81 (s, 3F)

Resin (C):

The structure, molecular weight and degree of molecular weight dispersion of each resin (C) used in Examples are shown below. The number on the right hand of each repeating unit is a molar ratio, and the rest is the same.

(RA-1)

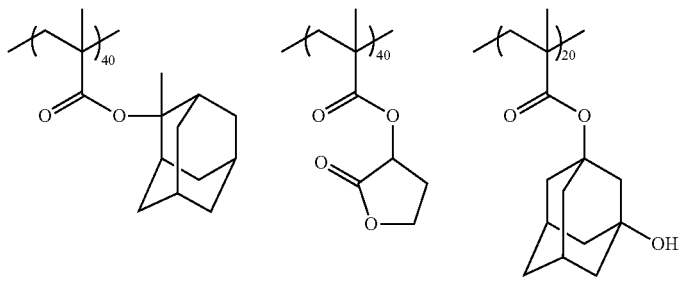

Mw = 10700
Mw/Mn = 1.81

-continued
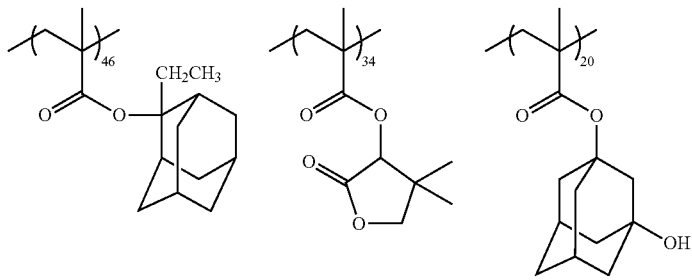
(RA-2)
Mw = 9400
Mw/Mn = 1.78
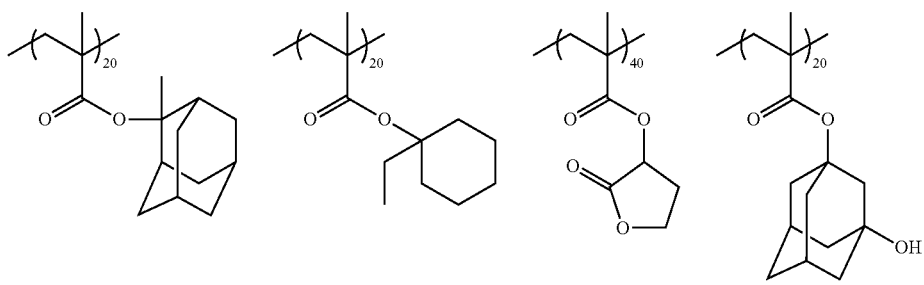
(RA-3)
Mw = 13700
Mw/Mn = 1.89
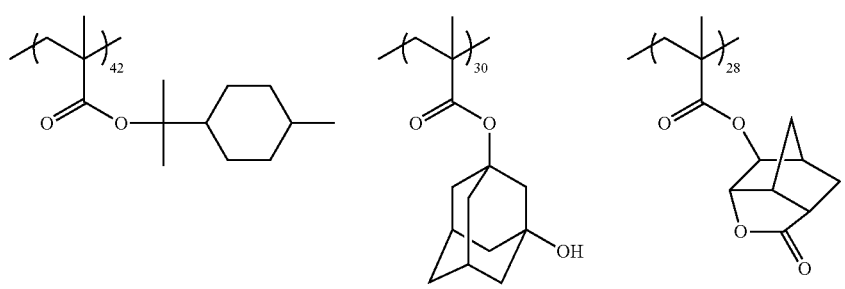
(RA-4)
Mw = 10300
Mw/Mn = 1.90
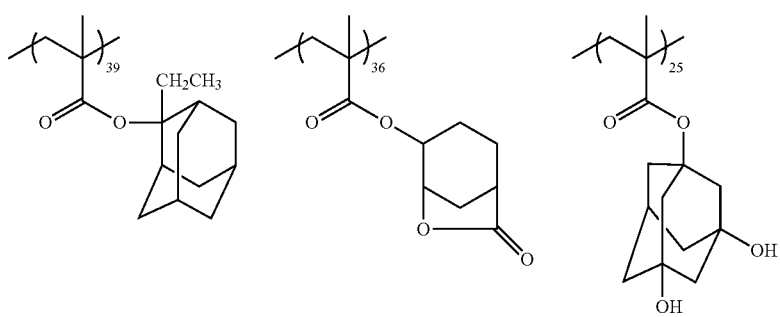
(RA-5)
Mw = 8900
Mw/Mn = 1.80
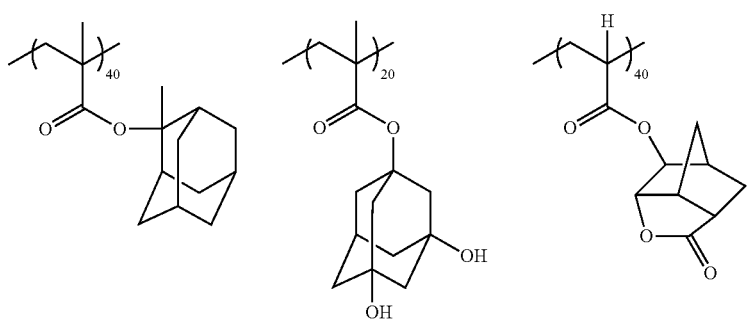
(RA-6)
Mw = 7900
Mw/Mn = 1.73

-continued
(RA-7)
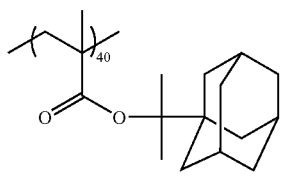 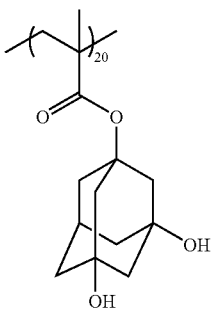 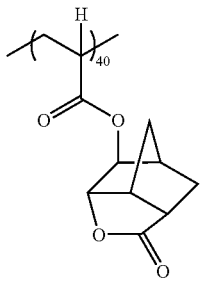
Mw = 8300
Mw/Mn = 1.81
(RA-8)
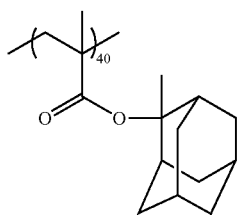 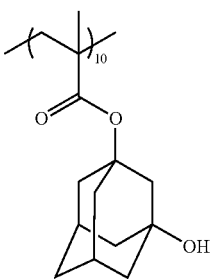 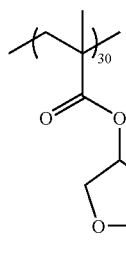 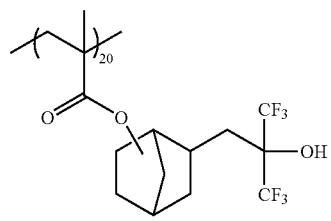
Mw = 15600
Mw/Mn = 2.03
(RA-9)
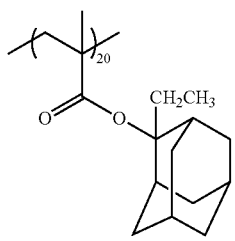 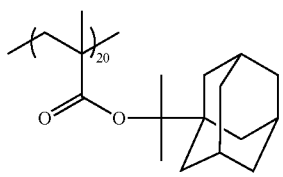 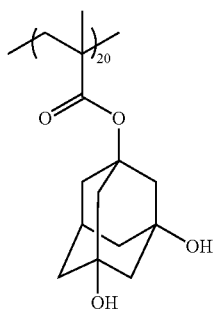 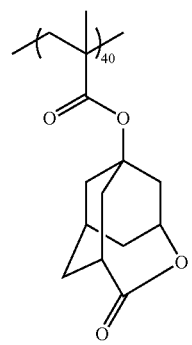
Mw = 9800
Mw/Mn = 1.86
(RA-10)
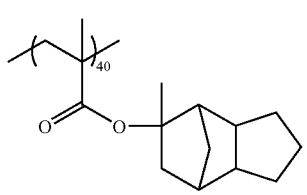 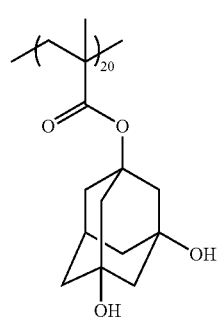 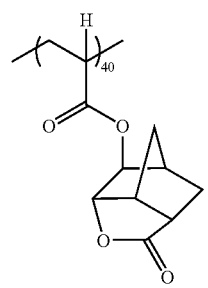
Mw = 18300
Mw/Mn = 2.10
(RA-11)
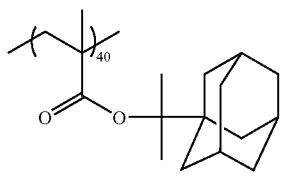 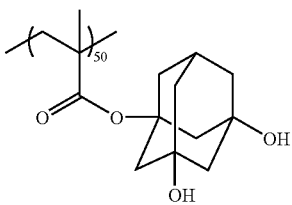 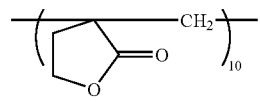
Mw = 6900
Mw/Mn = 1.71

-continued
(RA-12)
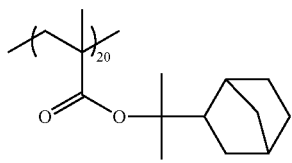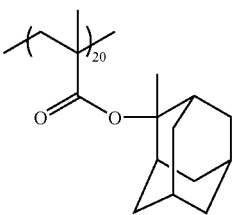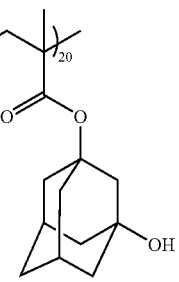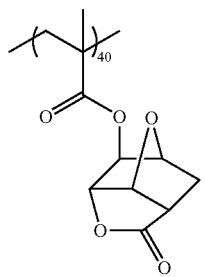
Mw = 8300
Mw/Mn = 1.81
(RA-13)
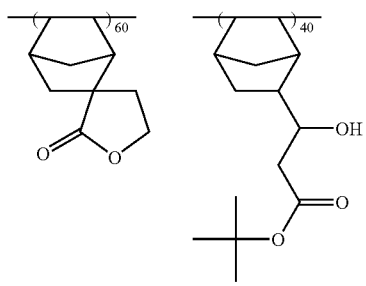
Mw = 9600
Mw/Mn = 1.81
(RA-14)
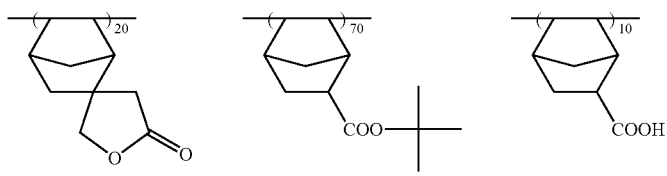
Mw = 5800
Mw/Mn = 1.69
(RA-15)
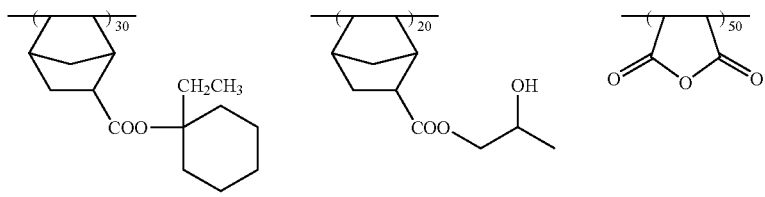
Mw = 4700
Mw/Mn = 1.70
(RA-16)
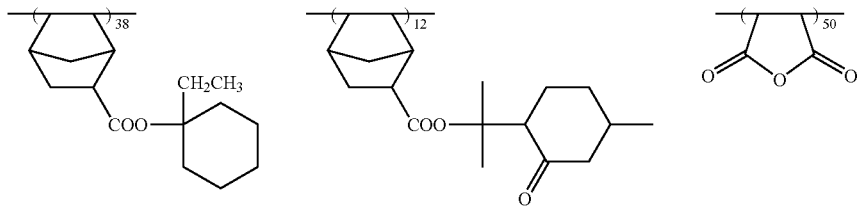
Mw = 8900
Mw/Mn = 1.81
(RA-17)
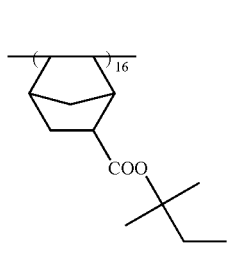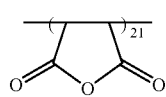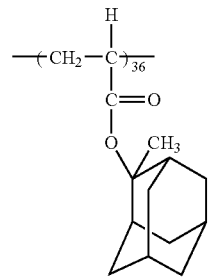
Mw = 13900
Mw/Mn = 1.98

-continued
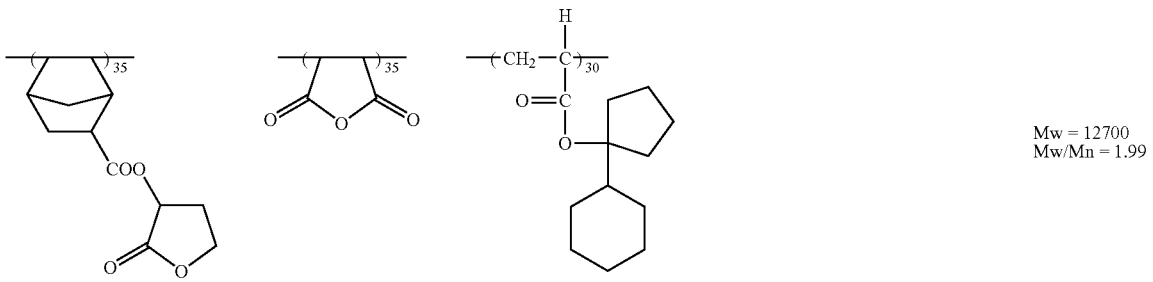
(RA-18)
Mw = 12700
Mw/Mn = 1.99
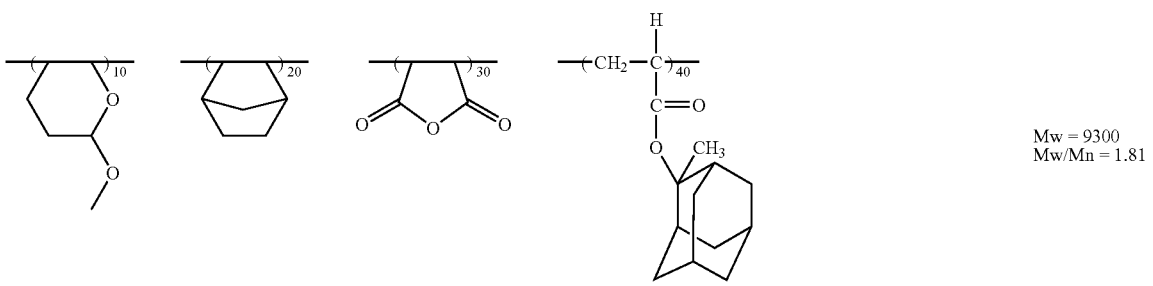
(RA-19)
Mw = 9300
Mw/Mn = 1.81
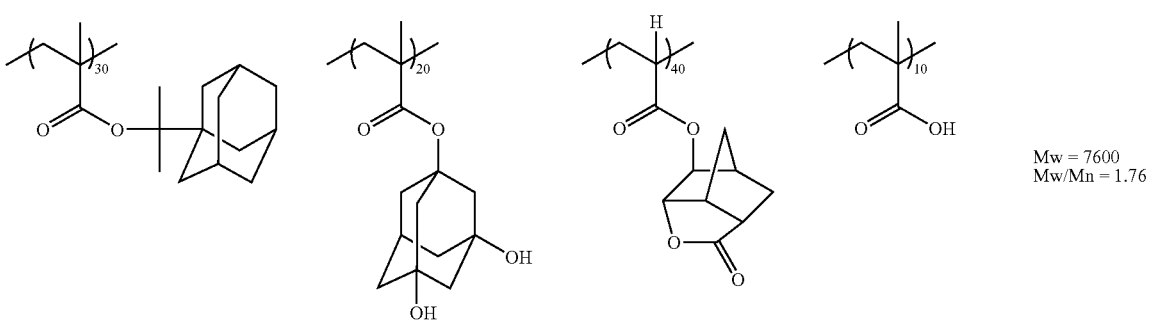
(RA-20)
Mw = 7600
Mw/Mn = 1.76
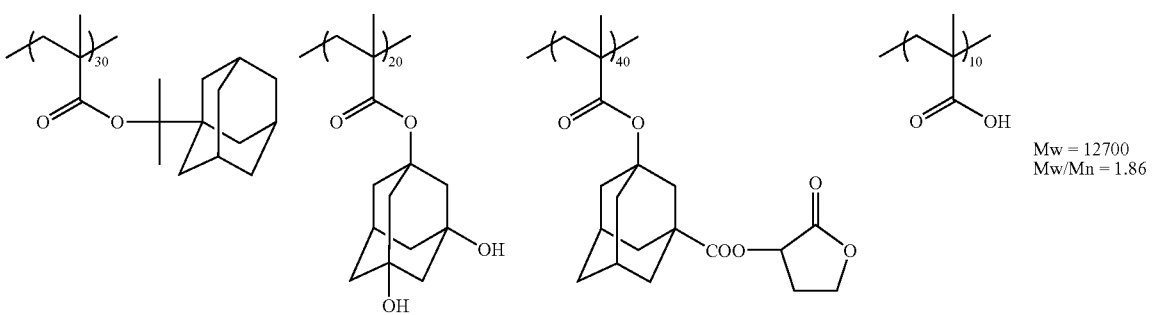
(RA-21)
Mw = 12700
Mw/Mn = 1.86
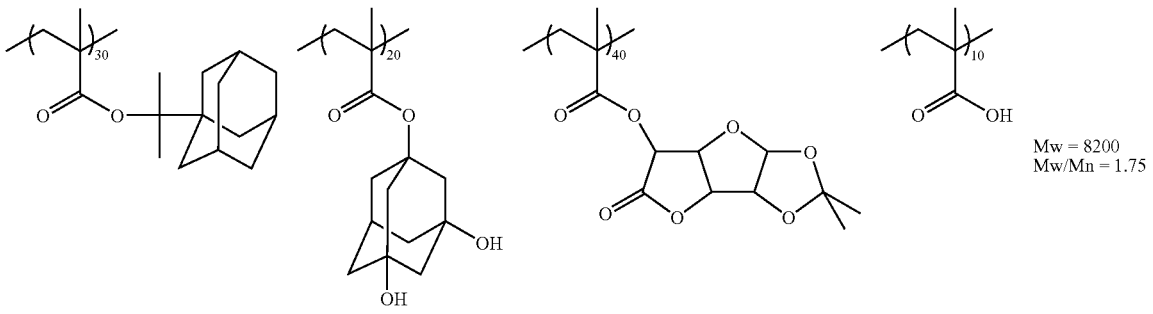
(RA-22)
Mw = 8200
Mw/Mn = 1.75

-continued
(RA-23)
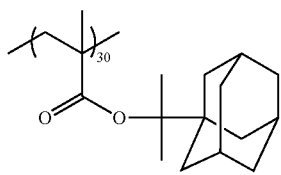 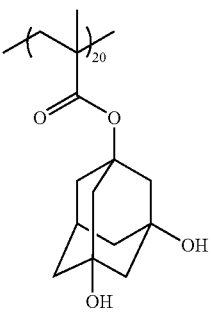 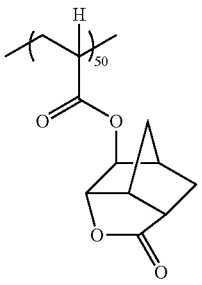
Mw = 8500
Mw/Mn = 1.77
(RA-24)
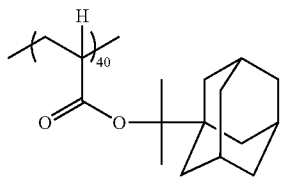 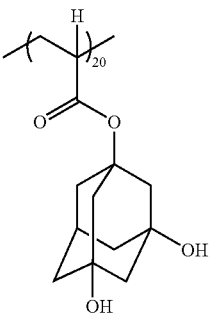 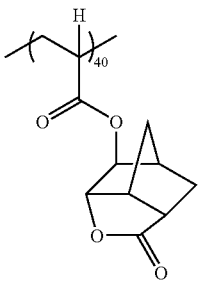
Mw = 18900
Mw/Mn = 2.13
(RA-25)
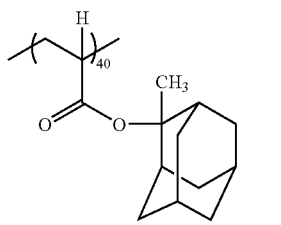 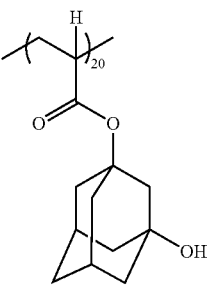 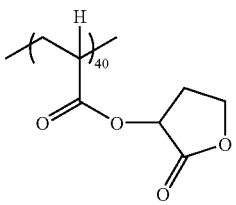
Mw = 20800
Mw/Mn = 2.25
(RA-26)
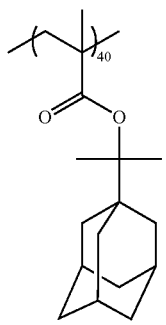 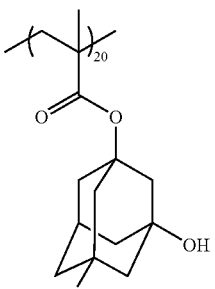 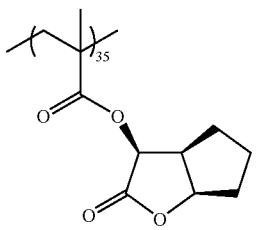 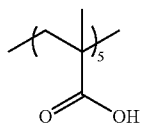
Mw = 12000
Mw/Mn = 2.1
(RA-27)
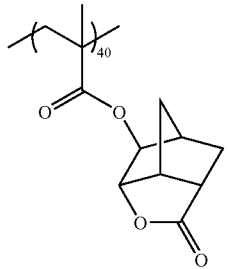 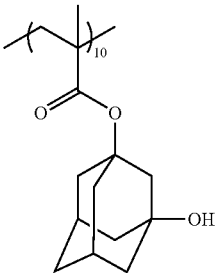 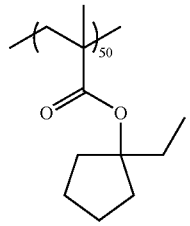
Mw = 8700
Mw/Mn = 1.55

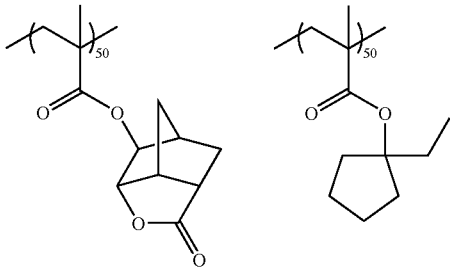

(RA-28)

Mw = 6500
Mw/Mn = 1.56

Examples 1 to 19 and Comparative Examples 1 to 5 and Examples 56 to 73

Preparation of Resist

A solution having the concentration of solids content of 12 mass % was prepared by dissolving the components shown in Table 2 below in the solvent shown in Table 2, and a positive resist solution was prepared by filtrating the above-prepared solution through a polytetrafluoroethylene filter or a polyethylene filter having a pore size of 0.1 μm. The thus prepared positive resist solution was evaluated as follows. The results obtained are shown in Table 2.

Evaluation of Resist:

Exposure Condition (1)

An antireflection film DUV-42 (manufactured by Brewer Science) was uniformly coated on a silicone substrate subjected to hexamethyldisilazane treatment in a thickness of 600 Å by a spin coater, and dried on a hot plate at 100° C. for 90 seconds, and then dried by heating at 190° C. for 240 seconds. After that, each positive resist solution was coated thereon by a spin coater and dried at 120° C. for 90 seconds to form a resist film having a thickness of 0.25 μm.

The resist film was subjected to exposure through a mask with an ArF excimer laser stepper (NA: 0.6, manufactured by ISI Co.), and heated on a hot plate at 120° C. for 90 seconds just after exposure. Further, the resist film was developed with a 2.38 mass % tetramethylammonium hydroxide aqueous solution at 23° C. for 60 seconds, rinsed with pure water for 30 seconds, and then dried, whereby a line pattern was formed.

Exposure Condition (2)

In condition (2), a resist pattern was formed by immersion exposure with pure water.

An organic antireflection film ARC29A (manufactured by Nissan Chemical Industries, Ltd.) was coated on a silicon wafer, and the coated layer was baked at 205° C. for 60 seconds to form an antireflection film having a thickness of 78 nm. The positive resist solution prepared was coated on the antireflection film and baked at 120° C. for 60 seconds, whereby a resist film having a thickness of 250 nm was formed. The obtained wafer was subjected to pattern exposure with an ArF excimer laser immersion scanner (NA: 0.75). Super pure water of impurities of 5 ppb or less was used as the immersion liquid. After that, the resist film was heated at 120° C. for 60 seconds, developed with a 2.38 mass % tetramethylammonium hydroxide aqueous solution for 30 seconds, rinsed with pure water, and then dried by spinning to obtain a resist pattern.

Exposure Condition (3)

An organic antireflection film, ARC29SR (produced by Nissan Chemical Industries, Ltd.), was coated on a silicon wafer and baked at 205° C. for 60 seconds to form an antireflection film having a film thickness of 95 nm, and the positive resist composition prepared was coated thereon and baked at 85° C. for 60 seconds to form a resist film having a film thickness of 100 nm. The obtained wafer was exposed through a 6% halftone mask having a 1:1 line-and-space pattern with a line width of 48 nm by using an ArF excimer laser immersion scanner (XT-1700Fi, manufactured by ASML, NA: 1.20, σo/σi=0.94/0.74). As for the immersion liquid, ultrapure water was used. Thereafter, the wafer was heated at 90° C. for 60 seconds, developed with an aqueous tetramethylammonium hydroxide solution (2.38 mass %) for 30 seconds, rinsed with pure water and spin-dried to obtain a resist pattern.

In Examples 1 to 19 and Comparative Examples 1 to 5, resist patterns formed by exposure conditions (1) and (2) were evaluated as follows. In Examples 56 to 73, resist patterns formed by exposure condition (3) were evaluated as follows.

Pattern Profile:

In exposure conditions (1) and (2), taking the exposure amount required to reproduce the mask pattern of line and space of line width 90 nm as the optimal exposure amount, a profile at the optimal exposure amount was observed with a scanning electron microscope (SEM).

In exposure condition (3), taking the exposure amount required to reproduce the mask pattern of line and space of line width 48 nm as the optimal exposure amount, a profile at the optimal exposure amount was observed with a scanning electron microscope (SEM).Line edge roughness:

In regard to the edge of the range of 5 μm in the machine direction of the line pattern, the distance from the intrinsic base line of the edge was measured at 50 points with an SEM (S-8840, manufactured by Hitachi, Ltd.), and the standard deviation was found, from which 3σ was computed. The smaller the value, the better is the performance.

TABLE 2

ArF Positive

| Ex. No. | Compound (A) (g) | Acid Generator Used in Combination (g) | Resin (10 g) | Basic Compound (g) | Surfactant (0.03 g) | Solvent (mass ratio) | Dissolution Inhibiting Compound (g) | Exposure Condition (1) Pattern Profile | Exposure Condition (1) Line Edge Roughness (nm) | Exposure Condition (2) Pattern Profile | Exposure Condition (2) Line Edge Roughness (nm) |
|---|---|---|---|---|---|---|---|---|---|---|---|
| Ex. 1 | A-1 (0.3) | z38 (0.3) | RA-20 | PEA/TPA (0.01/0.02) | W-4 | A1/B1 (60/40) | | Rectangle | 4.0 | Rectangle | 4.5 |
| Ex. 2 | A-1 (0.2) | z60 (0.3) z38 (0.4) | RA-20 | PEA/DIA (0.01/0.02) | W-4 | A1/B1 (80/20) | LCB (0.2) | Rectangle | 4.1 | Rectangle | 3.7 |
| Ex. 3 | A-3 (0.2) | z68 (0.4) | RA-22 | PEA (0.02) | W-4 | A1/B1 (60/40) | | Rectangle | 6.4 | Rectangle | 3.2 |
| Ex. 4 | A-5 (0.3) | z78 (0.3) | RA-20 | DIA (0.02) | W-4 | A1/B2 (80/20) | | Rectangle | 5.7 | Rectangle | 3.4 |
| Ex. 5 | A-7 (0.2) | z60 (0.4) | RA-24 | PEA/DIA (0.02/0.02) | W-4 | A1/B2 (80/20) | | Rectangle | 6.4 | Rectangle | 3.7 |
| Ex. 6 | A-16 (0.3) | z34 (0.4) | RA-25 | PEA/DIA (0.01/0.02) | W-4 | A1/B1 (60/40) | | Rectangle | 3.4 | Rectangle | 4.5 |
| Ex. 7 | A-22 (0.3) | z66 (0.3) | RA-24 | PEA/DIA (0.02/0.02) | W-4 | A1/B1 (80/20) | | Rectangle | 4.0 | Rectangle | 2.5 |
| Ex. 8 | A-31 (0.4) | z65 (0.4) | RA-4 | PEA (0.02) | W-4 | A1/A3 (60/40) | | Rectangle | 4.3 | Rectangle | 3.4 |
| Ex. 9 | A-4 (0.2) | z63 (0.15) | RA-23 | PEA (0.02) | W-2 | A1/B1 (70/30) | LCB (0.3) | Rectangle | 5.0 | Rectangle | 2.8 |
| Ex. 10 | A-39 (0.3) | z63 (0.3) | RA-20 | PEA (0.02) | W-4 | A1/A4 (60/40) | | Rectangle | 3.0 | Rectangle | 3.4 |
| Ex. 11 | A-34 (0.2) | z38 (0.4) z63 (0.4) | RA-22 | PEA (0.02) | W-4 | A1/B1 (60/40) | LCB (0.1) | Rectangle | 4.2 | Rectangle | 4.2 |
| Ex. 12 | A-46 (0.3) | z63 (0.3) | RA-21 | PEA (0.02) | W-2 | A1/B1 (70/30) | | Rectangle | 3.9 | Rectangle | 3.4 |
| Ex. 13 | A-48 (0.3) | z69 (0.5) | RA-26 | PEA/DIA (0.01/0.01) | W-4 | A1/B1 (80/20) | LCB (0.2) | Rectangle | 4.7 | Rectangle | 3.5 |
| Ex. 14 | A-53 (0.3) | z60 (0.3) | RA-8 | PEA (0.03) | W-4 | A1/A3 (60/40) | | Rectangle | 3.6 | Rectangle | 3.7 |
| Ex. 15 | A-25 (0.2) | z61 (0.3) | RA-21 | PEA (0.02) | W-1 | A1/A4 (60/40) | | Rectangle | 3.6 | Rectangle | 4.8 |
| Ex. 16 | A-34 (0.4) | z50 (0.4) | RA-15 | PEA (0.03) | W-4 | A1/B1 (80/20) | | Rectangle | 3.9 | Rectangle | 3.3 |
| Ex. 17 | A-31 (0.4) | z60 (0.4) | RA-25 | TMEA (0.03) | W-2 | A1/A3 (80/20) | | Rectangle | 3.7 | Rectangle | 3.7 |
| Ex. 18 | A-21 (0.35) | z38 (0.5) | RA-20 | DIA (0.02) | W-4 | A1/B1 (80/20) | | Rectangle | 4.3 | Rectangle | 3.6 |
| Ex. 19 | A-34 (0.3) | — (—) | RA-1 | — (—) | — | A1/B1 (60/40) | | Rectangle | 4.0 | Rectangle | 2.8 |

| Ex. No. | Comparative Compound (g) | Acid Generator Used in Combination (g) | Resin (10 g) | Basic Compound (g) | Surfactant (0.03 g) | Solvent (mass ratio) | Dissolution Inhibiting Compound (g) | Exposure Condition (1) | Exposure Condition (2) | | |
|---|---|---|---|---|---|---|---|---|---|---|---|
| Comp. Ex. 1 | — (—) | z38 (0.3) | RA-1 | PEA/DIA (0.01/0.02) | W-4 | A1/B1 (60/40) | | Taper | 8.0 | Taper | 9.5 |
| Comp. Ex. 2 | TPSB (0.3) | z38 (0.4) | RA-20 | PEA (0.03) | W-4 | A1/B1 (80/20) | | Taper | 9.9 | Taper | 11.8 |
| Comp. Ex. 3 | m-TPSB (0.3) | z38 (0.4) | RA-19 | DIA (0.03) | W-1 | A1/B1 (70/30) | | Taper | 10.2 | Taper | 9.6 |
| Comp. Ex. 4 | p-TPSB (0.3) | z38 (0.4) | RA-21 | PEA (0.03) | W-4 | A1/B1 (70/30) | | Taper | 10.2 | Taper | 10.9 |
| Comp. Ex. 5 | TPSPB (0.2) | z38 (0.3) | RA-20 | TMEA (0.03) | W-4 | A1/B1 (60/40) | LCB (0.2) | Taper | 10.9 | Taper | 11.2 |

| Ex. No. | Compound (A) (g) | Acid Generator Used in Combination (g) | Resin (10 g) | Basic Compound/ Compound (J) (g) | Surfactant (0.03 g) | Hydrophobic Resin (50 mg) | Solvent (mass ratio) | Dissolution Inhibiting Compound (g) | Exposure Condition (3) Pattern Profile | Exposure Condition (3) Line Edge Roughness (nm) |
|---|---|---|---|---|---|---|---|---|---|---|
| Ex. 56 | A-1 (0.2) | z38 (0.3) | RA-20 | PEA (0.03) | W-4 | HR-26 | A1/B1 (60/40) | | Rectangle | 4.0 |
| Ex. 57 | A-1 (0.2) | z38 (0.3) z66 (0.2) | RA-23 | DIA (0.02) | W-4 | HR-53 | A1/B1 (60/40) | | Rectangle | 3.8 |
| Ex. 58 | A-1 (0.2) | z38 (0.3) | RA-27 | APCA (0.03) | W-4 | HR-47 | A1 (100) | | Rectangle | 4.2 |
| Ex. 59 | A-1 (0.4) | z60 (0.2) | RA-28 | DIA (0.02) | W-4 | HR-49 | A1/A4 (98/2) | | Rectangle | 3.5 |

TABLE 2-continued

ArF Positive

| | | | | | | | | | | |
|---|---|---|---|---|---|---|---|---|---|---|
| Ex. 60 | A-1 (0.2) | z66 (0.3) | RA-27 | APCA (0.03) | W-4 | HR-28 | A1 (100) | | Rectangle | 3.2 |
| Ex. 61 | A-1 (0.2) | z66 (0.2) | RA-28 | APCA (0.03) | W-4 | HR-26 | A1 (100) | | Rectangle | 3.4 |
| Ex. 62 | A-2 (0.3) | z38 (0.3) | RA-20 (5 g) RA-28 (5 g) | DIA (0.02) | W-4 | HR-53 | A1/B1 (60/40) | | Rectangle | 3.5 |
| Ex. 63 | A-2 (0.2) | z38 (0.2) | RA-23 | DIA (0.02) | W-4 | HR-47 | A1/B1 (60/40) | | Rectangle | 3.5 |
| Ex. 64 | A-2 (0.2) | z60 (0.3) | RA-27 | PEA (0.03) | — | HR-49 | A1 (100) | | Rectangle | 3.9 |
| Ex. 65 | A-2 (0.2) | z60 (0.3) | RA-28 | DIA (0.02) | — | HR-28 | A1 (100) | | Rectangle | 4.0 |
| Ex. 66 | A-2 (0.3) | z66 (0.2) | RA-27 | PEA (0.03) | W-4 | HR-26 | A1/A4 (98/2) | | Rectangle | 3.5 |
| Ex. 67 | A-2 (0.2) | z66 (0.2) | RA-28 | DIA (0.02) | W-4 | HR-53 | A1 (100) | | Rectangle | 3.7 |
| Ex. 68 | A-21 (0.3) | z38 (0.2) z60 (0.4) | RA-27 | APCA (0.03) | W-4 | HR-47 | A1 (100) | | Rectangle | 3.8 |
| Ex. 69 | A-21 (0.3) | z60 (0.3) | RA-28 | APCA (0.03) | W-4 | HR-49 | A1 (100) | | Rectangle | 3.5 |
| Ex. 70 | A-21 (0.2) | z66 (0.3) | RA-27 | APCA (0.03) | — | HR-28 | A1/A4 (98/2) | | Rectangle | 3.6 |
| Ex. 71 | A-28 (0.3) | z38 (0.2) | RA-20 (5 g) RA-28 (5 g) | APCA (0.03) | — | HR-49 | A1 (100) | | Rectangle | 3.7 |
| Ex. 72 | A-28 (0.2) | z60 (0.3) | RA-27 | APCA (0.03) | W-4 | HR-28 | A1 (100) | | Rectangle | 3.8 |
| Ex. 73 | A-28 (0.2) | z66 (0.2) | RA-28 | APCA (0.03) | W-4 | HR-28 | A1 (100) | | Rectangle | 3.7 |

The abbreviations common to each table are enumerated together below.

Comparative Compounds:

The abbreviations of comparative compounds used in Comparative Examples are as follows.

TPSB: Triphenylsulfonium pentafluorobenzenesulfonate

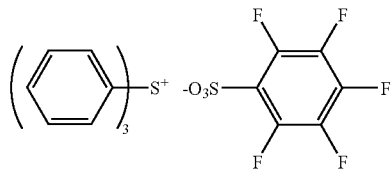

TPSPB: Triphenylsulfonium perfluorobutanesulfonate

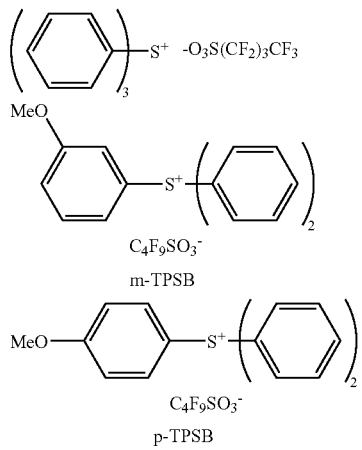

m-TPSB p-TPSB

Basic Compounds:
TPI: 2,4,5-Triphenylimidazole
TPSA: Triphenylsulfonium acetate
HEP: N-Hydroxyethylpiperidine
DIA: 2,6-Diisopropylaniline
DCMA: Dicyclohexylmethylamine
TPA: Tripentylamine
HAP: Hydroxyantipyrine
TBAH: Tetrabutylammonium hydroxide
TMEA: Tris(methoxyethoxyethyl)amine
PEA: N-Phenyldiethanolamine
TOA: Trioctylamine
DBN: 1,5-Diazabicyclo[4.3.0]non-5-ane
APCA: 4-Hydroxy-1-tert-butoxycarbonylpiperidine Surfactants:
W-1: Megafac F176 (fluorine surfactant, manufactured by Dainippon Ink and Chemicals Inc.)
W-2: Megafac R08 (fluorine/silicon surfactant, manufactured by Dainippon Ink and Chemicals Inc.)
W-3: Polysiloxane polymer KP-341 (silicon surfactant, manufactured by Shin-Etsu Chemical Co., Ltd.)
W-4: Troy Sol S-366 (manufactured by Troy Chemical Co., Ltd.)

Hydrophobic Resin:
The hydrophobic resins represented by the abbreviations in Table 2 above are the same as the specific examples in the hydrophobic resin (HR) mentioned above.

Solvents:
A1: Propylene glycol monomethyl ether acetate
A2: 2-Heptanone
A3: Cyclohexanone
A4: γ-Butyrolactone
B1: Propylene glycol monomethyl ether
B2: Ethyl lactate Dissolution Inhibiting Compounds:
LCB: t-Butyl lithocholate From the results shown in Table 2, it is apparently seen that the photosensitive compositions in the invention are excellent in pattern profile and line edge roughness in ArF ordinary exposure and ArF immersion exposure.

Examples 20 to 25 and Comparative Examples 6 to 10

(1) Formation of Lower Resist Layer

FHi-028DD resist (resist for i-ray, manufactured by Fuji Film Olin Co., Ltd.) was coated on a 6 inch silicon wafer with a spin coater Mark 8 (manufactured by Tokyo Electron Limited), baked at 90° C. for 90 seconds, whereby a uniform film having a thickness of 0.55 μm was obtained.

The obtained film was further heated at 200° C. for 3 minutes to obtain a lower resist layer having a thickness of 0.40 μm.

(2) Formation of Upper Resist Layer

A solution having the concentration of solids content of 11 mass % was prepared by dissolving the components shown in Table 3 below in the solvent shown in Table 3. The solution was filtrated through a membrane filter having a pore diameter of 0.1 μm, whereby a composition for an upper resist layer was prepared.

The upper resist layer coating composition was coated on the lower resist layer in the same manner as in the lower layer, and heated at 130° C. for 90 seconds, whereby an upper resist layer having a thickness of 0.20 μm was formed.

Resins (SI-1) to (SI-5) in Table 3 are as follows.

(3) Evaluation of Resist

The thus-obtained wafer was subjected to exposure with ArF Excimer Stepper 9300 (manufactured by ISI Co.) attached with a resolution mask with varying the exposure amount.

Subsequently, after heating at 120° C. for 90 seconds, the wafer was developed with a 2.38 mass % tetrahydroammo-

| | Molecular Weight |
|---|---|
| (SI-1) | 15000 |
| (SI-2) | 14500 |
| (SI-3) | 9600 |
| (SI-4) | 8900 |
| (SI-5) | 10800 | nium hydroxide developing solution for 60 seconds, rinsed with distilled water and dried to form an upper layer pattern. The pattern profile and line edge roughness of the resist were evaluated in the same manner as in Example 1.

The results obtained are shown in Table 3 below.

TABLE 3

Silicon-containing Positive

| Example No. | Acid Generator Used in Combination (g) | Resin (10 g) | Basic Compound (g) | Surfactant (0.03 g) | Solvent (mass ratio) | Pattern Profile | Line Edge Roughness (nm) |
|---|---|---|---|---|---|---|---|
| | Compound (A) (g) | | | | | | |
| Ex. 20 | A-1 (0.4) | z38 (0.4) | SI-1 | PEA (0.02) | W-4 | A1/A3 (80/20) | Rectangle | 3.8 |
| Ex. 21 | A-5 (0.3) | z60 (0.3) | SI-1 | PEA (0.03) | W-1 | A1/A3 (50/50) | Rectangle | 3.2 |
| Ex. 22 | A-7 (0.3) | z38 (0.4) | SI-2 | PEA (0.02) | W-3 | A1/A3 (80/20) | Rectangle | 6.5 |
| Ex. 23 | A-39 (0.3) | z38 (0.4) | SI-3 | TPA (0.03) | W-4 | A1 (100) | Rectangle | 5.9 |
| Ex. 24 | A-31 (0.3) | z38 (0.3) | SI-4 | DIA (0.03) | W-4 | A1 (100) | Rectangle | 4.1 |
| Ex. 25 | A-34 (0.25) | z60 (0.4) | SI-5 | TMEA (0.03) | W-3 | A1/A3 (80/20) | Rectangle | 3.0 |
| | Comparative Compound (g) | | | | | | |
| Comp. Ex. 6 | — (—) | z38 (0.4) | SI-1 | PEA (0.02) | W-1 | A1 (100) | Taper | 10.5 |
| Comp. Ex. 7 | TPSB (0.3) | z60 (0.3) | SI-2 | DIA (0.03) | W-4 | A1/A3 (60/40) | Taper | 9.9 |
| Comp. Ex. 8 | m-TPSB (0.4) | z38 (0.4) | SI-5 | PEA (0.03) | W-4 | A1/B1 (70/30) | Taper | 10.1 |
| Comp. Ex. 9 | p-TPSB (0.3) | z38 (0.3) | SI-4 | DIA (0.03) | W-4 | A1/A3 (70/30) | Taper | 9.1 |
| Comp. Ex. 10 | TPSPB (0.3) | z66 (0.4) | SI-4 | TPA (0.04) | W-1 | A1/A3 (60/40) | Taper | 10.7 |

From the results shown in Table 3, it is apparently seen that the photosensitive compositions in the invention are also excellent in pattern profile and line edge roughness when used as two-layered resists.

Examples 26 to 31 and Comparative Examples 11 to 15

Preparation of Resist

A positive resist solution having the concentration of solids content of 14 mass % was prepared by dissolving the components shown in Table 4 below in the solvent, and filtrating the solution through a polytetrafluoroethylene filter having a pore size of 0.1 μm.

Evaluation of Resist:

The prepared positive resist solution was uniformly coated on a silicon substrate having been subjected to hexamethyldisilazane treatment by a spin coater, and dried by heating on a hot plate at 120° C. for 90 seconds to form a resist film having a thickness of 0.4

The resist film was subjected to pattern exposure through a mask for line and space with a KrF excimer laser stepper (NA: 0.63), and heated on a hot plate at 110° C. for 90 seconds just after exposure. Further, the resist film was developed with a 2.38 mass % tetramethylammonium hydroxide aqueous solution at 23° C. for 60 seconds, rinsed with pure water for 30 seconds, and then dried, whereby a line pattern was formed. The pattern profile and line edge roughness of the resist were evaluated in the same manner as in Example 1.

The results obtained are shown in Table 4 below.

TABLE 4

KrF Positive

| Ex. No. | Acid Generator Used in Combination (g) | Resin (10 g) | Basic Compound (g) | Surfactant (0.03 g) | Solvent (mass ratio) | Dissolution Inhibiting Compound (g) | Pattern Profile | Line Edge Roughness (nm) |
|---|---|---|---|---|---|---|---|---|
| | Compound (A) (g) | | | | | | | |
| Ex. 26 | A-1 (0.4) | z38 (0.4) | R-2 | PEA (0.04) | W-4 | A1/B1 (60/40) | | Rectangle | 3.7 |
| Ex. 27 | A-5 (0.3) | z60 (0.3) | R-7 | PEA/DIA (0.01/0.02) | W-1 | A1/B1 (60/40) | | Rectangle | 4.4 |
| Ex. 28 | A-7 (0.3) | z38 (0.4) | R-8 | TMEA (0.02) | W-4 | A1/A3 (60/40) | LCB (0.1) | Rectangle | 3.3 |
| Ex. 29 | A-39 (0.3) | z38 (0.4) | R-9 | PEA (0.04) | W-4 | A1/B1 (70/30) | | Rectangle | 3.9 |

TABLE 4-continued

| | | | | | | | | | |
|---|---|---|---|---|---|---|---|---|---|
| | KrF Positive | | | | | | | | |
| Ex. No. | Acid Generator Used in Combination (g) | Resin (10 g) | Basic Compound (g) | Surfactant (0.03 g) | Solvent (mass ratio) | Dissolution Inhibiting Compound (g) | Pattern Profile | Line Edge Roughness (nm) | |
| Ex. 30 | A-31 (0.4) | z38 (0.3) | R-14 | PEA (0.02) | W-2 | A1/A4 (80/20) | | Rectangle | 3.7 |
| Ex. 31 | A-34 (0.4) Comparative Compound (g) | z60 (0.4) | R-17 | DIA (0.03) | W-3 | A1/B1 (60/40) | | Rectangle | 4.5 |
| Comp. Ex. 11 | — (—) | z38 (0.4) | R-2 | PEA (0.02) | W-4 | A1/B1 (60/40) | | Taper | 9.0 |
| Comp. Ex. 12 | TPSB (0.3) | z60 (0.3) | R-7 | DIA (0.03) | W-4 | A1/B1 (80/20) | | Taper | 8.4 |
| Comp. Ex. 13 | m-TPSB (0.4) | z38 (0.4) | R-8 | PEA (0.03) | W-1 | A1/B1 (70/30) | | Taper | 12.7 |
| Comp. Ex. 14 | p-TPSB (0.4) | z38 (0.3) | R-9 | PEA (0.03) | W-4 | A1/B1 (70/30) | | Taper | 13.0 |
| Comp. Ex. 15 | TPSPB (0.3) | z66 (0.4) | R-14 | DIA (0.02) | W-1 | A1/A3 (60/40) | | Taper | 12.1 |

The molar ratio of repeating units and weight average molecular weight of each of resins (R-2), (R-7), (R-8), (R-9), (R-14) and (R-17) used in Table 4 are shown in Table 5 below.

TABLE 5

| Resin | Molar Ratio of Repeating Units (correspondent from the left in order) | Weight Average Molecular Weight (Mw) |
|---|---|---|
| R-2 | 60/20/20 | 12,000 |
| R-7 | 60/30/10 | 18,000 |
| R-8 | 60/20/20 | 12,000 |
| R-9 | 60/40 | 13,000 |
| R-14 | 60/15/25 | 12,000 |
| R-17 | 80/20 | 15,000 |

From the results shown in Table 4, it is apparently seen that the photosensitive compositions in the invention are also excellent in pattern profile and line edge roughness as the positive resist compositions in KrF excimer laser exposure.

Examples 32 to 37 and Comparative Examples 16 to 20

Preparation of Resist

A negative resist solution having the concentration of solids content of 14 mass % was prepared by dissolving the components shown in Table 6 below in the solvent, and filtrating the solution through a polytetrafluoroethylene filter having a pore size of 0.1 μm.

Each of the prepared negative resist solutions was evaluated in the same manner as in Example 26, and the results obtained are shown in Table 6.

TABLE 6

| | | | | | | | | | |
|---|---|---|---|---|---|---|---|---|---|
| | KrF Negative | | | | | | | | |
| Example No. | Acid Generator Used in Combination (g) Compound (A) (g) | Resin (10 g) | Basic Compound (g) | Surfactant (0.03 g) | Solvent (mass ratio) | Crosslinking Agent (g) | Pattern Profile | Line Edge Roughness (nm) | |
| Ex. 32 | A-1 (0.4) | z38 (0.5) | P-1 | PEA (0.02) | W-4 | A1/B1 (60/40) | CL-1 (3) | Rectangle | 3.7 |
| Ex. 33 | A-5 (0.3) | z60 (0.3) | P-1 | DIA (0.03) | W-3 | A1/B1 (60/40) | CL-4 (4) | Rectangle | 2.5 |
| Ex. 34 | A-7 (0.5) | z38 (0.4) | P-2 | PEA (0.03) | W-1 | A1/B1 (80/20) | CL-1 (2) | Rectangle | 3.6 |
| Ex. 35 | A-39 (0.3) | z38 (0.4) | P-2 | PEA (0.02) | W-2 | A1/B1 (70/30) | CL-1 (2) | Rectangle | 3.1 |
| Ex. 36 | A-31 (0.4) | z38 (0.3) | P-2 | PEA/DIA (0.01/0.02) | W-4 | A1/A3 (80/20) | CL-1 (2) | Rectangle | 4.2 |
| Ex. 37 | A-34 (0.3) Comparative Compound (g) | z60 (0.4) | P-3 | PEA (0.02) | W-4 | A1/B1 (60/40) | CL-3 (2) | Rectangle | 3.4 |
| Comp. Ex. 16 | — (—) | z38 (0.4) | P-1 | HAP (0.02) | W-1 | A1/B1 (60/40) | CL-1 (2) | Taper | 10.5 |

TABLE 6-continued

| | | KrF Negative | | | | | | | |
|---|---|---|---|---|---|---|---|---|---|
| Example No. | Acid Generator Used in Combination (g) | Resin (10 g) | Basic Compound (g) | Surfactant (0.03 g) | Solvent (mass ratio) | Crosslinking Agent (g) | Pattern Profile | Line Edge Roughness (nm) |
| Comp. Ex. 17 | TPSB (0.4) | z38 (0.3) | P-1 | DIA (0.03) | W-4 | A1/B1 (60/40) | CL-4 (4) | Reverse taper | 8.0 |
| Comp. Ex. 18 | m-TPSB (0.4) | z38 (0.4) | P-2 | PEA (0.03) | W-4 | A1/A4 (80/20) | CL-2 (4) | Taper | 9.9 |
| Comp. Ex. 19 | p-TPSB (0.4) | z60 (0.3) | P-3 | DIA (0.04) | W-4 | A1/B1 (80/20) | CL-1 (2) | Taper | 10.2 |
| Comp. Ex. 20 | TPSPB (0.3) | z66 (0.4) | P-3 | PEA (0.02) | W-4 | A1/A3 (60/40) | CL-5 (2) | Taper | 10.5 |

The structures, molecular weights, and molecular weight distributions of the alkali-soluble resins and crosslinking agents in Table 6 are shown below.

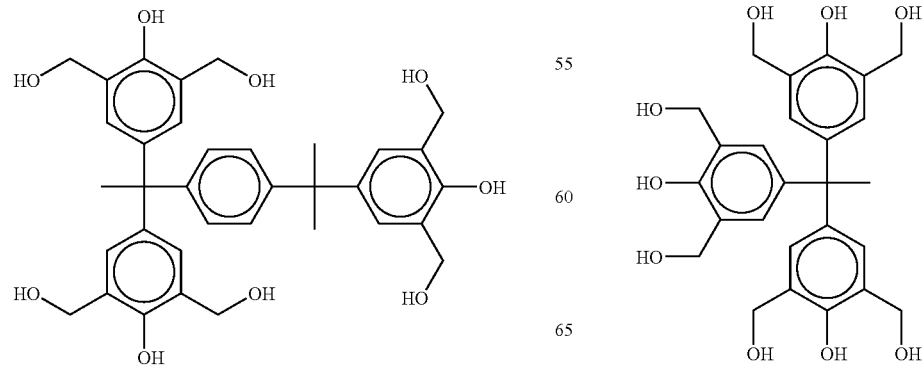

VP-5000 (manufactured by Nippon Soda Co., Ltd.)

-continued

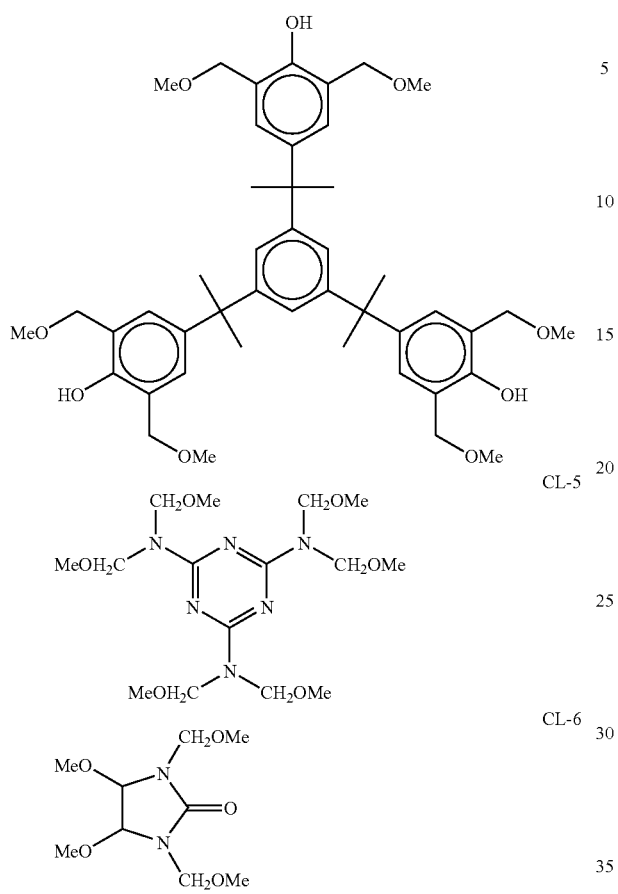

From the results shown in Table 6, it is apparently seen that the photosensitive compositions in the invention are also excellent in pattern profile and line edge roughness as the negative resist compositions in KrF excimer laser exposure.

Examples 38 to 43 and Comparative Examples 21 to 25

Preparation of Resist

A positive resist solution having the concentration of solids content of 12 mass % was prepared by dissolving the components shown in Table 4 in the solvent, and filtrating the solution through a polytetrafluoroethylene filter having a pore size of 0.1 μm.
Evaluation of Resist:

The prepared positive resist solution was uniformly coated on a silicon substrate having been subjected to hexamethyldisilazane treatment by a spin coater, and dried by heating on a hot plate at 120° C. for 60 seconds to form a resist film having a thickness of 0.3 μm.

The resist film was irradiated with an electron beam projection lithographic apparatus (accelerating voltage: 100 keV, manufactured by Nikon Corporation), and heated on a hot plate at 110° C. for 90 seconds just after irradiation. Further, the resist film was developed with a 2.38 mass % tetramethylammonium hydroxide aqueous solution at 23° C. for 60 seconds, rinsed with pure water for 30 seconds, and then dried, whereby a line and space pattern was formed. The pattern profile and line edge roughness of the resist were evaluated in the same manner as in Example 1.

The results obtained are shown in Table 7 below.

TABLE 7

| | EB Positive | |
|---|---|---|
| | Pattern Profile | Line Edge Roughness (nm) |
| Example No. | | |
| Example 38 | Rectangle | 3.5 |
| Example 39 | Rectangle | 3.4 |
| Example 40 | Rectangle | 3.6 |
| Example 41 | Rectangle | 3.6 |
| Example 42 | Rectangle | 3.9 |
| Example 43 | Rectangle | 4.0 |
| Comparative Example No. | | |
| Comparative Example 21 | Taper | 10.2 |
| Comparative Example 22 | Taper | 8.7 |
| Comparative Example 23 | Taper | 7.5 |
| Comparative Example 24 | Taper | 9.6 |
| Comparative Example 25 | Taper (a little) | 12.1 |

From the results shown in Table 7, it is apparently seen that the photosensitive compositions in the invention are also excellent in pattern profile and line edge roughness as the positive resist compositions for electron beam irradiation.

Examples 44 to 49 and Comparative Examples 26 to 30

Preparation of Resist

A negative resist solution having the concentration of solids content of 12 mass % was prepared by dissolving the components shown in Table 6 in the solvent, and filtrating the solution through a polytetrafluoroethylene filter having a pore size of 0.1 μm.

Evaluation of Resist:

The prepared negative resist solution was uniformly coated on a silicon substrate having been subjected to hexamethyldisilazane treatment by a spin coater, and dried by heating on a hot plate at 120° C. for 60 seconds to form a resist film having a thickness of 0.3 μm.

The resist film was irradiated with an electron beam projection lithographic apparatus (accelerating voltage: 100 keV, manufactured by Nikon Corporation), and heated on a hot plate at 110° C. for 90 seconds just after irradiation. Further, the resist film was developed with a 2.38 mass % tetramethylammonium hydroxide aqueous solution at 23° C. for 60 seconds, rinsed with pure water for 30 seconds, and then dried, whereby a line and space pattern was formed. The pattern profile and line edge roughness of the resist were evaluated in the same manner as in Example 1.

The results obtained are shown in Table 8 below.

TABLE 8

| | | EB Negative |
|---|---|---|
| Example No. | Pattern Profile | Line Edge Roughness (nm) |
| Example 44 | Rectangle | 4 |
| Example 45 | Rectangle | 2.9 |
| Example 46 | Rectangle | 3.4 |
| Example 47 | Rectangle | 3 |
| Example 48 | Rectangle | 3.4 |
| Example 49 | Rectangle | 3.7 |
| Comparative Example 26 | Taper | 10.2 |
| Comparative Example 27 | Taper | 10.9 |
| Comparative Example 28 | Taper | 10.5 |
| Comparative Example 29 | Taper | 9.9 |
| Comparative Example 30 | Taper | 11 |

From the results shown in Table 8, it is apparently seen that the photosensitive compositions in the invention are also excellent in pattern profile and line edge roughness as the negative resist compositions for electron beam irradiation.

Examples 50 to 55 and Comparative Examples 31 to 35

A positive resist solution having the concentration of solids content of 8 mass % was prepared by dissolving the components shown in Table 4 in the solvent, and filtrating the solution through a polytetrafluoroethylene filter having a pore size of 0.1 μm.

Evaluation of Resist:

The prepared positive resist solution was uniformly coated on a silicone substrate having been subjected to hexamethyldisilazane treatment by a spin coater, and dried by heating on a hot plate at 120° C. for 60 seconds to form a resist film having a thickness of 0.15 μm. The obtained resist film was subjected to areal exposure with EUV ray (wavelength: 13 nm) with varying exposure amount 0.5 by 0.5 mJ within the range of exposure amount of from 0 to 10.0 mJ, and the resist film was further baked at 110° C. for 90 seconds. After that, a dissolving rate of the resist film at each exposure amount was measured with a 2.38% tetramethylammonium hydroxide (TMAH) aqueous solution, and a sensitivity curve was obtained. In the sensitivity curve, the exposure amount at the time when the dissolving rate of the resist was saturated was taken as sensitivity, and dissolving contrast (γ value) was computed from the gradient of the straight line part of the sensitivity curve. The greater the γ value, the better is the dissolving contrast.

The results of evaluations obtained are shown in Table 9 below.

TABLE 9

| | Extreme Ultraviolet Radiation | |
|---|---|---|
| Example No. | Sensitivity (mJ/cm$^2$) | γ Value |
| Example 50 | 2.7 | 17.3 |
| Example 51 | 2.8 | 16.2 |
| Example 52 | 2.9 | 18.1 |
| Example 53 | 2.2 | 16.6 |
| Example 54 | 2.5 | 17.4 |
| Example 55 | 2.3 | 16.8 |

TABLE 9-continued

| | Extreme Ultraviolet Radiation | |
|---|---|---|
| Example No. | Sensitivity (mJ/cm$^2$) | γ Value |
| Comparative Example 31 | 5.1 | 8.2 |
| Comparative Example 32 | 5.3 | 8.8 |
| Comparative Example 33 | 5.6 | 8.6 |
| Comparative Example 34 | 6.2 | 9.1 |
| Comparative Example 35 | 6.2 | 10.1 |

From the results shown in Table 9, it can be seen that the resist compositions in the invention are high sensitivity, high contrast and excellent in the characteristic evaluation by irradiation with EUV rays as compared with comparative compositions.

The invention can provide a photosensitive composition that shows good line edge roughness and pattern profile, and improved in the contrast of sensitivity and dissolution in EUV exposure, a pattern-forming method using the photosensitive composition, and compounds for use in the photosensitive composition. The invention can further provide a photosensitive composition suitable for immersion exposure having good performances as described above even in immersion exposure, a pattern-forming method using the photosensitive composition, and compounds for use in the photosensitive composition.

The entire disclosure of each and every foreign patent application from which the benefit of foreign priority has been claimed in the present application is incorporated herein by reference, as if fully set forth.

What is claimed is:
1. A photosensitive composition, which comprises:
(A) a sulfonium salt compound represented by formula (I);
(C) a resin capable of decomposing by an action of an acid to increase a solubility in an alkali developing solution which does not have an aromatic group; and
(HR) a hydrophobic resin having at least either a fluorine atom or a silicon atom:

(I)

wherein A represents an (m+1)-valent linking group, when a plurality of A's are present, the plurality of A's may be the same or different, and the plurality of A's may be bonded to each other to form a cyclic structure;
R represents a monovalent organic group, when two R's are present, the two R's may be the same or different, and the two R's may be bonded to each other to form a cyclic structure;
L represents a lactone ring structure, when a plurality of L's are present, the plurality of L's may be the same or different;
X$^-$ represents an anion;
n represents an integer of from 1 to 3; and
m represents an integer of 1 or 2;
wherein when m is 1, A represents a divalent linking group for linking S$^+$ and L, the divalent linking group being selected from the group consisting of an arylene group, an alkylene group, a cycloalkylene group, an alkenylene group, an ether group, an ester group, —NH—, —SO$_2$— and a group formed by a combination thereof, each of which may have a substituent, and when m is 2, A is a group in which an arbitrary hydrogen atom in the divalent linking group selected from the corresponding case where m is 1 replaced by the other L.

2. The photosensitive composition according to claim 1, wherein the (m+1)-valent linking group represented by A has an aromatic ring.

3. The photosensitive composition according to claim 1, wherein the anion represented by X$^-$ in formula (I) is an organic sulfonate anion (R$^1$—SO$_3^-$), an organic carboxylate anion (R$^1$—CO$_2^-$), an organic imidate anion (N$^-$(SO$_2$—R$^1$)$_2$, N$^-$(SO$_2$—R$^1$)(CO—R$^1$)) or an organic methidate anion (C$^-$(SO$_2$—O$_3$), wherein R$^1$ represents a monovalent organic group.

4. The photosensitive composition according to claim 1, wherein the hydrophobic resin (HR) contains at least one group selected from the group consisting of the following (x) to (z):
(x) an alkali-soluble group;
(y) a group capable of decomposing by an action of an alkali developing solution to increase a solubility in an alkali developing solution; and
(z) a group capable of decomposing by an action of an acid.

5. The photosensitive composition according to claim 1, which further comprises (B) a compound capable of generating an acid upon irradiation with actinic ray or radiation.

6. The photosensitive composition according to claim 5, wherein the compound of component (B) is a sulfonium salt of a fluoro-substituted alkanesulfonic acid, a fluorine-substituted benzenesulfonic acid or a fluorine-substituted imidic acid.

7. The photosensitive composition according to claim 1, wherein the resin of component (C) has a monocyclic or polycyclic alicyclic hydrocarbon structure.

8. The photosensitive composition according to claim 1, wherein the resin of component (C) has a repeating unit having a lactone structure.

9. A resist film, which is formed from a photosensitive composition according to claim 1.

10. A pattern-forming method, which comprises:
forming a photosensitive film with a photosensitive composition according to claim 1; and
exposing and developing the photosensitive film.

11. The pattern-forming method according to claim 10, wherein the photosensitive film is exposed via an immersion liquid.

12. A photosensitive composition, which comprises:
(A) a sulfonium salt compound represented by formula (I);
(C) a resin capable of decomposing by an action of an acid to increase a solubility in an alkali developing solution which does not have an aromatic group; and
(HR) a hydrophobic resin having at least either a fluorine atom or a silicon atom:

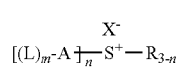

(I)

wherein A represents an (m+1)-valent linking group, when a plurality of A's are present, the plurality of A's may be the same or different, and the plurality of A's may be bonded to each other to form a cyclic structure;

R represents a monovalent organic group, when two R's are present, the two R's may be the same or different, and the two R's may be bonded to each other to form a cyclic structure;
L represents a lactone ring structure, when a plurality of L's are present, the plurality of L's may be the same or different;
X$^-$ represents an anion;
n represents an integer of from 1 to 3; and
m represents an integer of 1 or 2;
wherein when m is 1, A represents a divalent linking group for linking S$^+$ and L, the divalent linking group being selected from the group and combination of groups consisting of an arylene group, the combination of an arylene group and an alkylene group, the combination of an aryelene group and an ether group, the combination of an arylene group and an ester group, the combination of an alkylene group and an ester group, the combination of an arylene group and an alkenylene group, the combination of an arylene group, an alkylene group and an ester group, the combination of an arylene group, —NH—, and —CO—, the combination of an arylene group, —NH— and —SO$_2$—, the combination of an arylene group, an alkylene group and —NH—, the combination of an arylene group, an ether group, a cycloalkylene group and an ester group, the combination of an arylene group, an alkylene group, an alkenylene group and an ester group, and the combination of an arylene group, an alkylene group —CO—, and an ether group, each of which may have a substituent, and when m is 2, A is a group in which an arbitrary hydrogen atom in the divalent linking group selected from the corresponding case where m is 1 replaced by the other L.

13. The photosensitive composition according to claim 12, wherein the anion represented by X$^-$ in formula (I) is an organic sulfonate anion (R$^1$—SO$_3^-$), an organic carboxylate anion (R$^1$—CO$_2^-$), an organic imidate anion (N$^-$(SO$_2$—R$^1$)$_2$, N$^-$(SO$_2$—R$^1$)(CO—R$^1$)) or an organic methidate anion (C$^-$(SO$_2$—R$^1$)$_3$), wherein R$^1$ represents a monovalent organic group.

14. The photosensitive composition according to claim 12, wherein the hydrophobic resin (HR) contains at least one group selected from the group consisting of the following (x) to (z):
(x) an alkali-soluble group;
(y) a group capable of decomposing by an action of an alkali developing solution to increase a solubility in an alkali developing solution; and
(z) a group capable of decomposing by an action of an acid.

15. The photosensitive composition according to claim 12, which further comprises (B) a compound capable of generating an acid upon irradiation with actinic ray or radiation.

16. The photosensitive composition according to claim 15, wherein the compound of component (B) is a sulfonium salt of a fluoro-substituted alkanesulfonic acid, a fluorine-substituted benzenesulfonic acid or a fluorine-substituted imidic acid.

17. The photosensitive composition according to claim 12, wherein the resin of component (C) has a monocyclic or polycyclic alicyclic hydrocarbon structure.

18. The photosensitive composition according to claim 12, wherein the resin of component (C) has a repeating unit having a lactone structure.

19. A resist film, which is formed from a photosensitive composition according to claim 12.

20. A pattern-forming method, which comprises:
forming a photosensitive film with a photosensitive composition according to claim 12; and
exposing and developing the photosensitive film.

21. The pattern-forming method according to claim 20, wherein the photosensitive film is exposed via an immersion liquid.

22. A photosensitive composition, which comprises:
(A) a sulfonium salt compound represented by formula (I);
(C) a resin capable of decomposing by an action of an acid to increase a solubility in an alkali developing solution which does not have an aromatic group; and
(HR) a hydrophobic resin having at least either a fluorine atom or a silicon atom:

(I)

wherein A represents an (m+1)-valent linking group, when a plurality of A's are present, the plurality of A's may be the same or different, and the plurality of A's may be bonded to each other to form a cyclic structure;
R represents a monovalent organic group, when two R's are present, the two R's may be the same or different, and the two R's may be bonded to each other to form a cyclic structure;
L represents a lactone ring structure, when a plurality of L's are present, the plurality of L's may be the same or different;
$X^-$ represents an anion;
n represents an integer of from 1 to 3; and
m represents an integer of 1 or 2;
wherein when m is 1, A represents a divalent linking group for linking $S^+$ and L, the divalent linking group being selected from the group consisting of an arylene group, an alkylene group, a cycloalkylene group, an alkenylene group, an ether group, an ester group, —CO—, —NH—, —SO$_2$— and a group formed by a combination thereof, each of which may have a substituent, and when m is 2, A is a group in which an arbitrary hydrogen atom in the divalent linking group selected from the corresponding case where m is 1 replaced by the other L,
wherein the (m+1)-valent linking group represented by A comprises an arylene group.

23. The photosensitive composition according to claim 22, wherein the anion represented by $X^-$ in formula (I) is an organic sulfonate anion ($R^1$—$SO_3^-$), an organic carboxylate anion ($R^1$—$OO_2^-$), an organic imidate anion ($N^-(SO_2$—$R^1)_2$, $N^-(SO_2$—$R^1)(CO$—$R^1)$) or an organic methidate anion ($C^-(SO_2$—$O_3)$, wherein $R^1$ represents a monovalent organic group.

24. The photosensitive composition according to claim 22, wherein the hydrophobic resin (HR) contains at least one group selected from the group consisting of the following (x) to (z):
(x) an alkali-soluble group;
(y) a group capable of decomposing by an action of an alkali developing solution to increase a solubility in an alkali developing solution; and
(z) a group capable of decomposing by an action of an acid.

25. The photosensitive composition according to claim 22, which further comprises (B) a compound capable of generating an acid upon irradiation with actinic ray or radiation.

26. The photosensitive composition according to claim 25, wherein the compound of component (B) is a sulfonium salt of a fluoro-substituted alkanesulfonic acid, a fluorine-substituted benzenesulfonic acid or a fluorine-substituted imidic acid.

27. The photosensitive composition according to claim 22, wherein the resin of component (C) has a monocyclic or polycyclic alicyclic hydrocarbon structure.

28. The photosensitive composition according to claim 22, wherein the resin of component (C) has a repeating unit having a lactone structure.

29. A resist film, which is formed from a photosensitive composition according to claim 22.

30. A pattern-forming method, which comprises:
forming a photosensitive film with a photosensitive composition according to claim 22; and
exposing and developing the photosensitive film.

31. The pattern-forming method according to claim 30, wherein the photosensitive film is exposed via an immersion liquid.

32. A photosensitive composition, which comprises:
(A) a sulfonium salt compound represented by formula (I);
(C) a resin capable of decomposing by an action of an acid to increase a solubility in an alkali developing solution which does not have an aromatic group; and
(HR) a hydrophobic resin having at least either a fluorine atom or a silicon atom:

(I)

wherein A represents an (m+1)-valent linking group, when a plurality of A's are present, the plurality of A's may be the same or different, and the plurality of A's may be bonded to each other to form a cyclic structure;
R represents a monovalent organic group, when two R's are present, the two R's may be the same or different, and the two R's may be bonded to each other to form a cyclic structure;
L represents a lactone ring structure, when a plurality of L's are present, the plurality of L's may be the same or different;
$X^-$ represents an anion;
n represents an integer of from 1 to 3; and
m represents an integer of 1 or 2;
wherein when m is 1, A represents a divalent linking group for linking $S^+$ and L, the divalent linking group being selected from the group consisting of an arylene group, an alkylene group, a cycloalkylene group, an alkenylene group, an ether group, an ester group, —CO—, —NH—, —SO$_2$— and a group formed by a combination thereof, each of which may have a substituent, and when m is 2, A is a group in which an arbitrary hydrogen atom in the divalent linking group selected from the corresponding case where m is 1 replaced by the other L, and
wherein the (m+1)-valent linking group represented by A has an aromatic ring directly bonded to the sulfur atom ($S^+$).

33. The photosensitive composition according to claim 32, wherein the anion represented by $X^-$ in formula (I) is an organic sulfonate anion ($R^1$—$SO_3^-$), an organic carboxylate anion ($R^1$—$CO_2^-$), an organic imidate anion ($N^-(SO_2$—$R^1)_2$, $N^-(SO_2$—$R^1)(CO$—$R^1)$) or an organic methidate anion ($C^-(SO_2-R^1)_3$), wherein $R^1$ represents a monovalent organic group.

34. The photosensitive composition according to claim 32, wherein the hydrophobic resin (HR) contains at least one group selected from the group consisting of the following (x) to (z):
(x) an alkali-soluble group;
(y) a group capable of decomposing by an action of an alkali developing solution to increase a solubility in an alkali developing solution; and
(z) a group capable of decomposing by an action of an acid.

35. The photosensitive composition according to claim 32, which further comprises (B) a compound capable of generating an acid upon irradiation with actinic ray or radiation.

36. The photosensitive composition according to claim 35, wherein the compound of component (B) is a sulfonium salt of a fluoro-substituted alkanesulfonic acid, a fluorine-substituted benzenesulfonic acid or a fluorine-substituted imidic acid.

37. The photosensitive composition according to claim 32, wherein the resin of component (C) has a monocyclic or polycyclic alicyclic hydrocarbon structure.

38. The photosensitive composition according to claim 32, wherein the resin of component (C) has a repeating unit having a lactone structure.

39. A resist film, which is formed from a photosensitive composition according to claim 32.

40. A pattern-forming method, which comprises:
forming a photosensitive film with a photosensitive composition according to claim 32; and
exposing and developing the photosensitive film.

41. The pattern-forming method according to claim 40, wherein the photosensitive film is exposed via an immersion liquid.

42. The photosensitive composition according to claim 1, wherein the (m+1)-valent linking group represented by A has an aromatic ring directly bonded to the sulfur atom ($S^+$).

43. The photosensitive composition according to claim 12, wherein the (m+1)-valent linking group represented by A has an aromatic ring directly bonded to the sulfur atom ($S^+$).

* * * * *